US012297274B2

(12) United States Patent
Kuball et al.

(10) Patent No.: US 12,297,274 B2
(45) Date of Patent: May 13, 2025

(54) METHOD OF CELL THERAPY

(71) Applicants: UMC UTRECHT HOLDING B.V., Utrecht (NL); Gadeta B.V., Utrecht (NL); Albert-Ludwigs-Universität Freiburg, Freiburg (DE)

(72) Inventors: Jürgen Herbert Ernst Kuball, Hilversum (NL); Anke Janssen, Utrecht (NL); Dennis Beringer, Utrecht (NL); Paul Fisch, Freiburg im Breisgau (DE); Jose Alberto Villacorta Hidalgo, Gundelfingen (DE)

( * ) Notice: Subject to any disclaimer, the term of this patent is extended or adjusted under 35 U.S.C. 154(b) by 951 days.

(21) Appl. No.: 17/124,667

(22) Filed: Dec. 17, 2020

(65) Prior Publication Data

US 2021/0177901 A1 Jun. 17, 2021

Related U.S. Application Data

(60) Division of application No. 16/215,456, filed on Dec. 10, 2018, now Pat. No. 11,166,984, which is a continuation of application No. PCT/EP2017/064325, filed on Jun. 12, 2017.

(30) Foreign Application Priority Data

Jun. 10, 2016 (EP) .................................. 16173970.1
Jun. 10, 2016 (EP) .................................. 16173986.7

(51) Int. Cl.

| | |
|---|---|
| ***A61K 35/17*** | (2025.01) |
| ***A61K 39/00*** | (2006.01) |
| ***A61P 35/00*** | (2006.01) |
| ***C07K 14/725*** | (2006.01) |
| ***C07K 16/28*** | (2006.01) |
| ***C07K 16/30*** | (2006.01) |
| ***C12N 5/078*** | (2010.01) |
| ***C12N 5/0783*** | (2010.01) |
| ***C12N 15/62*** | (2006.01) |
| ***C12N 15/90*** | (2006.01) |
| ***C12Q 1/6809*** | (2018.01) |
| ***G01N 33/569*** | (2006.01) |
| *A61K 38/00* | (2006.01) |

(52) U.S. Cl.

CPC ...... *C07K 16/2833* (2013.01); *A61K 39/4611* (2023.05); *A61K 39/4632* (2023.05); *A61K 39/4644* (2023.05); *A61P 35/00* (2018.01); *C07K 14/7051* (2013.01); *C07K 16/30* (2013.01); *C12N 5/0634* (2013.01); *C12N 5/0636* (2013.01); *C12N 5/0638* (2013.01); *C12N 15/62* (2013.01); *C12N 15/907* (2013.01); *C12Q 1/6809* (2013.01); *G01N 33/56977* (2013.01); *A61K 38/00* (2013.01); *A61K 2239/31* (2023.05); *A61K 2239/38* (2023.05); *A61K 2239/49* (2023.05); *C07K 2317/32* (2013.01); *G01N 2800/7028* (2013.01)

(58) Field of Classification Search

CPC ...................................................... A61K 35/17

See application file for complete search history.

(56) References Cited

U.S. PATENT DOCUMENTS

| | | | |
|---|---|---|---|
| 5,260,223 | A | 11/1993 | Brenner |
| 5,350,674 | A | 9/1994 | Boenisch et al. |
| 5,585,362 | A | 12/1996 | Wilson et al. |
| 5,723,309 | A | 3/1998 | Bonneville |
| 5,962,272 | A | 10/1999 | Chenchik et al. |
| 6,165,782 | A | 12/2000 | Naldini et al. |
| 6,207,455 | B1 | 3/2001 | Chang |
| 6,218,181 | B1 | 4/2001 | Verma et al. |
| 6,277,633 | B1 | 8/2001 | Olsen |
| 6,323,031 | B1 | 11/2001 | Cichutek |
| 8,999,715 | B2 | 7/2015 | Bonini et al. |
| 9,891,211 | B2 | 2/2018 | Kuball et al. |
| 10,324,083 | B2 | 6/2019 | Kuball et al. |
| 2002/0011914 | A1 | 1/2002 | Ikeura et al. |
| 2002/0142389 | A1 | 3/2002 | Jakobsen et al. |
| 2002/0119149 | A1 | 8/2002 | Jakobsen et al. |
| 2004/0101519 | A1 | 5/2004 | June et al. |
| 2005/0249743 | A1 | 11/2005 | Boon-Falleur et al. |
| 2005/0255105 | A1 | 11/2005 | Chien et al. |
| 2006/0034810 | A1 | 2/2006 | Riley et al. |
| 2006/0093613 | A1 | 4/2006 | Jakobsen et al. |
| 2006/0155115 | A1 | 7/2006 | Jakobsen et al. |
| 2007/0036812 | A1 | 2/2007 | Sato et al. |
| 2008/0131415 | A1 | 5/2008 | Riddell et al. |

(Continued)

FOREIGN PATENT DOCUMENTS

| | | | |
|---|---|---|---|
| CA | 2996887 | A1 | 3/2017 |
| CN | 1308674 | A | 8/2001 |

(Continued)

OTHER PUBLICATIONS

Agrati et al., 2016, Cell Death and Disease, vol. 7, pp. 1-8 (Year: 2016).*

(Continued)

*Primary Examiner* — Anoop K Singh
*Assistant Examiner* — David A Montanari
(74) *Attorney, Agent, or Firm* — POLSINELLI PC

(57) ABSTRACT

The present invention relates to a method for identifying δT-cell (or γT-cell) receptors chains or parts thereof that mediate an anti-tumor or anti-infection response by identifying amino acid sequences comprising δT-cells (or γT-cell) receptors chains or parts thereof that are shared between different donors.

13 Claims, 16 Drawing Sheets

Specification includes a Sequence Listing.

(56) References Cited

U.S. PATENT DOCUMENTS

| | | | |
|---|---|---|---|
| 2009/0105133 | A1 | 4/2009 | Boulter |
| 2010/0151467 | A1 | 6/2010 | Wohlgemuth |
| 2014/0120622 | A1 | 1/2014 | Gregory et al. |
| 2014/0356398 | A1 | 4/2014 | Riddell et al. |
| 2014/0219975 | A1 | 7/2014 | June et al. |
| 2014/0308250 | A1 | 10/2014 | Handgretinger et al. |
| 2015/0017137 | A1 | 1/2015 | Spencer et al. |
| 2015/0050670 | A1 | 2/2015 | Kuball et al. |
| 2015/0344844 | A1 | 3/2015 | Better et al. |
| 2015/0306142 | A1 | 10/2015 | Bonini et al. |
| 2015/0353643 | A1 | 10/2015 | Olive et al. |
| 2016/0367664 | A1 | 12/2016 | Wang et al. |
| 2017/0174741 | A1 | 6/2017 | Kuball et al. |
| 2018/0188234 | A1 | 5/2018 | Kuball et al. |
| 2020/0345845 | A1 | 11/2020 | Kahvejian et al. |

FOREIGN PATENT DOCUMENTS

| | | | |
|---|---|---|---|
| CN | 1379041 | A | 11/2002 |
| CN | 1849395 | A | 10/2006 |
| CN | 101155829 | A | 4/2008 |
| CN | 101287754 | A | 10/2008 |
| CN | 102272153 | A | 12/2011 |
| CN | 102532269 | A | 4/2012 |
| CN | 102453701 | A | 5/2012 |
| CN | 102532269 | B | 9/2014 |
| CN | 105296431 | A | 3/2016 |
| EP | 0403156 | B1 | 9/1997 |
| EP | 1080193 | A2 | 7/2001 |
| EP | 1066380 | B1 | 11/2001 |
| EP | 2099902 | A1 | 9/2009 |
| EP | 1956080 | B1 | 9/2011 |
| EP | 2710123 | A2 | 3/2014 |
| EP | 2686417 | B1 | 8/2016 |
| EP | 3091074 | A1 | 11/2016 |
| EP | 3102609 | A2 | 12/2016 |
| EP | 3144388 | | 3/2017 |
| FR | 901228 | A | 7/1945 |
| JP | 2009508517 | A | 3/2009 |
| WO | 9412648 | A2 | 9/1994 |
| WO | 9958557 | A2 | 11/1999 |
| WO | WO9960120 | A2 | 11/1999 |
| WO | 0224718 | A1 | 3/2002 |
| WO | 03060097 | A2 | 7/2003 |
| WO | 03090694 | A2 | 11/2003 |
| WO | 2004016225 | A2 | 2/2004 |
| WO | 2005016962 | A2 | 2/2005 |
| WO | 2005019258 | A2 | 3/2005 |
| WO | WO2005/019258 | | 3/2005 |
| WO | WO2005/051988 | | 6/2005 |
| WO | 2005051988 | A3 | 7/2005 |
| WO | 2005016962 | A3 | 9/2005 |
| WO | 2006056733 | A1 | 1/2006 |
| WO | WO2006/026051 | | 3/2006 |
| WO | 2007034489 | A2 | 3/2007 |
| WO | 2007034489 | A3 | 6/2007 |
| WO | 2006026051 | A3 | 12/2007 |
| WO | 2009136874 | A1 | 12/2009 |
| WO | 2010087335 | A1 | 5/2010 |
| WO | WO2010058023 | A1 | 5/2010 |
| WO | 2013147606 | A1 | 3/2013 |
| WO | WO2013/147606 | | 10/2013 |
| WO | 2015075939 | | 5/2015 |
| WO | WO2014/179202 | A1 | 5/2015 |
| WO | 2015063069 | A1 | 7/2015 |
| WO | 2015174439 | | 11/2015 |
| WO | 2016195086 | A1 | 8/2016 |
| WO | 2017096239 | A1 | 8/2017 |
| WO | 2017197347 | A1 | 11/2017 |
| WO | 2017201019 | A1 | 11/2017 |
| WO | 2017212072 | A1 | 12/2017 |
| WO | 2017212074 | A1 | 12/2017 |
| WO | 2018162563 | A1 | 9/2018 |
| WO | 2018211115 | A1 | 11/2018 |
| WO | 2019219979 | A1 | 11/2019 |

OTHER PUBLICATIONS

Walker et al., 2012, Cold Spring Harb Perspect Med, vol. 2, pp. 1-19 (Year: 2012).*

Saura-Esteller et al. (2022, Frontiers in Immunology, vol. 13, pp. 1-11) (Year: 2022).*

Schonefeldt et al. (2021, Cancers, vol. 13, pp. 1-31) (Year: 2021).*

Frey et al. (2019, J. Clinical Oncology, vol. 38(5), pp. 415-422) (Year: 2019).*

Gardner et al. (2017, Blood, vol. 129(25), pp. 3322-3331) (Year: 2017).*

Adams, Erin J. et al., An autonomous CDR3δ is sufficient for γδ T cell recognition of the nonclassical MHC-I T10/T22, Nat Immunol., 2008, vol. 9, Issue 7, pp. 777-784.

European Office Action 17733994.2 issued Feb. 24, 2020, 7 pages.

Guo, Xi-zhi J. et al., Rapid cloning, expression, and functional characterization of paired ap and yS T-cell receptor chains from single-cell analysis, Methods & Clinical Development, Jan. 2016, vol. 3 , Article 15054.

Lafarge, Xavier et al., Expression of MHC class I receptors confers functional intraclonal heterogeneity to a reactive expansion of γδ T cells, Eropean Journal of Immunology, 2005, vol. 35, Issue 6, pp. 1896-1905.

Sadelain, Michael et al., The Basic Principles of Chimeric Antigen Receptor Design, Cancer Discovery, Apr. 2013, vol. 3, Issue 4, pp. 388-398.

Altschul S.F., et al., "Basic Local Alignment Search Tool," Journal of Molecular Biology, Oct. 1990, vol. 215(3), pp. 403-410.

Anderson W.F., "Human Gene Therapy," Nature, Apr. 30, 1998, vol. 392, pp. 25-30.

Ausubel, et al., "Current Protocols in Molecular Biology," Greene Publishing and Wiley-Interscience, 1987, 8 pages.

Berge, et al., "Selective Expansion of a Peripheral Blood CD8+ Memory T Cell Subset Expressing Both Granzyme B and L-Selectin During Primary Viral Infection in Renal Allograft Recipients," Transplant Proceedings, 1998, vol. 30, No. 8, pp. 3975-3977.

Ciccone, et al., "Specificity of Human T Lymphocytes Expressing a γ/δ T Cell Antigen Receptor", European Journal of Immunology, 1989, vol. 19, pp. 1267-1271.

Corrected Notice of Allowability for U.S. Appl. No. 14/388,675, dated Aug. 23, 2016, 3 pages.

Corrected Notice of Allowability U.S. Appl. No. 14/388,675, dated Dec. 13, 2016, 6 pages.

David A., et al., "Transient Transgenesis in The Endocrine System: Viral Vectors for Gene Delivery," Journal of Gene Virology, 2001, vol. 80, pp. 195-232.

Erikson C., et al., "Future Supply and Demand for Oncologists: Challenges to Assuring Access to Oncology Services," Journal of Oncology Practice, 2007, vol. 3, No. 2, pp. 79-86.

Extended European Search Report for European Application No. 17203843.2, mailed Mar. 9, 2018, 14 Pages.

Garland R.J, et al., "The Use of Teflon Cell Culture Bags to Expand Functionally Active CD8+ Cytotoxic T Lymphocytes," Journal of Immunological Methods, 1999, vol. 227, pp. 53-63.

Gherardi E, et al., "A Single-Step Procedure for Cloning and Selection of Antibody-Secreting Hybridomas," Journal Immunology Methods, 1990, vol. 126, pp. 61-68.

Goncalves, "Adeno-Associated Virus: From Defective Virus to Effective Vector," Virology Journal, 2005, vol. 2, No. 1, 43, 17 pages.

Grunder C., et al., "Gamma 9-and Delta 2-CDR3 Domains Regulate Functional Avidity of T Cells Harboring gamma9delta2 T Cell Receptors," Journal of Immunotherapy, Nov.-Dec. 2012, vol. 35, No. 9, pp. 723.

Haanen, et al., "Selective Expansion of Cross-reactive CD8 1 Memory T Cells by Viral Variants," Journal Experimental Medicine, 1999, vol. 190, No. 9, pp. 1319-1328.

Henikoff S., et al., "Amino Acid Substitution Matrices from Protein Blocks," Proceedings of National Academy of Sciences, USA, Nov. 15, 1992, vol. 89, pp. 10915-10919, Comparison matrix: BLOSSUM62.

(56) References Cited

OTHER PUBLICATIONS

"Human TCR V-gamma-9 chain, Seq Id 93," Geneseq, Jan. 11, 2018, Database Accession No. BEP59562, URL: EBI, XP002789044, 2 pages.
International Preliminary Report on Patentability for International Application No. PCT/EP2017/064323, mailed Dec. 20, 2018, 12 Pages.
International Preliminary Report on Patentability for International Application No. PCT/EP2017/064325, mailed Dec. 20, 2018, 15 Pages.
International Search Report and Written Opinion for International Application No. PCT/EP2017/064323, mailed Oct. 4, 2017, 16 Pages.
International Search Report and Written Opinion for International Application No. PCT/EP2019/063004, mailed Sep. 26, 2019, 17 Pages.
International Search Report and Written Opinion for International Application No. PCT/NL2013/050235, mailed Sep. 10, 2013, 12 Pages.
International Preliminary Report on Patentability for International Application No. PCT/EP2015/077286, mailed May 23, 2017, 8 pages.
International Search Report and Written Opinion for International Application No. PCT/EP2017/064325, mailed Sep. 22, 2017, 21 Pages.
International Search Report for International Application No. PCT/EP2015/077286, mailed Jan. 27, 2016, 5 pages.
International Search Report for International Application No. PCT/NL2013/050235, mailed Oct. 9, 2013, 6 pages.
Kunkel T.A, "Rapid and Efficient Site-Specific Mutagenesis without Phenotypic Selection," Proceedings of the National Academy of Sciences of the United States of America, 1985, vol. 82, pp. 488-492.
Mandel R.J., et al., "Clinical Trials in Neurological Disorders using AAV Vectors: Promises and Challenges," Current Opinion in Molecular Therapeutics, 2004, vol. 6, No. 5, pp. 482-490.
Mellacheruvu D., et al., "The CRAPome: A Contaminant Repository for Affinity Purification Mass Spectrometry Data," Nature Methods, 2013, vol. 10, No. 8, pp. 730-736.
Needleman S.B., et al., "A General Method Applicable to the Search for Similarities in the Amino Acid Sequence of WO Proteins," Journal of Molecular Biology, Mar. 28, 1970, vol. 48(3), pp. 443-453.
Non-Final Office Action for U.S. Appl. No. 16/275,070 (51887-701.303), dated Feb. 7, 2020, 9 pages.
Notice of Allowance for U.S. Appl. No. 15/374,613, dated Jul. 6, 2018, 9 pages.
Notice of Allowance for U.S. Appl. No. 14/388,675, dated Aug. 15, 2016, 7 pages.
Office Action for U.S. Appl. No. 14/388,675, dated Jul. 20, 2017, 4 pages.
Office Action for U.S. Appl. No. 15/374,613, dated Mar. 22, 2018, 13 pages.
Office Action for U.S. Appl. No. 15/842,784, dated Jul. 5, 2018, 11 pages.
Office Action for U.S. Appl. No. 14/388,675, dated Apr. 26, 2016, 4 pages.
Office Action for U.S. Appl. No. 14/388,675, dated Dec. 29, 2015, 7 pages.
Office Action for U.S. Appl. No. 15/374,613, dated Nov. 20, 2017, 20 pages.
Paul W.E., "Fundamental Immunology, Third Edition," Structure and Function of Immunoglobulins, Raven Press, 1993, pp. 292-295.
Peng K.-W., et al., "Viral Vector Targeting," Current Opinion Biotechnology, 1999, vol. 10: 454-457.
Riddel G., et al., "The Use of Anti-CD3 and Anti-CD28 Monoclonal Antibodies to Clone and Expand Human Antigen-Specific T Cells," Journal Immunology Methods 1990, vol. 128, No. 2, pp. 189-201.
Scheper W., et al., "477. Multipotent Vσ2-Negative γσT-Cells after CMV-Reactivation in Allogeneic Stem Cell Transplantation," Molecular Therapy, May 2012, vol. 20, Supplement 1, pp. S185.
Scheper W., et al., "Hunting for Clinical Translation with Innate-like Immune Cells and their Receptors," Leukemia, 2014, vol. 28, pp. 1181-1190.
Schneider C.A., et al., "NIH Image to ImageJ: 25 Years of Image Analysis," Nature Methods, Jul. 2012, vol. 9, No. 7, pp. 671-675.
Sebestyen Z, et al., "Long Wavelength Fluorophores and Cell-by-Cell Correction for Autofluorescence Significantly Improves the Accuracy of Flow Cytometric Energy Transfer Measurements on a Dual-Laser Benchtop Flow Cytometer," Cytometry, 2002, vol. 48, No. 3, pp. 124-135.
Smith D.W., Biocomputing: Informatics and Genome Projects, Academic Press, 1993.
Spits, et al., "Cytotoxic activity and lymphokine production of T cell receptor (TCR)-alpha beta+ and TCR-gamma delta+ cytotoxic T lymphocyte (CTL) clones recognizing HLA-A2 and HLA-A2 mutants. Recognition of TCR-gamma delta+ CTL clones is affected by mutations at positions 152 and 156," The Journal of Immunology, 1990, vol. 144, pp. 4156-4162.
"TCR delta CDR3 Peptide VD2 #4," Geneseq, Feb. 8, 2018, Database Accession No. BES28452, URL: EBI, XP002789045, 2 pages.
Voss R.- H., et al., "Designing TCR for Cancer Immunotherapy," Adoptive Immunotherapy: Methods and Protocols, Part of the Methods in Molecular Medicine™ book series, 2005, vol. 109, pp. 229-256.
Jonathan Fisher, Jennifer Heuijerjans, Mengyong Yan, Kenth Gustafsson &John Anderson, 2014: γδ T cells for cancer immunotherapy: A systematic review of clinical trials. Oncommunology 3: e27572.
Uldrich, A.P., et al., (2013) CDId-lipid antigen recognition by the gamma delta TCR. Nat Immunol 14: 1137-45.
Venturi V., et al., (2008), The molecular basis for public T-cell responses? Nat Rev Immunol B: 231-8.
Pauza, C. David, et al. Evolution and function of the TCR Vgamma9 chain repertoire: It's good to be public. Cellular Immunology, vol. 296, No. 1, Jul. 1, 2015 (Jul. 1, 2015), pp. 22-30, XP055320697, US ISSN: 0008-8749, DOI: 10.1016/j.cellimm.2015.02.010.
Wang, C., et al., (2015), B-cell repertoire responses to varicella-zoster vaccination in human Identical twins., Proc Natl Acad Sci U S A 112: 500-5.
Ravens, S., et al., (2017). Human gamma delta T cells are quickly reconstituted after stem-cell transplantation and show adaptive clonal expansion in response to viral infection. Nature Immunology, 18, 393-401.
Reiser,J. (2000), Production and concentration of pseudotyped HIV-1-based gene transfer vectors. Gene Ther. 7: 910-913.
Roberts, S. et al. (1987), Generation of an antibody with enhanced affinity and specificity for ts antigen by protein engineering. Nature 328:731-734.
Rudikoff et al. Single amino acid substitution altering antigen-binding Specificity. PNAS USA 79:1979-1983 (1982).
Russell, W.C., 2000, Update on adenovirus and its vectors, J. Gen. Virol. 81: 2573-604.
Salgado, R, (2015), Tumor-Infiltrating Lymphocytes and Associations With Pathological Complete Response and Event-Free Survival in HER2-Positive Early-Stage Breast Cancer Treated With Lapatinib and Trastuzumab: A Secondary Analysis of the NeoALTTO Trial. JAMA Oncol 1: 448-54.
Sandstrom, A, (2014), The intracellular B30.2 domain of butyrophilin 3A1 binds phosphoantigens to mediate activation of human Vgamma9Vdelta2 T cells. Immunity 40: 490500.
Scheper, W. 2014. Cancer immunotherapy using γδT cells: dealing with diversity. Thesis.
Scheper W., et al., (2013), gamma deltaT cells elicited by CMV reactivation after allo-SCT cross-recognize CMV and leukemia. Leukemia 27: 1328-38.
Wang et al., A comprehensive study of optimal conditions for naked plasmid DNA transfer into skeletal muscle by electroporation, (2005), J Gene Med. Sep. 7(9):12325-45.
Scheper, W., et al., (2014), Cancer Immunotherapy Using gamma deltaT Cells: Dealing with Diversity. Front Immunol 5: 601.

(56) References Cited

OTHER PUBLICATIONS

Vigna, E. et al., (2000), Lentiviral vectors: excellent tools for experimental gene transfer and promising candidates for gene therapy, J. Gene Med. 2: 308-16.
Sebestyen, Z. et al., (2016), RhoB Mediates Rhosphoantigen Recognition by Vgamma9Vdelta2 T Cell Receptor. Cell Rep 15: 1973-85.
Shugay, M., et al., (2014). Towards error-free profiling of immune repertoires. Nat Methods 11: 653-5.
Simmonelli, Francesca et al. Gene Therapy for Leber's Congenital Amaurosis is Safe and Effective Through 1.5 Years After Vector Administration, American Society of Gene & Cell Ther. Mar. 2010, 18(3): 643-50. Epub2009 Decl.
Sittig, S.P,.et al.,( 2013), Clonal expansion of renal cell carcinoma-infiltrating T lymphocytes. Oncoimmunology 2: e26014.
Stanislawski et al.. Circumventing tolerance to a human MDM2-derived tumor antigen by TCR gene transfer. Nat Immunol. 2001; 2(10): 962-970.
Straetemans T et al. Towards gamma/delta TCR gene therapy: the optimal gamma/delta TCR transgene cassette. Bone Marrow Transplantation, vol. 48 No. Suppl. 2, pp. $72, Apr. 2013, XP002700187.
Straetemans, T., et al., (2015), Untouched GMP-ready purified engineered immune cells to treat cancer. Clin Cancer Res., 21 (17); 3957-68.
Tripodo, et al. Gamma-delta T-cell lymphomas. 2009, Nat. Rev. Clin. Oncol. 6: 707-717.
Devereux et al., A comprehensive set of sequence analysis programs for the VAX. Nucleic Acids Res. Jan. 1, 19841;12(1 Pt 1):387-95.
Xi, X. et al. The Recognition Of TCR Protein Antigen Does Not Depend on the Hydrophobic 197 Residue of CDR3. International Immunology, vol. 22, No. 4, pp. 299-306, Apr. 1, 2010, XP055069895.
Elmaagacli, A.H., et al., (2016), Cytomegalovirus replication reduces the relapse incidence in patients with acute myeloid leukemia. Blood 128: 456-9.
Nathwani et al.,. Adenovirus-Associated Virus Vector-Mediated Gene Transfer in Hemophilia B. N Eng J Med. Dec. 22, 2011;365(25):2357-65.
Federico, Maurizio, Lentiviruses as gene delivery vectors, (1999), Curr. Opin. Biotechnol. 10: 448-53.
Fisch, P. et al. Recognition By Human V-Gamma-9-V-Delta-2 T Cells of a GroEL Homolog on Daudi Burkitt's Lymphoma Cell. vol. 250, No. 4985, pp. 1269-1273, 1990.
Fooksman, David et al.. Clustering Class I MHC Modulates Sensitivity of T-cell Recognition, Jun. 1, 2006 (Jun. 1, 2006), Retrieved from the Internet: URL:https://http://www.ncbi.nlm.nih.gov/pmc/articles/PMC1524854/pdf/nihms11101 .pdf [retrieved on Feb. 15, 2021].
Gentles, A.J., et al., (2015). The prognostic landscape of genes and infiltrating immune cells across human cancers. Nat Med 21: 938-45.
Gomes, A., et al,. Targeting gamma delta T Lymphocytes for Cancer Immunotherapy: From Novel Mechanistic Insight to Clinical Application. 2010, Cancer Res. 70: 10024-10027.
Grunder C., et al., 2012. gammaO and delta2CDR3 domains regulate functional avidity of T cells harboring gamma9delta2TCRs. Blood 120: 5153-62.
Grunder, et al. Individual T-Cell Receptors of y9δ2T-Cells Mediate Differential Anti-Tumorreactivity. Abstract Only. From Blood 2011; 118:4312.
Harly C., Guillaume Y, (2012), Key implication of CD277/butyrophilin-3 (BTN3A) in cellular stress sensing by a major human gamma delta T-cell subset. Blood 120: 2269-79.
Hildalgo, J.V., et al., (2014). Histological Analysis of gamma delta T Lymphocytes Infiltrating Human Triple-Negative Breast Carcinomas. Front Immunol 5: 632.
Ho, S.N., et al.. Site-directed mutagenesis by overlap extension using the polymerase chain reaction. Gene, 1989. 77(1): p. 51-9.
Holtmeier, W., et al. (1995), The delta T cell receptor repertoire in human colon and peripheral blood is oligoclonal irrespective of V region usage, J Clin Invest 96: 1108-17.
Nielsen, T.O., (2004), Immunohistochemical and clinical characterization of the basal-like subtype of invasive breast carcinoma. Clin Cancer Res 10: 5367-74.
Nicol, et al., (2011) Clinical evaluation of autologous gamma delta T cell-based Immunotherapy for metastatic solid tumors, Br. J. Cancer 105: 778-786.
Wang, Hong et al. Vgamma2Vdelta2 T Cell Receptor Recognition of Prenyl Pyrophosphates is Dependent on All CDRs. 2010, J. Immunol. 184: 6209-6222.
Kabelitz, D., et al., (2007) Perspectives of T Cells in Tumor Immunology. Cancer Research, vol. 67, No. 1, pp. 5-8.
Kabelitz, D., et al.. Potential of Human [gamma][delta] T Lymphocytes For Immunotherapy of Cancer. International Journal of Cancer, 112:727-732 (2004).
Kay et al.. Viral vectors for gene therapy: the art of the turning infectious agents into vehicles of therapeutics, (2001), Nat. Med. 7: 33-40.
Kershaw et al. Gene-engineered T cells for cancer therapy. Nat Rev Cancer 13(8):525-541 (2013).
Kim, S.K., et al., (2005), Private specificities of CD8 T cell responses control patterns of heterologous immunity, J Exp Med 201: 523-33.
Kuball, et al. Increasing functional avidity of TCR-redirected T cells by removing defined Nglycosylation sites in the TCR constant domain. J Exp Med. Feb. 16, 2009;206(2):463-75.
Kuball, et al. Multipotent Vδ2-negative γδT-cells after CMV-reactivation in allogeneic stem cell transplantation (162.36). Abstract Only. From J Immunol May 1, 2012, 188 (1 Supplement) 162.36. (abstract only).
Kuball, J, et al., 2007, Facilitating matched pairing and expression of TCR chains introduced Into human T cells. Blood 109: 2331-8.
Li, B., et al. (2016), Landscape of tumor-infiltrating T cell repertoire of human cancers. Nature Genetics 48,725-732.
Lim, W.A., (2017). The Principles of Engineering Immune Cells to Treat Cancer. Cell 168: 724-40.
Loi, S., et al., (2016), RAS/MAPK Activation Is Associated with Reduced Tumor-Infiltrating Lymphocytes in Triple-Negative Breast Cancer: Therapeutic Cooperation Between MEK and PD-1/PD-L1 Immune Checkpoint Inhibitors. Clin Cancer Res 22: 1499-509.
M. Ferez et al.: "Cognate Peptide-MHC Complexes are Expressed as Tightly Apposed Nanoclusters in Virus-Infected Cells To Allow TCR Crosslinking", The Journal of Immunology, vol. 192, No. 1,4 (accessed Feb. 15, 2021).
Mamedov, I.Z., et al. (2013), Preparing unbiased T-cell receptor and antibody cDNA libraries for the deep next generation sequencing profiling. Front Immunol 4: 456.
Mami-Chouaib, F. et al: "Further evidence for a gamma/delta T cell receptor-mediated TCT.1/CD48 recognition". The Journal of Immunology, Nov. 1, 1991 (Nov. 1, 1991), pp. 2864-2867, XP055403236, United States Retrieved from the Internet: URL:http://www.ji m mu nol.org/content/147/9/2864.full-text.pdf.
Willcox, C.R., et al., (2012),.Cytomegalovirus and tumor stress surveillance by binding of a human gammadelta T cell antigen receptor to endothelial protein C receptor, Nat.Immunol. 13: 872-9.
Marcu-Malina et al. Re-targeting T-cells against cancer by gene-transfer of tumor-reactive receptors. 2009, Expert Opin. Biol. Ther. 9: 579-591.
Marcu-Malina et al. Redirecting alpha betaT cells against cancer cells by transfer of a broadly tumor-reactive gamma deltaT-cell receptor. 2011, Blood 118: 50-59.
Marin, M. et al., (1997) Towards efficient cell targeting by recombinant retroviruses. Mol. Med. Today 3: 396-403.
Martin, K.R.G., et al., (2004), Gene therapy for optic nerve disease, , Eye 18(11):1049-55.
Meeh, P.F., (2006), Characterization of the gamma delta T cell response to acute leukemia. Cancer Immunol. Immunother. 55: 1072-80.
Metzger, D., et al., (1988), The human oestrogen receptor functions in yeast. Nature, 334: 31-36.
Miles, JJ, et al., 2005. CTL recognition of a bulged viral peptide involves biased TCR selection. J Immunol 175: 3826-34.

(56) References Cited

OTHER PUBLICATIONS

Miyagawa, et al., (2001), Essential Contribution of Germline-Encoded Lysine Residues in J gamma 1.2 Segment to the Recognition of Nonpeptide Antigens by Human gamma delta T Cells, J. Immunol. 167: 6773-6779.

Miyazaki, K., (2011) MEGAWHOP cloning: a method of creating random mutagenesis libraries via megaprimer PCR of whole plasmids. Methods Enzymol, 498: p. 399-406.

Moser Bernhard. Tumor-Killing [gamma] [delta]—TCRs take center stage. Blood, vol. 120, No. 26, pp. 5093-5094, Dec. 20, 2012, XP002700185.

Yan Ding et al: "Characteristics of the V[delta]2 CDR3 Sequence of Peripheral [gamma][delta] T Cells in Patients with Pulmonary Tuberculosis and Identification of a New Tuberculosis-Related Antigen Peptide", Clinical and Vaccine Immunology, vol. 22, No. 7, May 6, 2015, pp. 761-768, US ISSN: 1556-6811, DOI: 10.1128/CVI.00612-14.

Database WPI Week 201301 Thomson Scientific, London, GB; an 2012-K99769 XP002764637, -& CN 102 532 269 A (Inst Basic Medical Sci Chinese Acad Medi) Jul. 4, 2012.

Database WPI Week 201640 Thomson Scientific, London, GB; An 2016-09855T, XP002764638, -& CN 105 296 431 A (Inst Basic Medical Sci Chinese Acad Medi) Feb. 3, 2016.

C. David Pauza et al: "Evolution and function of the TCR Vgamma9 chain repertoire: It's good to be public", Cellular Immunology., vol. 296, No. 1, Jul. 1, 2015, pp. 22-30, US ISSN: 0008-8749, DOI: 10.1016/j.cellimm.2015.02.010.

Paul F Meeh et al: "Characterization of the [gamma][delta] T cell response to acute leukemia", Cancer Immunology, Immunotherapy, Springer, Berlin, DE, vol. 55, No. 9, Nov. 23, 2005, pp. 1072-1080, ISSN: 1432-0851.

F Mami-Chouaib et al.: "Further evidence for a gamma/delta T cell receptor-mediated TCT.1/CD48 recognition". The Journal of Immunology, Nov. 1, 1991, pp. 2864-2867.

Xu et al: "Gamma delta T cells recognize tumor cells via CDR3delta region", Molecular Immunol, Pergamon, GB, vol. 44, No. 4, Jan. 1, 2007, pp. 302-310.

Anonymous: "UPI0000117293", Mar. 28, 2003 (Mar. 28, 2003), XP055403635.

Anonymous: "UPI0000480E66", Mar. 23, 2007 (Mar. 23, 2007), XP055403650.

Anonymous: "EM_STD:BC030554", Dec. 2, 2006 (Dec. 2, 2006),XP055403988.

Chen, H., et al. "Characterization of Complementary Determinant Region 3δ in Human MutS Homologue 2-Specific γδ T Cells." Scandinavian Journal of Immunology 81.2 (2015): 121-128.

Chen, Hui, et al. "Characterization of the diversity of T cell receptor γδ complementary determinant region 3 in human peripheral blood by Immune Repertoire Sequencing." Journal of Immunological Methods 443 (2017): 9-17.

Davodeau, Frangois, et al. "Close correlation between Daudi and mycobacterial antigen recognition by human gamma delta T cells and expression of V9JPC1 gamma/V2DJC delta-encoded T cell receptors." The Journal of Immunology 151.3 (1993): 1214-1223.

Xi-zhi, J. Guo, et al. "Rapid cloning, expression, and functional characterization of paired αβ and γδ T-cell receptor chains from single-cell analysis." Molecular Therapy-Methods & Clinical Development 3 (2016): 15054.

Lafarge, Xavier, et al. "Cytomegalovirus infection in transplant recipients resolves when circulating γδ T lymphocytes expand, suggesting a protective antiviral role." The Journal of infectious diseases 184.5 (2001): 533-541.

Li, Bo, et al. "Landscape of tumor-infiltrating T cell repertoire of human cancers." Nature genetics 48.7 (2016): 725-732.

Walther W., et al., "Viral Vectors for Gene Transfer," Drugs, Aug. 2000, vol. 60, No. 2, pp. 249-271.

Wells J.A., et al., "Cassette Mutagenesis: An Efficient Method for Generation of Multiple Mutations at Defined Sites," Gene, 1985, vol. 34, pp. 315-323.

Xu et al. (PNAS, 108(6): 2414-2419, 2011).

Zhu Y.Y, et al., "Reverse Transcriptase Template Switching: A Smart™ Approach for Full-Length cDNA Library Construction," BioTechniques, 2001, vol. 30, pp. 892-897.

Yu, Songtao et al. T cell receptor γδ phenotypic lymphocyte with tumor immunity, "Overseas Medicine (Immunology division)", No. 2, 1997 (machine translation of the abstract provided).

Ferez et al: Cognate Peptide-MHC Complexes Are Expressed as Tightly Apposed Nanoclusters in Virus-Infected Cells to Allow TCR Crosslinking, The Journal of Immunology, vol. 192, No. 1,Dec. 4, 2013 (Dec. 4, 2013), pp. 52-58, XP55406156, US ISSN: 0022-1767, DOI: 10.4049/jimmunol.1301224.

Yan Ding et al: Characteristics of the V[delta]2 CDR3 Sequence of Peripheral [gamma][delta] T Cells in Patients with Pulmonary Tuberculosis and Identification of a New Tuberculosis-Related Antigen Peptide, 2015, Clinical and Vaccine Im., DOI: 10.1128/CVI.00612-14.

Volker, et al. Tumor-promoting Versus Tumor-antagonizing Roles of γδ T Cells in Cancer Immunotherapy: Results from a Prospective Phase I/II Trial, Journal of Immunotherapy (2012) vol. 35, Issue 2, p. 205-213.

Xiang, Z., (2014), Targeted activation of human Vgamma9Vdelta2-T cells controls Epstein-Barr virus-induced B cell lymphoproliferative disease. Cancer Cell 26: 565-76<a></a>.

Morita, Craig T., et al.. Nonpeptide antigens, presentation mechanisms, and immunological memory of human Vγ2Vδ2 T cells: discriminating friend from foe through the recognition of brenyl pyrophosphate antigens. Immunological Reviews 2007, vol. 215: 59-76.

Davey et al.. Recasting Human Vδ1 Lymphocytes in an Adaptive Role. Davey et al. Willcox Trends Immunol. Jun. 2018; 39(6): 446-459.

Halary et al. Shared reactivity of V2neg T cells against cytomegalovirus-infected cells and tumor intestinal epithelial cells, J Exp Med. May 16, 2005; 201(10): 1567-1578.

Davis et al. Development of human anti-murine T-cell receptor antibodies in both responding and nonresponding patients enrolled in TCR gene therapy trials. Clin Cancer Res. Dec. 1, 2010;16(23):5852-61.

Lal, Nareej et al.. Endothelial protein C receptor is overexpressed in colorectal cancer as a result of amplification and hypomethylation of chromosome 20q, The Journal of Pathology Clinical Research, Jul. 2017; 3(3):155-170.

Melandri et al.. The γδ T cell receptor combines innate with adaptive immunity by utilizing spatially distinct regions for agonist-selection and antigen responsiveness, Nat Immunol. Dec. 1, 2019; 19(12): 1352-1365.

Willcox et al., Butyrophilin-like 3 Directly Binds a Human Vγ4+T Cell Receptor Using a Modality Distinct from Clonally-Restricted Antigen, Immunity. Nov. 19, 2019; 51(5): 813-825.

Bernatchez, Chantale et al.. Adoptive T Cell Transfer and Cell Therapy as Cancer Immunotherapy (CARS), Abstracts forthe 27th Annual Scientific Meeting of the Society for Immunotherapy of Cancer (SITC), J. Immunother, vol. 35, No. 9, Nov 9, Nov.-Dec. 2012, p. 721-791.

Gonzalez-Villasana, et al., Rac1/Pak1/p38/MMP-2 Axis Regulates Angiogenesis in Ovarian Cancer, Clinical Cancer Research, vol. 21, No. 9,Jan. 16, 2015 (Jan. 26, 2015), pp. 2127-2137, XP055411010, US ISSN: 1078-0432, DOI: 10.1158/1078-0432.CCR-14-2279.

Huang, M., RhoB facilitates c-Myc turnover by supporting efficient nuclear accumulation of GSK-3, Oncogene, vol. 25, No. 9, Oct. 17, 2005 (Oct. 17, 2005), pp. 1281-1289, XP055496792, London ISSN: 0950-9232, DOI: 10.1038/sj.onc.1209174.

Paterson et al: "Cost-effectiveness of Oral Clodronate Compared with Oral Ibandronate, Intravenous Zoledronate or Intravenous Pamidronate in Breast Cancer Patients", Journal of International Medical Research, vol. 36, No. 3, May 1, 2008 (May 1, 2008), pp. 400413, XP055496644, GB ISSN: 0300-0605, DOI: 10.1177/147323000803600304.

Zhao, et al. CDR3δ-grafted γ9δ2T cells mediate effective antitumor reactivity. Cell Mol Immunol. Mar. 2012;9(2):147-54. doi: 10.1038/cmi.2011.28. EpubSep. 12, 2011.

XP-002778544 (Database Geneseq [online] May 20, 2004 (May 20, 2004), "Human tumourassociated antigenic target (TAT) polypep-

(56) References Cited

OTHER PUBLICATIONS tide #22.", XP002778544, retrieved from EBI accession No. GSP:ADL06523 Database accession No. ADL06523 & WO 2004016225 A2 20040226—Genentech Inc [US]) (See WO 2004016225 A2).

XP-002778546 ( DATABASE Geneseq [online] Mar. 5, 2009 (Mar. 5, 2009), "Human PRO amino acid sequence Seq Id No.2103.", XP002778546, retrieved from EBI accession No. GSP:AUZ26487 Database accession No. AUZ26487 & WO 2005016962 A2 20050224—Genentech Inc [US], et al) (See W02005016962A2).

XP-002778547 (Database Geneseq [online] Jun. 15, 2007 (Jun. 15, 2007), "Human lymphocyte clone G 115 soluble TCR Vgamma chain.", XP002778547, retrieved from EBI accession No. GSP:AAR55705 Database accession No. AAR55705 & WO 9412648 A2 19940609—Inst Nat Sante Rech Med [FR], et al) (See W09412648A2).

XP-002778548 ([X] Database USPTO Proteins [online] Aug. 10, 1998 (Aug. 10, 1998), "Sequence 17 from patent U.S. Pat. No. 5723309.", XP002778548, retrieved from EBI accession No. USPOP:I90500 Database accession No. AAC30862 & U.S. Pat. No. 5723309 A Mar. 3, 1998—Bonneville Marc [FR] (See U.S. Pat. No. 5,723,309).

Niemeyer, G., et al. Long-term correction of inhibitor-prone hemophilia B dogs treated with liver-directed AAV2-mediated factor IX gene therapy. Blood. Jan. 22, 2009;113(4):797-806.

Airoldi, I., et al. (2015). Gamma delta T-cell reconstitution after HLA-haploidentical hematopoietic transplantation depleted of TCR-alphabeta+/CD19+ lymphocytes. Blood 125: 2349-58.

Amado and Chen, Lentiviral vectors-the promise of gene therapy within reach?, 1999, Science 285: 674-6.

Xu, Chungping et al. γδ T Cells Recognize Tumor Cells Via CDR3δ Region. Molecular Immunology, 2007, vol. 44, pp. 302-310.

Anonymous: "EM_STD:BC030554", Dec. 2, 2006 (Dec. 2, 2006), XP055403988, Retrieved from the Internet: URL:http://ibis.internal.epo.org/exam/dbfetch.jsp?id=EM_STD:BC030554 [retrieved on Sep. 5, 2017].

Anonymous: "UP10000480E66," Mar. 23, 2007 (Mar. 23, 2007), XP055403650, Retrieved from the Internet: URL:http://www.uniprot.org/uniparc/UPI0000480E66 [retrieved on Sep. 4, 2017].

Anonymous: "UPI0000117293," Mar. 28, 2003 (Mar. 28, 2003), XP055403635, Retrieved from the Internet: URL:http://www.uniprot.org/ uniparc/UPIOOOOI 17293 [retrieved on Sep. 4, 2017].

Apparailly, M., et al., Adeno-Associated Virus Pseudotype 5 Vector Improves Gene Transfer in Arthritic Joints, Hum Gene Ther, Apr. 2005; 16(4): 426-34.

Bender, C, et al. (2009). Analysis of colorectal cancers for human cytomegalovirus presence. Infect Agent Cancer 4: 6.

Bolotin, DA, et al. (2015), MiXCR: software for comprehensive adaptive immunity profiling. Nat Methods 12: 380-1.

Born, et al.. Peptide antigens for gamma/delta T cells. 2011, Cell Mol. Life Sci., 68: 23352343.

Bosnes, Vidar et al.: "Recognition of a particular HLA-DQ heterodimer by a human y/6 T cell clone*",Eur. J. Immunol, Jan. 1, 1990 (Jan. 1, 1990), pp. 1429-1433.

Bouchie, A. et al., 2017. Nature Biotechnology's academic spinouts of 2016, Nat Biotechnol 35: 322-33.

Bowness, P. et al., Th17 Cells Expressing KIR3DL2+ and Responsive to HLA-B27 Homodimers Are Increased in Ankylosing Spondylitis, The Journal of Immunology, vol. 186, No. 4, Feb. 15, 2011 (Feb. 15, 2011), pp. 2672-2680, XP55373331, US ISSN: 00221767, DOI: 10.4049/jimmuno1.1002653.

Brauninger, A., (1999). Identification of common germinal-center B-cell precursors in two patients with both Hodgkin's disease and non-Hodgkin's lymphoma, N Engl J Med 340: 1239-47.

Bukowski, et al., (1998) Crucial Role of TCRgamma Chain Junctional Region in Prenyl Pyrophosphate Antigen Recognition by gamma delta T cells, J. Immunol. 161: 286-293.

Carillo et al. The Multiple Sequence Alignment Problem in Biology. SIAM J. Appl. Math 48(5):907-1082 (1988).

Castella, et al., (2011) V gamma 9 V delta 2 T cell-based immunotherapy in hematological malignancies: from bench to bedside. Cell Mol. Life Sci. 68: 2419-2432.

Chien, Y.H., et al., (2014) gamma delta T Cells: First Line of Defense and Beyond. Annu. Rev Immunol., vol. 32:121-155.

Coffelt, S.B., (2015). IL-17-producing gamma delta T cells and neutrophils conspire to promote breast cancer metastasis. Nature 522: 345-8.

Colman et al.. Effects of amino acid sequence changes on antibody-antigen interactions. Research in Immunology, 1994; 145(1):33-36.

De Witte, M.A., et al. (2015), Orchestrating an immune response against cancer with engineered immune cells expressing alphabetaTCRs, CARs, and innate immune receptors: an Immunological and regulatory challenge. Cancer Immunol Immunother. 64: 893-902.

Deniger, D.C., et al., (2014), Clinical applications of gamma delta T cells with multivalent Immunity. Front Immunol 5: 636.

Couzin-Frankel, J., (2013), Breakthrough of the year 2013. Cancer immunotherapy. Science 342: 1432-3.

Dadi, S., et al., (2016). Cancer Immunosurveillance by Tissue-Resident Innate Lymphoid Cells and Innate-like T Cells. Cell 164: 365-77.

Davey, MS, et al., (2017), Clonal selection in the human Vdeltal T cell repertoire indicates gamma delta TCR-dependent adaptive immune surveillance. Nat Commun. 8: 14760.

Allison, et al., "Structure of a Human Y8 T-cell Antigen Receptor," Nature, 2001, vol. 411, pp. 820-824, DOI:10.1038/35081115, XP055324441.

Allison T.J., et al., "Structure of Gammadelta T Cell Receptors and Their Recognition of Non-Peptide Antigens," Molecular Immunology, 2001, vol. 38, pp. 1051-1061.

Asnafi V., et al., "Analysis of TCR, pTalpha, and RAG-1 in T-Acute Lymphoblastic Leukemias Improves Understanding of Early Human T-Lymphoid Lineage Commitment," Blood, Apr. 1, 2003, vol. 101, No. 7, pp. 2693-2703.

Bethune M.T., et al., "Domain-Swapped T Cell Receptors Improve the Safety of TCR Gene Therapy," Elife, Nov. 8, 2016, vol. 5, 24 pages.

Betts M.R., et al., "Sensitive and Viable Identification of Antigen-Specific CD8+ T Cells by a Flow Cytometric Assay for Degranulation," Journal of Immunological Methods, 2003, vol. 281, pp. 65-78.

Born W., et al., "Immunoregulatory Functions of GammaDelta T Cells," Advances in Immunology, 1999, vol. 71, pp. 77-144.

Champagne E., "Gammadelta T Cell Receptor Ligands and Modes of Antigen Recognition," Archivum Immunologiae et Therapiae Experimentalis, 2011, vol. 59, pp. 117-137.

Couedel C., et al., "Allelic Exclusion at the TCR Delta Locus and Commitment to Gamma Delta Lineage: Different Modalities Apply To Distinct Human Gamma Delta Subsets," Journal of Immunology, May 1, 2004, vol. 172, No. 9, pp. 5544-5552.

Davodeau F., et al., "Secretion of Disulfide-Linked Human T-Cell Receptor Gamma Delta Heterodimers," Journal of Biological Chemistry, Jul. 25, 1993, vol. 268, No. 21, pp. 15455-15460.

Eilat D., et al., "Secretion of a Soluble, Chimeric Y8 T-Cell Receptor-Immunoglobulin Heterodimer," Proceedings of the National Academy of Sciences of the United States of America, Aug. 1992, vol. 89, pp. 6871-6875.

Garboczi D.N., et al., "Assembly, Specific Binding, and Crystallization of a Human TCR-Alphabeta with an Antigenic Tax Peptide from Human T Lymphotropic Virus Type 1 and the Class I MHC Molecule HLA-A2," Journal of Immunology, Dec. 15, 1996, vol. 157, No. 12, pp. 5403-5410.

Green A.E., et al., "Recognition of Nonpeptide Antigens by Human VGamma9VDelta2 T Cells Requires Contact with Cells of Human Origin," Clinical and Experimental Immunology, 2004, vol. 136, pp. 472-482.

Gregoire C., et al., "Engineered Secreted T-Cell Receptor Alpha Beta Heterodimers," Proceedings of the National Academy of Sciences of the United States of America, Sep. 1991, vol. 88, pp. 8077-8081.

(56) References Cited

OTHER PUBLICATIONS

Holtmeier W., et al., "The TCR-Delta Repertoire in Human Intestine Undergoes Characteristic Changes During Fetal to Adult Development," Journal of Immunology, Jun. 1997, vol. 158, No. 12, pp. 5632-5641.
Jones H.F., et al., "Empirical and Rational Design of T Cell Receptor-Based Immunotherapies," Frontiers in Immunology, Jan. 2021, vol. 11, No. 585385, 21 pages.
Kerrigan J.J., et al., "Production of Protein Complexes via Co-Expression," Protein Expression and Purification, Jan. 2011, vol. 75, No. 1, pp. 1-14.
Langerak A.W., et al., "Immunophenotypic and Immunogenotypic Characteristics of Tcrgammadelta+ T Cell Acute Lymphoblastic Leukemia," Leukemia, Feb. 1999, vol. 123, No. 21, pp. 206-214.
Li H., et al., "Structure of the Vdelta Domain of a Human Gammadelta T-Cell Antigen Receptor," Nature, Jan. 29, 1998, vol. 391, pp. 502-506.
Loh E.Y., et al., "Identification and Sequence of a Fourth Human T Cell Antigen Receptor Chain," Nature, Dec. 10, 1987, vol. 330, No. 6148, pp. 569-572.
MacDougall A.V., et al., "Vgamma2 TCR Repertoire Overlap in Different Anatomical Compartments of Healthy, Unrelated Rhesus Macaques," Journal of Immunology, Feb. 15, 2001, vol. 166, No. 4, pp. 2296-2302.
Mathioudakis G., et al., "Preferential Rearrangements of the V Gamma I Subgroup of the Gamma-Chain of the T-Cell Antigen Receptor to J Gamma 2C Gamma 2 Gene Segments in Peripheral Blood Lymphocyte Transcripts from Normal Donors," Scandinavian Journal of Immunology, 1993, vol. 38, pp. 31-36.
Ozawa T., et al., "The Binding Affinity of a Soluble TCR-Fc Fusion Protein is Significantly Improved by Crosslinkage with an Anti-CBeta antibody," Biochemical and Biophysical Research Communications, 2012, vol. 422, pp. 245-249.
Petersen T.R., et al., "A Chimeric T Cell Receptor with Super-Signaling Properties," International Immunology, May 17, 2004, 6 pages.
Scotet E., et al., "Tumor Recognition Following Vgamma9Vdelta2 T cell Receptor Interactions with a Surface F1-ATpase-Related Structure and Apolipoprotein A-I," Immunity, Jan. 2005, vol. 22, pp. 71-80.
Sebestyen Z., et al., "Translating Gammadelta (Gammadelta) T Cells and Their Receptors into Cancer Cell Therapies," Nature Reviews Drug Discovery, Mar. 2020, vol. 19, No. 3, pp. 169-184.
Spada F.M., et al., "Self-Recognition of CD1 by Gamma/Delta T Cells: Implications for Innate Immunity," Journal of Experimental Medicine, Mar. 20, 2000, vol. 191, No. 6, pp. 937-948.
Starick L., et al., "Butyrophilin 3A (BTN3A, CD277)-Specific Antibody 20.1 Differentially Activates Vgamma9Vdelta2 TCR Clonotypes and Interferes With Phosphoantigen Activation," European Journal of Immunology, 2017, vol. 47, pp. 982-992.
Tao C., et al., "Gammadelta TCR Immunoglobulin Constant Region Domain Exchange In Human Alfa-Betaters Improves TCR Pairing Without Altering TCR Gene-Modified T Cell Function," Molecular Medicine Reports, 2017, vol. 15, pp. 1555-1564.
Wang H., et al., "Conservation of Nonpeptide Antigen Recognition by Rhesus Monkey Vgamma2Vdelta2 T Cells," Journal of Immunology, Apr. 1, 2003, vol. 170, No. 7, pp. 3696-3706.
Wei H., et al., "Definition of APC Presentation of Phosphoantigen (E)-4-hydroxy-3-methyl-but-2-enyl Pyrophosphate to Vgamma2Vdelta 2 TCR," Journal of Immunology, Oct. 1, 2008, vol. 181, No. 7, pp. 4798-4806.
Xiong X., et al., "Identification of Guinea Pig Gammadelta T Cells and Characterization during Pulmonary Tuberculosis," Veterinary Immunology and Immunopathology, Nov. 2004, vol. 102, No. 1-2, pp. 33-44.
Zhang L., et al., "Gamma Delta T-Cell Receptors Confer Autonomous Responsiveness to the Insulin-Peptide B: 9-23," Journal of Autoimmunity, 2010, vol. 34, pp. 478-484.
Zheng J., et al., "A Novel Antibody-Like TCRGamma delta-Ig Fusion Protein Exhibits Antitumor Activity against Human Ovarian Carcinoma," Cancer Letters, 2013, 9 pages.
Agrati, C et al., Longitudinal characterization of dysfunctional T cell-activation during human acute Ebola infection, Cell Death Dis., 2016, vol. 7, No. 3, pp. 1-8.
Frey, N.V et al., Optimizing Chimeric Antigen Receptor T-Cell Therapy for Adults With Acute Lymphoblastic Leukemia, J. Clin. Oncol., 2020, vol. 38, No. 5, pp. 415-422.
Gardner, R.A., Intent-to-treat leukemia remission by CD19 Car T cells of defined formulation and dose in children and young adults, Blood, 2017, vol. 129, No. 25, pp. 3322-3331.
Saura-Esteller, J et al., Gamma Delta T-Cell Based Cancer Immunotherapy: Past-Present-Future, Front Immunol., 2022, vol. 13, pp. 1-11.
Schonefeldt, S., The Diverse Roles of yo T Cells in Cancer: From Rapid Immunity to Aggressive Lymphoma. Cancers (Basel), vol. 13, No. 24, pp. 1-31.
Walker, B. and Mcmichael, A., The T-Cell Response to HIV, Cold Spring Harb Perspect Med, 2012, 2:a007054, 31 pages.

* cited by examiner

Fig. 4A
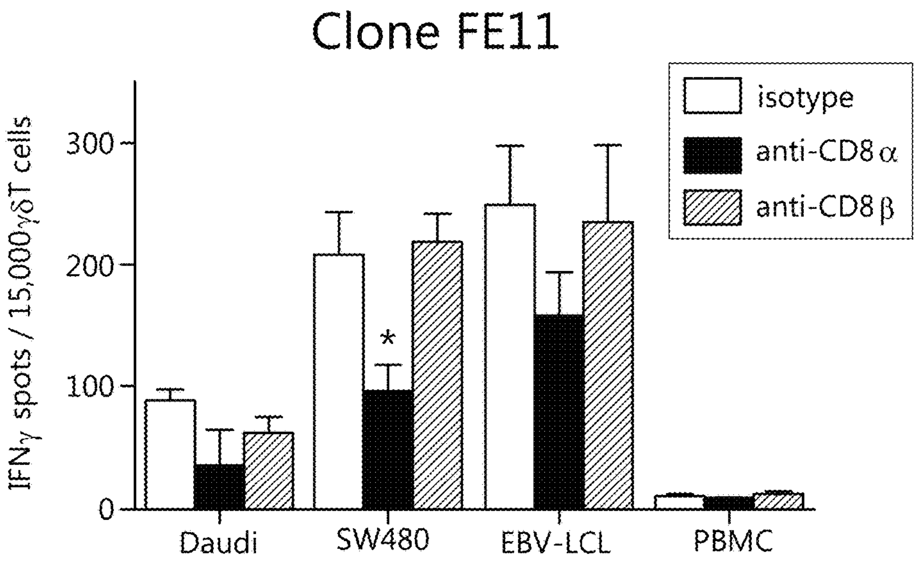
Fig. 4B(i) Fig. 4B(ii) Fig. 4B(iii)
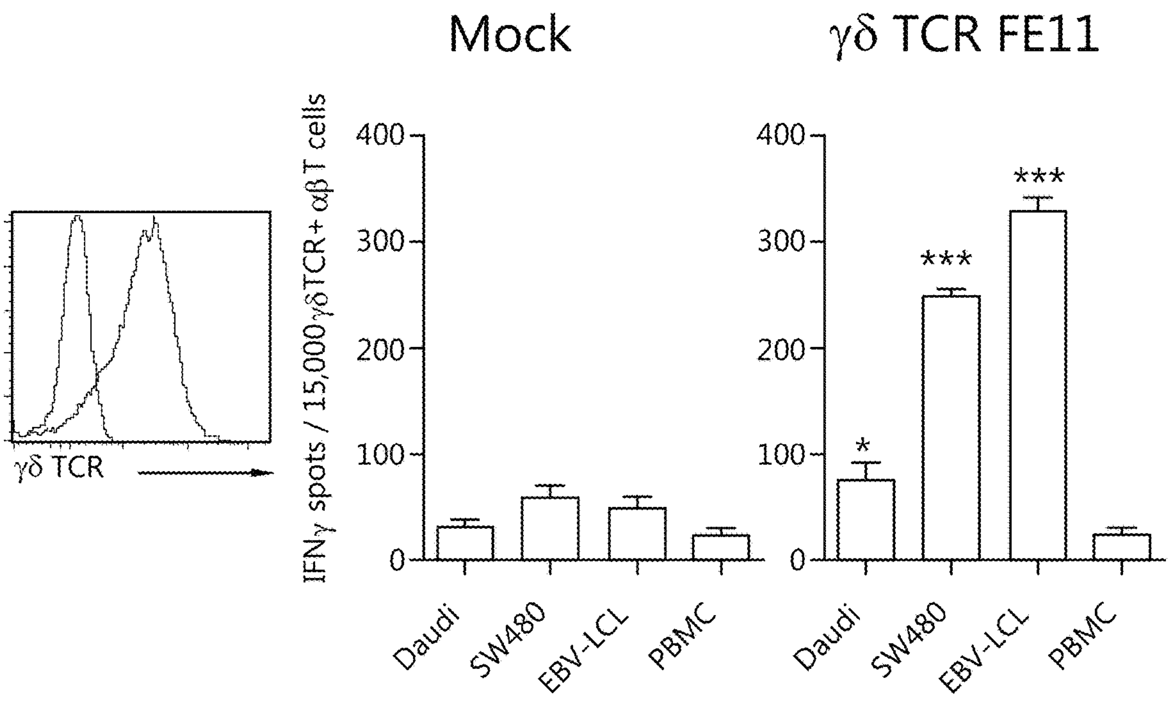

Fig. 4C(i)
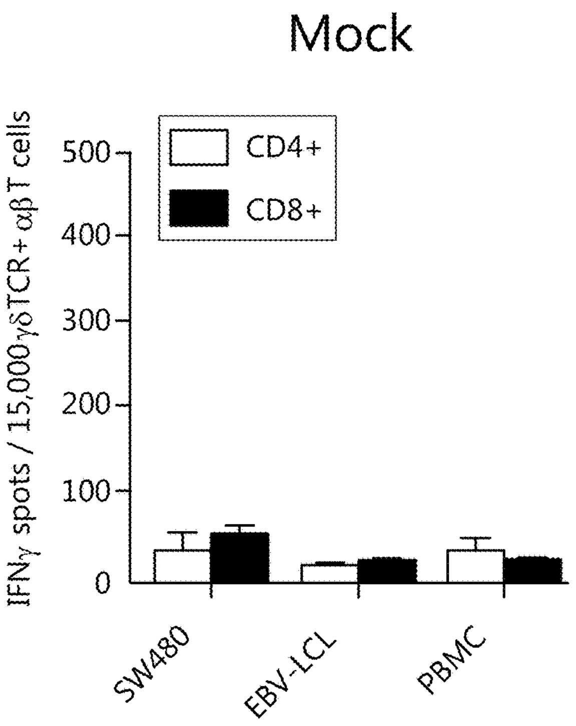
Fig. 4C(ii)
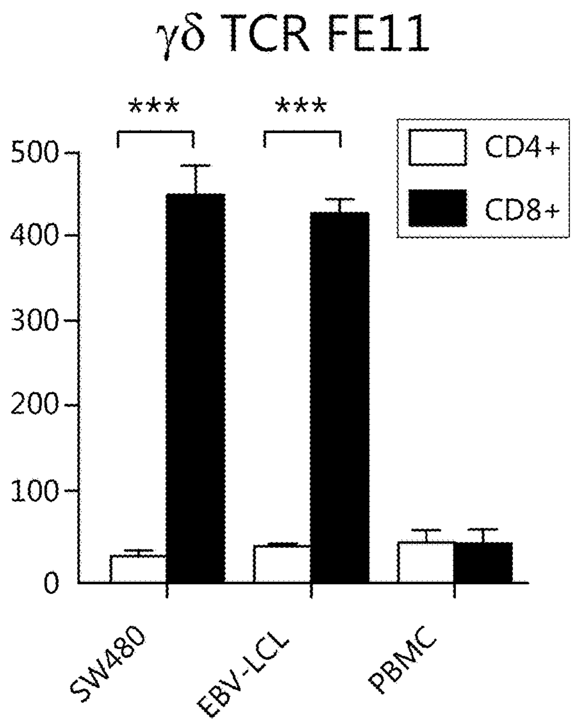
Fig. 4D
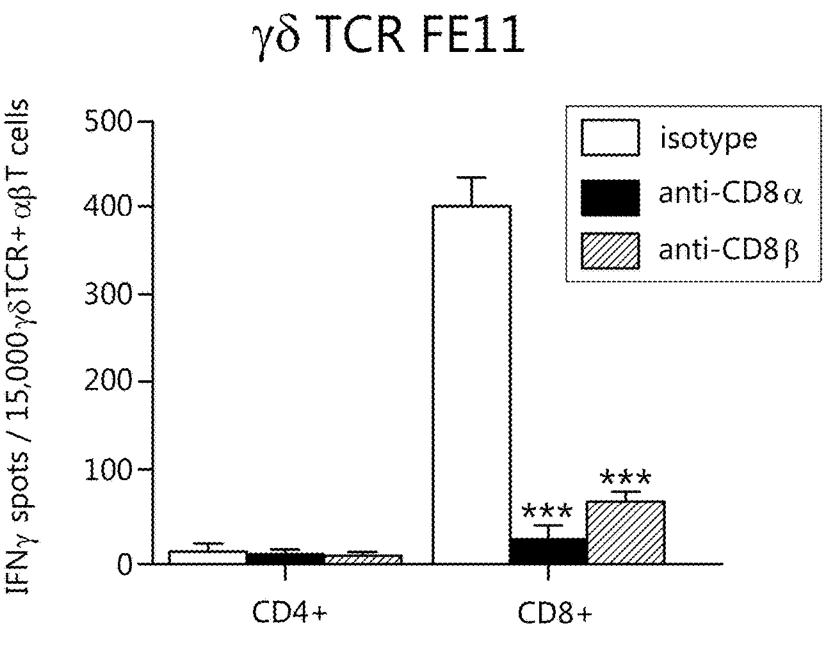

Fig. 5A

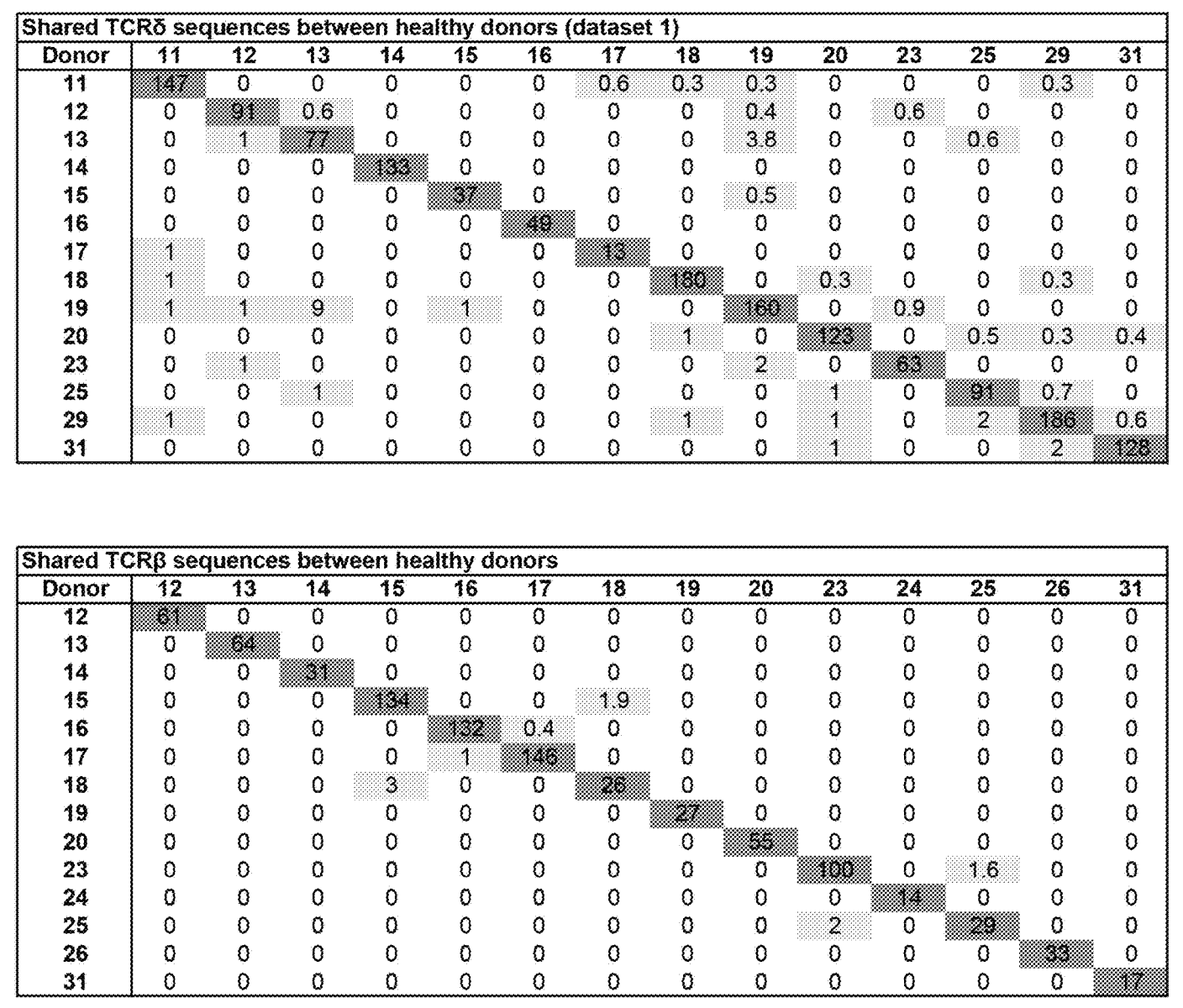

Shared TCRδ sequences between healthy donors (dataset 1)

| Donor | 11 | 12 | 13 | 14 | 15 | 16 | 17 | 18 | 19 | 20 | 23 | 25 | 29 | 31 |
|---|---|---|---|---|---|---|---|---|---|---|---|---|---|---|
| 11 | 147 | 0 | 0 | 0 | 0 | 0 | 0.6 | 0.3 | 0.3 | 0 | 0 | 0 | 0.3 | 0 |
| 12 | 0 | 91 | 0.6 | 0 | 0 | 0 | 0 | 0 | 0.4 | 0 | 0.6 | 0 | 0 | 0 |
| 13 | 0 | 1 | 77 | 0 | 0 | 0 | 0 | 0 | 3.8 | 0 | 0 | 0.6 | 0 | 0 |
| 14 | 0 | 0 | 0 | 133 | 0 | 0 | 0 | 0 | 0 | 0 | 0 | 0 | 0 | 0 |
| 15 | 0 | 0 | 0 | 0 | 37 | 0 | 0 | 0 | 0.5 | 0 | 0 | 0 | 0 | 0 |
| 16 | 0 | 0 | 0 | 0 | 0 | 49 | 0 | 0 | 0 | 0 | 0 | 0 | 0 | 0 |
| 17 | 1 | 0 | 0 | 0 | 0 | 0 | 13 | 0 | 0 | 0 | 0 | 0 | 0 | 0 |
| 18 | 1 | 0 | 0 | 0 | 0 | 0 | 0 | 180 | 0 | 0.3 | 0 | 0 | 0.3 | 0 |
| 19 | 1 | 1 | 9 | 0 | 1 | 0 | 0 | 0 | 160 | 0 | 0.9 | 0 | 0 | 0 |
| 20 | 0 | 0 | 0 | 0 | 0 | 0 | 0 | 1 | 0 | 123 | 0 | 0.5 | 0.3 | 0.4 |
| 23 | 0 | 1 | 0 | 0 | 0 | 0 | 0 | 0 | 2 | 0 | 63 | 0 | 0 | 0 |
| 25 | 0 | 0 | 1 | 0 | 0 | 0 | 0 | 0 | 0 | 1 | 0 | 91 | 0.7 | 0 |
| 29 | 1 | 0 | 0 | 0 | 0 | 0 | 0 | 1 | 0 | 1 | 0 | 2 | 186 | 0.6 |
| 31 | 0 | 0 | 0 | 0 | 0 | 0 | 0 | 0 | 0 | 1 | 0 | 0 | 2 | 178 |

Fig. 5B

Shared TCRβ sequences between healthy donors

| Donor | 12 | 13 | 14 | 15 | 16 | 17 | 18 | 19 | 20 | 23 | 24 | 25 | 26 | 31 |
|---|---|---|---|---|---|---|---|---|---|---|---|---|---|---|
| 12 | 61 | 0 | 0 | 0 | 0 | 0 | 0 | 0 | 0 | 0 | 0 | 0 | 0 | 0 |
| 13 | 0 | 64 | 0 | 0 | 0 | 0 | 0 | 0 | 0 | 0 | 0 | 0 | 0 | 0 |
| 14 | 0 | 0 | 31 | 0 | 0 | 0 | 0 | 0 | 0 | 0 | 0 | 0 | 0 | 0 |
| 15 | 0 | 0 | 0 | 154 | 0 | 0 | 1.9 | 0 | 0 | 0 | 0 | 0 | 0 | 0 |
| 16 | 0 | 0 | 0 | 0 | 132 | 0.4 | 0 | 0 | 0 | 0 | 0 | 0 | 0 | 0 |
| 17 | 0 | 0 | 0 | 0 | 1 | 146 | 0 | 0 | 0 | 0 | 0 | 0 | 0 | 0 |
| 18 | 0 | 0 | 0 | 3 | 0 | 0 | 26 | 0 | 0 | 0 | 0 | 0 | 0 | 0 |
| 19 | 0 | 0 | 0 | 0 | 0 | 0 | 0 | 27 | 0 | 0 | 0 | 0 | 0 | 0 |
| 20 | 0 | 0 | 0 | 0 | 0 | 0 | 0 | 0 | 55 | 0 | 0 | 0 | 0 | 0 |
| 23 | 0 | 0 | 0 | 0 | 0 | 0 | 0 | 0 | 0 | 100 | 0 | 1.6 | 0 | 0 |
| 24 | 0 | 0 | 0 | 0 | 0 | 0 | 0 | 0 | 0 | 0 | 14 | 0 | 0 | 0 |
| 25 | 0 | 0 | 0 | 0 | 0 | 0 | 0 | 0 | 0 | 2 | 0 | 29 | 0 | 0 |
| 26 | 0 | 0 | 0 | 0 | 0 | 0 | 0 | 0 | 0 | 0 | 0 | 0 | 33 | 0 |
| 31 | 0 | 0 | 0 | 0 | 0 | 0 | 0 | 0 | 0 | 0 | 0 | 0 | 0 | 17 |

Fig. 5C

| Shared Vδ2 TCR sequences between different datasets | | | | | | | | |
|---|---|---|---|---|---|---|---|---|
| | Source | Dataset 1 | Dataset 2 | Dataset 3 | Dataset 4 | Dataset 5 | Dataset 6 | Dataset 7 |
| Dataset 1 - Healthy donors | Peripheral blood | 1225 | | | | | | |
| Dataset 2 - Ravens et al | Peripheral blood | 30 | 1206 | | | | | |
| Dataset 3 - Davey et al | Peripheral blood | 95 | 107 | 9800 | | | | |
| Dataset 4 - Published sequences | Peripheral blood and tissue (healthy) | 4 | 4 | 23 | 320 | | | |
| Dataset 5 - Published γδ TIL's | Various tumor tissue | 5 | 6 | 20 | 0 | 184 | | |
| Dataset 6 - Breast cancer single cell | Breast cancer tissue | 0 | 0 | 0 | 0 | 0 | 7 | |
| Datazet 7 - Breast cancer NGS | Breast cancer tissue | 17 | 14 | 40 | 1 | 3 | 1 | 482 |

Fig. 5D

| Shared Vδ1 TCR sequences between different datasets | | | | | | | | |
|---|---|---|---|---|---|---|---|---|
| | Source | Dataset 1 | Dataset 2 | Dataset 3 | Dataset 4 | Dataset 5 | Dataset 6 | Dataset 7 |
| Dataset 1 - Healthy donors | Peripheral blood | 202 | | | | | | |
| Dataset 2 - Ravens et al | Peripheral blood | 0 | 126 | | | | | |
| Dataset 3 - Davey et al | Peripheral blood | 0 | 0 | 27368 | | | | |
| Dataset 4 - Published sequences | Peripheral blood and tissue (healthy) | 0 | 0 | 0 | 94 | | | |
| Dataset 5 - Published γδTIL's | Various tumor tissue | 0 | 0 | 11 | 0 | 624 | | |
| Dataset 6 - Breast cancer single cell | Breast cancer tissue | 0 | 0 | 0 | 0 | 0 | 22 | |
| Datazet 7 - Breast cancer NGS | Breast cancer tissue | 0 | 0 | 0 | 0 | 0 | 2 | 482 |

Fig. 5E

| Shared Vδ3 TCR sequences between different datasets | | | | | | | | |
|---|---|---|---|---|---|---|---|---|
| | Source | Dataset 1 | Dataset 2 | Dataset 3 | Dataset 4 | Dataset 5 | Dataset 6 | Dataset 7 |
| Dataset 1 - Healthy donors | Peripheral blood | 14 | | | | | | |
| Dataset 2 - Ravens et al | Peripheral blood | 0 | 26 | | | | | |
| Dataset 3 - Davey et al | Peripheral blood | 0 | 0 | 687 | | | | |
| Dataset 4 - Published sequences | Peripheral blood and tissue (healthy) | 0 | 0 | 0 | 22 | | | |
| Dataset 5 - Published γδTIL's | Various tumor tissue | 0 | 0 | 0 | 0 | 81 | | |
| Dataset 6 - Breast cancer single cell | Breast cancer tissue | 0 | 0 | 0 | 0 | 0 | 13 | |
| Datazet 7 - Breast cancer NGS | Breast cancer tissue | 0 | 0 | 0 | 0 | 1 | 1 | 43 |

Fig. 8A(i)

| Patient | Identified seq. | Unique seq. |
|---|---|---|
| A | 2 | 1 |
| B | 8 | 6 |
| C | 9 | 8 |
| D | 5 | 3 |
| E | 10 | 6 |
| F | 8 | 8 |
| G | 5 | 5 |
| H | 2 | 2 |
| I | 0 | 0 |
| K | 2 | 2 |
| Z | 4 | 4 |
| Total | 55 | 41 |

Fig. 8A(ii)

Shared TCRδ sequences in triple negative breast cancer

| HD | A | B | C | D | E | F | G | H | I | K | Z |
|---|---|---|---|---|---|---|---|---|---|---|---|
| A | 1 | | | | | | | | | | |
| B | 0 | 6 | | | | | | | | | |
| C | 0 | 1 | 8 | | | | | | | | |
| D | 0 | 1 | 1 | 3 | | | | | | | |
| E | 0 | 1 | 1 | 1 | 6 | | | | | | |
| F | 0 | 1 | 1 | 1 | 1 | 8 | | | | | |
| G | 0 | 1 | 1 | 1 | 1 | 1 | 5 | | | | |
| H | 0 | 1 | 0 | 0 | 0 | 0 | 0 | 2 | | | |
| I | ND | ND | ND | ND | ND | ND | ND | ND | 0 | | |
| K | 0 | 0 | 0 | 0 | 0 | 0 | 0 | 0 | ND | 2 | |
| Z | 0 | 0 | 0 | 1 | 0 | 0 | 0 | 0 | ND | 0 | 4 |

| Shared sequences | Vdelta | Clone# | Shared by no of patients |
|---|---|---|---|
| CAASSPIRGYTGSDKLIF | Vdelta5 | C132 | 6 |
| CALGDYLGDKYPSYDLLGDTTDKL | Vdelta1 | Ze11 | 2 |

Fig. 8B(i)

| Patient | Identified seq. | Unique seq. |
|---|---|---|
| A | 18 | 16 |
| B | 13 | 11 |
| C | 16 | 16 |
| D | 8 | 7 |
| E | 12 | 10 |
| F | 8 | 7 |
| G | 9 | 9 |
| H | 0 | 0 |
| I | 2 | 2 |
| K | 1 | 1 |
| Z | 3 | 2 |
| Total | 90 | 66 |

Fig. 8B(ii)

Shared TCRγ sequences in triple negative breast cancer

| HD | A | B | C | D | E | F | G | H | I | K | Z |
|---|---|---|---|---|---|---|---|---|---|---|---|
| A | 16 | | | | | | | | | | |
| B | 2 | 11 | | | | | | | | | |
| C | 2 | 0 | 16 | | | | | | | | |
| D | 0 | 1 | 0 | 7 | | | | | | | |
| E | 1 | 1 | 0 | 1 | 10 | | | | | | |
| F | 0 | 0 | 0 | 1 | 3 | 7 | | | | | |
| G | 0 | 0 | 0 | 0 | 0 | 0 | 9 | | | | |
| H | ND | ND | ND | ND | ND | ND | ND | 0 | | | |
| I | 1 | 1 | 0 | 0 | 1 | 0 | 0 | ND | 2 | | |
| K | 0 | 0 | 0 | 0 | 1 | 0 | 0 | ND | 0 | 1 | |
| Z | 1 | 2 | 0 | 0 | 1 | 0 | 0 | ND | 1 | 0 | 2 |

| Shared sequences | Vgamma | Clone # | Shared by no of patients |
|---|---|---|---|
| CATWDGFYYKKLF | Vgamma4 | C132 | 2 |
| CATWDGQKKLF | Vgamma2 | F4 | 3 |
| CATWDGPPYYKKLF | Vgamma4 | E113, F2 | 2 |
| CATWDNYKKLF | Vgamma8 | B23, Zi11, Zei | 5 |

METHOD OF CELL THERAPY

FIELD OF THE INVENTION

The present invention relates to a method for identifying δT-cell (or γT-cell) receptors chains or parts thereof that mediate an anti-tumour or an anti-infection response by identifying amino acid sequences comprising δT-cell (or γT-cell) receptors chains or parts thereof that are shared between different donors.

BACKGROUND OF THE INVENTION

Our immune system utilizes different lines of defenses to protect us from infections as well as cancer. In order to cover the magnitude of potential invaders and internal threats our adaptive immune system has the possibility to raise up to $10^{16}$ αβ TCR combinations as well as $10^{11}$ variations in immunoglobulins (1). Although threats are frequently identical and many HLA types are shared between individuals, only little overlap in the usage of defined CDR3 regions in the α and βTCR chains between individuals has been reported so far. "Private specificities", thus α or βTCRs with a very distinct sequences, which are only observed in one individual, are usually dominant (2). Occasionally also public specificities are observed. These consist of highly shared βTCR sequences and are only observed in the presence of the very same peptide MHC complex in the context of chronic infections such as EBV, CMV, influenza, or allo-reactive immune responses (3, 4). Analyses of the diversity of immunoglobulin responses imply a similar diversity and random usage of CDR3 sequences. Though an increased correlation in antibody gene segment usages, junctional features, and mutation rates are observed in twins, antibody pools show little similarity in clonal responses to acute stimuli against the very same antigen (5). These data suggest that protective immune responses are usually not shared in detail in sequences between different individuals in the highly diverse αβTCR and immunoglobulin repertoire. Consequently each individual needs to raise its very own army of α as well as βTCR chains and immunoglobulins. Analyses of sequences only will therefore not allow the identification of sequences with large therapeutic interest. This is also reflected by the fact that protective α as well as βTCR chains (6) and immunoglobulins, which are currently used in the clinic are usually identified by functional analyses followed by sequence analysis and not vice versa.

Among all immune receptor chains, TCR δs have even the highest potential diversity in the CDR3 loop (approximately $10^{16}$ combinations for murine TCR δ) owing to the presence of multiple D gene segments (two in mice, three in human, and up to five in cattle) that can join together. Each D gene segment can be read in all three open reading frames, and N nucleotides can be inserted into the junctions of the joining segments. Thus, despite the limited diversity at the VJ junctions of TCR γ chains, the potential diversity generated at the combined CDR3 junctions (approximately $10^{18}$ combinations) is still higher than that of αβ TCRs (~$10^{16}$) and immunoglobulins (~$10^{11}$). (1) This suggests also a highly diverse usage of CDR3 regions for δTCR chains in each individual and is again in line with mentioned considerations for the usage of αβ TCR chains or immunoglobulins, that sequence analysis only will not result in the identification of therapeutically relevant δTCR chains.

Surprisingly we were able to identify shared δT-cell (or γT-cell) receptor chains or parts thereof that mediate an anti-tumour or an anti-infection response.

DESCRIPTION OF THE FIGURES

FIG. 4A, 4B(i)-4B(iii), 4C(i)-4C(ii), 4D. The γδTCR FE11 critically depends on the CD8 co-receptor for tumour recognition. (FIG. 4A) γδT cell clone FE11 was generated by limiting dilution. To assess tumour reactivity, FE11 cells were incubated with Daudi, SW480 or EBV-LCL tumour targets in the presence of control antibody or antibodies blocking CD8α or CD8β. IFNγ secretion was measured by ELISPOT. Healthy PBMCs served as negative control targets. (FIGS. 4B(i), 4B(ii) and 4B(iii)) The TCR γ and δ chains of clone FE11 were sequenced and retrovirally transduced into αβT cells (FIG. 4B(i) left panel; δTCR expression on mock-transduced (light curve) and γδTCR-transduced T cells is indicated). Transfer of γδTCR-mediated tumour-reactivity was tested by co-incubating γδTCR- or mock-transduced T cells (FIG. 4B(ii)), with indicated target cells in an IFNγ ELISPOT (FIG. 4B(iii), right panel). (FIGS. 4C(i) and 4C(ii)) CD4+ and CD8+ αβT cells transduced with the FE11 γδTCR were sorted and co-cultured with indicated target cells. T cell activation was assessed by IFNγ ELISPOT. (FIG. 4C(i), mock transduced; FIG. 4C(ii), FE11 transduced). (FIG. 4D) CD4+ and CD8+ αβT cells expressing the FE11 γδTCR were co-incubated with SW480 target cells as in (FIGS. 4C(i) and 4C(ii)) but now in the presence of a control antibody or blocking antibodies against CD8α or CD8β. Data are representative of three (FIGS. 4A, 4D), two (FIG. 4B(i)-4B(iii)), and five (FIG. 4C(i)-4C(ii)) separate experiments. Error bars represent S.E.M. (*P<0.01; ***P<0.001).

FIG. 5A-5E. Overview of shared TCRδ and TCRβ sequences. (FIG. 5A) Overview of shared TCRδ sequences found within healthy donors (dataset 1). The included sequences in the healthy donors all had a clonal frequency>0.1%. On the horizontal axis the number of shared sequences between donors. On the vertical axis the percentage of shared sequences of the total of sequences of those two donors. (FIG. 5B) Overview of shared TCRβ sequences found within healthy donors. On the horizontal axis the number of shared sequences between donors. On the vertical axis the percentage of shared sequences of the total of sequences of those two donors. (FIG. 5C) Overview of shared Vδ2 sequences between the different datasets. On the horizontal axis the number of shared sequences between donors. (FIG. 5D) Overview of shared Vδ1 sequences between the different datasets. On the horizontal axis the number of shared sequences between donors. (FIG. 5E)

Overview of shared Vδ3 sequences between the different datasets. On the horizontal axis the number of shared sequences between donor.

Figure 6:
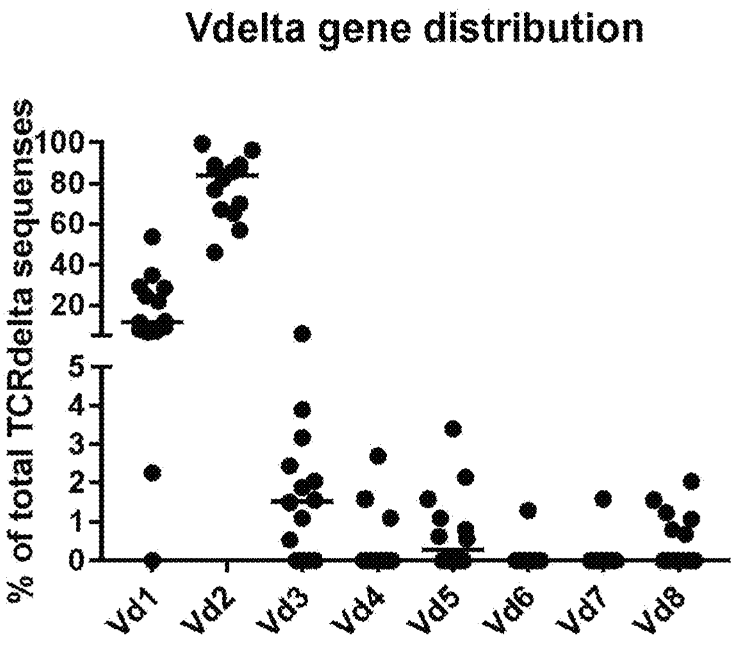

FIG. 6. Vδ gene distribution. The majority of the identified TCRδ sequences by NGS in the peripheral blood are of Vδ2 γδ T cells. The frequencies and median of the Vδ gene distribution in 14 healthy donors are shown.

Figure 7A:
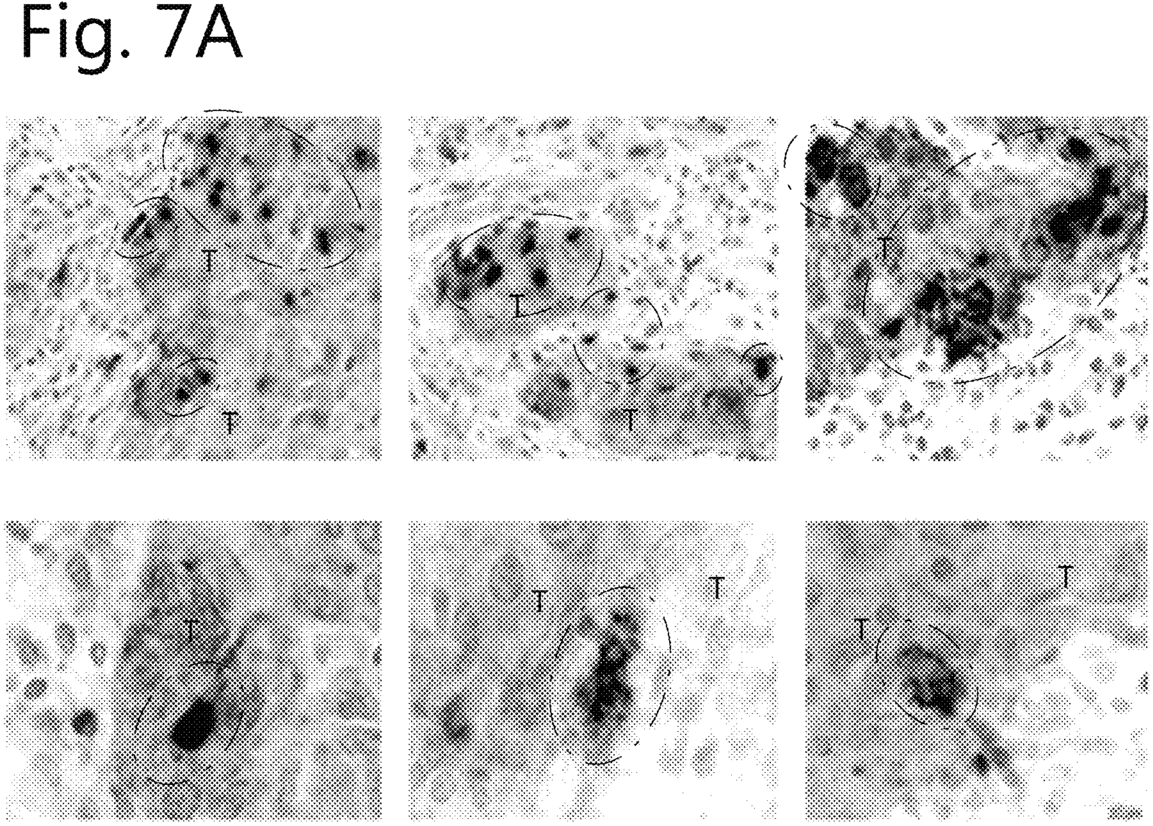
Figure 7B:
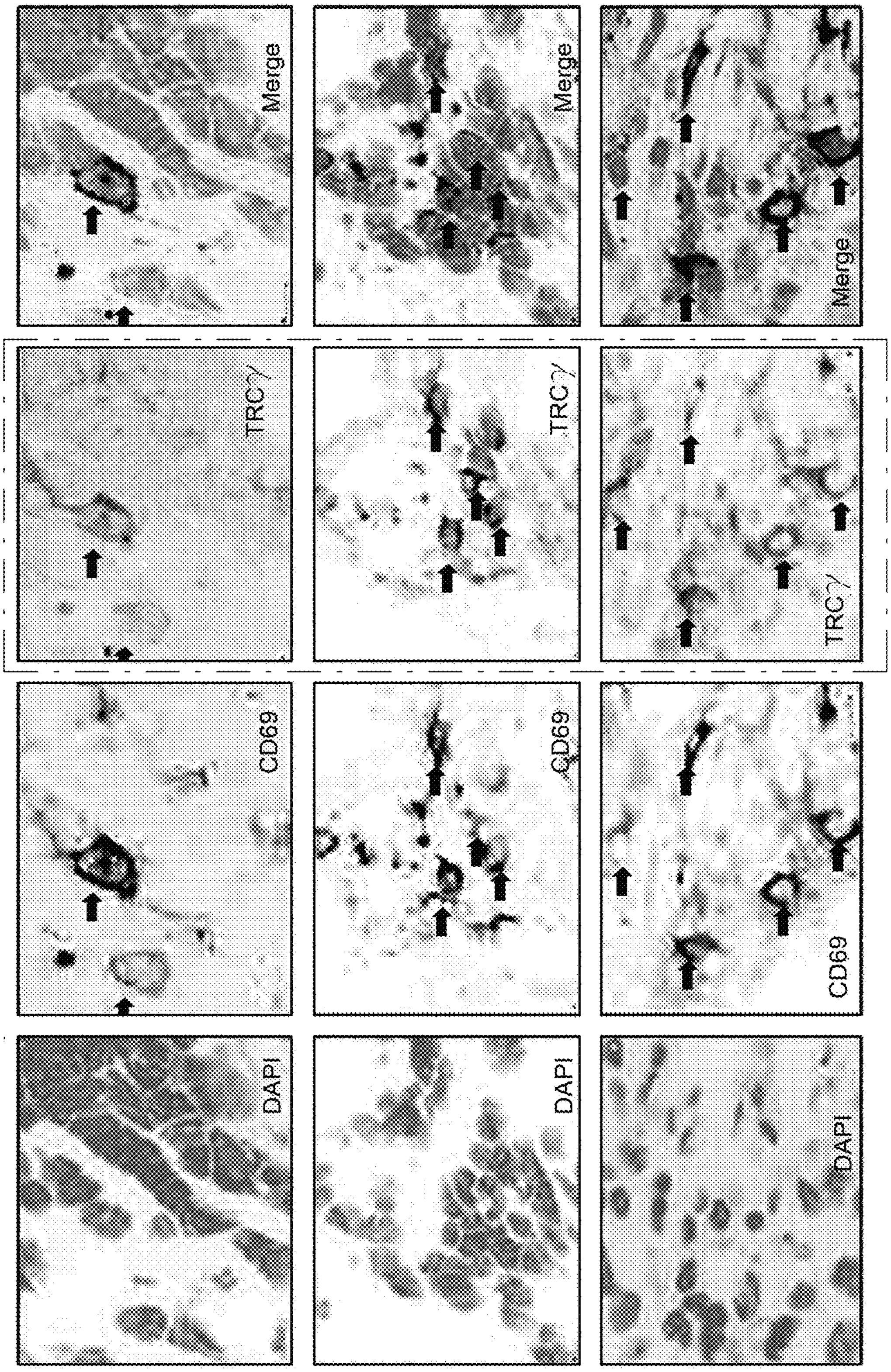

FIG. 7A-7B. Activated γδ T cells are in contact with the apoptotic tumors positive cells. (FIG. 7A) Double Immunohistochemistry using TCRγ antibody and cleaved caspase 3 (Areas with double positive T cells are indicated with a circle). T in these images indicates tumor tissue (FIG. 7B) Analyses of γδ TILs in TNBC froze section with CD69 as activation marker. Arrow show positive cells, nuclei are stained with DAPI blue.

FIG. 8A(i)-8A(ii), 8B(i)-8B(ii). Shared TCRδ and TCRγ sequences from γδ TIL. Overview of shared (FIG. 8A(i)-8A(ii)) TCRδ and (FIG. 8B(i)-8B(ii)) TCRγ sequences found in tumor samples of patients with triple negative breast cancer. On the right (FIG. 8A(ii) or FIG. 8B (ii)), the total identified sequences and the unique sequences per patients are shown. On the left (FIG. 8A(i) or FIG. 8B(i)), the overlap between patients is represented by the numbers in the table.

Figure 9A:
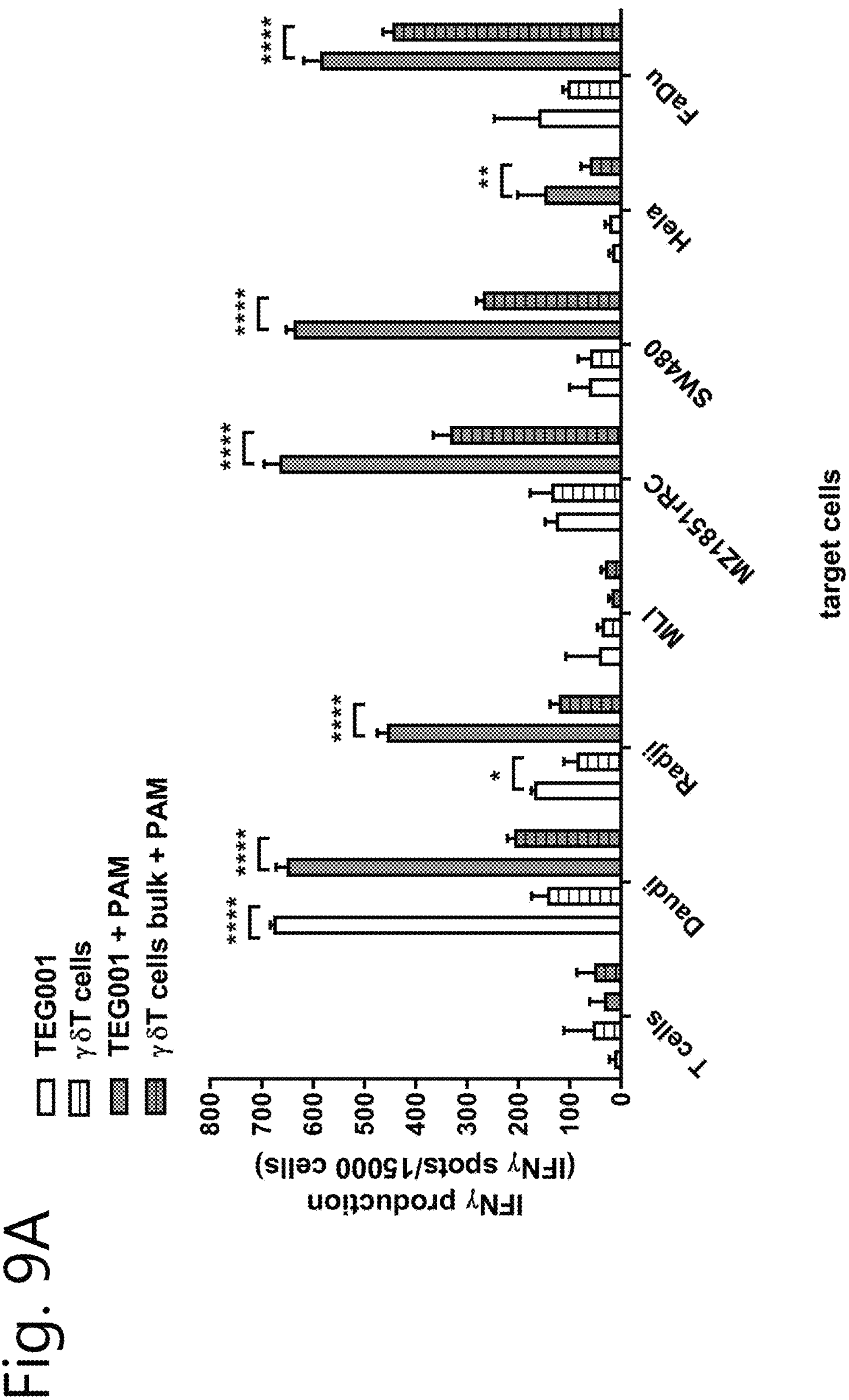
Figure 9B:
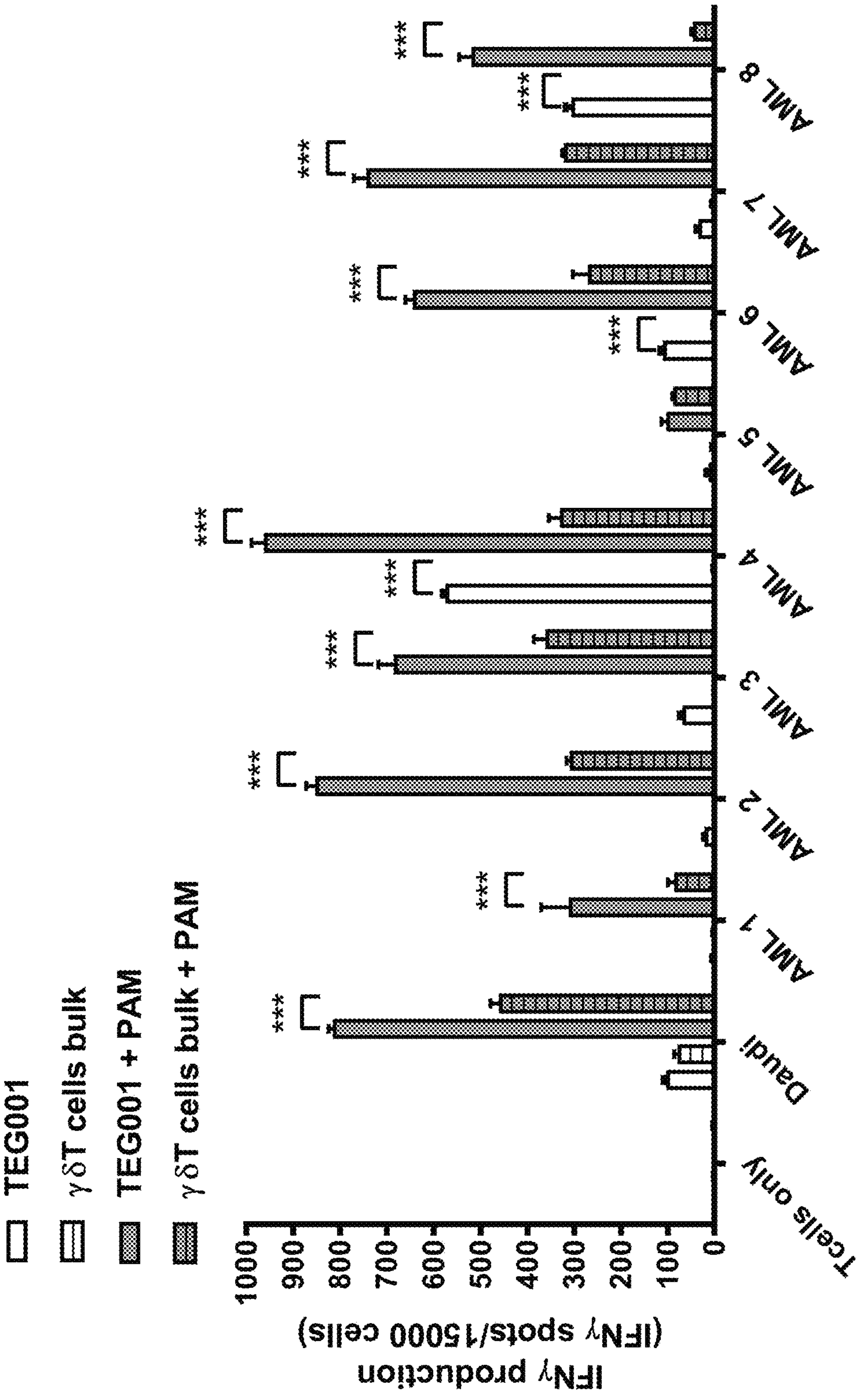

FIG. 9A-9B. Improved anti-tumor activity of TEG001 when compared to a bulk population of Vγ9Vδ2 T cells. A panel of tumor cell lines (FIG. 9A) or primary AML tumor samples (FIG. 9B) was incubated with TEG001 or with a bulk population of primary γδ T cells with or without 10 μM pamidronate (PAM) for 20 h and IFNγ secretion was measured by ELISPOT. IFNγ spots per 15.000 T cells is shown as mean of triplicates (+SD). Statistical significances were calculated by two-way anova; *$p<0.05$; $p<0.01$; *$p<0.001$.

Figure 10A:
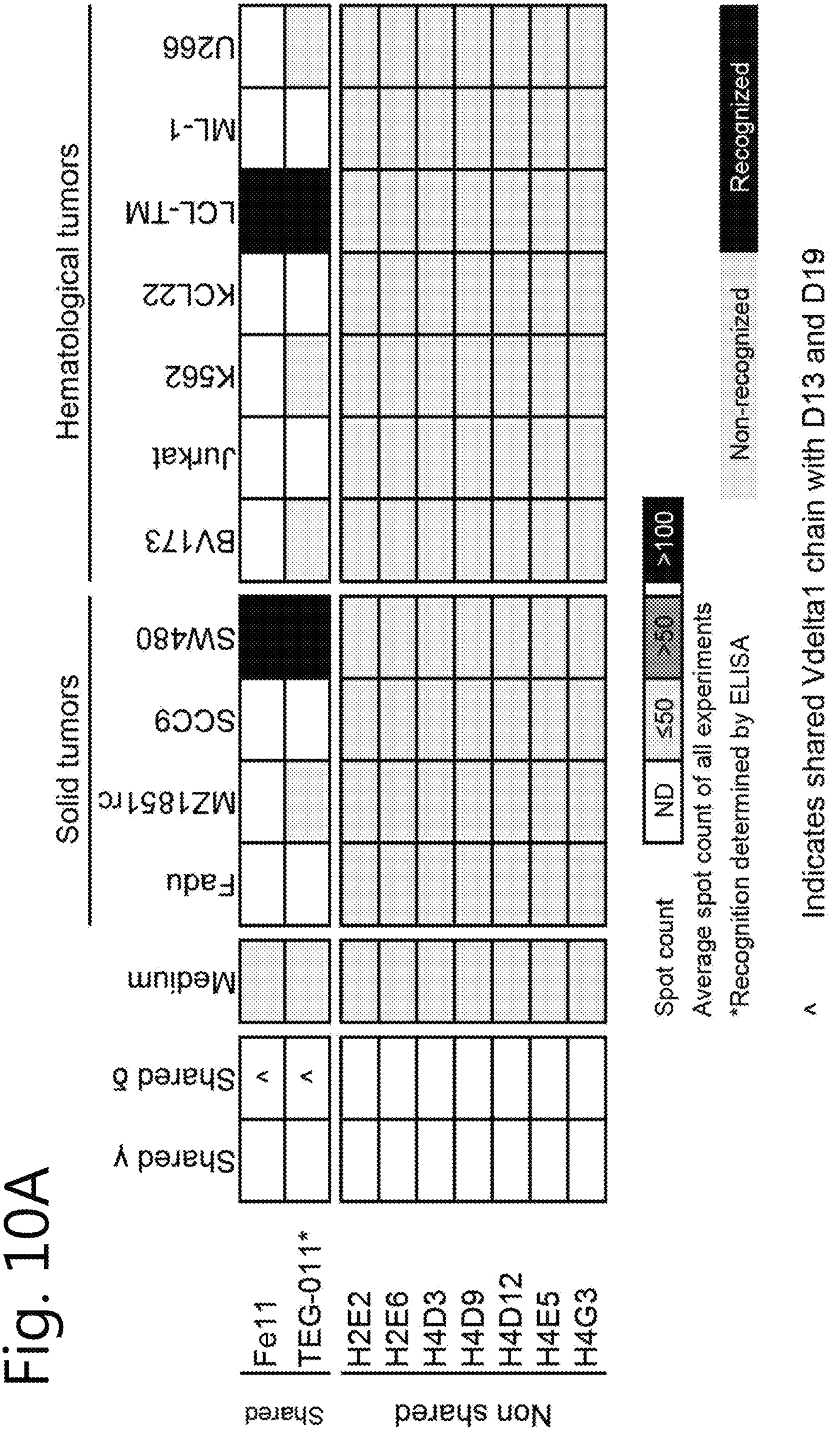
Figure 10B:
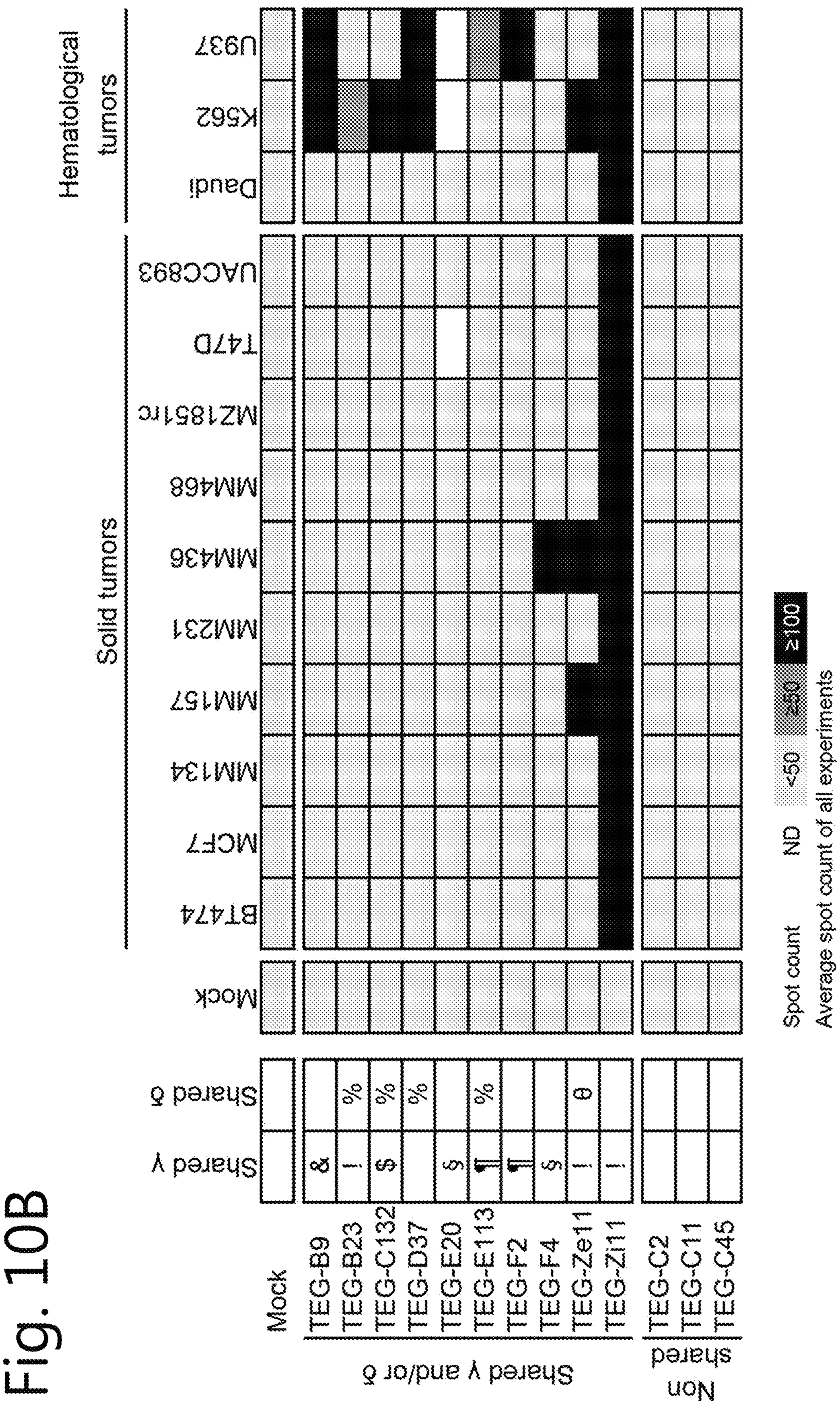

FIG. 10A-10B. γδ T cell clones and TEGs with shared γ or δ TCR chains. (FIG. 10A) Vδ1 clones isolated from the peripheral repertoire and TEGs engineered with shared δ TCR chains show reactivity against different tumor cell lines. $V\delta2^{neg}$γδ T cell clones of a healthy donor were tested against a broad panel of tumor cell lines by an ELISPOT assay. The reactivity of Fe11 in TEG (TEG-011) format was measured by ELISA. ^ Indicates shared Vdelta1 chain with D13 and D19. (FIG. 10B) TEG's engineered with shared γ or δ TCR chains isolated from γδ TILs show reactivity against tumor cell lines. Reactivity towards tumor cell lines of γδ TIL TCRs in TEG format as measured was measured by ELISPOT. $ Indicates shared Vγ4 sequence published by Lafarge et al. (51). % Indicates shared Vδ5 sequence within γδ TILs and also published by Lafarge et al (51), & Indicates γ TCR chains sequence published by Uldirch et al. (32). ! Indicates shared Vγ8 sequence. § Indicates shared Vγ2 sequence. ¶ Indicates shared Vγ4 sequence 0 Indicates shared Vδ1 within γδ TILs.

Figure 11A:
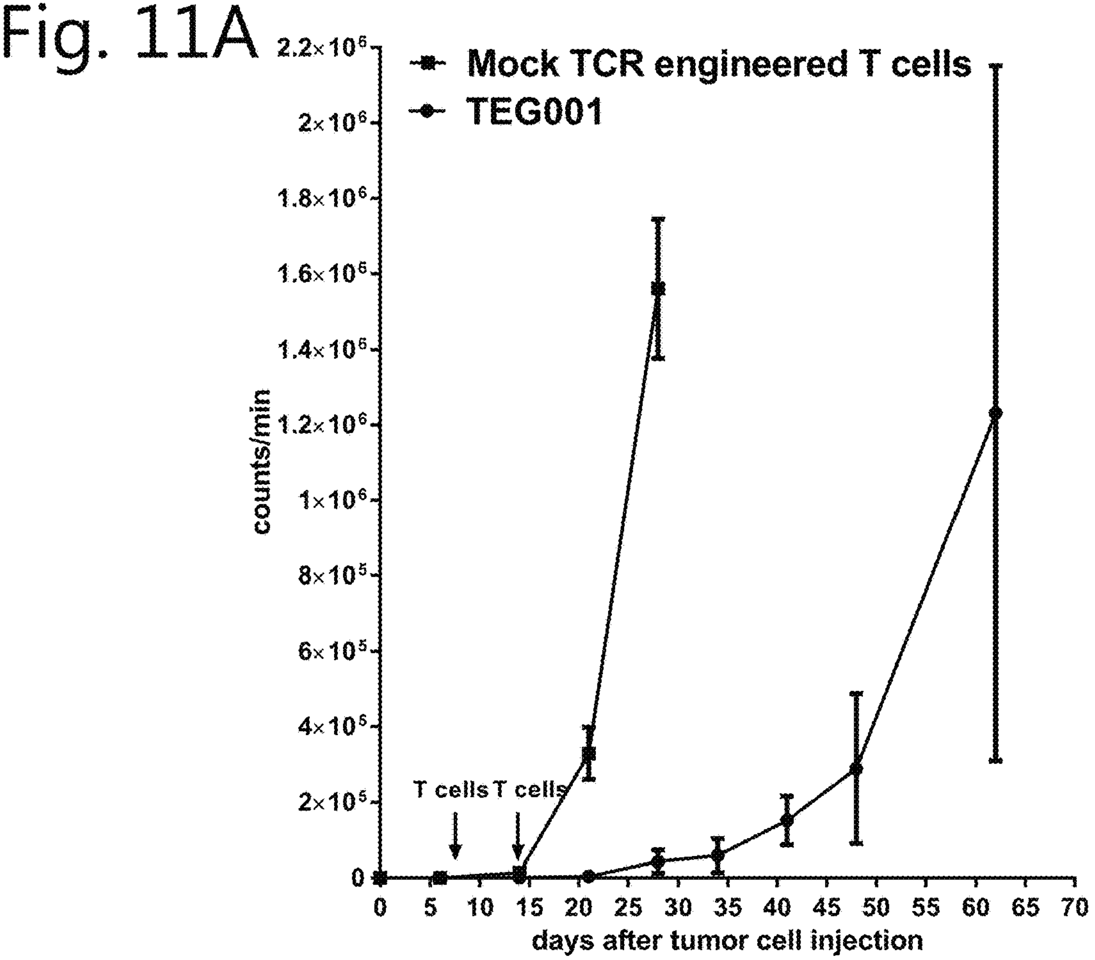
Figure 11B:
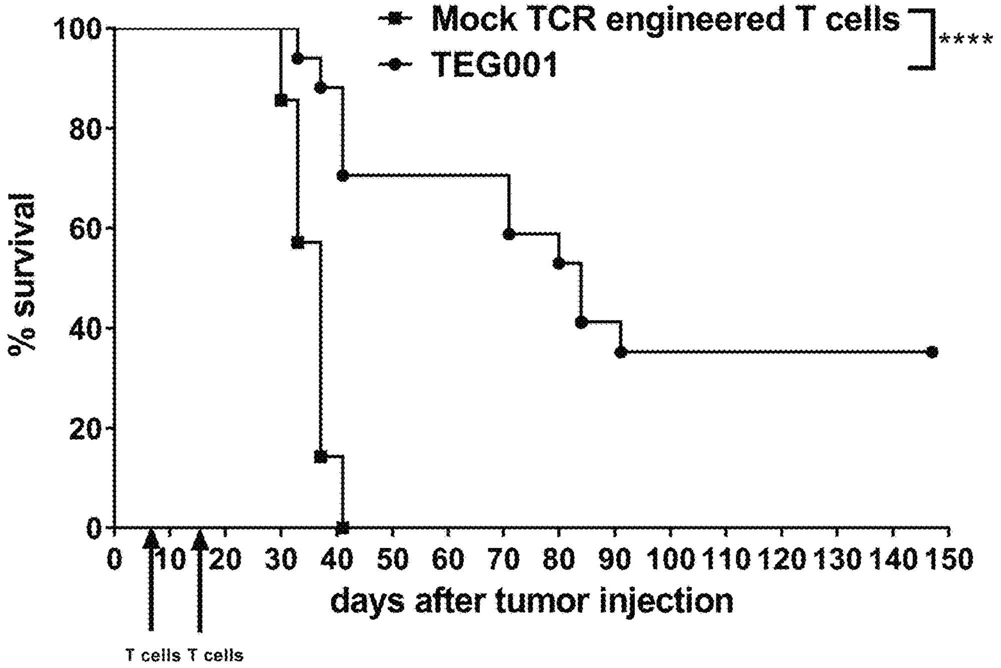

FIG. 11A-11B. Inhibition of tumor growth and increased overall survival in TEG001 treated tumor bearing mice. NSG mice were treated with TEG001 (n=17) or Mock cells (TEG-LM1, n=7) at day 7 and day 14 after tumor engraftment. (FIG. 11A) Bioluminescence Imaging was used to monitor tumor growth every 7 days. Data represent mean of all mice per group (+/−SEM). (FIG. 11B) Overall survival of treated mice was monitored until the end of the experiment and is presented in the right panel. Statistical significances were calculated by log-rank (Mantel-Cox) test; ****$p<0.0001$.

Figure 12:
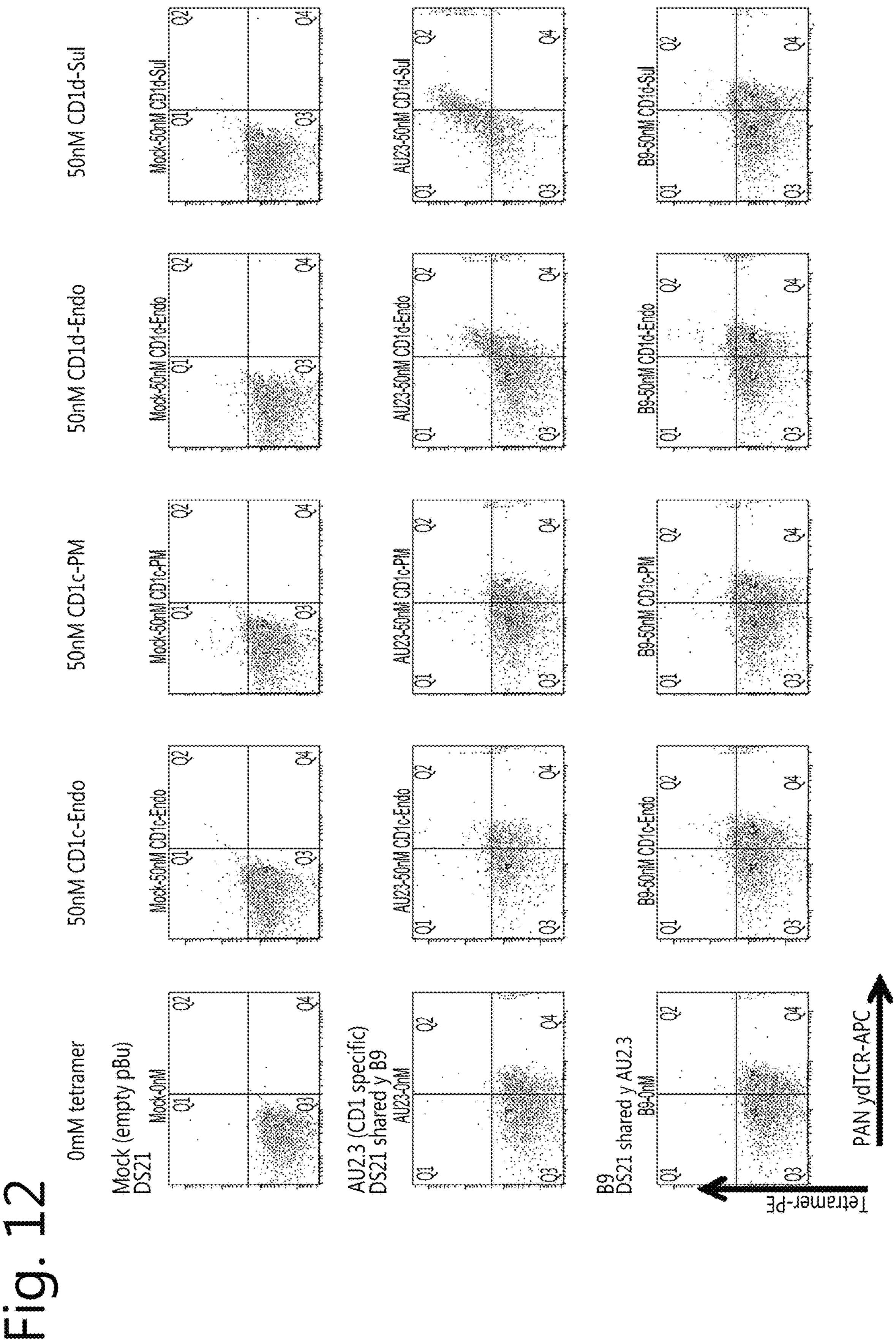

FIG. 12. Tetramer staining of TEG-AU2.3 (CD1d-specific) and TEG-B9.

DESCRIPTION OF THE INVENTION

Method

In a first aspect the invention provides a method for identifying δT-cell receptors chains or parts thereof that mediate an anti-tumour or anti-infection response comprising the steps of:

a) providing amino acid sequences obtained from a donor, comprising δT-cell receptor chains or parts thereof each of said receptor chains or parts thereof comprising a CDR3 region;

b) identifying amino acid sequences comprising δT-cell receptors chains or parts thereof obtained in step a) that are shared between different donors;

c) confirming the anti-tumour or anti-infection response of the δT-cell receptors chains or parts thereof identified in step b) by assessing the anti-tumour or anti-infection response of a T cell expressing a nucleic acid molecule encoding the amino acid sequence provided in step a).

In a second aspect the invention provides a method for identifying γT-cell receptors chains or parts thereof that mediate an anti-tumour or anti-infection response comprising the steps of:

a) providing amino acid sequences obtained from a donor, comprising γT-cell receptor chains or parts thereof each of said receptor chains or parts thereof comprising a CDR3 region;

b) identifying amino acid sequences comprising γT-cell receptors chains or parts thereof obtained in step a) that are shared between different donors;

c) confirming the anti-tumour or anti-infection response of the γT-cell receptors chains or parts thereof identified in step b) by assessing the anti-tumour or anti-infection response of a T cell expressing a nucleic acid molecule encoding the amino acid sequence provided in step a).

Unless otherwise indicated herein, the explanation provided for each feature of the method of the first aspect below also holds for each feature of the method of the second aspect; the only difference being that the method of the second aspect deals with the identification of γT-cell receptor chains or parts thereof whereas the method of the first aspect deals with the identification of δT-cell receptor chains or parts thereof.

Step a of the Method of the First and Second Aspects

Step a) comprises the provision of the amino acid sequences from a donor, comprising δT-cell (or γT-cell for the method of the second aspect) receptor chains or parts thereof comprising a CDR3 region. In a first place, T cells or T lymphocytes should be first isolated.

T cells, or T lymphocytes, belong to a group of white blood cells named lymphocytes, which play a role in cell-mediated immunity. T cells originate from hematopoietic stem cells in the bone marrow, mature in the thymus (that is where the T is derived from), and gain their full function in peripheral lymphoid tissues. During T-cell development, $CD4^{-}CD8^{-}$T-cells (negative for both the CD4 and CD8 co-receptor) are committed either to an αβ or γδ fate as a result of an initial β or δ TCR gene rearrangement. Cells that undergo early β chain rearrangement express a pre-TCR structure composed of a complete β chain and a pre-TCRα chain on the cell surface. Such cells switch to a $CD4^{+}CD8^{+}$ state, rearrange the TCRα chain locus, and express a mature αβTCR on the surface. $CD4^-CD8^-$ T cells that successfully complete the γ gene rearrangement before the β gene rearrangement express a functional γδTCR and remain $CD4^-$ $CD8^-$. (Claudio Tripodo et al. Gamma delta T cell lymphomas Nature Reviews Clinical Oncology 6, 707-717 (December 2009)). The T cell receptor associates with the CD3 protein complex. Mature T cells, i.e. expressing a αβTCR or a γδ TCR, express the T cell receptor complex on the cell surface. The γδT-cells, which constitute about 1-5% of the total population of T cells, can be divided in further subpopulations. A subpopulation of γδT-cells constitutes γ9δ2T-cells, which express a γ9δ2TCR. Within the extracellular domain of a T cell receptor three complementarity determining regions (CDR1, CDR2, CDR3) are located. These regions are in general the most variable domains and contribute significantly to the diversity among TCRs. CDR regions are composed during the development of a T-cell where so-called Variable-(V), Diverse-(D), and Joining-(J)-gene segments are randomly combined to generate diverse TCRs. Of the three CDR regions CDR3, for both αβ T-cells and γδ T-cells, is the most variable one, and is therefore the key player in antigen/ligand recognition.

αβT cells may be defined with respect to function as T lymphocytes that express an αβTCR, which recognize peptides bound to MHC molecules (major histocompatibility complex), which are expressed on the surface of various cells. MHC molecules present peptides derived from the proteins of a cell. When for example a cell is infected with a virus, the MHC will present viral peptides, and the interaction between the αβTCR on the T cell and the MHC-complex on the target cell (i.e. the virus infected cell) activates specific types of T-cells which initiate and immune responses to eliminate the infected cell. Hence, αβT cells may be functionally defined as being cells capable of recognizing peptides bound to MHC molecules. αβT cells may be selected from peripheral blood for example via the CD3 antigen as described below and in the examples, as the large majority of T cells have the αβTCR. αβT cells may also be selected with an antibody specific for the αβTCR, such as described below. From such selected cells, the nucleic acid (or amino acid) sequence corresponding to the αT-cell receptor chain and the βT-cell receptor chain may be determined by sequencing, preferably as carried out in the experimental part. Hence, αβT-cells may also be defined as being cells comprising a nucleic acid (or amino acid) sequence corresponding to the αT-cell receptor chain and/or the βT-cell receptor chain.

γδT-cells may be functionally defined in that they are specifically and rapidly activated by e.g. a set of non-peptidic phosphorylated isoprenoid precursors, collectively named phosphoantigens or stress signals medicated by non classical HLA molecules like CD1. Phosphoantigens are produced by virtually all living cells, though the levels are usually very low in healthy cells, and increased in transformed/malignant cells or cells infected with e.g. *Mycobacterium tuberculosis*, which deliver a derivate of phosphoantigens. The most common phosphoantigen found in human cells (including cancer cells) is isopentenyl pyrophosphate (IPP) and its isomer dimethylallyl pyrophosphate (DMAPP). Activation of γδT-cells comprises clonal expansion, cytoxic activity and expression and release of cytokines. γδT-cells are also defined by expression of the γδ T cell receptor. For example, cells may be selected using an antibody specific for the γδ T cell receptor such as described below. From such selected cells, the nucleic acid (or amino acid sequence) sequence corresponding to the γT-cell receptor chain and/or the δT-cell receptor chain may be determined by sequencing, preferably as carried out in the experimental part. Hence, γδT-cells may also be defined as being cells naturally comprising a nucleic acid (or amino acid) sequence corresponding to a γT-cell receptor chain and/or a δT-cell receptor chain.

The person skilled in the art is well capable of selecting and/or identifying cell populations characterized by expression of an antigen or receptor on the surface of the cell such as described throughout herein. It is understood that with regard to expression on the surface of cells, such as CD3, CD4, CD8, αβTCR, and γδ TCR, this is typically done in a population of cells of which a portion of cells have a much higher level of expression of the antigen when compared to cells having a lower level of expression.

Hence, the terms positive or negative are to be understood as being relative, i.e. positive cells have a much higher expression level as compared to cells being negative. Cells being negative in this sense may thus still have an expression level which may be detected.

Expression on the surface of cells may be analyzed using Fluorescence Activated Cell Sorting (FACS), and many specific antibodies are commercially available, e.g. such as for CD3, CD4, CD8, αβTCR, and γδTCR that are suitable for such FACS analysis, such as described in the examples and as available. γδTCR may be γ9δ2TCR. As an example, αβ T cells can also be defined and selected as being positive for αβTCR in FACS. The same holds for γδ T cells. Antibodies suitable for FACS or similar separation techniques (such as e.g. antibodies conjugated to magnetic beads) are widely available. Conditions are selected, such as provided by the antibody manufacturer that allows the selection of negative and/or positive cells. Examples of antibodies that may be suitable for selection of γδ-T cells, or engineered γδT cells or 1982 T cells or engineered γ9δ2 T cells such as available from BD Pharmingen (BD, 1 Becton Drive, Franklin Lakes, NJ USA) are Vγ9-PE (clone B3, #555733), Vδ2-FITC (clone B6, #555738), γδTCR-APC (clone B1, #555718) or such as available from Beckman Coulter is pan-γδ TCR-PE (clone IMMU510, #IM 1418U) Similarly, suitable antibodies for αβ-T cell selection, such as anti-CD3 antibodies may be such as available from BD Pharmingen is CD3-FITC (#345763) or such as anti-αβTCR antibodies such as available from Beckman Coulter is pan-αβTCR-PE (#A39499) or pan-αβTCR-PC5 (#A39500). An alternative antibody that binds to the human endogenous αβT cell receptor is available commercially from Miltenyi (Miltenyi Biotec GmbH, Friedrich-Ebert-Straße 68, 51429 Bergisch Gladbach, Germany). This antibody is from cell clone BW242/412 which is of the mouse isotype IgG2b. A FITC labeled BW242/412 antibody is available from Miltenyi under order no. 130-098-688. The BW242/412 cell clone and the antibody expressed by BW242/412 is described in detail i.a. EP0403156B1 which is herein incorporated by reference.

Accordingly, in the method of the invention, first T-cells are provided. The T-cells may be primary cells, for example from a subject, such as described in the examples for a human subject. The T-cells may be αβ or γδ T-cells derived from a human subject. Alternatively, the T-cells may be T cell lines, such as SupT-1, Jurkat, or Raji cells or any other widely available cell line. Any cell type, being a primary cell or any other cell line will suffice, as long as the cell population, or a substantial part thereof, expresses the T-cell receptor, i.e. such as being positive for the αβT-cell or the γδ TCR receptor in a FACS sorting or the like as described above, such a cell population may be contemplated. Also, any cell or cell population may be contemplated that, when provided with a γδ TCR according to the invention is capable of forming a functional TCR complex and exerting e.g. a functional cytoxic response and/or cytokine production. The cell that is provided may also be a progenitor cell, preferably a blood progenitor cell such as a thymocyte or a blood stem cell, which after it has been provided with the right stimuli can develop into T cells.

Preferably, T cells provided express or are able to express a γδ TCR. T cells may have been transduced to express a γδ TCR or already express a γTCR and have been transduced to express a δTCR (or respectively already express a δTCR and have been transduced to express a γTCR), comprising the nucleic acid sequences encoding the sequence obtained in step a). All theoretical combinations of a γ with a δ chain of the TCR is encompassed. In an embodiment, the γδTCR is γ9δ2TCR. In another embodiment the γδTCR is γ5δ1TCR. In another embodiment, the γδTCR is γ8δ5TCR. In another embodiment, the γδTCR is γ4δ5TCR. In another embodiment, the γδTCR is γ2δ1TCR. In another embodiment the γδTCR is γ8δ1TCR.

Step a) comprising "providing amino acid sequences obtained from a donor, comprising δT-cell receptor chains or parts thereof each of said receptor chains or parts thereof comprising a CDR3 region" may be replaced by "obtaining from a plurality of donors, δT-cell receptor chains, γT-cell receptor chains or parts thereof, said receptor chains or parts thereof comprising a CDR3 region, and determining amino acid sequences of said receptors chains or parts thereof or nucleic acid sequences encoding the same".

In step a) at least two different donors are used. This is important in the method of the invention as one wishes to identify δTCR (or γTCR) chains or part thereof that are shared by different donors. A preferred δTCR chain is a δ2 TCR chain. Another preferred δTCR chain is a δ1 TCR chain. Another preferred δTCR chain is a δ3 TCR chain. Another preferred δTCR chain is a δ4 TCR chain. Another preferred δTCR chain is a δ5 TCR chain. A preferred γTCR chain is a γ2TCR chain. Another preferred γTCR chain is a γ4TCR chain. Another preferred γTCR chain is a γ5TCR chain. Another preferred γTCR chain is a γδTCR chain. Another preferred γTCR chain is a γ9TCR chain.

In an embodiment, a γδTCR is a γ9δ2TCR. In another embodiment the γδTCR is γ5δ1TCR. In another embodiment the γδTCR is γ9δ4TCR. In another embodiment the γδTCR is γ4δ5TCR. In another embodiment the γδTCR is γ8δ5TCR. In another embodiment the γδTCR is γ2δ1TCR. In another embodiment the γδTCR is γ8δ1TCR. In another embodiment the γδTCR is γ4δ3TCR.

The number of different donors used may be as high as possible. At least 2 different donors are used. However it is preferred that 3, 4, 5, 6, 7, 8, 9, 10 or more different donors are used.

In an embodiment, at least one of the donors may be healthy. However, it is also encompassed that all donors are healthy.

In another embodiment, at least one of the donors may be diseased. However, it is also encompassed that all donors are diseased or elite controller of a disease. It means that a donor could be nor healthy nor diseased but got a cancer or an infection and was able to control it. The TCR's of such a "controlled" infection are of particular interest.

A disease in this context may be cancer or any infection. Infection include infections immediate by viruses bacteria and fungi such as the Hepatitis virus, the Herpes Viruses (CMV, EBV, and more) or a *Mycobacterium.*

In another embodiment, it is also envisaged to have part of the donors being healthy and the remaining part of the donors being diseased.

A donor is preferably a human being.

Accordingly in a preferred embodiment of the step a) of the method of the invention:

a. the donors are human beings, b. at least 2 different donors are used, c. at least one donor, preferably all donors are healthy and/or d. at least one donor is diseased.

Step b of the Method of the First and Second Aspects

Step b) comprises the identification of amino acid sequences comprising δT-cells (or γT-cells) receptors chains or parts thereof obtained in step a) that are shared between different donors.

Such amino acid sequences are preferably defined by InMunoGeneTics information system (www.imgt.org/IMGTScientificChart/Nomenclature/IMGT-FRCDRdefinition-.html).

It is to be understood that the expression "δT-cell receptors chains or parts thereof that are shared between different donors" means that it is not per se the whole "δT-cell receptors chains" that are shared or are identical between different donors. Part of such chain may be shared or may be identical between different donors. In theory each part of a δT-cell receptor may be shared between donors. The same holds for "γT-cell receptors chains or parts thereof that are shared between different donors".

It is also encompassed that the parts that are shared may not be identical but comprises conservative substitutions of a given amino acid. A list of amino acids that are considered to be a conservative substitution of another amino acid is provided in the general part of the description dedicated to the definitions under identity/similarity. In an embodiment said shared part is comprised within a CDR3 region of a δT-cell (or 1-cell) receptor chain or comprises a CDR3 region of a δT-cell (or γT-cell) receptor chain or consists of a δT-cell (or γT-cell) receptor chain. In another embodiment, said shared part is from 3 to 53 amino acids or from 5 and 40 or from 10 and 30. More preferably said shared part is comprised within a CDR3 region of a δT-cell (or γT-cell) receptor chain and is from 3 to 53 amino acids.

It is clear that the number of donors sharing a δT-cell (or γT-cell) receptor chain or part thereof depends on the number of donors used in step a). In a preferred embodiment, the sequences identified are shared between at least 2, 3, 4, 5 different donors.

Step c of the Method of the First and Second Aspects

Step c) comprises the confirmation or the validation of sequences identified as shared in step b). In order to validate the biological relevance of such sequence, the anti-tumour or anti-infection response of a T-cell expressing a defined nucleic acid molecule encoding an amino acid sequence as provided in step a) is determined. The T-cell may already express a δT-cell (or γT-cell) receptor chain identified as shared in step b). It is clear that even if step b) has led to the identification of a part of a δT-cell (or γT-cell) receptor chain being shared, in order to assess the biological relevance of the corresponding δT-cell (or γT-cell) receptor chain, a T cell is transduced with the corresponding δT-cell (or γT-cell) receptor chain comprising the part identified in step b). In an embodiment, an anti-tumour or anti-infection response of such sequence is assessed in a T-cell that does not endogenously express a gamma or delta chain of the TCR. Such a cell may be an αβ-T cell or a NK cell.

The nucleic acid sequences encoding the δT-, preferably the δ2-T cell receptor chain may be introduced into T-cells to provide an engineered T-cell as explained in the general part of the description dedicated to the definitions.

Alternatively in the method of the second aspect, the nucleic acid sequences encoding the γT-, preferably the γ9-T cell receptor chain may be introduced into T-cells to provide an engineered T-cell as explained in the general part of the description dedicated to the definitions.

It is clear to a skilled person that the T cells used should also express a γT cell receptor chain in order to assess the biological relevance of a δT cell receptor chain. In other words a γδTCR is preferably expressed in said T cells, the δTCR being the one identified in the method of the invention as being shared between different donors.

In the method of the second aspect, it is also clear to a skilled person that the T cells used should also express a δT cell receptor chain in order to assess the biological relevance of a γT cell receptor chain. In other words a γδTCR is preferably expressed in said T cells, the TCR being the one identified in the method of the invention as being shared between different donors.

In a preferred embodiment, the nucleic acid molecule encoding the δT-cell (or γT-cell) receptor chain or part thereof is provided in an expression vector or in a retroviral or lentiviral vector in a T cell. This has been extensively explained in the general part of the description dedicated to the definitions.

T cells may be expanded before or after the transfer of the nucleic acids encoding the δT- and/or γT-cell receptor chain. Preferably, the expansion is after the transfer such that the amount of nucleic acids that needs to be transferred is as low as possible. This expansion of T cells may be performed by stimulation with anti-CD3/CD28 Dynabeads in the presence of IL-2. The expanded cells comprising the engineered γδ T-cell receptor, may be selected e.g. via a selectable marker and may be further selected for the presence of the CD4 antigen and the CD8 antigen, e.g. using the MACS separating system as described in the examples. The engineered T-cells may be subsequently further expanded using the REP protocol as described by Riddel and Greenberg, 1990 J Immunol Methods. 128(2): 189-201, which is incorporated herein by reference, or using similar further expansion methods thereto. Briefly, the expansion method involves using antibodies directed against T cell activation molecules, such as TCR, CD3 and CD28 and/or feeder cells and/or stimulating cytokines.

The anti-tumour response of the provided T-cell expressing a δT-cell (or γT-cell) receptor chain may be assessed using any technique known to the skilled person. A δT-cell receptor chain may be a δ2-T cell receptor chain. A γT-cell receptor chain may be a γ9-T cell receptor chain.

In one embodiment, the step of determining an anti-tumour response or reactivity comprises contacting the T cells with tumour cells. The step of determining anti-tumour reactivity may include any assay in which an anti-tumour effect may be determined, such as having an effect on tumour cell division rate, i.e. the speed with which the tumour cells divide, cell death, binding to the tumour cells, induction of the production of a cytokine such as IFN, IL-2 or TNFα.

Tumour cells may be any kind of tumour cells. For example, primary tumour cells from a patient. The tumour cells may be tumour cells from cell lines, such as the cell lines listed in the examples named Daudi, RPMI8226/S, OPM2, LME1, K562, Saos2, MZ1851 RC, SCC9, Fadu, MDA-MB231, MCF7, BT549, SW480, which are well known in the art. Tumour cell lines may easily be obtained from the American Type Culture Collection (ATCC, Manassas, Virginia) and the like.

In a preferred embodiment, determining the anti-tumour responses includes contacting the T cell expressing a defined nucleic acid molecule encoding an amino acid comprising a δT-cell (or γT-cell) receptor chain identified as shared in step b) with a tumour cell and measuring its ability to lyse the tumour cell and/or induce the production of a cytokine such as IFN-γ, IL-2 or TNFα. This contacting, culturing or incubation step may have a duration from 10 hours to 1, 2, 3, 4, 5 days. The ability to lyse the tumour cells include providing a fixed amount of tumour cells with which T cell expressing a defined nucleic acid molecule encoding an amino acid comprising a δT-cell (or γT-cell) receptor chain identified as shared in step b), is contacted and after an incubation period the number of viable tumour cells is counted.

An anti-tumour response may have been identified or determined when the number of viable tumor cells at the end of the incubation step is less than 90%, less than 80%, less than 70%, less than 60%, less than 50%, less than 40%, less than 30%, less than 20%, less than 10% of the number of initial tumour cells at the onset of the incubation step. Alternatively, an anti-tumour response may have been identified or determined when the number of viable tumour cells at the end of the incubation step with the engineered T cells is lower than the number of tumour cells at the end of a similar incubation step with control T cells not engineered with sequences identified as shared. Lower in this context may mean at least 10% lower, at least 20% lower, at least 30% lower, at least 40% lower, at least 50% lower, at least 60% lower, at least 70% lower, at least 80% lower, at least 90% lower.

In addition or as alternative to the counting of the number of viable tumour cells at the end of the incubation step, one may also perform a $^{51}$Chromium-release assay which is known to the skilled person. The amount of $^{51}$Chromium release is a measure of the number of cells that have been lysed.

Similarly, the production of a cytokine such as IFN-γ, IL-2 or TNFα or the secretion or the expression of activation markers may also be determined, e.g. via antibody staining, ELISA and/or quantitative PCR for the expressed mRNA. Assays for determining the production of a cytokine such as IFN-γ, IL-2 or TNFα are commercially widely available. When the production of a cytokine such as IL-2, TNFα or IFNγ is detected at the end of the contacting step, the T cell expressing a defined nucleic acid molecule encoding an amino acid comprising a δT-cell (or γT-cell) receptor chain identified as shared in step b) is said to exhibit an anti-tumour response. Alternatively and preferably, when the amount of IFNγ, IL-2 or TNFα produced at the end of the contacting step with engineered T cells is higher (preferably at least 10%, at least 20%, at least 30%, at least 40%, at least 50%, at least 60%, at least 70%, at least 80%, at least 90%, at least 100% or more) than the amount of IFNγ IL-2 or TNFα produced when tumour cells are contacted with control T cells, the T cells is said to exhibit an anti-tumour response. Control T cells do not express a defined nucleic acid molecule encoding an amino acid comprising a δT-cell (or γT-cell) receptor chain identified as shared in step b).

An anti-tumour response may also be determined by assessing the binding of the engineered T cells to the tumour cell at the end of the incubation step. When binding of the T cell expressing a defined nucleic acid molecule encoding an amino acid comprising a δT-cell (or γT-cell) receptor chain identified as shared in step b) to the tumour cell is detected at the end of the contacting step, the T cell expressing a defined nucleic acid molecule encoding an amino acid comprising a δT-cell (or γT-cell) receptor chain identified as shared in step b) is said to exhibit an anti-tumour response. Alternatively and preferably, when the binding of the T cell expressing a defined nucleic acid molecule encoding an amino acid comprising a δT-cell (or γT-cell) receptor chain identified as shared in step b) at the end of the contacting step is higher (preferably at least 10%, at least 20%, at least 30%, at least 40%, at least 50%, at least 60%, at least 70%, at least 80%, at least 90%, at least 100% or more) than the binding of control T cells (see earlier definition) to the same tumour cell, the T cells is said to exhibit an anti-tumour response.

The contacting step may be carried out in the presence of a phosphoantigen, such as pamidronate.

In a preferred method the step of confirming the anti-tumour response comprises contacting the T cell expressing a defined nucleic acid molecule encoding an amino acid comprising a δT-cell (or γT-cell) receptor chain identified as shared in step b) with a tumour cell and measuring its ability to lyse the tumour cell and/or induce a cytokine such as IFN-γ, IL-2 or TNFα.

In a preferred embodiment, determining the anti-infection responses includes contacting the T cell expressing a defined nucleic acid molecule encoding an amino acid comprising a δT-cell (or γT-cell) receptor chain identified as shared in step b) with the infectious agent or cells comprising the infectious agent and measuring its ability to kill the infectious agent or cells comprising the infectious agent and/or induce the production of a cytokine such as IFN-γ, IL-2 or TNFα. This contacting, culturing or incubation step may have a duration from 10 hours to 1, 2, 3, 4, 5 days. The ability to kill the infectious agent or cells comprising the infectious agent includes providing a fixed amount of infectious agent or cells comprising the infectious agent or inducing indirectly an expression of a natural danger signal at the cell surface by the infectious agent with which the T-cell expressing a γTCR as explained earlier herein (or a T cell expressing a defined nucleic acid molecule encoding an amino acid comprising a δT-cell (or γT-cell) receptor chain identified as shared in step b)), is contacted and after an incubation period the number of alive infectious agent or cells comprising the infectious agent is counted.

An anti-infectious response may have been identified or determined when the number of infectious agent or cells comprising the infectious agent at the end of the incubation step is less than 90%, less than 80%, less than 70%, less than 60%, less than 50%, less than 40%, less than 30%, less than 20%, less than 10% of the number of initial infectious agent or cells comprising the infectious agent at the onset of the incubation step.

Alternatively, an anti-infectious response may have been identified or determined when the number of viable infectious agent or cells comprising the infectious agent at the end of the incubation step with the T cells is lower than the number of infectious agent or cells comprising the infectious agent at the end of a similar incubation step with control T cells (earlier defined herein). Lower in this context may mean at least 10% lower, at least 20% lower, at least 30% lower, at least 40% lower, at least 50% lower, at least 60% lower, at least 70% lower, at least 80% lower, at least 90% lower.

In a preferred method the step of confirming the anti-infectious response comprises contacting the T cell expressing a defined nucleic acid molecule encoding an amino acid comprising a δT-cell (or γT-cell) receptor chain identified as shared in step b) with an infectious agent or cells comprising the infectious agent and measuring its ability to kill the infectious agent or cells comprising the infectious agent and/or induce a cytokine such as IFN-γ, IL-2 or TNFα.

δT-Cell Receptor Chain or a Part Thereof in General

Provided in certain aspects described herein are polypeptides comprising a δT-cell receptor chain or a variant or functional portion thereof. In a further aspect the invention provides a δT-cell receptor chain or a part thereof, comprising a CDR3 region, and which δT-cell receptor chain or part thereof is represented by an amino acid sequence as defined in step 1 c) of the method of the invention and which is obtainable by the method of the first aspect. Each of these δT-cell receptor chain or part thereof is represented by an amino acid sequence that could be identified using a SEQ ID NO. In an embodiment, a δT-cell receptor chain is a δ2T-cell receptor chain. In another embodiment, a δT-cell receptor chain is a δ1T-cell receptor chain or a δ4T-cell receptor chain.

γT-Cell Receptor Chain or a Part Thereof in General

Provided in certain aspects described herein are polypeptides comprising a γT-cell receptor chain or a variant or functional portion thereof. In a further aspect the invention provides a γT-cell receptor chain or a part thereof, comprising a CDR3 region, and which γT-cell receptor chain or part thereof is represented by an amino acid sequence as defined in step 1 c) of the method of the invention and which is obtainable by the method of the first aspect. Each of these γT-cell receptor chain or part thereof is represented by an amino acid sequence that could be identified using a SEQ ID NO. In an embodiment, a γT-cell receptor chain is a γ9T-cell receptor chain or a γ5T-cell receptor chain.

Each of the δT-cell receptor chain or part thereof comprising a CDR3 region identified herein may also be represented by its coding nucleic acid sequence instead of its amino acid sequence. Therefore the invention also relates to a nucleic acid molecule encoding said receptor chain or part thereof. The same holds for each of the γT-cell receptor chain or part thereof comprising a CDR3 region identified herein. The same also holds for the TCR identified herein: it can be identified by the receptor chains it expresses or by the nucleic acid molecules encoding these chains it comprises. The same also holds for the T cell expressing said TCR: the T cell can be defined by reference to the receptor chains or parts thereof it expresses or by the nucleic acid molecules encoding these chains or parts thereof it comprises.

Preferred δT-Cell or γT-Cell Receptor Chain or a Part Thereof

Provided in certain aspects described herein are polypeptides comprising a δT-cell receptor CDR or a variant or functional portion thereof.

In another preferred embodiment, there is provided a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 7 and/or 17 and/or 96.

In another preferred embodiment, there is provided a nucleic acid molecule represented by a nucleotide sequence comprising a nucleotide sequence that has at least 60% sequence identity with SEQ ID NO: 50 and/or 62 and/or a nucleotide sequence that encodes an amino acid sequence that has at least 60% amino acid identity or similarity with an amino acid sequence encoded by a nucleotide sequence SEQ ID NO: 50 and/or 62.

Preferably, the identity is of at least 65%, 70%, 75%, 80%, 85%, 90%, 95%, 97%, 98%, 99% or 100%.

Each of these preferred δT-cell or γT-cell receptor chains or parts thereof defined above by sequence identity and as encompassed by the invention are preferably considered to be able to exhibit an anti-tumour or anti-infective activity as assessed in step c) of the method of the invention.

Provided in certain aspects described herein are polypeptides comprising a γT-cell receptor CDR or a variant or functional portion thereof. There is also provided a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 10, 18, 64 and/or 97.

In another preferred embodiment, there is provided a nucleic acid molecule represented by a nucleotide sequence comprising a nucleotide sequence that has at least 60% sequence identity with SEQ ID NO: 51 and/or 63 and/or a nucleotide sequence that encodes an amino acid sequence that has at least 60% amino acid identity or similarity with an amino acid sequence encoded by a nucleotide sequence SEQ ID NO: 51 and/or 63.

Preferably, the identity is of at least 65%, 70%, 75%, 80%, 85%, 90%, 95%, 97%, 98%, 99% or 100%.

In another preferred embodiment, there is provided a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:18 Preferably, the identity is of at least 65%, 70%, 75%, 80%, 85%, 90%, 95%, 97%, 98%, 99% or 100%.

In another preferred embodiment, there is provided a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 19 and/or 30.

In another preferred embodiment, there is provided a nucleic acid molecule represented by a nucleotide sequence comprising a nucleotide sequence that has at least 60% sequence identity with SEQ ID NO: 41 and/or 53 and/or a nucleotide sequence that encodes an amino acid sequence that has at least 60% amino acid identity or similarity with an amino acid sequence encoded by a nucleotide sequence SEQ ID NO: 41 and/or 53.

Preferably, the identity is of at least 65%, 70%, 75%, 80%, 85%, 90%, 95%, 97%, 98%, 99% or 100%.

In another preferred embodiment, there is provided a γT-cell receptor chain or part thereof comprising a CDR3 region, said T-cell receptor chain or part thereof being represented by an amino acid sequence, said amino acid sequence comprising at least 60% sequence identity or similarity with amino acid sequence SEQ ID NO: 20 and/or 32.

In another preferred embodiment, there is provided a nucleic acid molecule represented by a nucleotide sequence comprising a nucleotide sequence that has at least 60% sequence identity with SEQ ID NO: 43 and/or 55 and/or a nucleotide sequence that encodes an amino acid sequence that has at least 60% amino acid identity or similarity with an amino acid sequence encoded by a nucleotide sequence SEQ ID NO: 43 and/or 55.

Preferably, the identity is of at least 65%, 70%, 75%, 80%, 85%, 90%, 95%, 97%, 98%, 99% or 100%.

In another preferred embodiment, there is provided a γT-cell receptor chain or part thereof comprising a CDR3 region, said T-cell receptor chain or part thereof being represented by an amino acid sequence, said amino acid sequence comprising at least 60% sequence identity or similarity with amino acid sequence SEQ ID NO: 21 and/or 34.

In another preferred embodiment, there is provided a nucleic acid molecule represented by a nucleotide sequence comprising a nucleotide sequence that has at least 60% sequence identity with SEQ ID NO: 45 and/or 57 and/or a nucleotide sequence that encodes an amino acid sequence that has at least 60% amino acid identity or similarity with an amino acid sequence encoded by a nucleotide sequence SEQ ID NO: 45 and/or 57.

Preferably, the identity is of at least 65%, 70%, 75%, 80%, 85%, 90%, 95%, 97%, 98%, 99% or 100%.

In another preferred embodiment, there is provided a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 40 and/or 70.

In another preferred embodiment, there is provided a nucleic acid molecule represented by a nucleotide sequence comprising a nucleotide sequence that has at least 60% sequence identity with SEQ ID NO: 76 and/or 82 and/or a nucleotide sequence that encodes an amino acid sequence that has at least 60% amino acid identity or similarity with an amino acid sequence encoded by a nucleotide sequence SEQ ID NO: 76 and/or 82.

Preferably, the identity is of at least 65%, 70%, 75%, 80%, 85%, 90%, 95%, 97%, 98%, 99% or 100%.

In another preferred embodiment, there is provided a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 65 and/or 71.

In another preferred embodiment, there is provided a nucleic acid molecule represented by a nucleotide sequence comprising a nucleotide sequence that has at least 60% sequence identity with SEQ ID NO: 77 and/or 83 and/or a nucleotide sequence that encodes an amino acid sequence that has at least 60% amino acid identity or similarity with an amino acid sequence encoded by a nucleotide sequence SEQ ID NO: 77 and/or 83.

Preferably, the identity is of at least 65%, 70%, 75%, 80%, 85%, 90%, 95%, 97%, 98%, 99% or 100%.

In another preferred embodiment, there is provided a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 66 and/or 72.

In another preferred embodiment, there is provided a nucleic acid molecule represented by a nucleotide sequence comprising a nucleotide sequence that has at least 60% sequence identity with SEQ ID NO: 78 and/or 84 and/or a nucleotide sequence that encodes an amino acid sequence that has at least 60% amino acid identity or similarity with an amino acid sequence encoded by a nucleotide sequence SEQ ID NO: 78 and/or 84.

Preferably, the identity is of at least 65%, 70%, 75%, 80%, 85%, 90%, 95%, 97%, 98%, 99% or 100%.

In another preferred embodiment, there is provided a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 67 and/or 73.

In another preferred embodiment, there is provided a nucleic acid molecule represented by a nucleotide sequence comprising a nucleotide sequence that has at least 60% sequence identity with SEQ ID NO:79 and/or 85 and/or a nucleotide sequence that encodes an amino acid sequence that has at least 60% amino acid identity or similarity with an amino acid sequence encoded by a nucleotide sequence SEQ ID NO: 79 and/or 85.

Preferably, the identity is of at least 65%, 70%, 75%, 80%, 85%, 90%, 95%, 97%, 98%, 99% or 100%.

In another preferred embodiment, there is provided a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 68 and/or 74.

In another preferred embodiment, there is provided a nucleic acid molecule represented by a nucleotide sequence comprising a nucleotide sequence that has at least 60% sequence identity with SEQ ID NO: 80 and/or 86 and/or a nucleotide sequence that encodes an amino acid sequence that has at least 60% amino acid identity or similarity with an amino acid sequence encoded by a nucleotide sequence SEQ ID NO: 80 and/or 86.

Preferably, the identity is of at least 65%, 70%, 75%, 80%, 85%, 90%, 95%, 97%, 98%, 99% or 100%.

In another preferred embodiment, there is provided a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 69 and/or 75.

In another preferred embodiment, there is provided a nucleic acid molecule represented by a nucleotide sequence comprising a nucleotide sequence that has at least 60% sequence identity with SEQ ID NO: 81 and/or 87 and/or a nucleotide sequence that encodes an amino acid sequence that has at least 60% amino acid identity or similarity with an amino acid sequence encoded by a nucleotide sequence SEQ ID NO: 81 and/or 87.

Preferably, the identity is of at least 65%, 70%, 75%, 80%, 85%, 90%, 95%, 97%, 98%, 99% or 100%.

In another preferred embodiment, there is provided a γT-cell receptor chain or part thereof comprising a CDR3 region, said T-cell receptor chain or part thereof being represented by an amino acid sequence, said amino acid sequence comprising at least 60% sequence identity or similarity with amino acid sequence SEQ ID NO: 89 and/or 91.

In another preferred embodiment, there is provided a nucleic acid molecule represented by a nucleotide sequence comprising a nucleotide sequence that has at least 60% sequence identity with SEQ ID NO: 93 and/or 95 and/or a nucleotide sequence that encodes an amino acid sequence that has at least 60% amino acid identity or similarity with an amino acid sequence encoded by a nucleotide sequence SEQ ID NO: 93 and/or 95.

Preferably, the identity is of at least 65%, 70%, 75%, 80%, 85%, 90%, 95%, 97%, 98%, 99% or 100%.

Each of these preferred δT-cell receptor chains or parts thereof defined above by sequence identity and as encompassed by the invention are preferably considered to be able to exhibit an anti-tumour or anti-infective activity when expressed in a T cell already expressing a γT-cell receptor as assessed in step c) of the method of the invention. The same holds for preferred γT-cell receptor chains or parts thereof defined above by sequence identity, the T cell already expressing a δT cell receptor.

Further Aspects Linked to the Use of a δT-Cell (or γT-Cell) Receptor Chain or a Part Thereof In this part, all aspects described below applied for any δT-cell (or γT-cell) receptor chain or variant or part thereof obtainable by the present invention, and especially for the preferred δT cell (or γT-cell) receptor chain or variant or part thereof identified above.

In an embodiment, a variant or part of a δT-cell (or γT-cell) receptor chain described herein is a soluble polypeptide. Such a soluble polypeptide may also be called a binding unit. Such a soluble polypeptide can include various forms to binding entities such as a TCR, antibody, scFv, BCR, or any combination thereof. In some cases, at least a portion of a TCR, such as a Vγ9Vδ2 or Vγ5Vδ1 or Vγ4Vδ5 or Vγ8Vδ5 or Vγ2Vδ1 or Vγ8Vδ1 can be generated and utilized in a pharmaceutical composition as described herein. For example, TCR-antibody chimeras can be generated and tested before arriving at a desired chimera. For example, γδ-variable domains can replace heavy and light chain variable domains of an antibody. In addition to enhanced binding, an Fc domain of an antibody can mediate cytotoxicity through Fcγ-receptor positive immune cells and/or a complementary system. In some cases, TCR-antibody chimeras can be generated using HEK293 cells and subsequently purified using protein A affinity chromatography followed by size exclusion chromatography. A proper folding of chimeras can be probed using conformational-specific antibodies that can target γ and δ variable domains. Chimeras can be used in antibody dependent cell mediated cytotoxicity (ADCC) and complement dependent cytotoxicity (CDC) assays to determine functional efficacy. After performing in vitro assays, functional efficacy of TCR-antibody chimeras can be tested in vitro and/or in vivo.

In a further aspect, the invention also relates to a conjugate comprising (a part of) the δT-cell (or γT-cell) receptor chain as defined above which is linked to an agent. The type of agent used depends from the type of applications envisaged. Such conjugates may be linked to substrates (e.g. chemicals, nanoparticles) and may be used e.g. to deliver chemotherapy to a target of interest. In addition, in diagnostics expression of defined ligands may be tested by taking advantage of the soluble TCRs linked to fluorochromes which are then used as staining tool or for the biochemical isolation of the ligand.

In a further aspect, the invention relates to a nucleic acid construct comprising the δT-cell (and/or γT-cell) receptor chain or a part thereof represented by an amino acid sequence as identified in step c) of the method of the invention, preferably the δT-cell (and/or T-cell) receptor chain or part thereof identified in the part entitled “Preferred δT-cell (or γT-cell) receptor chain or a part thereof”.

In an aspect, there is therefore provided a γδTCR comprising:

a δT-cell receptor chain or part thereof comprising a CDR3 region, said δT-cell receptor chain or part thereof and a γT-cell receptor chain or part thereof comprising a CDR3 region, said T-cell receptor chain or part thereof, each having been identified by a method as disclosed herein.

In another preferred embodiment, there is therefore provided a γδTCR comprising:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 7 and/or 17 and/or 96, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 10, 18 64 and/or 97.

In another preferred embodiment, there is provided a nucleic acid molecule encoding a γδ TCR, said nucleic acid molecule being represented by a nucleotide sequence comprising:

a nucleotide sequence that has at least 60% sequence identity with SEQ ID NO: 50 and/or 62 and/or a nucleotide sequence that encodes an amino acid sequence that has at least 60% amino acid identity or similarity with an amino acid sequence encoded by a nucleotide sequence SEQ ID NO: 50 and/or 62, and preferably a nucleotide sequence that has at least 60% sequence identity with SEQ ID NO: 51 and/or 63 and/or a nucleotide sequence that encodes an amino acid sequence that has at least 60% amino acid identity or similarity with an amino acid sequence encoded by a nucleotide sequence SEQ ID NO: 51 and/or 63.

Preferably, the identity is of at least 65%, 70%, 75%, 80%, 85%, 90%, 95%, 97%, 98%, 99% or 100%.

In another preferred embodiment, there is therefore provided a γδTCR comprising:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:22 and/or 35, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:39 and/or 36.

In another preferred embodiment, there is provided a nucleic acid molecule encoding a γδ TCR, said nucleic acid molecule being represented by a nucleotide sequence comprising:

a nucleotide sequence that has at least 60% sequence identity with SEQ ID NO: 46 and/or 58 and/or a nucleotide sequence that encodes an amino acid sequence that has at least 60% amino acid identity or similarity with an amino acid sequence encoded by a nucleotide sequence SEQ ID NO:46 and/or 58, and preferably a nucleotide sequence that has at least 60% sequence identity with SEQ ID NO: 47 and/or 59 and/or a nucleotide sequence that encodes an amino acid sequence that has at least 60% amino acid identity or similarity with an amino acid sequence encoded by a nucleotide sequence SEQ ID NO: 47 and/or 59.

Preferably, the identity is of at least 65%, 70%, 75%, 80%, 85%, 90%, 95%, 97%, 98%, 99% or 100%.

In another preferred embodiment, there is therefore provided a γδTCR comprising:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 23 and/or 29 and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 19 and/or 30.

In another preferred embodiment, there is provided a nucleic acid molecule encoding a γδ TCR, said nucleic acid molecule being represented by a nucleotide sequence comprising:

a nucleotide sequence that has at least 60% sequence identity with SEQ ID NO: 26 and/or 52 and/or a nucleotide sequence that encodes an amino acid sequence that has at least 60% amino acid identity or similarity with an amino acid sequence encoded by a nucleotide sequence SEQ ID NO: 26 and/or 52, and preferably a nucleotide sequence that has at least 60% sequence identity with SEQ ID NO: 41 and/or 53 and/or a nucleotide sequence that encodes an amino acid sequence that has at least 60% amino acid identity or similarity with an amino acid sequence encoded by a nucleotide sequence SEQ ID NO: 41 and/or 53.

Preferably, the identity is of at least 65%, 70%, 75%, 80%, 85%, 90%, 95%, 97%, 98%, 99% or 100%.

In another preferred embodiment, there is therefore provided a γδTCR comprising:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 24 and/or 31, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 20 and/or 32.

In another preferred embodiment, there is provided a nucleic acid molecule encoding a γδ TCR, said nucleic acid molecule being represented by a nucleotide sequence comprising:

a nucleotide sequence that has at least 60% sequence identity with SEQ ID NO: 42 and/or 54 and/or a nucleotide sequence that encodes an amino acid sequence that has at least 60% amino acid identity or similarity with an amino acid sequence encoded by a nucleotide sequence SEQ ID NO:42 and/or 54, and preferably a nucleotide sequence that has at least 60% sequence identity with SEQ ID NO: 43 and/or 55 and/or a nucleotide sequence that encodes an amino acid sequence that has at least 60% amino acid identity or similarity with an amino acid sequence encoded by a nucleotide sequence SEQ ID NO: 43 and/or 55.

Preferably, the identity is of at least 65%, 70%, 75%, 80%, 85%, 90%, 95%, 97%, 98%, 99% or 100%.

In another preferred embodiment, there is therefore provided a γδTCR comprising:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 25 and/or 33 and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 21 and/or 34

In another preferred embodiment, there is provided a nucleic acid molecule encoding a γδ TCR, said nucleic acid molecule being represented by a nucleotide sequence comprising:

a nucleotide sequence that has at least 60% sequence identity with SEQ ID NO: 44 and/or 56 and/or a nucleotide sequence that encodes an amino acid sequence that has at least 60% amino acid identity or similarity with an amino acid sequence encoded by a nucleotide sequence SEQ ID NO: 44 and/or 56, and preferably a nucleotide sequence that has at least 60% sequence identity with SEQ ID NO: 45 and/or 57 and/or a nucleotide sequence that encodes an amino acid sequence that has at least 60% amino acid identity or similarity with an amino acid sequence encoded by a nucleotide sequence SEQ ID NO: 45 and/or 57.

Preferably, the identity is of at least 65%, 70%, 75%, 80%, 85%, 90%, 95%, 97%, 98%, 99% or 100%.

In another preferred embodiment, there is therefore provided a γδTCR comprising:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:28 and/or 37, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:27 and/or 38

In another preferred embodiment, there is provided a nucleic acid molecule encoding a γδ TCR, said nucleic acid molecule being represented by a nucleotide sequence comprising:

a nucleotide sequence that has at least 60% sequence identity with SEQ ID NO: 48 and/or 60 and/or a nucleotide sequence that encodes an amino acid sequence that has at least 60% amino acid identity or similarity with an amino acid sequence encoded by a nucleotide sequence SEQ ID NO: 48 and/or 60, and preferably a nucleotide sequence that has at least 60% sequence identity with SEQ ID NO: 49 and/or 61 and/or a nucleotide sequence that encodes an amino acid sequence that has at least 60% amino acid identity or similarity with an amino acid sequence encoded by a nucleotide sequence SEQ ID NO: 49 and/or 61.

Preferably, the identity is of at least 65%, 70%, 75%, 80%, 85%, 90%, 95%, 97%, 98%, 99% or 100%.

In another preferred embodiment, there is therefore provided a γδTCR comprising:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:40 and/or 70, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:65 and/or 71.

In another preferred embodiment, there is provided a nucleic acid molecule encoding a γδ TCR, said nucleic acid molecule being represented by a nucleotide sequence comprising:

a nucleotide sequence that has at least 60% sequence identity with SEQ ID NO: 76 and/or 82 and/or a nucleotide sequence that encodes an amino acid sequence that has at least 60% amino acid identity or similarity with an amino acid sequence encoded by a nucleotide sequence SEQ ID NO: 76 and/or 82, and preferably a nucleotide sequence that has at least 60% sequence identity with SEQ ID NO: 77 and/or 83 and/or a nucleotide sequence that encodes an amino acid sequence that has at least 60% amino acid identity or similarity with an amino acid sequence encoded by a nucleotide sequence SEQ ID NO: 77 and/or 83.

Preferably, the identity is of at least 65%, 70%, 75%, 80%, 85%, 90%, 95%, 97%, 98%, 99% or 100%.

In another preferred embodiment, there is therefore provided a γδTCR comprising:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:66 and/or 72, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:67 and/or 73.

In another preferred embodiment, there is provided a nucleic acid molecule encoding a γδ TCR, said nucleic acid molecule being represented by a nucleotide sequence comprising:

a nucleotide sequence that has at least 60% sequence identity with SEQ ID NO: 78 and/or 84 and/or a nucleotide sequence that encodes an amino acid sequence that has at least 60% amino acid identity or similarity with an amino acid sequence encoded by a nucleotide sequence SEQ ID NO: 78 and/or 84, and preferably a nucleotide sequence that has at least 60% sequence identity with SEQ ID NO: 79 and/or 85 and/or a nucleotide sequence that encodes an amino acid sequence that has at least 60% amino acid identity or similarity with an amino acid sequence encoded by a nucleotide sequence SEQ ID NO: 79 and/or 85.

Preferably, the identity is of at least 65%, 70%, 75%, 80%, 85%, 90%, 95%, 97%, 98%, 99% or 100%.

In another preferred embodiment, there is therefore provided a γδTCR comprising:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:68 and/or 74, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:69 and/or 75.

In another preferred embodiment, there is provided a nucleic acid molecule encoding a γδ TCR, said nucleic acid molecule being represented by a nucleotide sequence comprising:

a nucleotide sequence that has at least 60% sequence identity with SEQ ID NO: 80 and/or 86 and/or a nucleotide sequence that encodes an amino acid sequence that has at least 60% amino acid identity or similarity with an amino acid sequence encoded by a nucleotide sequence SEQ ID NO:80 and/or 86, and preferably a nucleotide sequence that has at least 60% sequence identity with SEQ ID NO: 81 and/or 87 and/or a nucleotide sequence that encodes an amino acid sequence that has at least 60% amino acid identity or similarity with an amino acid sequence encoded by a nucleotide sequence SEQ ID NO: 81 and/or 87.

Preferably, the identity is of at least 65%, 70%, 75%, 80%, 85%, 90%, 95%, 97%, 98%, 99% or 100%.

In another preferred embodiment, there is therefore provided a γδTCR comprising:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:88 and/or 90, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:89 and/or 91.

In another preferred embodiment, there is provided a nucleic acid molecule encoding a γδ TCR, said nucleic acid molecule being represented by a nucleotide sequence comprising:

a nucleotide sequence that has at least 60% sequence identity with SEQ ID NO: 92 and/or 94 and/or a nucleotide sequence that encodes an amino acid sequence that has at least 60% amino acid identity or similarity with an amino acid sequence encoded by a nucleotide sequence SEQ ID NO:92 and/or 94, and preferably a nucleotide sequence that has at least 60% sequence identity with SEQ ID NO: 93 and/or 95 and/or a nucleotide sequence that encodes an amino acid sequence that has at least 60% amino acid identity or similarity with an amino acid sequence encoded by a nucleotide sequence SEQ ID NO: 93 and/or 95.

Preferably, the identity is of at least 65%, 70%, 75%, 80%, 85%, 90%, 95%, 97%, 98%, 99% or 100%.

In a further aspect, the invention further relates to a vector comprising the nucleic acid construct defined above. A preferred vector is a retroviral vector or a lentiviral vector.

In a further aspect, the invention provides a cell comprising the nucleic acid construct or the vector as defined above. This cell is preferably a T cell.

A preferred T cell expresses a δT-cell (or γT-cell) receptor chain or a part thereof identified in the part entitled "Preferred δT-cell (or γT-cell) receptor chain or a part thereof".

The general part of the description dedicated to the definitions provides detailed explanation as to nucleic acid molecules and polypeptide encompassed by the invention, nucleic construct, viral vector and cells comprising said construct or vector.

Each of the δT-cell (or γT-cell) receptor chain or part thereof isolated using the method of the invention is expected to be biologically relevant for designing a medicament for preventing, treating, regressing, curing and/or delaying cancer or an infection since each of these chain or part thereof exhibits an anti-tumour or an anti-infectious activity (step c of the methods of the invention).

A δT-cell (or γT-cell) receptor chain, or a part thereof, a conjugate, a nucleic acid construct, a vector, a cell all as defined earlier herein are preferably for use as a medicament. In an embodiment, a δT-cell receptor chain is a δ2T-cell, a δ1T-cell, δ5T-cell, or a δ4T-cell receptor chain. In an embodiment, a γT-cell receptor chain is a γ9T-cell, γδT-cell, γ4T-cell receptor chain or a γ5T-cell receptor chain. The medicament is preferably for the prevention, suppression, treatment of cancer or an infection. Accordingly the invention also relates to a composition, preferably a pharmaceutical composition comprising a δT-cell (or γT-cell) receptor chain, or a part thereof, a conjugate, a nucleic acid construct, a vector, a cell all as defined earlier herein.

In a further aspect, the invention relates to a method for preventing, treating, regressing, curing and/or delaying cancer or an infection in a subject wherein a δT-cell (or γT-cell) receptor chain, or a part thereof, a conjugate, a nucleic acid construct, a vector, a cell all as defined earlier herein are administered to said subject. A preferred subject is a human being.

In a further aspect, the invention relates to a use of a δT-cell (or γT-cell) receptor chain, or a part thereof, a conjugate, a nucleic acid construct, a vector, a cell all as defined earlier herein for the manufacture of a medicament for preventing, treating, regressing, curing and/or delaying cancer or an infection in a subject. A preferred subject is a human being.

A preferred T cell used as a medicament as explained is preferably a T cell expressing:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 7 and/or 17 and/or 96, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 10, 18, 64 and/or 97.

Another preferred T cell used as a medicament comprises a nucleic acid molecule encoding a γδ TCR, said nucleic acid molecule being represented by a nucleotide sequence comprising:

a nucleotide sequence that has at least 60% sequence identity with SEQ ID NO: 50 and/or 62 and/or a nucleotide sequence that encodes an amino acid sequence that has at least 60% amino acid identity or similarity with an amino acid sequence encoded by a nucleotide sequence SEQ ID NO: 50 and/or 62, and preferably a nucleotide sequence that has at least 60% sequence identity with SEQ ID NO: 51 and/or 63 and/or a nucleotide sequence that encodes an amino acid sequence that has at least 60% amino acid identity or similarity with an amino acid sequence encoded by a nucleotide sequence SEQ ID NO: 51 and/or 63.

Preferably, the identity is of at least 65%, 70%, 75%, 80%, 85%, 90%, 95%, 97%, 98%, 99% or 100%.

Another preferred T cell used as a medicament as explained is preferably a T cell expressing:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:22 and/or 35, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:39 and/or 36.

Another preferred T cell used as a medicament comprises a nucleic acid molecule encoding a γδ TCR, said nucleic acid molecule being represented by a nucleotide sequence comprising:

a nucleotide sequence that has at least 60% sequence identity with SEQ ID NO: 46 and/or 58 and/or a nucleotide sequence that encodes an amino acid sequence that has at least 60% amino acid identity or similarity with an amino acid sequence encoded by a nucleotide sequence SEQ ID NO: 46 and/or 58, and preferably a nucleotide sequence that has at least 60% sequence identity with SEQ ID NO: 47 and/or 59 and/or a nucleotide sequence that encodes an amino acid sequence that has at least 60% amino acid identity or similarity with an amino acid sequence encoded by a nucleotide sequence SEQ ID NO: 47 and/or 59.

Preferably, the identity is of at least 65%, 70%, 75%, 80%, 85%, 90%, 95%, 97%, 98%, 99% or 100%.

Another preferred T cell used as a medicament as explained is preferably a T cell expressing:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 23 and/or 29, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 19 and/or 30.

Another preferred T cell used as a medicament comprises a nucleic acid molecule encoding a γδ TCR, said nucleic acid molecule being represented by a nucleotide sequence comprising:

a nucleotide sequence that has at least 60% sequence identity with SEQ ID NO: 26 and/or 52 and/or a nucleotide sequence that encodes an amino acid sequence that has at least 60% amino acid identity or similarity with an amino acid sequence encoded by a nucleotide sequence SEQ ID NO: 26 and/or 52, and preferably a nucleotide sequence that has at least 60% sequence identity with SEQ ID NO: 41 and/or 53 and/or a nucleotide sequence that encodes an amino acid sequence that has at least 60% amino acid identity or similarity with an amino acid sequence encoded by a nucleotide sequence SEQ ID NO: 41 and/or 53.

Preferably, the identity is of at least 65%, 70%, 75%, 80%, 85%, 90%, 95%, 97%, 98%, 99% or 100%.

Another preferred T cell used as a medicament as explained is preferably a T cell expressing:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 24 and/or 31, and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 20 and/or 32.

Another preferred T cell used as a medicament comprises a nucleic acid molecule encoding a γδ TCR, said nucleic acid molecule being represented by a nucleotide sequence comprising:

a nucleotide sequence that has at least 60% sequence identity with SEQ ID NO: 42 and/or 54 and/or a nucleotide sequence that encodes an amino acid sequence that has at least 60% amino acid identity or similarity with an amino acid sequence encoded by a nucleotide sequence SEQ ID NO: 42 and/or 54, and preferably a nucleotide sequence that has at least 60% sequence identity with SEQ ID NO: 43 and/or 55 and/or a nucleotide sequence that encodes an amino acid sequence that has at least 60% amino acid identity or similarity with an amino acid sequence encoded by a nucleotide sequence SEQ ID NO: 43 and/or 55.

Preferably, the identity is of at least 65%, 70%, 75%, 80%, 85%, 90%, 95%, 97%, 98%, 99% or 100%.

Another preferred T cell used as a medicament as explained is preferably a T cell expressing:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO: 25 and/or 33 and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO: 21 and/or 34.

Another preferred T cell used as a medicament comprises a nucleic acid molecule encoding a γδ TCR, said nucleic acid molecule being represented by a nucleotide sequence comprising:

a nucleotide sequence that has at least 60% sequence identity with SEQ ID NO: 44 and/or 56 and/or a nucleotide sequence that encodes an amino acid sequence that has at least 60% amino acid identity or similarity with an amino acid sequence encoded by a nucleotide sequence SEQ ID NO: 44 and/or 56, and preferably a nucleotide sequence that has at least 60% sequence identity with SEQ ID NO: 45 and/or 57 and/or a nucleotide sequence that encodes an amino acid sequence that has at least 60% amino acid identity or similarity with an amino acid sequence encoded by a nucleotide sequence SEQ ID NO: 45 and/or 57.

Preferably, the identity is of at least 65%, 70%, 75%, 80%, 85%, 90%, 95%, 97%, 98%, 99% or 100%.

Another preferred T cell used as a medicament as explained is preferably a T cell expressing:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:28 and/or 37 and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:28 and/or 38.

Another preferred T cell used as a medicament comprises a nucleic acid molecule encoding a γδ TCR, said nucleic acid molecule being represented by a nucleotide sequence comprising:

a nucleotide sequence that has at least 60% sequence identity with SEQ ID NO: 48 and/or 60 and/or a nucleotide sequence that encodes an amino acid sequence that has at least 60% amino acid identity or similarity with an amino acid sequence encoded by a nucleotide sequence SEQ ID NO: 48 and/or 60, and preferably a nucleotide sequence that has at least 60% sequence identity with SEQ ID NO: 49 and/or 61 and/or a nucleotide sequence that encodes an amino acid sequence that has at least 60% amino acid identity or similarity with an amino acid sequence encoded by a nucleotide sequence SEQ ID NO: 49 and/or 61.

Preferably, the identity is of at least 65%, 70%, 75%, 80%, 85%, 90%, 95%, 97%, 98%, 99% or 100%.

Another preferred T cell used as a medicament as explained is preferably a T cell expressing:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:40 and/or 70 and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:65 and/or 71.

Another preferred T cell used as a medicament comprises a nucleic acid molecule encoding a γδ TCR, said nucleic acid molecule being represented by a nucleotide sequence comprising:

a nucleotide sequence that has at least 60% sequence identity with SEQ ID NO: 76 and/or 82 and/or a nucleotide sequence that encodes an amino acid sequence that has at least 60% amino acid identity or similarity with an amino acid sequence encoded by a nucleotide sequence SEQ ID NO: 76 and/or 82, and preferably a nucleotide sequence that has at least 60% sequence identity with SEQ ID NO: 77 and/or 83 and/or a nucleotide sequence that encodes an amino acid sequence that has at least 60% amino acid identity or similarity with an amino acid sequence encoded by a nucleotide sequence SEQ ID NO: 77 and/or 83.

Preferably, the identity is of at least 65%, 70%, 75%, 80%, 85%, 90%, 95%, 97%, 98%, 99% or 100%.

Another preferred T cell used as a medicament as explained is preferably a T cell expressing:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:66 and/or 72 and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:67 and/or 73.

Another preferred T cell used as a medicament comprises a nucleic acid molecule encoding a γδTCR, said nucleic acid molecule being represented by a nucleotide sequence comprising:

a nucleotide sequence that has at least 60% sequence identity with SEQ ID NO: 78 and/or 84 and/or a nucleotide sequence that encodes an amino acid sequence that has at least 60% amino acid identity or similarity with an amino acid sequence encoded by a nucleotide sequence SEQ ID NO: 78 and/or 84, and preferably a nucleotide sequence that has at least 60% sequence identity with SEQ ID NO: 79 and/or 85 and/or a nucleotide sequence that encodes an amino acid sequence that has at least 60% amino acid identity or similarity with an amino acid sequence encoded by a nucleotide sequence SEQ ID NO: 79 and/or 85.

Preferably, the identity is of at least 65%, 70%, 75%, 80%, 85%, 90%, 95%, 97%, 98%, 99% or 100%.

Another preferred T cell used as a medicament as explained is preferably a T cell expressing:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:68 and/or 74 and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:69 and/or 75.

Another preferred T cell used as a medicament comprises a nucleic acid molecule encoding a γδ TCR, said nucleic acid molecule being represented by a nucleotide sequence comprising:

a nucleotide sequence that has at least 60% sequence identity with SEQ ID NO: 80 and/or 86 and/or a nucleotide sequence that encodes an amino acid sequence that has at least 60% amino acid identity or similarity with an amino acid sequence encoded by a nucleotide sequence SEQ ID NO: 80 and/or 86, and preferably a nucleotide sequence that has at least 60% sequence identity with SEQ ID NO: 81 and/or 87 and/or a nucleotide sequence that encodes an amino acid sequence that has at least 60% amino acid identity or similarity with an amino acid sequence encoded by a nucleotide sequence SEQ ID NO: 81 and/or 87.

Preferably, the identity is of at least 65%, 70%, 75%, 80%, 85%, 90%, 95%, 97%, 98%, 99% or 100%.

Another preferred T cell used as a medicament as explained is preferably a T cell expressing:

a δT-cell receptor chain or part thereof comprising a CDR3 region, said δT-cell receptor chain or part thereof being represented by an amino acid sequence, said amino acid sequence comprising at least 60% sequence identity or similarity with amino acid sequence SEQ ID NO:88 and/or 90 and preferably a γT-cell receptor chain or part thereof comprising a CDR3 region, said γT-cell receptor chain or part thereof being represented by an amino acid sequence, said amino acid sequence comprising at least 60% sequence identity or similarity with amino acid sequence SEQ ID NO:89 and/or 91.

Another preferred T cell used as a medicament comprises a nucleic acid molecule encoding a γδ TCR, said nucleic acid molecule being represented by a nucleotide sequence comprising:

a nucleotide sequence that has at least 60% sequence identity with SEQ ID NO: 92 and/or 94 and/or a nucleotide sequence that encodes an amino acid sequence that has at least 60% amino acid identity or similarity with an amino acid sequence encoded by a nucleotide sequence SEQ ID NO: 92 and/or 94, and preferably a nucleotide sequence that has at least 60% sequence identity with SEQ ID NO: 93 and/or 95 and/or a nucleotide sequence that encodes an amino acid sequence that has at least 60% amino acid identity or similarity with an amino acid sequence encoded by a nucleotide sequence SEQ ID NO: 93 and/or 95.

Preferably, the identity is of at least 65%, 70%, 75%, 80%, 85%, 90%, 95%, 97%, 98%, 99% or 100%.

In the general part dedicated to definitions, more detailed information is provided as to the formulation of a pharmaceutical composition. The way the δT-cell (or γT-cell) receptor chain or part thereof or nucleic acid construct or viral vector or cells may be administered to a subject in a method of treatment or in a pharmaceutical use of each of these compounds has already been defined herein in the context of the method of the first aspect (see step c) and in the general part of the description dedicated to the definitions.

General Part Dedicated to Definitions

Polypeptide/Nucleic Acid

In the context of the invention, a polypeptide is represented by an amino acid sequence. Preferred polypeptides are δT-cell (or γT-cell) receptor chains or parts thereof which mediates an anti-tumour response as explained herein.

In the context of the invention, a nucleic acid molecule as a nucleic acid molecule encoding such a δT-cell (or γT-cell) receptor chain or part thereof is represented by a nucleic acid or nucleotide sequence which encodes such a polypeptide. A nucleic acid molecule may comprise a regulatory region.

It is to be understood that each nucleic acid molecule or polypeptide or construct as identified herein by a given Sequence Identity Number (SEQ ID NO) is not limited to this specific sequence as disclosed. Throughout this application, each time one refers to a specific nucleotide sequence SEQ ID NO (take SEQ ID NO: X as example) encoding a given polypeptide, one may replace it by:

i. a nucleotide sequence comprising a nucleotide sequence that has at least 60% sequence identity or similarity with SEQ ID NO: X;
ii. a nucleotide sequences the complementary strand of which hybridizes to a nucleic acid molecule of sequence of (i);
iii. a nucleotide sequence the sequence of which differs from the sequence of a nucleic acid molecule of (i) or (ii) due to the degeneracy of the genetic code; or,
iv. a nucleotide sequence that encodes an amino acid sequence that has at least 60% amino acid identity or similarity with an amino acid sequence encoded by a nucleotide sequence SEQ ID NO: X.

Throughout this application, each time one refers to a specific amino acid sequence SEQ ID NO (take SEQ ID NO: Y as example), one may replace it by: a polypeptide comprising an amino acid sequence that has at least 60% sequence identity or similarity with amino acid sequence SEQ ID NO: Y.

Each nucleotide sequence or amino acid sequence described herein by virtue of its identity or similarity percentage (at least 60%) with a given nucleotide sequence or amino acid sequence respectively has in a further preferred embodiment an identity or a similarity of at least 65%, 70%, 75%, 80%, 85%, 90%, 95%, 97%, 98%, 99% or more identity or similarity with the given nucleotide or amino acid sequence respectively. In a preferred embodiment, sequence identity or similarity is determined by comparing the whole length of the sequences as identified herein. Unless otherwise indicated herein, identity or similarity with a given SEQ ID NO means identity or similarity based on the full length of said sequence (i.e. over its whole length or as a whole).

Sequence Identity

"Sequence identity" is herein defined as a relationship between two or more amino acid (polypeptide or protein) sequences or two or more nucleic acid (polynucleotide) sequences, as determined by comparing the sequences. The identity between two amino acid or two nucleic acid sequences is preferably defined by assessing their identity within a whole SEQ ID NO as identified herein or part thereof. Part thereof may mean at least 50% of the length of the SEQ ID NO, or at least 60%, or at least 70%, or at least 80%, or at least 90%.

In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, MD 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, WI. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg, Gln or Glu; Met to Leu or Ile; Phe to Met, Leu or Tyr; Ser to Thr; Thr to Ser; Trp to Tyr; Tyr to Trp or Phe; and Val to Ile or Leu.

Conjugate

A polypeptide comprising a δT-cell (or γT-cell) receptor chain or part thereof which mediates an anti-tumour response as explained herein may be coupled or linked to an agent to form a conjugate. The agent may be selected from the group consisting of a diagnostic agent, a therapeutic agent, an anti-cancer agent, a chemical, a nanoparticle, a chemotherapeutic agent or a fluorochrome.

Gene or Coding Sequence

"Gene" or "coding sequence" or "nucleic acid" or "nucleic" refers to a DNA or RNA region (the transcribed region) which "encodes" a particular polypeptide such as a δT-cell receptor. A coding sequence is transcribed (DNA) and translated (RNA) into a polypeptide when placed under the control of an appropriate regulatory region, such as a promoter. A gene may comprise several operably linked fragments, such as a promoter, a 5' leader sequence, an intron, a coding sequence and a 3'nontranslated sequence, comprising a polyadenylation site or a signal sequence. A chimeric or recombinant gene (such as the one encoding a δTCR or γTCR chain comprising the polypeptide as identified herein and operably linked to a promoter) is a gene not normally found in nature, such as a gene in which for example the promoter is not associated in nature with part or all of the transcribed DNA region. "Expression of a gene" refers to the process wherein a gene is transcribed into an RNA and/or translated into an active protein.

Promoter

As used herein, the term "promoter" refers to a nucleic acid fragment that functions to control the transcription of one or more genes (or coding sequence), located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most physiological and developmental conditions. An "inducible" promoter is a promoter that is regulated depending on physiological or developmental conditions. A "tissue specific" promoter is preferentially active in specific types of differentiated cells/tissues, such as preferably a T cell.

Operably Linked

"Operably linked" is defined herein as a configuration in which a control sequence such as a promoter sequence or regulating sequence is appropriately placed at a position relative to the nucleotide sequence of interest, preferably coding for a δTCR (or a γTCR) chain comprising the polypeptide as identified such that the promoter or control or regulating sequence directs or affects the transcription and/ or production or expression of the nucleotide sequence of interest, preferably encoding a δTCR (or γTCR) chain comprising the polypeptide as identified in a cell and/or in a subject. For instance, a promoter is operably linked to a coding sequence if the promoter is able to initiate or regulate the transcription or expression of a coding sequence, in which case the coding sequence should be understood as being "under the control of" the promoter.

Viral Expression Construct

An expression construct carries a genome that is able to stabilize and remain episomal in a cell. Within the context of the invention, a cell may mean to encompass a cell used to make the construct or a cell wherein the construct will be administered. Alternatively a construct is capable of integrating into a cell's genome, e.g. through homologous recombination or otherwise. A particularly preferred expression construct is one wherein a nucleotide sequence encoding a δTCR (or TCR) chain or part thereof is operably linked to a promoter as defined herein wherein said promoter is capable of directing expression of said nucleotide sequence (i.e. coding sequence) in a cell. Such a preferred expression construct is said to comprise an expression cassette. An expression cassette as used herein comprises or consists of a nucleotide sequence encoding a δTCR (or γTCR) chain or part thereof. A viral expression construct is an expression construct which is intended to be used in gene therapy. It is designed to comprise part of a viral genome as later defined herein.

Expression constructs disclosed herein could be prepared using recombinant techniques in which nucleotide sequences encoding said δTCR (or TCR) chain or part thereof are expressed in a suitable cell, e.g. cultured cells or cells of a multicellular organism, such as described in Ausubel et al., "Current Protocols in Molecular Biology", Greene Publishing and Wiley-Interscience, New York (1987) and in Sambrook and Russell (2001, supra); both of which are incorporated herein by reference in their entirety. Also see, Kunkel (1985) Proc. Natl. Acad. Sci. 82:488 (describing site directed mutagenesis) and Roberts et al. (1987) Nature 328:731-734 or Wells, J. A., et al. (1985) Gene 34: 315 (describing cassette mutagenesis).

Typically, a nucleic acid or nucleotide sequence encoding a δTCR (or γTCR) chain is used in an expression construct or expression vector. The phrase "expression vector" generally refers to a nucleotide sequence that is capable of effecting expression of a gene in a host compatible with such sequences. These expression vectors typically include at least suitable promoter sequences and optionally, transcription termination signals. An additional factor necessary or helpful in effecting expression can also be used as described herein. A nucleic acid or DNA or nucleotide sequence encoding a δTCR (or γTCR) chain is incorporated into a DNA construct capable of introduction into and expression in an in vitro cell culture. Specifically, a DNA construct is suitable for replication in a prokaryotic host, such as bacteria, e.g., *E. coli*, or can be introduced into a cultured mammalian, plant, insect, (e.g., Sf9), yeast, fungi or other eukaryotic cell lines.

A DNA construct prepared for introduction into a particular host may include a replication system recognized by the host, an intended DNA segment encoding a desired polypeptide, and transcriptional and translational initiation and termination regulatory sequences operably linked to the polypeptide-encoding segment. The term "operably linked" has already been defined herein. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of a polypeptide. Generally, a DNA sequence that is operably linked are contiguous, and, in the case of a signal sequence, both contiguous and in reading frame. However, enhancers need not be contiguous with a coding sequence whose transcription they control. Linking is accomplished by ligation at convenient restriction sites or at adapters or linkers inserted in lieu thereof, or by gene synthesis.

The selection of an appropriate promoter sequence generally depends upon the host cell selected for the expression of a DNA segment. Examples of suitable promoter sequences include prokaryotic, and eukaryotic promoters well known in the art (see, e.g. Sambrook and Russell, 2001, supra). A transcriptional regulatory sequence typically includes a heterologous enhancer or promoter that is recognised by the host. The selection of an appropriate promoter depends upon the host, but promoters such as the trp, lac and phage promoters, tRNA promoters and glycolytic enzyme promoters are known and available (see, e.g. Sambrook and Russell, 2001, supra). An expression vector includes the replication system and transcriptional and translational regulatory sequences together with the insertion site for the polypeptide encoding segment can be employed. In most cases, the replication system is only functional in the cell that is used to make the vector (bacterial cell as *E. coli*). Most plasmids and vectors do not replicate in the cells infected with the vector. Examples of workable combinations of cell lines and expression vectors are described in Sambrook and Russell (2001, supra) and in Metzger et al. (1988) Nature 334: 31-36. For example, suitable expression vectors can be expressed in, yeast, e.g. *S. cerevisiae*, e.g., insect cells, e.g., Sf9 cells, mammalian cells, e.g., CHO cells and bacterial cells, e.g., *E. coli*. A cell may thus be a prokaryotic or eukaryotic host cell. A cell may be a cell that is suitable for culture in liquid or on solid media.

Alternatively, a host cell is a cell that is part of a multicellular organism such as a transgenic plant or animal.

Viral Vector

A viral vector or a gene therapy vector is a vector that comprises a viral expression construct as defined above.

A viral vector or a gene therapy vector is a vector that is suitable for gene therapy. Vectors that are suitable for gene therapy are described in Anderson 1998, Nature 392: 25-30; Walther and Stein, 2000, Drugs 60: 249-71; Kay et al., 2001, Nat. Med. 7: 33-40; Russell, 2000, J. Gen. Virol. 81: 2573-604; Amado and Chen, 1999, Science 285: 674-6; Federico, 1999, Curr. Opin. Biotechnol. 10: 448-53; *Vigna* and Naldini, 2000, J. Gene Med. 2: 308-16; Marin et al., 1997, Mol. Med. Today 3: 396-403; Peng and Russell, 1999, Curr. Opin. Biotechnol. 10: 454-7; Sommerfelt, 1999, J. Gen. Virol. 80: 3049-64; Reiser, 2000, Gene Ther. 7: 910-3; and references cited therein.

A particularly suitable gene therapy vector includes an Adenoviral and Adeno-associated virus (AAV) vector. These vectors infect a wide number of dividing and non-dividing cell types including synovial cells and liver cells. The episomal nature of the adenoviral and AAV vectors after cell entry makes these vectors suited for therapeutic applications. (Russell, 2000, J. Gen. Virol. 81: 2573-2604; Goncalves, 2005, Virol J. 2(1):43) as indicated above. AAV vectors are even more preferred since they are known to result in very stable long term expression of transgene expression (up to 9 years in dog (Niemeyer et al, *Blood.* 2009 Jan. 22; 113(4):797-806) and 2 years in human (Nathwani et al, *N Eng J Med.* 2011 Dec. 22; 365(25):2357-

65, Simonelli et al, *Mol Ther.* 2010 March; 18(3):643-50. Epub 2009 Dec. 1)). Preferred adenoviral vectors are modified to reduce the host response as reviewed by Russell (2000, supra). Method for gene therapy using AAV vectors are described by Wang et al., 2005, J Gene Med. March 9 (Epub ahead of print), Mandel et al., 2004, Curr Opin Mol Ther. 6(5):482-90, and Martin et al., 2004, Eye 18(11):1049-55, Nathwani et al, *N Eng J Med.* 2011 Dec. 22; 365(25): 2357-65, Apparailly et al, *Hum Gene Ther.* 2005 April; 16(4):426-34.

Another suitable gene therapy vector includes a retroviral vector. A preferred retroviral vector for application in the present invention is a lentiviral based expression construct. Lentiviral vectors have the ability to infect and to stably integrate into the genome of dividing and non-dividing cells (Amado and Chen, 1999 Science 285: 674-6). Methods for the construction and use of lentiviral based expression constructs are described in U.S. Pat. Nos. 6,165,782, 6,207,455, 6,218,181, 6,277,633 and 6,323,031 and in Federico (1999, Curr Opin Biotechnol 10: 448-53) and Vigna et al. (2000, J Gene Med 2000; 2: 308-16).

Other suitable gene therapy vectors include a herpes virus vector, a polyoma virus vector or a vaccinia virus vector.

A gene therapy vector comprises a nucleotide encoding a δTCR chain (or γTCR), whereby each of said nucleotide sequence is operably linked to the appropriate regulatory sequences. Such regulatory sequence will at least comprise a promoter sequence. Suitable promoters for expression of such a nucleotide sequence from gene therapy vectors include e.g. cytomegalovirus (CMV) intermediate early promoter, viral long terminal repeat promoters (LTRs), such as those from murine moloney leukaemia virus (MMLV) rous sarcoma virus, or HTLV-1, the simian virus 40 (SV 40) early promoter and the herpes simplex virus thymidine kinase promoter. Transposon or other non-viral delivery systems may also be used in this context. All systems can be used in vitro or in vivo.

A gene therapy vector may optionally comprise a further nucleotide sequence coding for a further polypeptide. A further polypeptide may be a (selectable) marker polypeptide that allows for the identification, selection and/or screening for cells containing the expression construct. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual (3rd edition), Cold Spring Harbor Laboratory, Cold Spring Harbor Laboratory Press, New York.

A gene therapy vector is preferably formulated in a pharmaceutical composition as defined herein. In this context, a pharmaceutical composition may comprise a suitable pharmaceutical carrier as earlier defined herein.

Transgene

A "transgene" is herein defined as a gene or a nucleic acid molecule (i.e. a molecule encoding a δTCR (or a γTCR) chain) that has been newly introduced into a cell, i.e. a gene that may be present but may normally not be expressed or expressed at an insufficient level in a cell. The transgene may comprise sequences that are native to the cell, sequences that naturally do not occur in the cell and it may comprise combinations of both. A transgene may contain sequences coding for a δTCR (or a γTCR) chain and comprising the polypeptide as identified and/or additional proteins as earlier identified herein that may be operably linked to appropriate regulatory sequences for expression of the sequences coding for a δTCR (or a γTCR) chain. Preferably, the transgene is not integrated into the host cell's genome.

Transduction

"Transduction" refers to the delivery of a δTCR (or a γTCR) chain or parts thereof into a recipient host cell by a viral vector. For example, transduction of a target cell by a retroviral or lentiviral vector of the invention leads to transfer of the genome contained in that vector into the transduced cell.

Host Cell/Target Cell

"Host cell" or "target cell" refers to the cell into which the DNA delivery takes place, such as the T cells of a donor.

Engineered Cells

"Engineered cells" refers herein to cells having been engineered, e.g. by the introduction of an exogenous nucleic acid sequence as defined herein. Such a cell has been genetically modified for example by the introduction of for example one or more mutations, insertions and/or deletions in the endogenous gene and/or insertion of a genetic construct in the genome. An engineered cell may refer to a cell in isolation or in culture. Engineered cells may be "transduced cells" wherein the cells have been infected with e.g. a modified virus, for example, a retrovirus may be used, such as described in the examples, but other suitable viruses may also be contemplated such as lentiviruses. Non-viral methods may also be used, such as transfections. Engineered cells may thus also be "stably transfected cells" or "transiently transfected cells". Transfection refers to non-viral methods to transfer DNA (or RNA) to cells such that a gene is expressed. Transfection methods are widely known in the art, such as calciumphosphate transfection, PEG transfection, and liposomal or lipoplex transfection of nucleic acids. Such a transfection may be transient, but may also be a stable transfection wherein cells can be selected that have the gene construct integrated in their genome. In some cases genetic engineering systems such as CRISPR or Argonaute maybe utilized to design engineered cells that express a polypeptide described herein.

Pharmaceutical Composition/Method of Treatment

In therapeutic applications, an effective amount of a δTCR (or γTCR) chain or parts thereof or nucleic acid construct or viral vector or cell expressing these molecules as defined herein is administered to a subject.

The term "effective amount" as used herein is defined as the amount of the molecules of the present invention that are necessary to result in the desired physiological change in the cell or tissue to which it is administered. The term "therapeutically effective amount" as used herein is defined as the amount of the molecules of the present invention that achieves a desired effect with respect to cancer. In this context, a "desired effect" is synonymous with "an anti-tumour activity" as earlier defined herein. A skilled artisan readily recognizes that in many cases the molecules may not provide a cure but may provide a partial benefit, such as alleviation or improvement of at least one symptom or parameter. In some embodiments, a physiological change having some benefit is also considered therapeutically beneficial. Thus, in some embodiments, an amount of molecules that provides a physiological change is considered an "effective amount" or a "therapeutically effective amount."

Pharmaceutical compositions of the present invention comprise an effective amount of one or more molecules (i.e. a polypeptide comprising a δTCR or γTCR chain or variants or parts thereof or nucleic acid construct or viral vector or cell expressing these molecules as defined herein) optionally dissolved or dispersed in a pharmaceutically acceptable carrier. The phrases "pharmaceutical or pharmacologically acceptable" refers to molecular entities and compositions that do not produce or produce acceptable adverse, allergic or other untoward reaction when administered to an animal, such as, for example, a human, as appropriate. Whether certain adverse effects are acceptable is determined based on the severity of the disease. The preparation of a pharmaceutical composition that contains at least one active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated. In certain embodiments, a pharmaceutical composition described herein comprising a population of cells described herein, further comprises a suitable amount of an antifungal agent. In some cases, a pharmaceutical composition described herein comprises an antifungal agent in an amount sufficient for the pharmaceutical composition to retain at least 20%, 30%, 40%, 50%, 60%, 70%, 80% or 90% of its desired activity for a period of at least 1 month, 2 months, 3 months, 6 months, 1 year, 1.5 years, 2 years, 2.5 years or 3 years.

The actual dosage amount of a composition of the present invention administered to an animal or a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

T Cell as Pharmaceutical Composition

Prior to expansion and genetic modification of the T cells of the invention, a source of T cells is obtained from a subject. T cells can be obtained from a number of sources, including PBMCs, bone marrow, lymph node tissue, cord blood, thymus tissue, tissue from a site of infection, ascites, pleural effusion, spleen tissue, and tumors. In certain embodiments of the present invention, T cells can be obtained from a unit of blood collected from a subject using any number of techniques known to the skilled artisan, such as Ficoll™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In a particular embodiment, the engineered cell can be a T cell. The engineered cell can be an effector ($T_{EFF}$), effector-memory ($T_{EM}$), central-memory ($T_{CM}$), T memory stem ($T_{SCM}$), naïve ($T_N$), or CD4+ or CD8+ T cell. The T cells can also be selected from a bulk population, for example, selecting T cells from whole blood. The T cells can also be expanded from a bulk population. The T cells can also be skewed towards particular populations and phenotypes. The engineered cell can also be expanded ex vivo. The engineered cell can be formulated into a pharmaceutical composition. The engineered cell can be formulated into a pharmaceutical composition and used to treat a subject in need thereof as earlier explained herein. The engineered cell can be autologous to a subject in need thereof. The engineered cell can be allogeneic to a subject in need thereof. The engineered cell can also be a good manufacturing practices (GMP) compatible reagent. The engineered cell can be part of a combination therapy to treat a subject in need thereof. The engineered cell can be a human cell. The subject that is being treated can be a human.

A method of attaining suitable cells can comprise sorting cells. In some cases, a cell can comprise a marker that can be selected for the cell. For example, such marker can comprise GFP, a resistance gene, a cell surface marker, an endogenous tag. Cells can be selected using any endogenous marker. Suitable cells can be selected or sorted using any technology. Such technology can comprise flow cytometry and/or magnetic columns. The selected cells can then be infused into a subject. The selected cells can also be expanded to large numbers. The selected cells can be expanded prior to infusion.

Vectors can be delivered to cells ex vivo, such as cells explanted from an individual patient (e.g., lymphocytes, T cells, bone marrow aspirates, tissue biopsy), followed by re-implantation of the cells into a patient, usually after selection for cells which have incorporated the vector. Prior to or after selection, the cells can be expanded.

Ex vivo cell transfection can also be used for diagnostics, research, or for gene therapy (e.g. via re-infusion of the transfected cells into the host organism). In some cases, cells are isolated from the subject organism, transfected with a nucleic acid (e.g., gene or DNA), and re-infused back into the subject organism (e.g. patient). Further, also in vivo cell transfection can be used for gene therapy, in order to reduced immune reactions of the patient.

In some cases, populations of engineered T cells may be formulated for administration to a subject using techniques known to the skilled artisan. Formulations comprising populations of engineered T cells may include pharmaceutically acceptable excipient(s). Excipients included in the formulations will have different purposes depending, for example, on the subpopulation of T cells used and the mode of administration. Examples of generally used excipients included, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising populations of engineered T cells will typically have been prepared and cultured in the absence of any non-human components, such as animal serum.

A formulation may include one population of engineered T cells, or more than one, such as two, three, four, five, six or more population of engineered T cells. The formulations comprising population(s) of engineered T cells may be administered to a subject using modes and techniques known to the skilled artisan. Exemplary modes include, but are not limited to, intravenous injection. Other modes include, without limitation, intratumoral, intradermal, subcutaneous (s.c., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection of infusion of the formulations can be used to effect such administration. The formulations comprising population(s) of engineered T cells that are administered to a subject comprise a number of engineered T cells that is effective for the treatment and/or prophylaxis of the specific indication or disease. Thus, therapeutically-effective populations of engineered T cells are administered to subjects when the methods of the present invention are practiced. In general, formulations are administered that comprise between about $1\times10^4$ and about $1\times10^{10}$ engineered T cells. In most cases, the formulation will comprise between about $1\times10^5$ and about $1\times10^9$ engineered T cells, from about $5\times10^5$ to about $5\times10^8$ engineered T cells, or from about $1\times10^6$ to about $1\times10^7$ engineered T cells. However, the number of engineered T cells administered to a subject will vary between wide limits, depending upon the location, source, identity, extent and severity of the cancer, the age and condition of the individual to be treated etc. A physician will ultimately determine appropriate dosages to be used.

General

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a method as defined herein may comprise additional step(s), respectively component(s) than the ones specifically identified, said additional step(s), respectively component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" when used in association with an integer (about 10) preferably means that the value may be the given value of 10 more or less 1 of the value: about 10 preferably means from 9 to 11. The word "about" when used in association with a numerical value (about 10.6) preferably means that the value may be the given value of 10.6 more or less 1% of the value 10.6.

All patent and literature references cited in the present specification are hereby incorporated by reference in their entirety. The following examples are offered for illustrative purposes only, and are not intended to limit the scope of the present invention in any way.

TABLE 1

Overview of the sequences of the sequence listing

| SEQ. ID NO | Name | Amino acid (aa) or DNA |
|---|---|---|
| 1 | Primer table 1 | DNA |
| 2 | Primer table 1 | DNA |
| 3 | Primer table 1 | DNA |
| 4 | Primer table 1 | DNA |
| 5 | Primer table 1 | DNA |
| 6 | Primer table 1 | DNA |
| 7 | CDR3 VD1 Fe11 | aa |
| 8 | CDR3 VD2 cl3 | aa |
| 9 | CD3 VD2 cl5 | aa |
| 10 | CDR3 VG5 Fe11 | aa |
| 11 | CDR3 VG cl3 | aa |
| 12 | CDR3 VG9 cl5 | aa |
| 13 | TRD cl3 | aa |
| 14 | TRG cl3 | aa |
| 15 | TRD cl5 | aa |
| 16 | TRG cl5 | aa |
| 17 | TRD Fe11 | aa |
| 18 | TRG Fe11 | aa |
| 19 | CDR3 VG4 E113 | aa |
| 20 | CDR3 VG2 F4 | aa |
| 21 | CDR3 VG8 Zi11 | aa |
| 22 | CDR3 VD5 D37 | aa |
| 23 | CDR3 VD5 E113 | aa |
| 24 | CDR3 VD1 F4 | aa |
| 25 | CDR3 VD1 Zi11 | aa |
| 26 | TRD E113 | DNA wild type |
| 27 | CDR3 VG4 C132 | aa |
| 28 | CDR3 VD5 C132 | aa |
| 29 | TRD E113 | aa |
| 30 | TRG E113 | aa |
| 31 | TRD F4 | aa |
| 32 | TRG F4 | aa |
| 33 | TRD Zi11 | aa |
| 34 | TRG Zi11 | aa |
| 35 | TRD D37 | aa |
| 36 | TRG D37 | aa |
| 37 | TRD C132 | aa |
| 38 | TRG C132 | aa |
| 39 | CDR3 VG8 D37 | aa |
| 40 | CDR3 VD3 F2 | aa |
| 41 | TRG E113 | DNA wild type |
| 42 | TRD F4 | DNA wild type |
| 43 | TRG F4 | DNA wild type |
| 44 | TRD Zi11 | DNA wild type |
| 45 | TRG Zi11 | DNA wild type |
| 46 | TRDD37 | DNA wild type |
| 47 | TRG D37 | DNA wild type |
| 48 | TRD C132 | DNA wild type |
| 49 | TRG C132 | DNA wild type |
| 50 | TRD Fe11 | DNA wild type |
| 51 | TRG Fe11 | DNA wild type |
| 52 | TRD E113 | DNA codon opt. |
| 53 | TRG E113 | DNA codon opt. |
| 54 | TRD F4 | DNA codon opt. |
| 55 | TRG F4 | DNA codon opt. |
| 56 | TRD Zi11 | DNA codon opt. |
| 57 | TRG Zi11 | DNA codon opt. |
| 58 | TRD D37 | DNA codon opt. |
| 59 | TRG D37 | DNA codon opt. |
| 60 | TRD C132 | DNA codon opt. |
| 61 | TRG C132 | DNA codon opt. |
| 62 | TRD Fe11 | DNA codon opt. |
| 63 | TRG Fe11 | DNA codon opt. |
| 64 | Longer CDR3 VG5 Fe11 | aa |
| 65 | CDR3 VG4 F2 | Aa |
| 66 | CDR3 VD1 Ze11 | aa |
| 67 | CDR3 VG8 Ze11 | aa |
| 68 | CDR3 VD5 B23 | aa |
| 69 | CDR3 VG8 B23 | aa |
| 70 | TRD F2 | aa |
| 71 | TRG F2 | aa |
| 72 | TRD Ze11 | aa |
| 73 | TRG Ze11 | aa |
| 74 | TRD B23 | aa |
| 75 | TRG B23 | aa |
| 76 | TRD F2 | DNA wild type |
| 77 | TRG F2 | DNA wild type |

TABLE 1-continued

| Overview of the sequences of the sequence listing | | |
|---|---|---|
| SEQ. ID NO | Name | Amino acid (aa) or DNA |
| 78 | TRD Ze11 | DNA wild type |
| 79 | TRG Ze11 | DNA wild type |
| 80 | TRD B23 | DNA wild type |
| 81 | TRG B23 | DNA wild type |
| 82 | TRD F2 | DNA codon opt. |
| 83 | TRG F2 | DNA codon opt. |
| 84 | TRD Ze11 | DNA codon opt. |
| 85 | TRG Ze11 | DNA codon opt. |
| 86 | TRD B23 | DNA codon opt. |
| 87 | TRG B23 | DNA codon opt. |
| 88 | CDR3 VD1 B9 | aa |
| 89 | CDR3 VG5 B9 | aa |
| 90 | TRD B9 | aa |
| 91 | TRG B9 | aa |
| 92 | TRD B9 | DNA wild type |
| 93 | TRG B9 | DNA wild type |
| 94 | TRD B9 | DNA codon opt. |
| 95 | TRG B9 | DNA codon opt. |
| 96 | TRD FE11 without signal pept. | aa |
| 97 | TRG FE11 without signal pept. | aa |
| 98 | TRD clone 3 without signal pept. | aa |
| 99 | TRG clone 3 without signal pept. | aa |
| 100 | TRD clone 5 without signal pept. | aa |
| 101 | TRG clone 5 without signal pept. | aa |

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

Unless specified, reagents employed in the examples are commercially available or can be prepared using commercially available instrumentation, methods, or reagents known in the art. The examples illustrate various aspects of the invention and practice of the methods of the invention. The examples are not intended to provide an exhaustive description of the many different embodiments of the invention. Thus, although the invention has been described in some detail by way of illustration and example for purposes of clarity of understanding, those of ordinary skill in the art will realize readily that many changes and modifications can be made thereto without departing from the spirit or scope of the appended claims.

Example 1

Material & Methods

Frozen PBMC's from healthy donors were thawed and stained with the following antibodies: CD3 (eFluor450 clone okt 3 1:40 eBioscience), αβ TCR (APC clone IP26 1:10, eBioscience), and pan γδ TCR (PE clone IMMU510 1:10 Boeckman Coulter), or with CD3 (PE clone UCHT1 1:20 BD), CD4 (APC clone RPA-T4 1:100 Biolegend), CD8 (PerCP-Cy5.5 clone RPA-T8 1:1000 Biolegend), CD27 (APC eFluor780 clone 0323 1:20 eBioscience), and CD45RA (PB clone HI100 1:50 Biolegend). Samples were sorted with flow cytometry on the ARIAII (BD) in an αβ-fraction (CD3+, αβ+), and a γδ-fraction (CD3+, γδ+), or in different subsets of CD4+ and CD4− T cells. RNA was isolated using Qiagen Rneasy Minikit for samples$\geq 0.5\times10^6$ cells or Qiagen Rneasy Microkit for samples$<0.5\times10^6$ cells following manufacturer's instructions. Specific cDNA for TRB and TRD was synthesized with Superscript® II Reverse Transcriptase (Thermofisher), using a specific primer at the 3' constant region of TRB or TRD. A universal template switch adaptor, containing a unique molecular identifier (UMI), was incorporated at the 5'end of the V region to be able to take PCR bias into account during the analysis. An overview of the used primers can be found in Table 1. After cDNA synthesis the cDNA was purified using NucleoSpin® Gel and PCR Clean-UP (Machery-Nagel). cDNA was amplified during with PCR using Q5® High Fidelity DNA polymerase (New England Biolabs). A specific nested primer at the constant region of TRB or TRD, and a step-out primer which anneals to the switch adaptor were used (Table 1). PCR amplification was performed on a T100 Thermal Cycler (Biorad) using the following steps 90 s at 98° C., 35 cycles of 7 s at 98° C., 20 s at 62° C., 50 s at 72° C., followed by 10 m at 72° C. PCR products were purified using NucleoSpin® Gel and PCR Clean-UP (Machery-Nagel). PCR products were analyzed with QIAxcel Advanced System (Qiagen).

TruSeq Barcode adapters (Illumina) were ligated to the PCR products using the ClaSeek Ligation Mix (Thermo Scientific), according to the recommendations of the manufacturer. Cleanup of the samples was performed with The Agencourt AMPure XP system (Beckman Coulter). Next-generation sequencing was performed on an Illumina MiSeq system 500 (2×250 bp) (Illumina).

Sequencing data were analyzed with the MiXCR program (Bolotin, et al. (7)). To correct for PCR bias UMI's were extracted from the sequencing data using the MIGEC pipeline (Shugay, et al. (8)) Only sequences with a valid UMI were used for further analyses. To search for shared CDR3 sequence regions within the different donors an interactive webtool was used (http://bioinformatics.psb.ugent.be/webtools/Venn/). Further methods for functional analyses have been described in Sebestyen et al (Cell Rep. 2016, 15: 1973-1985) and Scheper et al (Leukemia, 2013, 27: 1328-1338).

TABLE 2

| Overview primers | |
|---|---|
| cDNA synthesis | |
| Constant region TRB | CAGTATCTGGAGTCATTGA (SEQ ID NO: 1) |
| Constant region TRD | CTTGGATGACACGAGAT (SEQ ID NO: 2) |
| Template switch adaptor with UMI | AAGCAGUGGTAUCAACGCAGAGUNNNNUNNNNUNNNNUCTT(rG)4 (SEQ ID NO: 3) |

TABLE 2-continued

| Overview primers | |
|---|---|
| PCR amplification | |
| Nested primer constant region TRB | TGCTTCTGATGGCTCAAACAC (SEQ ID NO: 4) |
| Nested primer constant region TRD | AACGGATGGTTTGGTATGAG (SEQ ID NO: 5) |
| Step out primer (anneals to switch adaptor) | CACTCTATCCGACAAGCAGTGGTATCAACGCAG (SEQ ID NO: 6) |

rG=riboguanosine, necessary for the template switch adaptor to anneal. The backbone of this adaptor is cDNA, but in this part there are four RNA-G's. This template switch adapter is described in U.S. Pat. No. 5,962,272 and in Zhu Y et al (Zhu Y et al 2001, BioTechniques, 30: 892-897).

Results

Figure 1:
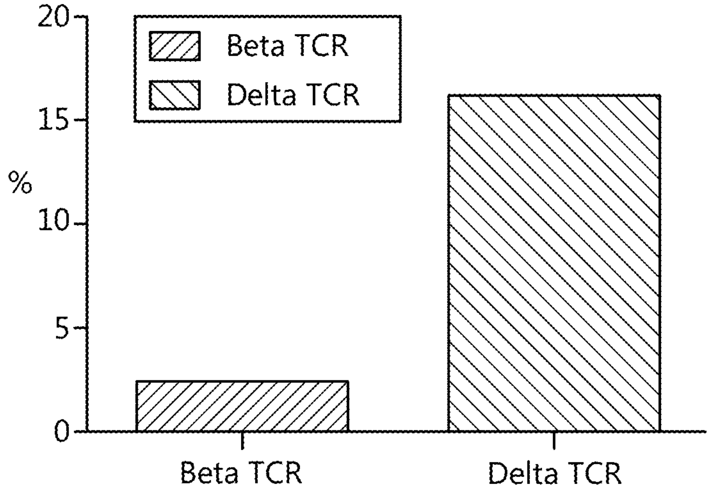
FIG. 1. Correction of unique clones for overlapping unique molecular identifiers (UMI's). Ratio between percentage of overlapping unique clones versus percentage of overlapping UMI's based on three healthy donors (HD 18 19 20) is shown.
Figure 2:
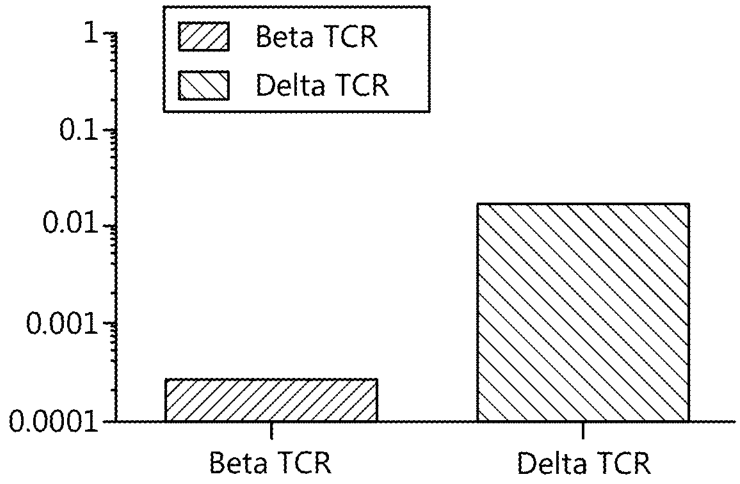
FIG. 2. Frequency of overlapping clones when corrected for UMI's and size of repertoire. Ratio between percentage of overlapping unique clones versus percentage of overlapping UMI's divided by the average repertoire size is shown on a logarithmic scale. Data are based on three healthy donors (HD18 19 20).

We hypothesized that rapid sequencing of γδTCR chains by next generation sequencing followed by comparison of (dominant) clones between different individuals can be used to rapidly identify functionally relevant clones, which are shared between different individuals. In order to test this hypothesis, we isolated γδT cells from 6 different donors and analyzed the δTCR repertoire by NGS as indicated in material and methods. For further analyses two strategies were used, either the individual analysis of three donors indicated as HD 18, 19, and 20 as well as a pool of three donors, depicted as "combined" (HD11, 12, and 15). In addition, we utilized as hypothetical 7$^{th}$ donor the randomly collected database of γδTCR chains obtained by single cell cloning and sequencing from many different donors, which are available in the public and our private database. After correction for the percentage of overlapping unique clones for overlapping UMI's a 7-fold higher amount of shared δTCR has been observed when compared to βTCR repertoire (FIG. 1). When further adjusting the corrected ratios for the average size of the found repertoire, the difference between the frequency of observed overlapping clones was even more pronounced with 1-2 log differences more overlapping clones observed for shared δTCR chains (FIG. 2). Thus, although the theoretical δTCR repertoire is substantially bigger than the theoretical βTCR repertoire; we show that the chance of finding an overlapping clone in the δTCR repertoire is 1-2 log-higher than when analyzing a βTCR repertoire. We hypothesized that these shared δTCR chains must provide a specific survival advantage and could be therefore essential in function, such as daily tumor surveillance.

Figure 3:
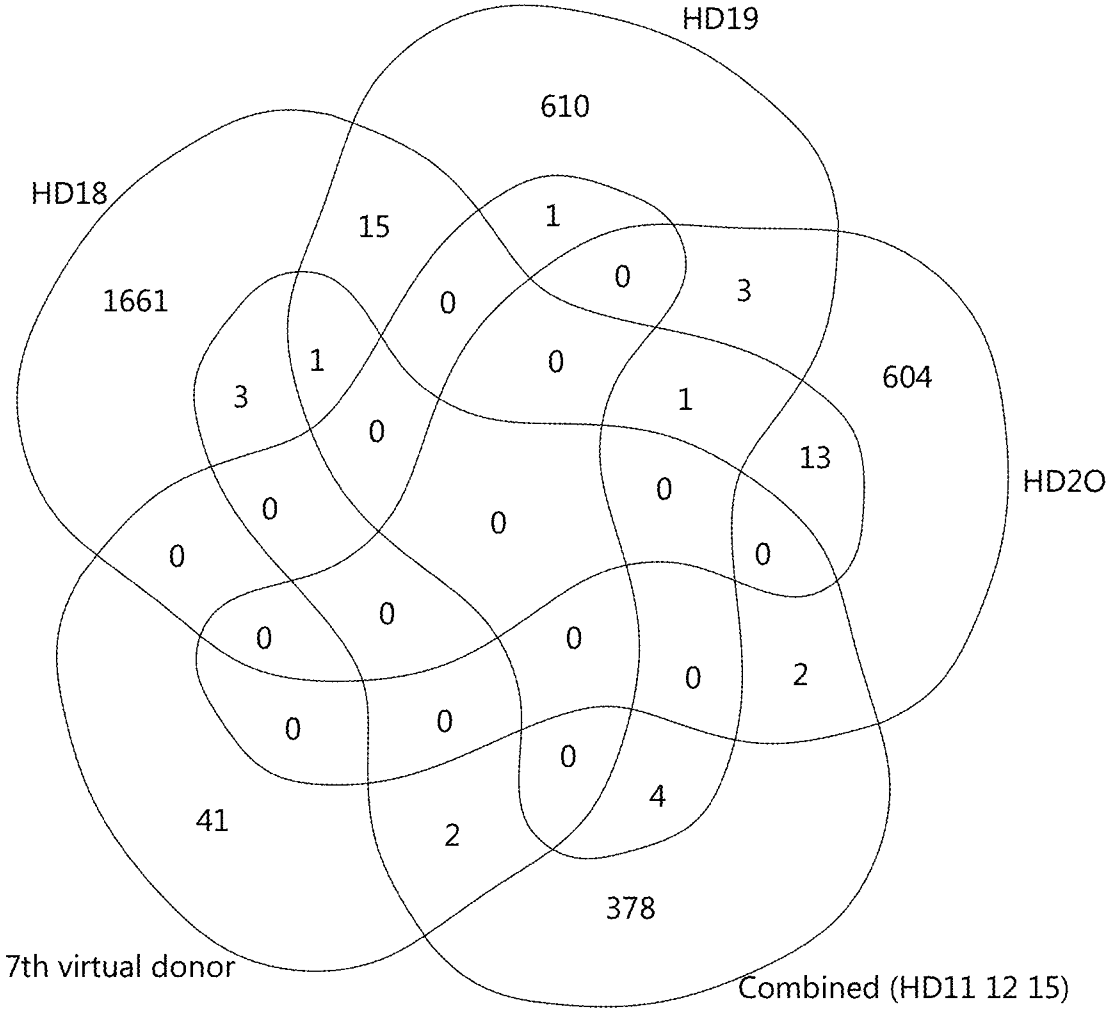
FIG. 3. Comparison of NGS sequencing results (amino acids) of the δTCR chains from 4 different donors and the 7$^{th}$ "virtual" donor as indicated in a Venn diagram. Healthy donor 18, 19, 20, the "combined donor" (HD 11, 12, 15), and the 7$^{th}$ virtual donor are depicted.

Comparing δTCR sequences between different NGS-donors results in the identification of a limited number of clones, which have been shared at least between two different donors (FIG. 3 and Table 2 and not shown). In addition, we compared our δTCR sequences from HDs with the 7$^{th}$ hypothetical donor. Thereby we identified additional δ2 negative TCR chain, which is the second most frequent sequence in donor HD19 (Tables 3 and 4) and δ2 positive TCR chains, which are shared at least between HD15 and the 7$^{th}$ hypothetical donor (Table 3). Some of these relevant clones are within the top 30 clones of at least one the healthy donors, indicating the potential biological relevance of these clones. As proof of concept for the functional and potential therapeutic relevance of identified shared δTCR sequences we further searched for described complete γδTCR sequences harboring by us so far identified dominant and shared δTCR sequences. We identified clone FE11 (Table 3), which has been described recently by our group (δ2 negative δTCR (9), Table 2). Clone Fe11 was the second most prevalent clone in HD19 (Table 4). Screening of tumor cell lines classified this clone as tumor reactive against malignant B cell and solid cancer cell lines ((10) and FIG. 4). In addition we could identify one overlapping δ2 positive δTCR sequence as part of the distinct clone 5, and one sequence corresponding to the so called clone 3, which have both also been extensively described by our group (Table 3 and (11)). Clone 5 was found in the top 20 of clones of HD15 (Table 4). This sequence has been reported to be very active against many types of hematological and solid cancer cells ((11, 12) and Table 4).

In summary, we provide proof of concept that we can down scale a highly diverse immune repertoire to very limited number of sequences, which are tumor reactive and therefore therapeutically relevant. In addition to anti-tumor reactivity identified sequences can also be active highly against infection as evidenced by the identification of shared Vδ2 positive TCR chain sequences. Thus, high throughput sequencing of δTCR chains followed by the comparison of sequences between different donors can be a very powerful tool and result in the rapid identification of γδTCR chains which can be interesting for therapeutic applications.

TABLE 3

| Shared clonotypes | Vdelta | Previously described |
|---|---|---|
| Vδ2 negative<br>CALGDSYGGGPLYTDKLIF<br>(SEQ ID NO: 7) | Vd1 | Fe11 |
| Vδ2 positive<br>CACDLLGYTDKLIF<br>(SEQ ID NO: 8) | Vd2 | C13 |
| CACDALKRTDTDKLIF<br>(SEQ ID NO: 9) | Vd2 | C15 |

TABLE 4

| Characteristics known clones | | |
|---|---|---|
| Clone | CDR3 δ chain | CDR3 γ chain |
| Fe11 | CALGDSYGGGPLYTDKLIF<br>SEQ ID NO: 7 | ATWDRPEIYYKKL<br>SEQ ID NO: 10 |
| C13 | CACDLLGYTDKLIF<br>SEQ ID NO: 8 | CALWEEELGKKIKVF<br>SEQ ID NO: 11 |
| C15 | CACDALKRTDTDKLIF<br>SEQ ID NO: 9 | CALWEIQELGKKIKMF<br>SEQ ID NO: 12 |

Discussion

Main finding of this study is that by comparing NGS data of Rand δTCR chains from different healthy donors we observe a substantial frequency of shared δTCR chains between different individuals, though the βTCR repertoire is as expected seldomly shared. Data mining of CDR3 regions within identified δTCR sequences and public data bases elucidated further that highly therapeutically interesting receptor chains such as the by us recently described chain of clone 5 from δ2-positive δTCR chains (11) was found among the dominant top 20 clones of HD15. Moreover, the δ2-negative δTCR chain of clone Fe11(9) was the second most prevalent clone in HD19. Main advantage is that such a strategy narrows down very quickly the potential very high diversity of δTCR chains from $10^1$ to literally less than $10^2$ sequences of therapeutic interest. This has practical and therapeutical consequences as high through put screening of γδTCR chain sequences followed by the identification of shared sequences in healthy and diseased patients can serve as rapid hub for the identification of novel therapeutic tools which can be used for e.g. T cells engineered with defined δTCRs, so called TEGs (13). In addition, repertoire analyses of diseased patients has the power to rapidly identify patients who might benefit from the addition of an immune repertoire with defined δTCR sequences.

TRD C13 Amino acid sequence:

SEQ ID NO: 13 m e r i s s l i h l s l f w a g v m s a i e l v p e h q t v p v s i g v p a t l r c s m k g e a i g n y y i n w y r k t q g n t m t f i y r e k d i y g p g f k d n f q g d i d i a k n l a v l k i l a p s e r d e g s y y c a c d l l g y t d k l i f g k g t r v t v e p r s q p h t k p s v f v m k n g t n v a c l v k e f y p k d i r i n l v s s k k i t e f d p a i v i s p s g k y n a v k l g k y e d s n s v t c s v q h d n k t v h s t d f e v k t d s t d h v k p k e t e n t k q p s k s c h k p k a i v h t e k v n m m s l t v l g l r m l f a k t v a v n f l l t a k l f f l

TRG C13 Amino acid sequence:

SEQ ID NO: 14 m v s l l h a s t l a v l g a l c v y g a g h l e q p q i s s t k t l s k t a r l e c v v s g i t i s a t s v y w y r e r p g e v i q f l v s i s y d g t v r k e s g i p s g k f e v d r i p e t s t s t l t i h n v e k q d i a t y y c a l w e e e l g k k i k v f g p g t k l i i t d k q l d a d v s p k p t i f l p s i a e t k l q k a g t y l c l l e k f f p d v i k i h w e e k k s n t i l g s q e g n t m k t n d t y m k f s w l t v p e k s l d k e h r c i v r h e n n k n g v d q e i i f p p i k t d v i t m d p k d n c s k d a n d t l l l q l t n t s a y y m y l l l l l k s v v y f a i i t c c l l r r t a f c c n g e k s

-continued

TRD C15 Amino acid sequence:

SEQ ID NO: 15 m e r i s s l i h l s l f w a g v m s a i d l v p e h q t v p v s i g v p a t l r c s m k g e a i g n y y i n w y r k t q g n t m t f i y r e k d i y g p g f k d n f q g d i d i a k n l a v l k i l a p s e r d e g s y y c a c d a l k r t d t d k l i f g k g t r v t v e p r s q p h t k p s v f v m k n g t n v a c l v k e f y p k d i r i n l v s s k k i t e f d p a i v i s p s g k y n a v k l g k y e d s n s v t c s v q h d n k t v h s t d f e v k t d s t d h v k p k e t e n t k q p s k s c h k p k a i v h t e k v n m m s l t v l g l r m l f a k t v a v n f l l t a k l f f l

TRG C15 Amino acid sequence:

SEQ ID NO: 16 m v s l l h a s t l a v l g a l c v y g a g h l e q p q i s s t k t l s k t a r l e c v v s g i t i s a t s v y w y r e r p g e v i q f l v s i s y d g t v r k e s g i p s g k f e v d r i p e t s t s t l t i h n v e k q d i a t y y c a l w e i q e l g k k i k v f g p g t k l i i t d k q l d a d v s p k p t i f l p s i a e t k l q k a g t y l c l l e k f f p d v i k i h w e e k k s n t i l g s q e g n t m k t n d t y m k f s w l t v p e k s l d k e h r c i v r h e n n k n g v d q e i i f p p i k t d v i t m d p k d n c s k d a n d t l l l q l t n t s a y y m y l l l l l k s v v y f a i i t c c l l r r t a f c c n g e k s

TRD Fe11 Amino acid sequence:

SEQ ID NO: 17 m v f s s l l c v f v a f s y s g s s v a q k v t q a q s s v s m p v r k a v t l n c l y e t s w w s y y i f w y k q l p s k e m i f l i r q g s d e q n a k s g r y s v n f k k a a k s v a l t i s a l q l e d s a k y f c a l g d s y g g g p l y t d k l i f g k g t r v t v e p r s q p h t k p s v f v m k n g t n v a c l v k e f y p k d i r i n l v s s k k i t e f d p a i v i s p s g k y n a v k l g k y e d s n s v t c s v q h d n k t v h s t d f e v k t d s t d h v k p k e t e n t k q p s k s c h k p k a i v h t e k v n m m s l t v l g l r m l f a k t v a v n f l l t a k l f f l

-continued

TRG Fell Amino acid sequence:

SEQ ID NO: 18

```
m g w a l l v h a f l s p a s q k s s n l e g g t

k s v t r p t r s s a e i t c d l t v i n a f y i

h w y l h q e g k a p q r l l y y d v s n s k d v

l e s g l s p g k y y t h t p r r w s w i l i l r

n l i e n d s g v y y c a t w d r p e i y y k k l

f g s g t t l v v t d k q l d a d v s p k p t i f

l p s i a e t k l q k a g t y l c l l e k f f p d

v i k i h w e e k k s n t i l g s q e g n t m k t

n d t y m k f s w l t v p e k s l d k e h r c i v

r h e n n k n g v d q e i i f p p i k t d v i t m

d p k d n c s k d a n d t l l l q l t n t s a y y

m y l l l l l k s v v y f a i i t c c l l r r t a

f c c n g e k s
```

Example 2

Material & Methods

Patient, Sample Collection and Cell Lines

All donor and patient material were collected according to GCP and Helsinki regulations. Peripheral blood mononuclear cell (PBMC) samples from healthy donors and acute myeloid leukemia (AML) patients were from the University Medical Center Utrecht Biobank. The use of the TNBC patient samples was approved by the ethics committee of the University of Freiburg Medical Center. From the archive of the Institute of Clinical Pathology, Freiburg we selected 16 formalin-fixed paraffin-embedded tissue specimens with the diagnosis of "TNBC". The histopathological diagnosis was performed according to the Union for the International Cancer Control (UICC) criteria. All the tumors were Grade III in the modified Bloom-Richardson classification (Elston). Conforming to the recommendations for the evaluation of TILs (14 15), the H&E stained samples contained at least 50% tumor infiltration. The cohort of 11 tumors (5 medullary breast carcinoma's and 6 invasive ductal carcinoma's) that we studied further was selected on the basis that the correspondent frozen tissue samples were available in the tumor bank of the Comprehensive Cancer Center Freiburg (CCCF). All these samples were classified as basal like subtype according to the expression of CK 5/6 or 14 and EGFR (16). The median age of the patients was 59 years in a range between 43 and 82 years.

Breast cancer cell lines and frozen tumor material were tested for HCMV using IHC nested PCR according to the protocol previously published by Bender et al (17), and real-time PCR with the Artus® CMV™ PCR kit (Qiagen, Hilden, Germany) in a 7900HT Fast real time PCR cycler (Applied Biosystems, CA, USA) according to the manufacturer instructions.

Next Generation Sequencing of TCRδ and TCRβ Repertoire

The protocol is adapted from Mamedov et al with modifications (18). Frozen PBMCs from healthy donors were thawed and stained with the following antibodies: CD3 eFluor 450, TCRαβ APC, and TCRγδ PE monoclonal antibodies (mAb). (Table 6. Samples were sorted on the ARIAII (BD) in an αβ-fraction ($CD3^+$, $αβ^+$), and a γδ-fraction ($CD3^+$, $γδ^+$). RNA was isolated using Qiagen Rneasy Minikit for samples≥$0.5×10^6$ cells or Qiagen Rneasy Microkit for samples<$0.5×10^6$ cells following manufacturer's instructions. Specific cDNA for TCRδ and TCRβ was synthesized with Superscript® II Reverse Transcriptase (Thermofisher), using a specific primer at the 3' constant region and an universal template switch adaptor was incorporated at the 5'end of the V region. cDNA was purified using NucleoSpin® Gel and PCR Clean-UP (Machery-Nagel) thereafter amplified with a first PCR amplification using Q5® High Fidelity DNA polymerase (New England Biolabs), on a T100 Thermal Cycler (Biorad) using the following steps 90 s at 98° C., 15 cycles of 7 s at 98° C., 20 s at 62° C., 50 s at 72° C., followed by 10 m at 72° C. A specific nested primer at the constant region, and a step-out primer which anneals to the switch adaptor were used (Table 5). PCR products were loaded on a 1.5% agarose gel for size selection of products between 400-600 base pairs. After purification of the gel with NucleoSpin® Gel and PCR Clean-UP (Machery-Nagel), the PCR product was used for a second PCR with a reverse nested primer on the constant region and a forward primer which annealed on the switch adaptor (Table 5), using the following steps: 90 s at 98° C., 20 cycles of 7 s at 98° C., 20 s at 62° C., 50 s at 72° C., followed by 10 m at 72° C. After purification with NucleoSpin® Gel and PCR Clean-UP (Machery-Nagel), the final PCR products were analyzed with QIAxcel Advanced System (Qiagen). Library preparation for NGS was done with NGSgo-LibrX kit with NGSgo-IndX indices from Gendx according to recommendations of the manufacturer. Cleanup of the samples was performed with HighPrep PCR beads from GC Biotech. Next-generation sequencing was performed on an Illumina MiSeq system 500 (2×250 bp) (Illumina). Sequencing data were analyzed with the MiXCR program (Bolotin, et al. (18)) and VDJ-tools for further analyses.

Immunohistochemistry (IHC) and Image Analysis of TNBC Samples

Serial FFPE 2 μm sections mounted on Superfrost plus glass slides (R Langenbrink, Germany), were dewaxed and rehydrated. After the proper antigen retrieval in a pressure cooker with citrate buffer (pH 6) and citrate buffer (pH 6.1) (Dako, Hamburg, Germany), blocking of nonspecific binding was performed using goat serum (5% in PBS). Mouse monoclonal anti-TCRγ-chain mAb and rabbit-anti-human cleaved caspase 3 (cC3) polyclonal antiserum (Table 6) as we previously reported (19). The HCMV detection was performed using the mouse anti-CMV mAb. Alkaline phosphatase-conjugated and Horseradish peroxidase-conjugated detection systems were used to visualize the primary antibodies in a separate or sequential protocols for single or double staining test with red and brown chromogen (Dako-REAL™ Alkaline Phosphatase/RED r/m and EnVision™FLEX Systems, Dako, USA). Acidic hematoxylin was used as a counterstain.

IHC samples were analyzed and tiled scanned using an AxioObserver Z1 with Apotome2 system with an ERc5s digital camera. The initial analysis was performed using the AxioVision 4.8 and ZEN BLUE image software (all from Carl Zeiss MicroImaging, Jena, Germany). Colocalization and quantitate analysis were performed with ImageJ (NIH images, USA) and QuPath (GitHub, San Francisco CA, USA) software with Bio-Formats, Stack Slicer and Cell counter plugins (20).

Immunofluorescence Imaging of TNBC Samples

Sections at 5 μm were mounted on Superfrost plus Adhesion glass slides, air-dried for 3 hours and fixed with pre-cooled acetone (−20° C.) for 10 minutes. Samples were rinsed with TBST for 5 minutes (3×) and blocking for nonspecific binding using normal human serum 5% in PBS for 30 min. The samples were incubated with corresponding primary mouse-anti-human mAbs: anti-TCRγ and anti-CD69 mAb or goat-anti-human polyclonal anti-IFN-γ and anti-IL-17 antisera. Fluorescence-conjugated secondary antibodies used to visualized the primary antibodies were rabbit-anti-mouse AlexaFluor 488, donkey-anti-rabbit AlexaFluor 568, donkey-anti-goat AlexaFluor 594, donkey-anti-goat AlexaFluor 647 (Table 6). Samples were mounted using the Prolong® Diamond Antifade medium with DAPI (Thermo Fischer).

Tissue Immunostaining and Laser Capture Microdissection of TNBC Samples

Frozen sections (8 μm thick) were air dried overnight on MembraneSlide 1.0 PEN™ membrane covered slides (Carl Zeiss, Munich, Germany), fixed in pre-cooled acetone (−20° C.) for 10 min, washed twice with TBST and incubated for 30 min with 5% human serum in PBS. The samples were incubated for 30 min at room temperature with the mouse anti-human TCRγ mAb (Table 6). To detect the primary antibody, a biotinylated anti-mouse secondary antibody with alkaline phosphatase detection system (Dako REAL™ Detection System Alkaline P/RED, rabbit-mouse). Mayer's hematoxylin was used as counterstain. Samples were dried at room temperature for 2 hours, examined under microscopy and stored at 4° C. until processing.

Laser microdissection was performed using an Axiovert microscope equipped with a PALM MicroBeam system (ZEISS Microscopy, Oberkochen, Germany). Energy parameters of cutting and catapulting were stablished individually for each sample. Only infiltrating single lymphocytes in close contact with cancer cells were selected at 40× magnification and microdissected at 63× magnification. Single cells were catapulted into the cap of an Adhesive Cap 500 Opaque™ 500 μl tube (Carl Zeiss, Göttingen, Germany). To improve isolation, the cap contained 5 μl of 1× Expand High Fidelity PCR buffer w/o $MgCl_2$ (Roche, Mannheim, Germany). Then, 15 μl of a 1:10 mix containing PCR buffer and Proteinase K (20 mg/ml, PCR grade, Roche, Mannheim, Germany) were added for the digestion. The tubes were incubated with the lid down for 4 h at 56° C., centrifuged for 2 min at 500 rpm and heat inactivated at 95° C. for 10 min. Additional tubes containing only membrane were dissected from each sample and used as negative controls. All PCR tubes were overlaid with mineral oil under a laminar flow hood before adding the PCR master mix.

Single-Cell PCR of TNBC γδ TILs

DNA isolation, the first and the second rounds of PCR were performed in different "single-cell rooms" under laminar flow cabinet previously decontaminated with UV lamp, ethanol and DNA Zap (Invitrogen, Bleiswijk, Netherlands). Separate sets of pipettes, consumables and reagents were used for each step and every two weeks all reagents were tested to prevent contamination. Corresponding to the single-cell PCR technique previously described for the analysis of rearranged immunoglobulin genes (21), a multiplex, semi-nested, hot-start PCR was prepared with 15 newly designed primers (Table 7). For the first round, a master mix was prepared with 5 μl dNTP (2 mM), 5 μl 10×PCR buffer (High Fidelity System), 5 μl primer mix (2.5 μM, forward and reverse primers), 3.2 μl 25 μM $MgCl_2$, 6.5 μl $H_2O$ and 15 μl from the DNA digestion. A volume of 0.3 μl Expand High Fidelity enzyme mix (3.5 units/μl) was added after the first denaturation step to a final volume of 40 μl. The cycler program was 95° C. 2 min, 80° C. pause (enzyme added), 72° C. 1 min, 39× (95° C. 50 s, 56° C. 30 s, 72° C. 60 s), 72° C. 5 min and 10° C. pause. For the second round, eight master mixes were prepared to detect TCRγ and δ chains: two mixes for TCRγ (Vγ1-8 and Vγ9) and six for TCRδ (Vδ1, Vδ2, Vδ3, Vδ4, Vδ5 and Vδ6) (Suppl. Table 4) with 2.5 μl dNTP (2 mM), 2.5 μl 10×PCR buffer, 1.25 μl of the respective Vγ and Vδ forward primers, 1.25 μl of the respective joint mix primers, 2 μl 25 mM $MgCl_2$, 12.2 μl $H_2O$, 3 μl of first round PCR product and 0.3 μl Expand High Fidelity enzyme mix (3.5 units/μl). The cycler program was 95° C. 5 min, 72° C. 1 min, 35× (95° C. 50 s, 55.5° C. 30 s, 72° C. 1 min), 72° C. 5 min, 15° C. 5 min and 4° C. pause. The PCR products were analyzed by 2% agarose gel electrophoresis and the positive bands were cut under UV light and purified from the gel with the Qiaex II gel extraction kit (Qiagen, Hilden, Germany). The clean DNA was sequenced using the BigDye Terminator 3.1 system (Applied Biosystems, CA, USA), the sequencing reactions consisted of 1 μl BigDye, 3.75 μl 15× sequencing buffer, 0.75 μl forward primer, 3-10 μl template and water to a final volume of 20 μl. The cycler conditions were 96° C. 5 min, 24× (95° C. 15 sec., 50° C. 10 sec., 60° C. 4 min), 10° C. pause. The sequence sample was cleaned using the DyeEx 2.0 Spin Kit (Quiagen) and analyzed on the ABI 3130XL capillary sequencer (Applied Biosystems, Darmstadt, Germany). The sequences we compared and evaluated with the IMGT database (http://www.imgt.org/) and the IgBlast tool (https://www.ncbi.nlm.nih.gov/igblast/)

Retroviral Expression of Plasmids from TNBC γδ TILs

Codon optimized DNA coding for the full length γ and δ TCR chains of the tumor infiltrating lymphocytes and for full length EPCR was ordered at Baseclear Inc. The synthetic genes were flanked with a 5' NcoI and a 3' BamHI site for subsequent cloning into a pBullet retroviral expression vector. The γ TCR genes were subcloned into pBullet-IRES-neo and the δ TCR genes as well as EPCR were subcloned into pBullet-IRES-puromycin.

Transduction of αβ T Cells.

For the generation of TEGs, PBMCs were transduced defined TCRγ and δ chains as described (22-24). In short, retroviral supernatant was produced by Phoenix-Ampho packaging cells, that were transfected with gag-pol (pHIT60), env (pCOLT-GALV) and pBullet retroviral constructs containing TCRγ or δ, using Fugene HD (Promega). PBMCs preactivated with αCD3 (30 ng/ml) (clone OKT3, Janssen-Cilag) and IL-2 (50 U/ml) were transduced twice with viral supernatant within 48 hours in the presence of 50 U/ml IL-2 and 4 μg/ml polybrene (Sigma-Aldrich). Transduced T cells were expanded by stimulation with αCD3/CD28 Dynabeads ($0.5\times10^6$ beads/$10^6$ cells) (Invitrogen) and IL-2 (50 U/ml) and selected with 800 μg/ml geneticin (Gibco) and 5 μg/ml puromycin (Sigma-Aldrich) for one week. Following transduction, transduced T cells were stimulated biweekly with 1 μg/ml PHA-L (Sigma-Aldrich), 50 U/ml IL-2 (Novartis Pharma), 5 ng/ml IL-15 (R&D Systems), and irradiated allogeneic PBMCs, Daudi and LCL-TM cells. Fresh IL-2 was added twice a week. Transgenic TCR expression was routinely assessed by flow cytometry.

Functional Assays of Primary Clones and TEG's

IFNγ ELISPOT was performed as previously described (25, 26). Briefly, 15,000 TCR-transduced or mock-transduced T cells and 50,000 target cells (ratio 0.3:1) were co-cultured for 24 hrs in nitrocellulose-bottomed 96-well plates (Millipore) precoated with anti-IFNγ antibody (clone 1-D1K) (Mabtech). Plates were washed and incubated with a second biotinylated anti-IFNγ antibody (clone 7-B6-1)

(Mabtech) followed by streptavidin-HRP (Mabtech). IFNγ spots were visualized with TMB substrate (Sanquin) and the number of spots was quantified using ELISPOT Analysis Software (Aelvis). IFNγ ELISA was performed using ELISA-ready-go! Kit (eBioscience, San Diego, CA, USA) following manufacturer's instructions. Effector and target cells (E:T 1:1) were incubated for 24 h in the presence of pamidronate when indicated.

CD1 Tetramer Staining

CD1c and CD1d tetramers were produced as described before (27). TEGs were stained with anti-γδ TCR-APC antibody (Table 5) and CD1 streptavidin-PE tetramers at a concentration of 50 nM in PBS+0.5% BSA for 30' at room temperature. After two wash steps the cells were analyzed by flow cytometry on a BD FACSCanto II.

Mouse Model for TEG001

The NOD.Cg-Prkcd$^{scid}$ IL2rg$^{tm1Wjl}$/SzJ (NSG) mice, originally obtained from JAX (Bar Harbor, ME, USA), were bred and housed in the specific pathogen-free (SPF) breeding unit of the Central Animal Facility of Utrecht University. Experiments were conducted according to Institutional Guidelines after acquiring permission from the local Ethical Committee and in accordance with current Dutch laws on Animal Experimentation. For the experiments mice from 8 to 12 weeks of age were used. At day 0 mice received sublethal total body irradiation (175 cGy) followed by i.v. injection of $5\times10^6$ OPM2-Luc tumor cells at day 1. Mice were treated with $10^7$ TEG001 cells or Mock TCR transduced T cells i.v. at day 7 and 14. Mice received $0.6\times10^6$ IU of IL-2 in IFA s.c. on day 7 and every 21 days till the end of the experiment. Pamidronate (10 mg/kg body weight) was applied at day 7 i.v. and every 21 days until the end of the experiment. Tumors were visualized in vivo by bioluminescent imaging. Mice were anesthetized by isoflurane before they received an i.p. injection (100 μl) of 25 mg/ml Beetle Luciferin (Promega, Madison WI). Bioluminescence images were acquired by using a third generation cooled GaAs intensified charge-coupled device camera, controlled by the Photo Vision software and analyzed with M$^3$Vision software (all from Photon Imager; Biospace Laboratory, Paris, France).

Results

Identification of Shared TCRδ Sequences with Next Generation Sequencing.

In order to understand the functional implication of shared immune receptors within the TCRδ repertoire we analyzed TCRδ chains from 14 different healthy donors (dataset 1). After sorting γδ T cells by flow cytometry. followed by TCRδ repertoire analyses by NGS, we found 9011 amino acids sequences of the TCRδ CDR3 (CDR3δ) region. Further analysis on the most abundant sequences per donor, defined as sequences with a clonal frequency of >0.1% (n=1478), showed that 1.8% of sequences where shared between at least two donors. Of these shared sequences one was shared between three different donors (Table 8). Overlap of TCRδ sequences between 2 different donors differed from 0 to 3.9% of the sequences of the 2 donors (FIG. 5A). In contrast in the TCRβ repertoire only 0.7% of sequences were shared. We identified 6 shared sequences, and the overlap between 2 different donors ranged from 0 to 1.9% (FIG. 5B). As expected for peripheral blood repertoires the majority of the identified sequences was Vδ2+ (FIG. 6A). In line with this the majority of the shared sequences was also Vδ2. In addition we identified four shared Vδ1 sequences.

Analyses of TCRδ Repertoires in the Tumor Infiltrating Tissues

Immune repertoires of γδ T cells in healthy individuals between peripheral blood and tissues differ substantially (28), although it is reported that TCRδ sequences identified in tissue could be traced back in the peripheral blood (28). To analyze whether the same holds true for γδ tumor infiltrating lymphocytes (γδ TILs) we compared the sequences of the peripheral TCRδ repertoire (dataset 1-4) with a fifth dataset consisting of published γδ TIL TCRδ sequences and a publicly available dataset of Li et al. The dataset of Li et al consisted of CDR3 sequences of TILs of various tumors with 1060 complete CDR3δ sequences. In line with the assumption that Vδ2$^{neg}$ γδ T cells are the dominant fraction in tissues, only 19% of TCRδ sequences were classified as Vδ2 TCRδ. The majority of the sequences were of Vδ1 origin, but compared to the healthy repertoires also the Vδ3, Vδ5, Vδ7 and Vδ8 fraction were increased. Although the percentage of Vδ2 TCRδ sequences in tumor tissue is relatively low, still 24 shared Vδ2 sequences could be identified (FIG. 5C). Interestingly, once peripheral T cells have been heavily enriched for Vδ1 γδ T cells before NGS analyses (dataset 3) 10 Vδ1 sequences could be characterized as shared between the peripheral blood and γδ TILs (FIG. 5D). Although these data demonstrate that it is possible to identify shared sequences between γδ TILs and the peripheral blood, it also illustrates the limitation of this method because of the different composition of the TCRδ repertoire between peripheral blood and cancer tissues.

Single Cell Analyses of γδ TILs in Patients with Triple Negative Breast Cancer

In order to further analyze in depth γδ TIL receptor sequences between individual cancer patients at the tumor site a previously characterized TNBC cohort was used. γδ TILs in TNBC have been associated with elevated levels of the apoptotic marker cleaved caspase 3 at the tumor site (29). In order to identify γδ TILs with close proximity to apoptotic tumor cells paraffin embedded tissues were co-stained for TCRγδ and cleaved caspase-3 using IHC. γδ TILs were observed at high frequency in all of the examined biopsies and apoptotic tumor cells were in contact with γδ T cells (FIG. 7A). Expression of CD69, as evident by IHC (FIG. 7B), suggested a T cell receptor-mediated activation of γδ TILs. Conflicting roles of γδ TILs have been described such as cancer immune surveillance (30) or tumor promoting properties through IL-17 (31). Therefore, IFNγ and IL-17 expression was further assessed by IHC. Most γδ TILs were IFNγ$^{pos}$ and did not substantiality stain for IL-17, suggesting that indeed investigated γδ TILs are activated with a Th1-type and that γδ T cells are an active participant of daily cancer immune surveillance.

Diversity and Sharing of TCRγ and δ Chains Derived from γδ TILs

Diversity and clonal expansion of γδ TILs in individual TNBC patients was first analyzed by spectratyping of Vγ and Vδ genes. These data confirmed that also tumor infiltrating γδ T cells Vγ and Vδ gene usage is polyclonal in most patients. These data were also confirmed for five of the breast cancer samples by NGS of the delta sequences (dataset 7, FIG. 6B). However, with a mean of 68.9%, the Vδ2 T cell proportion appeared higher in the NGS breast cancer data than observed for other tumor tissues (FIG. 6B). This is most likely due to the strong vascularization of investigated tissues. The Vδ3 and Vδ5 gene were again enriched in tumor tissue, suggesting that these subsets might be functionally important in cancer immune surveillance. Next we searched for public TCRδ sequences in the NGS breast cancer data. 52 Vδ2 sequences were shared with the healthy donor datasets and 3 sequences were shared with the γδ TIL dataset (FIG. 5C). Interestingly, a Vδ3 sequence which was also present in the γδ TIL sequences, was also found within this dataset of breast cancer TILs (FIG. 5E). No further Vδ1 shared sequences were observed (FIG. 5D). In summary, analysis of this rather unique and homogenous cohort indicates that the γδ T cell repertoire in tumor tissue is quite diverse, and that despite some increased frequency for Vδ3 and Vδ5 in our TNBC cohort, but also in a dataset of γδ TILs (32) of Li et al., no substantial clonal expansion can be observed among γδ TILs.

Next, we aimed to assess whether shared individual γ or δ TCR chains were involved in a cognate γδ T cell tumor interaction. Therefore, single cells were isolated from frozen TNBC sections using laser microdissection and transferred to a PCR tube to determine the TCR sequence using single cell sequencing. In total, 530 single γδ T cells were isolated from 11 different tumors and 27 paired TCR γ and δ sequences from 9 different patients could be identified. (dataset 6, Table 9). The other single cell sequencing reactions did not result in reliable sequencing data for both the γ and/or δ TCR chain, however we were able to determine 63 additional non-paired γ and 28 additional non-paired δ CDR3 sequences. The single cell sequencing data again confirmed a polyclonal population of tumor infiltrating γδ T cells, within patients some TCRδ and TCRγ sequences were seen multiple times. As expected from our analyses of TILs across many cancer patients, as well as our analysis tumor infiltrating γδ T cells in patients suffering from TNBC. Non-Vγ9 and non-Vδ2 genes, were most prominent in the sequences obtained. The Vδ2 gene was used in 7 out of the 55 TCRδ sequences and the Vγ9 gene in 21 out of the 90 TCRγ sequences. Interestingly, 4 of the 27 clones used an identical Vδ5 sequence paired with a different γ TCR sequence (Table 9). Additionally, this Vδ5 sequence was also identified in 6 non-paired δ CDR3 sequences (FIG. 8A). This sequence was found in 6 out of 11 patients, which classifies it as a public CDR3 sequence. This particular sequence has also been reported to associate with CMV- and tumor-reactivity (33). However, surprisingly none of the patients that had this particular shared TCRVδ5 sequence were CMV positive. Two Vδ1 sequences were shared between 2 different patients. As additional quality control we could retrieve four of the single cell TRD sequences within NGS dataset from TNBC: three sequences of patient E and one sequence of patient F, indicating that many receptors picked up by single cell sequencing might be of very low frequency and therefore not visible through NGS of TCRδ repertoires.

The TCRγ chain was more frequently shared between the isolated T cells out of the 90 obtained sequences in total, 10 different sequences were shared amongst the patients. One sequence was shared between 5 patients and was identified in 10 different isolated cells. This sequence was found back in 4 of the 27 paired γδ clones. One other CDR37 sequence was shared between 3 patients and some others were shared between two patients (FIG. 8B). Additionally, there was a T cell that shared the γ TCR chain reported with a previously identified CD1d-restricted T cell clone (34). In summary, many shared TCRγ chains and Vβ2$^{neg}$ TCR chains can be found within the local tumor microenvironment, however in contrast to γδ T cell repertoires in the peripheral blood, repertoires are dominated by Vβ2$^{neg}$ γδ T cells and lack a substantial clonal expansion.

Functional Assessment of Selected TCRγδ from the Peripheral and Tumor Infiltrating γδ T Cell Repertoire In order to test our hypothesis that either shared γ or shared δ TCR chains from the peripheral and tissue residing immune repertoire functionally contribute to daily cancer immune surveillance, we completed first the corresponding TCRγ for selected shared TCRδ from the peripheral repertoire. This was done by single cell cloning for Vδ2+(23) or Vδ2$^{ne}$(25) γδ T cells and we sequenced both, γ and δ TCR chains. We identified a corresponding γ chain of the shared Vδ2TCR chain, Clone 5 as reported recently (23). The TCRδ chain of the TCRVγ9δ2 expressing clone 5 was found in healthy donor 11 of dataset 1. This particular combination has been reported to be very active against many types of hematological and solid cancer cells (22, 23). In order to further extend analyses on activity of the TCRγ and δ chains isolated from clone 5 in comparison to bulk γδ T cells a T cells were engineered to express this defined TCRγδ (TEG001) (23, 25, 26). TEG001 showed not only superior activity to different tumor cell lines when compared to bulk γδ T cells (FIG. 9A) but also to a variety of primary AML blasts (FIG. 9B). These data suggest that the TCR Vγ9δ2 utilizing shared TCRδ chains can mediate a high functional activity and functionally outperform most γδ T cells.

To further functionally characterize shared TCRδ chains from Vδ2$^{neg}$ T cells from the peripheral repertoire healthy donors, Vδ2$^{neg}$ γδ T cells were isolated and cloned as reported (25) from an additional healthy donors, tested for reactivity by an IFNγ ELISPOT assay against a defined tumor cell panel, and sequenced for the corresponding γ and δ TCR chain. From the 10 isolated Vδ2$^{neg}$ γδ T-cell clones, 3 clones showed reactivity against different cancer cell lines (FIG. 10A). Sequencing of all functionally investigated clones identified clone FE11 as a clone, which shares its δ1 TCR chain also with donor 13 and 19 of dataset 1. In order to investigate whether tumor reactivity of FE11 is mediated by the TCRγδ chain only, we introduced γ and δ TCR chains of clone FE11 into a T cells (TEG-011), and tested activity of FE11 against a panel of tumor cell lines by an IFNγ ELISA assay, and confirmed the results as seen with the ELISPOT assay (FIG. 10A). In summary, a variety of Vδ2$^{neg}$ γδ T-cell clones can be identified from the peripheral blood, which recognize in a complementary way different tumor cell lines. In addition, clone FE11 with a shared TCRδ shows tumor reactivity.

In order to functionally confirm that also the TCRγδ from γδ TILs have the potential to mediate tumor reactivity and that this reactivity is at least partially mediated by their individual shared TCRγ or δ chains, we generated a series of 15 TEGs by expressing paired γ and δ TCR chains derived from our breast cancer γδ TILs (Table 9). In line with the observed reactivity of Vδ2neg γδ T cell clones from the peripheral blood 5 out of 10 TEGs with shared γ or δ TCR chains showed complementary reactivity against different types of cancer cell lines. One out of 15 TCRγδs with a shared receptor sequence showed a very broad reactivity, namely TEG-Zi11, while the 5 other clones had a more restricted reactivity against a distinct cancer cell lines within the tested panel (FIG. 10B). Notably, the broadly reactive TCRγδ complex of TEG-Zi11 uses a shared γ chain with TEG-B23 and TEG-Ze11 which are both unresponsive to tested cancer cell lines, indicating in this case that the unique δ chain of TEG-Zi11 is required for the tumor-reactivity. In line with this observation, the TCRγδ complex from TEG-F4 which has a restricted reactivity to some tumor cell lines shared its γ chain with the non-reactive TCR from TEG-E20, and TCRγδ complex from TEG-B9, which shares its γ chain with a previously reported CD1d-reactive TCRγδ (34), did not bind to CD1d tetramer when the reported unique TCRδ chain was not present (FIG. 12). Thus, a shared TCRγ chain can be part of a tumor-reactive γδTCR, but that in itself is not sufficient for reactivity. Vice versa, TEG-C132, TEG-D37, TEG-E113 and TEG-B23, who share the very same δ5 chain, were active against different cancer cell lines, namely K562 for TEG-B23, TEG-D37 and TEG-C132, U937 for TEG-B23, TEG-D37 and TEG-E113 (FIG. 10B). Thus, TCRγδ complexes comprised of shared Vδ2 and Vδ2$^{neg}$ chains have a comprehensive and complementary ability to attack different types of cancer cells and chains comprised of Vδ5 could be in particular important participants in cancer immune surveillance.

In Vivo Activity of Public TCRδ Chains within the Therapeutic Concept of TEGs

Engineering immune cells for cancer immune therapy has been recognized as scientific breakthrough (35) and the next generation of chimeric antigen receptors (CARs) is urgently needed to overcome current limitations such as restricted tumor antigen availability (36). TEGs have most recently been appreciated as a new interesting twist on this strategy (36) and therefore we tested whether not only artificial TCRγδ complexes (22, 23) but also natural TCRγδ complexes with partly public δ TCR sequences can be part of the next generation of TEGs. Therefore, TEG001 activity was tested in vivo in a multiple myeloma mouse model utilizing OPM2 as target (22). As negative control TEGs expressing a non-functional TCRγδ chain LM1 (23) were used. TEGs were infused 7 and 14 days after inoculation of OPM2. Treatment with TEG001 lead when compared to TEG-LM1 to a significant inhibition of tumor growth and associated in this treatment model also with a significant prolonged overall survival (FIG. 11), indicating that TCRγδ complexes comprised of partly public TCR chains are a valuable tool for cancer immune therapy with TEGs.

Discussion

Three types of immune cells undergo somatic DNA recombination during their ontogeny. Numerous functions of two of them, a T cells and B cells, during immune responses have been elucidated to a substantial extent. In contrast, relatively very limited information is available about the repertoire and immunological function of the third type of cells undergoing somatic DNA recombination during their ontogeny, γδ T cells. Here we attempted to illuminate this unknown territory by analyzing the γδ TCR repertoires using combined high-throughput next generation and single-cell sequencing techniques and found evidence of the involvement of public Vδ2$^+$ and Vδ2$^{neg}$ TCR chains in cancer immune surveillance.

While public βTCR chains have been reported to be mainly involved in infection and allo-reactivity, our data suggest that public γ and δ TCR pairs are an important pillar of daily cancer immune surveillance. Shared Vδ2 TCRs from the peripheral blood have the ability to mediate highest functional activity against various tumor types and can even outperform tumor reactivity of polyclonal γδ T cells, as shown in the in vitro experiments with TEG001. In addition also Vδ2$^{neg}$ TCRs can mediate strong anti-tumor reactivity against a set of different tumor cells, thus seem to cover surveillance against a variety of solid and hematological malignancies. However, in depth analyses of γδ TILs indicate that γδ TILs with potentially tumor reactive γδ TCR lack substantial clonal proliferation within tumor tissues. In addition, to this basic biological observation which indicates that public γ and δ TCR chains are an important but also vulnerable part of early cancer immune surveillance, identified receptors are a valuable tool for novel therapeutic compounds like TEGs.

Although clonal expansions of a TILs have been described (38), no substantial clonal dominance was observed within TNBC's γδ TIL populations when analyzed by spectratyping, NGS or single-cell PCR during our current study. This observed absence of significant clonal expansions in TNBC's γδ TILs is starkly contrasting the very skewed TCRδ1 repertoires in the adult peripheral blood (39, 40, 25) or in fetal CMV infections in utero containing several high-frequency clonotypes (31). Interestingly, proliferation proficiency of Vδ2$^+$ cells noticed in infectious challenges (41), is frequently absent in cancer patients (39). Also, elegant mouse model studies indicate that γδ T cells can prevent cancer development in the early disease stages (42, 43), but once the disease becomes more advanced, γδ TILs become rapidly proliferation-deficient, while maintaining other functional activities such as IFNγ or CD69 upregulation. Since we could not detect any γδ TILs with the Th17 phenotype, it's possible that the tumor microenvironment may be particularly inhibitory for this subset. The assumption of an early proliferation deficiency of γδ TILs would also favor single cell PCR instead of NGS for the identification of relevant receptors within the context of γδ TILs. However, a study as ours is technically challenging, and currently it is difficult to perform single cell sequencing analysis of tumor tissue in a high trough put manner.

Our data are compatible with the earlier findings of low relapse incidence of leukemia following cord blood transplantations (25). In this scenario, the high frequency of public Vδ2$^{neg}$ TCRδ chains in the cord blood cells could contribute substantially to a potential abundance of tumor-reactive receptors in the post-transplant repertoire (39, 40). In addition, CMV reactivation in patients who received non-T-cell-depleted peripheral blood stem cells after myeloablative conditioning regimens was associated with a reduced risk of leukemic relapse (44). We and others have suggested that this effect is partially mediated via γδ T cells (25, 45).

Willcox et al. have identified endothelial protein C receptor (EPCR) as a CMV-induced stress ligand for Vγ4Vδ5 T cells (22). We now classify the receptors chains of CMV-reactive clones partially as public. In one patient, we detected public TCRγ and TCRδ chains with the EPCR reactivity to be present at the tumor side, suggesting that these chains, particularly the Vδ5, could form receptors with tumor-reactivity. Indeed, γδ TILs in many TNBC patients expressed a shared Vδ5 TCR chain associated with anti-CMV responses. However, all TNBC patients with this particular shared Vδ5 TCR chain were CMV-negative. It is conceivable that CMV reactivations may not be clinically beneficial only in leukemias (46), but also could confer some protection against certain solid tumors. However, we also demonstrate with multiple TCR complexes comprised of public TCRγ or δ chains, that the corresponding chain is frequently private and key for anti-tumor activity. Therefore in these patients the corresponding counterpart might not mediate CMV or tumor reactivity when paired with a different opposing chain, as also suggested by our data and others (33).

Many clinical trials with ex vivo and in vitro expanded γδ T cells were not very successful (47) and the functional diversity within the γδ T cell repertoire may be a major factor contributing to these numerous failures of clinical translations of γδ T cell-based therapeutics (48). The observation that public TCRδ chains are frequently involved in the observed anti-tumor reactivity points toward possible strategies for creating potentially clinically-important T cells with defined γδ TCRs (TEGs) utilizing shared TCRγ and/or δ chains. Indeed, high-throughput analyses of CDR3 regions combined with single-cell sequencing of γδ TILs can narrow down very quickly the extremely diverse TCRδ repertoire from $10^{18}$ to literally perhaps less than $10^2$ sequences of therapeutic interest for generating novel therapeutic TEGs (49). Such receptors could be quickly analyzed functionally and custom made for each patient. Nevertheless, the absence of HLA restriction during the measured antitumor activities suggests the potential usage of these novel, freshly-created TEGs in numerous genetically unrelated patients.

For generating off the shelf products analyzing cord blood donors with a natural high frequency of public TCRγ and δ chains when compared to the adult repertoire could be a natural starting point. Shared TCRγ and δ chains have also been reported in patients with acute leukemia (50) and ovarian cancer (51) and such samples could also be an interesting source for further functional analyses. However, though the frequency and potency of tumor reactive receptors was in our analyses always higher within complexes harboring shared as compared to non-shared receptor chains, the identification of interesting receptors will always require a functional confirmation of defined receptors against a comprehensive tumor panel. Many analyzed receptor complexes harboring shared TCRγ or δ chains were complementary in reactivity against completely different types of cancer or not reactive at all suggesting that these receptors target complementary and so far unknown ligands.

Screening of TEGs against a limited panel of tumor cell lines and the potential absence of co-stimulatory signals that might be needed for the γδ T cell response somewhat restrict the interpretation of our data. Clearly, distinct TCRγδ pairs mediated different patterns of tumor reactivity, indicating that each individual pair of public TCRγδ chains may be reactive only against defined subsets of targets. One limitation of our studies clearly arises from screening of TEGs against a rather limited panel of tumor cell lines as we observed different patterns for tumor reactivity for different γδ TCR pairs. In addition, γδ TCR pairs might depend on additional co-stimulation not present within the TEG format. However, all tested receptors where active within the TEG format and expression within NEGs or GEGs did not show additional activity. This suggests that also for many Vδ2$^{neg}$ γδ T cells the TCR γδ chain alone is sufficient for full T cell activation but also that each individual pair with public TCR chains is apparently reactive only against defined subsets of targets. While an inside out mechanism involving CD277 (52, 53) and RhoB (24) has now been established for Vγ9Vδ2 TCR-mediated recognition, most ligands remain to be defined for many Vδ2$^{neg}$ TCRγδ combinations and testing of potentially interesting chains should therefore always include either a large and comprehensive tumor panels.

In summary, we describe frequencies of shared TCRδ chains within the peripheral blood γδ TCRs and γδ TILs. We also demonstrate that public TCRγ or δ chains are active and complementary participants in daily cancer immune surveillance. However, despite functional proofs of direct tumor-reactivity of involved receptors, we did not observe substantial clonal expansion of shared TCRδ repertoires within the local microenvironment, suggesting proliferation deficiency of γδ TILs in advanced cancer patients. In contrast, we detected shared tumor-reactive TCRδs within the peripheral blood repertoire of healthy individuals, which was compatible with the proposed role of the public tumor-reactive TCRδs in cancer immune surveillance. Thus, the identification of therapeutically relevant TCRs might be facilitated by analyzing shared TCRγδ repertories in different compartments in healthy and cancer patients. This involvement of public Vδ2$^+$ and Vδ2$^{neg}$ TCR clonotypes in tumor immune surveillance could be exploited for augmenting tumor-specific immunity. In particular, clarifying the precise nature of the recognized ligands, the exact mode of their recognition and their tissue distribution and regulation of expression may lead to developing novel therapeutic approaches and thus improving future γδ T cell-based cancer therapies.

TABLE 5

Overview used primers for NGS library preparation

| | |
|---|---|
| **cDNA synthesis** | |
| TRB reverse primer constant | CAGTATCTGGAGTCATTGA |
| TRD reverse primer constant | CTTGGATGACACGAGAT |
| Template switch adaptor | AAGCAGUGGTAUCAACGCAGAGUNNNNUNNNNUNNNNUCTT (rG)4 |
| **1st PCR** | |
| TRB nested reverse primer constant region | TGCTTCTGATGGCTCAAACAC |
| TRD nested reverse primer constant region | AACGGATGGTTTGGTATGAG |
| Forward primer (anneals to switch adaptor) | CACTCTATCCGACAAGCAGTGGTATCAACGCAG |
| **2nd PCR** | |
| TRB nested reverse primer constant region | ACACSTTKTTCAGGTCCTC |
| TRD nested reverse primer constant region | TTTGGTATGAGGCTGACTTC |
| Forward primer (anneals to switch adaptor) | CACTCTATCCGACAAGCAGT |

TABLE 6

Overview of used antibodies in different experiments.

| Antibody | Fluorchrome/color | Species | Dilution | Isotype | Clone | Cat No | Source |
|---|---|---|---|---|---|---|---|
| TCRγ | | Mouse monoclonal | 1:40 | IgG | γ3,20 | TCR1153 | Thermo Fisher |
| TCRγ | FITC | Mouse monoclonal | 1:20 | IgG1 | IMMU510 | IM1349 | Beckman Coulter |
| CD69 | | Mouse monoclonal | 1:30 | IgG | CH11 | NCLCD69 | Leica Biosystems |

TABLE 6-continued

Overview of used antibodies in different experiments.

| Antibody | Fluorchrome/color | Species | Dilution | Isotype | Clone | Cat No | Source |
|---|---|---|---|---|---|---|---|
| CMV | | Mouse monoclonal | Flex System | IgG1, K + L | CCH2 + DDG9 | IS752 | Dako |
| Cleaved Caspase 3 | | Rabbit monoclonal | 1:700 | IgG | 5A1E | mAb9664 | Cell Signalling |
| IFNγ | | Goat polyclonal | 1:200 | IgG | polyclonal | AF285NA | R&D Systems |
| IL-17 | | Goat polyclonal | 1:200 | IgG | polyclonal | AF317NA | R&D Systems |
| anti-rabbit/ Alexa Fluor 568 sec. Ab | | Donkey | 1:500 | IgG | polyclonal | Ab175470 | Abcam |
| anti-Mouse IgG/Alexa Fluor 488 sec. Ab | | Rabbit | 1:700 | IgG H + L | polyclonal | A11059 | Thermo Fisher |
| anti-goat IgG/Alexa Fluor 647 sec. Ab | | Donkey | 1:500 | IgG | polyclonal | ab150131 | Abcam |
| anti-goat IgG/Alexa Fluor 594 sec. Ab | | Donkey | 1:500 | IgG | polyclonal | Ab150132 | Abcam |
| CD3 | eFluor450 | Mouse monoclonal | 1:40 | IgG2a | OKT3 | 16-0037-81 | eBioscience |
| TCRαβ | APC | Mouse monoclonal | 1:10 | IgG1 | IP26 | 14-9986-42 | eBioscience |
| TCRγδ | PE | Mouse monoclonal | 1:10 | IgG1 | IMMU510 | B49716 | Beckman Coulter |
| TCRγδ | APC | Mouse monoclonal | 1:5 | IgG1 | B1 (RUO) | 555718 | BD biosciences |

TABLE 7

Overview of used primers for single cell PCR
Primers Single cell PCR

| Forward primers | |
|---|---|
| Vg18-F1 | AGGGGAAGGCCCCACAGCGTCTTC |
| Vg18-F2: | CAGCGTCTTCWGTACTATGAC |
| Vg9-F1 | TGACGGCACTGTCAGAAAGGAATC |
| Vg9-F2 | TGAGGTGGATAGGATACCTGAAAC |
| Vd1-F1 (Biomed) | ATGCAAAAAGTGGTCGCTATTCTG |
| Vd1-F2 | CAACTTCAAGAAAGCAGCGAAATC |
| Vd2-F1 (Biomed) | ATACCGAGAAAAGGACATCTATG |
| Vd2-F2 | CAAGGTGACATTGATATTGCAAAG |
| Vd3-F1 | GGTTTTCTGTGAAACACATTCTGAC |
| Vd3-F2 | CTTTCACTTGGTGATCTCTCCAG |
| Vd4-F1(Biorned) | ATGACCAGCAAAATGCAACAGAAG |
| Vd4-F2 | CGCTACTCATTGAATTTCCAGAAG |
| Vd5-F1(Biomed) | TACCCTGCTGAAGGTCCTACATTC |
| Vd5-F2 | CTGTCTTCTTAAACAAAAGTGCCAAG |
| Vd6-F1(Biomed) | CCCTGCATTATTGATAGCCATACG |
| Vd6-F2 | TGCCAAGCAGTTCTCATTGCATATC |

TABLE 7-continued

Overview of used primers for single cell PCR
Primers Single cell PCR

| Reverse primers | |
|---|---|
| TRg-JP1/2-R1 | TTACCAGGYGAAGTTACTATGAGC |
| TRg-J1/2-R1 | AAGTGTTGTTCCACTGCCAAAGAG |
| TRg-JP-R1 | AAGCTTTGTTCCGGGACCAAATAC |
| Jd1-R1 | TTGGTTCCACAGTCACACGGGTTC |
| Jd2-R1 | CTGGTTCCACGATGAGTTGTGTTC |
| Jd3-R1 | CAACTCACGGGGCTCCACGAAGAG |
| Jd4-R1 | TTGTACCTCCAGATAGGTTCCTTTG |

TABLE 8

Shared TCRδ sequences (dataset 1) clonal frequency >0.1%

| Sequence CDR3δ | Identified in donor |
|---|---|
| Vδ1 | |
| CALGDSYGGGPLYTDKLIF* | 13, 19 |
| Vδ2 | |
| CACDVLGDTDKLIF** | 18, 19, 20 |
| CACDLLGDTGDKLIF** | 25, 29 |
| CACDTAGGSWDTRQMFF** | 13, 19 |

TABLE 8-continued

| Shared TCRδ sequences (dataset 1) clonal frequency >0.1% | |
|---|---|
| Sequence CDR3δ | Identified in donor |
| CACDTLGAYTDKLIF** | 20, 25 |
| CACDTLGDTDKLIF** | 19, 23 |
| CACDTLLGDSSWDTRQMFF** | 13, 19 |
| CACDTPSSWDTRQMFF** | 13, 19 |
| CACDTTGGPSSWDTRQMFF** | 12, 23 |
| CACDTVGDTDKLIF** | 11, 29 |
| CACDTVGGTDKLIF** | 15, 19 |
| CACDTVGTYTDKLIF** | 13, 25 |
| CACDTVLGDTRSWDTRQMFF* | 20, 70 |
| CACDTWGTDKLIF** | 29, 31 |
| CACDTWGYTDKLIF** | 29, 31 |

Examples of shared sequences within 14 healthy donors were identified. CDR36 sequences obtained with NGS of dataset 1 with a clonal frequency>0.1% were compared to identify shared sequences between donors. * Indicates sequence of clone FE11 which has been isolated from an additional healthy donor. ** Indicates sequence was also identified in another dataset.

Example 3: Stability Testing

A pharmaceutical composition described herein containing at least one polypeptide described herein or an engineered cell expressing a polypeptide described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the pharmaceutical composition shall remain as determined by standard protocols.

While specific embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 9

| Pnt | Cln | TRG Rearrangement | TRG CDR3 | TRD Rearrangement | TRD CDR3 |
|---|---|---|---|---|---|
| B | 9[#] | TRGV5*GJ1** | CATWDRLYYKKLF[&] | TRDV1*DD3*DJ1 | CALGNGNHIGYWRYTDKLIF |
| B | 23[#] | TRGV8*GJ1 | **CATWDNYKKLF** | TRAV29/DV5DD3*DJ1* | **CAASSPIRGYTGSDKLIF**[%] |
| C | 132[#$] | TRGV4*GJ1* | CATWDGFYYKKLF | TRAV29/DV5DJ1DD2DD3* | **CAASSPIRGYTGSDKLIF**[%] |
| D | 37[#] | TRGV8*GJ1 | CATWDNYMKLF | TRAV29/DV5 *DD2*DD3*DJ1 | **CAASSPIRGYTGSDKLIF**[%] |
| E | 113[#] | TRGV4*GJ1 | **CATWDGPPYYKKLF** | TRAV29/DV5 *DD2DD3**DJ1 | **CAASSPIRGYTGSDKLIF**[%] |
| F | 2[#] | TRGV4*GJ1 | **CATWDGPPYYKKLF** | TRDV3 *DD2*DD3*DJ1 | CASSYTLKLGDTPGRVRDWKLIF |
| F | 4[#] | TRGV2GJ1 | **CATWDGQKKLF** | TRDV1*DD3*DJ1 | CALGELRYWGIVDKLIF |
| Z | e11[#] | TRGV8*GJ1 | **CATWDNYKKLF** | TRDV1*DD3*01DJ1 | **CALGDYLGDKYPSYDLLGDTTDKLIF** |
| Z | i11[#] | TRGV8*GJ1 | **CATWDNYKKLF** | TRDV1*DD1*DD2*DD3*DJ 1 | CALGELRGQISFLYLLGDTTDKLIF |

Overview of examples of paired sequences of γδ TIL's found in patients with triple negative breast cancer. Bold alphabets indicate identical sequences. # Indicates that these clones were used to generate TEG's for functional essays. $ Indicates clone published by Lafarge et al; doi:10.1002/eji.200425837. % Indicates delta chain published by Lafarge et al; doi:10.1002/eji.200425837. & Indicates gamma chain published by Uldirch et al.; doi:10.1038/ni.2713

LIST OF REFERENCES

1. Chien Y H, Meyer C, Bonneville M. 2014. gammadelta T Cells: First Line of Defense and Beyond. *Annu. Rev. Immunol.*
2. Kim S K, Cornberg M, Wang X Z, Chen H D, Selin L K, Welsh R M. 2005. Private specificities of CD8 T cell responses control patterns of heterologous immunity. *J Exp Med* 201: 523-33
3. Miles J J, Elhassen D, Borg N A, Silins S L, Tynan F E, Burrows J M, Purcell A W, Kjer-Nielsen L, Rossjohn J, Burrows S R, McCluskey J. 2005. CTL recognition of a bulged viral peptide involves biased TCR selection. *J Immunol* 175: 3826-34
4. Venturi V, Price D A, Douek D C, Davenport M P. 2008. The molecular basis for public T-cell responses? *Nat Rev Immunol* 8: 231-8

5. Wang C, Liu Y, Cavanagh M M, Le Saux S, Qi Q, Roskin K M, Looney T J, Lee J Y, Dixit V, Dekker C L, Swan G E, Goronzy J J, Boyd S D. 2015. B-cell repertoire responses to varicella-zoster vaccination in human identical twins. *Proc Natl Acad Sci USA* 112: 500-5

6. Kuball J, Dossett M L, Wolfl M, Ho W Y, Voss R H, Fowler C, Greenberg P D. 2007. Facilitating matched pairing and expression of TCR chains introduced into human T cells. *Blood* 109: 2331-8

7. Bolotin D A, Poslavsky S, Mitrophanov I, Shugay M, Mamedov I Z, Putintseva E V, Chudakov D M. 2015. MiXCR: software for comprehensive adaptive immunity profiling. *Nat Methods* 12:380-1

8. Shugay M, Britanova O V, Merzlyak E M, Turchaninova M A, Mamedov I Z, Tuganbaev T R, Bolotin D A, Staroverov D B, Putintseva E V, Plevova K, Linnemann C, Shagin D, Pospisilova S, Lukyanov S, Schumacher T N, Chudakov D M. 2014. Towards error-free profiling of immune repertoires. *Nat Methods* 11: 653-5

9. Scheper W, van Dorp S, Kersting S, Pietersma F, Lindemans C, Hol S, Heijhuurs S, Sebestyen Z, Grunder C, Marcu-Malina V, Marchant A, Donner C, Plachter B, Vermijlen D, van Baarle D, Kuball J. 2013. gammadeltaT cells elicited by CMV reactivation after allo-SCT cross-recognize CMV and leukemia. *Leukemia* 27: 1328-38

10. Scheper w. 2014. Cancer immunotherapy using γδT cells: dealing with diversity. *Thesis*

11. Grunder C, van D S, Hol S, Drent E, Straetemans T, Heijhuurs S, Scholten K, Scheper W, Sebestyen Z, Martens A, Strong R, Kuball J. 2012. gamma9 and delta2CDR3 domains regulate functional avidity of T cells harboring gamma9delta2TCRs. *Blood* 120: 5153-62

12. Straetemans T, Grunder C, Heijhuurs S, Hol S, Slaper-Cortenbach I, Bonig H, Sebestyen Z, Kuball J. 2015. Untouched GMP-ready purified engineered immune cells to treat cancer. *Clin Cancer Res*

13. de Witte M A, Kierkels G J, Straetemans T, Britten C M, Kuball J. 2015. Orchestrating an immune response against cancer with engineered immune cells expressing alphabetaTCRs, CARs, and innate immune receptors: an immunological and regulatory challenge. *Cancer Immunol Immunother* 64: 893-902

14. Salgado R, Denkert C, Campbell C, Savas P, Nuciforo P, Aura C, de Azambuja E, Eidtmann H, Ellis C E, Baselga J, Piccart-Gebhart M J, Michiels S, Bradbury I, Sotiriou C, Loi S. 2015. Tumor-Infiltrating Lymphocytes and Associations With Pathological Complete Response and Event-Free Survival in HER2-Positive Early-Stage Breast Cancer Treated With Lapatinib and Trastuzumab: A Secondary Analysis of the NeoALTTO Trial. *JAMA Oncol* 1: 448-54

15. Loi S, Dushyanthen S, Beavis P A, Salgado R, Denkert C, Savas P, Combs S, Rimm D L, Giltnane J M, Estrada M V, Sanchez V, Sanders M E, Cook R S, Pilkinton M A, Mallal S A, Wang K, Miller V A, Stephens P J, Yelensky R, Doimi F D, Gomez H, Ryzhov S V, Darcy P K, Arteaga C L, Balko J M. 2016. RAS/MAPK Activation Is Associated with Reduced Tumor-Infiltrating Lymphocytes in Triple-Negative Breast Cancer: Therapeutic Cooperation Between MEK and PD-1/PD-L1 Immune Checkpoint Inhibitors. *Clin Cancer Res* 22: 1499-509

16. Nielsen T O, Hsu F D, Jensen K, Cheang M, Karaca G, Hu Z, Hernandez-Boussard T, Livasy C, Cowan D, Dressler L, Akslen L A, Ragaz J, Gown A M, Gilks C B, van de Rijn M, Perou C M. 2004. Immunohistochemical and clinical characterization of the basal-like subtype of invasive breast carcinoma. *Clin Cancer Res* 10: 5367-74

17. Bender C, Zipeto D, Bidoia C, Costantini S, Zamo A, Menestrina F, Bertazzoni U. 2009. Analysis of colorectal cancers for human cytomegalovirus presence. *Infect Agent Cancer* 4: 6

18. Mamedov I Z, Britanova O V, Zvyagin I V, Turchaninova M A, Bolotin D A, Putintseva E V, Lebedev Y B, Chudakov D M. 2013. Preparing unbiased T-cell receptor and antibody cDNA libraries for the deep next generation sequencing profiling. *Front Immunol* 4: 456.

19. Hidalgo J V, Bronsert P, Orlowska-Volk M, Diaz L B, Stickeler E, Werner M, Schmitt-Graeff A, Kayser G, Malkovsky M, Fisch P. 2014. Histological Analysis of gammadelta T Lymphocytes Infiltrating Human Triple-Negative Breast Carcinomas. *Front Immunol* 5: 632

20. Schneider C A, Rasband W S, Eliceiri K W. 2012. NIH Image to ImageJ: 25 years of image analysis. *Nat Methods* 9: 671-5

21. Brauninger A, Hansmann M L, Strickler J G, Dummer R, Burg G, Rajewsky K, Kuppers R. 1999. Identification of common germinal-center B-cell precursors in two patients with both Hodgkin's disease and non-Hodgkin's lymphoma. *N Engl J Med* 340: 1239-47

22. Straetemans T, Grunder C, Heijhuurs S, Hol S, Slaper-Cortenbach I, Bonig H, Sebestyen Z, Kuball J. 2015. Untouched GMP-Ready Purified Engineered Immune Cells to Treat Cancer. *Clin Cancer Res* 21: 3957-68

23. Grunder C, van D S, Hol S, Drent E, Straetemans T, Heijhuurs S, Scholten K, Scheper W, Sebestyen Z, Martens A, Strong R, Kuball J. 2012. gamma9 and delta2CDR3 domains regulate functional avidity of T cells harboring gamma9delta2TCRs. *Blood* 120: 5153-62

24. Sebestyen Z, Scheper W, Vyborova A, Gu S, Rychnavska Z, Schiffler M, Cleven A, Cheneau C, van Noorden M, Peigne C M, Olive D, Lebbink R J, Oostvogels R, Mutis T, Schuurhuis G J, Adams E J, Scotet E, Kuball J. 2016. RhoB Mediates Phosphoantigen Recognition by Vgamma9Vdelta2 T Cell Receptor. *Cell Rep* 15: 1973-85

25. Scheper W, van Dorp S, Kersting S, Pietersma F, Lindemans C, Hol S, Heijhuurs S, Sebestyen Z, Grunder C, Marcu-Malina V, Marchant A, Donner C, Plachter B, Vermijlen D, van Baarle D, Kuball J. 2013. gammadeltaT cells elicited by CMV reactivation after allo-SCT cross-recognize CMV and leukemia. *Leukemia* 27: 1328-38

26. Marcu-Malina V, Heijhuurs S, van B M, Hartkamp L, Strand S, Sebestyen Z, Scholten K, Martens A, Kuball J. 2011. Redirecting alphabeta T cells against cancer cells by transfer of a broadly tumor-reactive gammadeltaT-cell receptor. *Blood* 118: 50-9

27. Holtmeier W, Chowers Y, Lumeng A, Morzycka-Wroblewska E, Kagnoff M F. 1995. The delta T cell receptor repertoire in human colon and peripheral blood is oligoclonal irrespective of V region usage. *J Clin Invest* 96: 1108-17

28. Chien Y H, Meyer C, Bonneville M. 2014. gammadelta T Cells: First Line of Defense and Beyond. *Annu. Rev. Immunol.*

29. Hidalgo J V, Bronsert P, Orlowska-Volk M, Diaz L B, Stickeler E, Werner M, Schmitt-Graeff A, Kayser G, Malkovsky M, Fisch P. 2014. Histological Analysis of gammadelta T Lymphocytes Infiltrating Human Triple-Negative Breast Carcinomas. *Front Immunol* 5: 632

30. Gentles A J, Newman A M, Liu C L, Bratman S V, Feng W, Kim D, Nair Vδ, Xu Y, Khuong A, Hoang C D, Diehn M, West R B, Plevritis S K, Alizadeh A A. 2015. The prognostic landscape of genes and infiltrating immune cells across human cancers. *Nat Med* 21: 938-45

31. Coffelt S B, Kersten K, Doornebal C W, Weiden J, Vrijland K, Hau C S, Verstegen N J, Ciampricotti M, Hawinkels L J, Jonkers J, de Visser K E. 2015. IL-17-producing gammadelta T cells and neutrophils conspire to promote breast cancer metastasis. *Nature* 522: 345-8

32. Li B, Li T, Pignon J C, Wang B, Wang J, Shukla S A, Dou R, Chen Q, Hodi F S, Choueiri T K, Wu C, Hacohen N, Signoretti S, Liu J S, Liu X S. 2016. Landscape of tumor-infiltrating T cell repertoire of human cancers. *Nat Genet*

33. Willcox C R, Pitard V, Netzer S, Couzi L, Salim M, Silberzahn T, Moreau J F, Hayday A C, Willcox B E, chanet-Merville J. 2012. Cytomegalovirus and tumor stress surveillance by binding of a human gammadelta T cell antigen receptor to endothelial protein C receptor. *Nat. Immunol.* 13: 872-9

34. Uldrich A P, Le Nours J, Pellicci D G, Gherardin N A, McPherson K G, Lim R T, Patel O, Beddoe T, Gras S, Rossjohn J, Godfrey D I. 2013. CD1d-lipid antigen recognition by the gammadelta TCR. *Nat Immunol* 14: 1137-45

35. Couzin-Frankel J. 2013. Breakthrough of the year 2013. Cancer immunotherapy. *Science* 342: 1432-3

36. Lim W A, June C H. 2017. The Principles of Engineering Immune Cells to Treat Cancer. *Cell* 168: 724-40

37. Bouchie A, DeFrancesco L, Sheridan C, Webb S. 2017. Nature Biotechnology's academic spinouts of 2016. *Nat Biotechnol* 35: 322-33

38. Sittig S P, Kollgaard T, Gronbaek K, Idorn M, Hennenlotter J, Stenzl A, Gouttefangeas C, Thor Straten P. 2013. Clonal expansion of renal cell carcinoma-infiltrating T lymphocytes. *Oncoimmunology* 2: e26014

39. Davey M S, Willcox C R, Joyce S P, Ladell K, Kasatskaya S A, McLaren J E, Hunter S, Salim M, Mohammed F, Price D A, Chudakov D M, Willcox B E. 2017. Clonal selection in the human Vdelta1 T cell repertoire indicates gammadelta TCR-dependent adaptive immune surveillance. *Nat Commun* 8: 14760

40. Ravens S, Schultze-Florey C, Raha S, Sandrock I, Drenker M, Oberdorfer L, Reinhardt A, Ravens I, Beck M, Geffers R, von Kaisenberg C, Heuser M, Thol F, Ganser A, Forster R, Koenecke C, Prinz I. 2017. Human gammadelta T cells are quickly reconstituted after stem-cell transplantation and show adaptive clonal expansion in response to viral infection. *Nat Immunol*

41. Ding Y, Ma F, Wang Z, Li B. 2015. Characteristics of the Vdelta2 CDR3 Sequence of Peripheral gammadelta T Cells in Patients with Pulmonary Tuberculosis and Identification of a New Tuberculosis-Related Antigen Peptide. *Clin Vaccine Immunol* 22: 761-8

42. Dadi S, Chhangawala S, Whitlock B M, Franklin R A, Luo C T, Oh S A, Toure A, Pritykin Y, Huse M, Leslie C S, Li M O. 2016. Cancer Immunosurveillance by Tissue-Resident Innate Lymphoid Cells and Innate-like T Cells. *Cell* 164: 365-77

43. Xiang Z, Liu Y, Zheng J, Liu M, Lv A, Gao Y, Hu H, Lam K T, Chan G C, Yang Y, Chen H, Tsao G S, Bonneville M, Lau Y L, Tu W. 2014. Targeted activation of human Vgamma9Vdelta2-T cells controls epstein-barr virus-induced B cell lymphoproliferative disease. *Cancer Cell* 26: 565-76

44. Elmaagacli A H, Koldehoff M. 2016. Cytomegalovirus replication reduces the relapse incidence in patients with acute myeloid leukemia. *Blood* 128: 456-9

45. Airoldi I, Bertaina A, Prigione I, Zorzoli A, Pagliara D, Cocco C, Meazza R, Loiacono F, Lucarelli B, Bernardo M E, Barbarito G, Pende D, Moretta A, Pistoia V, Moretta L, Locatelli F. 2015. gammadelta T-cell reconstitution after HLA-haploidentical hematopoietic transplantation depleted of TCR-alphabeta+/CD19+ lymphocytes. *Blood* 125: 2349-58

46. Scheper W, Grunder C, Straetemans T, Sebestyen Z, Kuball J. 2013. Hunting for clinical translation with innate-like immune cells and their receptors. *Leukemia*

47. Deniger D C, Moyes J S, Cooper U. 2014. Clinical applications of gamma delta T cells with multivalent immunity. *Front Immunol* 5: 636

48. Scheper W, Sebestyen Z, Kuball J. 2014. Cancer Immunotherapy Using gammadeltaT Cells: Dealing with Diversity. *Front Immunol* 5: 601

49. de Witte M A, Kierkels G J, Straetemans T, Britten C M, Kuball J. 2015. Orchestrating an immune response against cancer with engineered immune cells expressing alphabetaTCRs, CARs, and innate immune receptors: an immunological and regulatory challenge. *Cancer Immunol Immunother* 64: 893-902

50. Meeh P F, King M, O'Brien R L, Muga S, Buckhalts P, Neuberg R, Lamb L S, Jr. 2006. Characterization of the gammadelta T cell response to acute leukemia. *Cancer Immunol. Immunother.* 55: 1072-80

51. Xu C, Zhang H, Hu H, He H, Wang Z, Xu Y, Chen H, Cao W, Zhang S, Cui L, Ba D, He W. 2007. Gammadelta T cells recognize tumor cells via CDR3delta region. *Mol Immunol* 44: 302-10

52. Sandstrom A, Peigne C M, Leger A, Crooks J E, Konczak F, Gesnel M C, Breathnach R, Bonneville M, Scotet E, Adams E J. 2014. The intracellular B30.2 domain of butyrophilin 3A1 binds phosphoantigens to mediate activation of human Vgamma9Vdelta2 T cells. *Immunity* 40: 490-500

53. Harly C, Guillaume Y, Nedellec S, Peigne C M, Monkkonen H, Monkkonen J, Li J, Kuball J, Adams E J, Netzer S, chanet-Merville J, Leger A, Herrmann T, Breathnach R, Olive D, Bonneville M, Scotet E. 2012. Key implication of CD277/butyrophilin-3 (BTN3A) in cellular stress sensing by a major human gammadelta T-cell subset. *Blood* 120: 2269-79

The invention claimed is:

1. A method of treating a cancer or an infection in a subject in need thereof comprising: administering intravenously to the subject an engineered T cell, wherein said cell comprises a nucleic acid molecule encoding an exogenous γT-cell receptor chain or part thereof comprising a CDR3 region, wherein said nucleic acid molecule is represented by:

a) a nucleotide sequence that comprises at least 90% identity with any one of SEQ ID NO: 41, 43, 45, 47, 49, 77, 79, 81, or 93, or;

b) a nucleotide sequence that comprises at least 90% identity with any one of SEQ ID NO: 53, 55, 57, 59, 61, 83, 85, 87, or 95, or;

c) a nucleotide sequence that encodes an amino acid sequence that comprises at least 90% identity or similarity with any one of SEQ ID NO: 30, 32, 34, 36, 38, 71, 73, 75, or 91.

2. The method of claim 1, wherein the cell comprises an exogenous γT-cell receptor chain represented by an amino acid sequence that comprises at least 90% identity or similarity with any one of SEQ ID NO: 30, 32, 34, 36, 38, 71, 73, 75, or 91.

3. The method of claim 1, wherein the subject in need thereof is a human being.

4. The method of claim 1, wherein the disease is a cancer, and wherein said cancer is a solid cancer or a hematological cancer.

5. The method of claim 4, wherein the cancer is leukemia or breast cancer.

6. The method of claim 5, wherein the breast cancer is triple negative breast cancer.

7. The method of claim 1, wherein the disease is an infection caused by a virus, a bacterium, or a fungus.

8. The method of claim 1, wherein said cell further comprises a nucleic acid molecule encoding an exogenous δT-cell receptor chain or part thereof comprising a CDR3 region, wherein said nucleic acid molecule is represented by:

e) a nucleotide sequence that comprises at least 90% identity with any one of SEQ ID NO: 26, 42, 44, 46, 48, 76, 78, 80, or 82, or;

f) a nucleotide sequence that comprises at least 90% identity with any one of SEQ ID NO: 52, 54, 56, 58, 60, 82, 84, 86, or 94, or;

g) a nucleotide sequence that encodes an amino acid sequence that comprises at least 90% identity or similarity with any one of SEQ ID NO: 29, 31, 33, 35, 37, 70, 72, 74, or 90.

9. The method of claim 8, wherein the cell comprises an exogenous γT-cell receptor chain represented by an amino acid sequence that comprises at least 90% identity or similarity with any one of SEQ ID NO: 30, 32, 34, 36, 38, 71, 73, 75, or 91, and an exogenous δT-cell receptor chain represented by an amino acid sequence that comprises at least 90% identity or similarity with any one of SEQ ID NO: 29, 31, 33, 35, 37, 70, 72, 74, or 90.

10. The method of claim 1, wherein the nucleic acid molecule encoding the exogenous γT-cell receptor chain or part thereof comprising a CDR3 region is represented by:

a) a nucleotide sequence that comprises at least 90% identity with SEQ ID NO: 49, or;

b) a nucleotide sequence that comprises at least 90% identity with SEQ ID NO: 61, or;

c) a nucleotide sequence that encodes an amino acid sequence that comprises at least 90% identity or similarity with SEQ ID NO: 38.

11. The method of claim 8, wherein the nucleic acid molecule encoding the exogenous γT-cell receptor chain or part thereof comprising a CDR3 region is represented by:

a) a nucleotide sequence that comprises at least 90% identity with SEQ ID NO: 49, or;

b) a nucleotide sequence that comprises at least 90% identity with SEQ ID NO: 61, or;

c) a nucleotide sequence that encodes an amino acid sequence that comprises at least 90% identity or similarity with SEQ ID NO: 38 and;

the nucleic acid molecule encoding an exogenous δT-cell receptor chain or part thereof comprising a CDR3 region is represented by:

e) a nucleotide sequence that comprises at least 90% identity with SEQ ID NO: 48, or;

f) a nucleotide sequence that comprises at least 90% identity with SEQ ID NO: 60, or;

g) a nucleotide sequence that encodes an amino acid sequence that comprises at least 90% identity or similarity with SEQ ID NO: 37.

12. The method of claim 10, wherein the nucleic acid molecule encoding the exogenous γT-cell receptor chain or part thereof comprising a CDR3 region is represented by:

a) a nucleotide sequence that comprises SEQ ID NO: 49, or;

b) a nucleotide sequence that comprises SEQ ID NO: 61, or;

c) a nucleotide sequence that encodes an amino acid sequence that comprises SEQ ID NO: 38.

13. The method of claim 11, wherein the nucleic acid molecule encoding the exogenous γT-cell receptor chain or part thereof comprising a CDR3 region is represented by:

a) a nucleotide sequence that comprises SEQ ID NO: 49, or;

b) a nucleotide sequence that comprises SEQ ID NO: 61, or;

c) a nucleotide sequence that encodes an amino acid sequence that comprises SEQ ID NO: 38 and;

the nucleic acid molecule encoding an exogenous δT-cell receptor chain or part thereof comprising a CDR3 region is represented by:

e) a nucleotide sequence that comprises SEQ ID NO: 48, or;

f) a nucleotide sequence that comprises SEQ ID NO: 60, or;

g) a nucleotide sequence that encodes an amino acid sequence that comprises SEQ ID NO: 37.

* * * * *

SEQUENCE LISTING

```
<160> NUMBER OF SEQ ID NOS: 101

<210> SEQ ID NO 1
<211> LENGTH: 19
<212> TYPE: DNA
<213> ORGANISM: artificial
<220> FEATURE:
<223> OTHER INFORMATION: primer: Constant region TRB

<400> SEQUENCE: 1
```

```
cagtatctgg agtcattga                                                    19


<210> SEQ ID NO 2
<211> LENGTH: 17
<212> TYPE: DNA
<213> ORGANISM: artificial
<220> FEATURE:
<223> OTHER INFORMATION: primer: Constant region TRD

<400> SEQUENCE: 2

cttggatgac acgagat                                                      17


<210> SEQ ID NO 3
<211> LENGTH: 45
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (24)..(27)
<223> OTHER INFORMATION: n is a, c, g, t or u
<220> FEATURE:
<221> NAME/KEY: misc_feature
<222> LOCATION: (29)..(32)
<223> OTHER INFORMATION: n is a, c, g, t or u
<220> FEATURE:
<221> NAME/KEY: misc_feature
<222> LOCATION: (34)..(37)
<223> OTHER INFORMATION: n is a, c, g, t or u
<220> FEATURE:
<221> NAME/KEY: misc_feature
<222> LOCATION: (42)..(45)
<223> OTHER INFORMATION: riboguanosine

<400> SEQUENCE: 3

aagcaguggt aucaacgcag agunnnnunn nnunnnnuct tgggg                       45


<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4

tgcttctgat ggctcaaaca c                                                 21


<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5

aacggatggt ttggtatgag                                                   20


<210> SEQ ID NO 6
<211> LENGTH: 33
<212> TYPE: DNA
<213> ORGANISM: Artificial
<220> FEATURE:
<223> OTHER INFORMATION: Primer

<400> SEQUENCE: 6

cactctatcc gacaagcagt ggtatcaacg cag                                    33
```

```
<210> SEQ ID NO 7
<211> LENGTH: 19
<212> TYPE: PRT
<213> ORGANISM: Artificial
<220> FEATURE:
<223> OTHER INFORMATION: peptide, Vd1 Fe11

<400> SEQUENCE: 7

Cys Ala Leu Gly Asp Ser Tyr Gly Gly Gly Pro Leu Tyr Thr Asp Lys
1               5                   10                  15

Leu Ile Phe


<210> SEQ ID NO 8
<211> LENGTH: 14
<212> TYPE: PRT
<213> ORGANISM: Artificial
<220> FEATURE:
<223> OTHER INFORMATION: Peptide: Vd2, clone 3

<400> SEQUENCE: 8

Cys Ala Cys Asp Leu Leu Gly Tyr Thr Asp Lys Leu Ile Phe
1               5                   10


<210> SEQ ID NO 9
<211> LENGTH: 16
<212> TYPE: PRT
<213> ORGANISM: Artificial
<220> FEATURE:
<223> OTHER INFORMATION: Peptide: Vd2, clone 5

<400> SEQUENCE: 9

Cys Ala Cys Asp Ala Leu Lys Arg Thr Asp Thr Asp Lys Leu Ile Phe
1               5                   10                  15


<210> SEQ ID NO 10
<211> LENGTH: 13
<212> TYPE: PRT
<213> ORGANISM: Artificial
<220> FEATURE:
<223> OTHER INFORMATION: Peptide: CDR3 gamma chain, Fe11

<400> SEQUENCE: 10

Ala Thr Trp Asp Arg Pro Glu Ile Tyr Tyr Lys Lys Leu
1               5                   10


<210> SEQ ID NO 11
<211> LENGTH: 15
<212> TYPE: PRT
<213> ORGANISM: Artificial
<220> FEATURE:
<223> OTHER INFORMATION: Peptide: CDR3 gamma chain, clone 3

<400> SEQUENCE: 11

Cys Ala Leu Trp Glu Glu Glu Leu Gly Lys Lys Ile Lys Val Phe
1               5                   10                  15


<210> SEQ ID NO 12
<211> LENGTH: 16
<212> TYPE: PRT
<213> ORGANISM: Artificial
<220> FEATURE:
<223> OTHER INFORMATION: Peptide: CDR3 gamma chain, clone 5

<400> SEQUENCE: 12

Cys Ala Leu Trp Glu Ile Gln Glu Leu Gly Lys Lys Ile Lys Val Phe
1               5                   10                  15
```

```
<210> SEQ ID NO 13
<211> LENGTH: 288
<212> TYPE: PRT
<213> ORGANISM: Artificial
<220> FEATURE:
<223> OTHER INFORMATION: TRD Cl3

<400> SEQUENCE: 13

Met Glu Arg Ile Ser Ser Leu Ile His Leu Ser Leu Phe Trp Ala Gly
1               5                   10                  15

Val Met Ser Ala Ile Glu Leu Val Pro Glu His Gln Thr Val Pro Val
            20                  25                  30

Ser Ile Gly Val Pro Ala Thr Leu Arg Cys Ser Met Lys Gly Glu Ala
        35                  40                  45

Ile Gly Asn Tyr Tyr Ile Asn Trp Tyr Arg Lys Thr Gln Gly Asn Thr
    50                  55                  60

Met Thr Phe Ile Tyr Arg Glu Lys Asp Ile Tyr Gly Pro Gly Phe Lys
65                  70                  75                  80

Asp Asn Phe Gln Gly Asp Ile Asp Ile Ala Lys Asn Leu Ala Val Leu
                85                  90                  95

Lys Ile Leu Ala Pro Ser Glu Arg Asp Glu Gly Ser Tyr Tyr Cys Ala
            100                 105                 110

Cys Asp Leu Leu Gly Tyr Thr Asp Lys Leu Ile Phe Gly Lys Gly Thr
        115                 120                 125

Arg Val Thr Val Glu Pro Arg Ser Gln Pro His Thr Lys Pro Ser Val
    130                 135                 140

Phe Val Met Lys Asn Gly Thr Asn Val Ala Cys Leu Val Lys Glu Phe
145                 150                 155                 160

Tyr Pro Lys Asp Ile Arg Ile Asn Leu Val Ser Ser Lys Lys Ile Thr
                165                 170                 175

Glu Phe Asp Pro Ala Ile Val Ile Ser Pro Ser Gly Lys Tyr Asn Ala
            180                 185                 190

Val Lys Leu Gly Lys Tyr Glu Asp Ser Asn Ser Val Thr Cys Ser Val
        195                 200                 205

Gln His Asp Asn Lys Thr Val His Ser Thr Asp Phe Glu Val Lys Thr
    210                 215                 220

Asp Ser Thr Asp His Val Lys Pro Lys Glu Thr Glu Asn Thr Lys Gln
225                 230                 235                 240

Pro Ser Lys Ser Cys His Lys Pro Lys Ala Ile Val His Thr Glu Lys
                245                 250                 255

Val Asn Met Met Ser Leu Thr Val Leu Gly Leu Arg Met Leu Phe Ala
            260                 265                 270

Lys Thr Val Ala Val Asn Phe Leu Leu Thr Ala Lys Leu Phe Phe Leu
        275                 280                 285

<210> SEQ ID NO 14
<211> LENGTH: 313
<212> TYPE: PRT
<213> ORGANISM: Artificial
<220> FEATURE:
<223> OTHER INFORMATION: TRG Cl3

<400> SEQUENCE: 14

Met Val Ser Leu Leu His Ala Ser Thr Leu Ala Val Leu Gly Ala Leu
1               5                   10                  15

Cys Val Tyr Gly Ala Gly His Leu Glu Gln Pro Gln Ile Ser Ser Thr
```

```
            20                  25                  30

Lys Thr Leu Ser Lys Thr Ala Arg Leu Glu Cys Val Val Ser Gly Ile
        35                  40                  45

Thr Ile Ser Ala Thr Ser Val Tyr Trp Tyr Arg Glu Arg Pro Gly Glu
    50                  55                  60

Val Ile Gln Phe Leu Val Ser Ile Ser Tyr Asp Gly Thr Val Arg Lys
65                  70                  75                  80

Glu Ser Gly Ile Pro Ser Gly Lys Phe Glu Val Asp Arg Ile Pro Glu
                85                  90                  95

Thr Ser Thr Ser Thr Leu Thr Ile His Asn Val Glu Lys Gln Asp Ile
            100                 105                 110

Ala Thr Tyr Tyr Cys Ala Leu Trp Glu Glu Glu Leu Gly Lys Lys Ile
        115                 120                 125

Lys Val Phe Gly Pro Gly Thr Lys Leu Ile Ile Thr Asp Lys Gln Leu
    130                 135                 140

Asp Ala Asp Val Ser Pro Lys Pro Thr Ile Phe Leu Pro Ser Ile Ala
145                 150                 155                 160

Glu Thr Lys Leu Gln Lys Ala Gly Thr Tyr Leu Cys Leu Leu Glu Lys
                165                 170                 175

Phe Phe Pro Asp Val Ile Lys Ile His Trp Glu Glu Lys Lys Ser Asn
            180                 185                 190

Thr Ile Leu Gly Ser Gln Glu Gly Asn Thr Met Lys Thr Asn Asp Thr
        195                 200                 205

Tyr Met Lys Phe Ser Trp Leu Thr Val Pro Glu Lys Ser Leu Asp Lys
    210                 215                 220

Glu His Arg Cys Ile Val Arg His Glu Asn Asn Lys Asn Gly Val Asp
225                 230                 235                 240

Gln Glu Ile Ile Phe Pro Pro Ile Lys Thr Asp Val Ile Thr Met Asp
                245                 250                 255

Pro Lys Asp Asn Cys Ser Lys Asp Ala Asn Asp Thr Leu Leu Leu Gln
            260                 265                 270

Leu Thr Asn Thr Ser Ala Tyr Tyr Met Tyr Leu Leu Leu Leu Leu Lys
        275                 280                 285

Ser Val Val Tyr Phe Ala Ile Ile Thr Cys Cys Leu Leu Arg Arg Thr
    290                 295                 300

Ala Phe Cys Cys Asn Gly Glu Lys Ser
305                 310


<210> SEQ ID NO 15
<211> LENGTH: 290
<212> TYPE: PRT
<213> ORGANISM: Artificial
<220> FEATURE:
<223> OTHER INFORMATION: TRD C15

<400> SEQUENCE: 15

Met Glu Arg Ile Ser Ser Leu Ile His Leu Ser Leu Phe Trp Ala Gly
1               5                   10                  15

Val Met Ser Ala Ile Glu Leu Val Pro Glu His Gln Thr Val Pro Val
            20                  25                  30

Ser Ile Gly Val Pro Ala Thr Leu Arg Cys Ser Met Lys Gly Glu Ala
        35                  40                  45

Ile Gly Asn Tyr Tyr Ile Asn Trp Tyr Arg Lys Thr Gln Gly Asn Thr
    50                  55                  60

Met Thr Phe Ile Tyr Arg Glu Lys Asp Ile Tyr Gly Pro Gly Phe Lys
```

-continued

```
65                  70                  75                  80

Asp Asn Phe Gln Gly Asp Ile Asp Ile Ala Lys Asn Leu Ala Val Leu
                85                  90                  95

Lys Ile Leu Ala Pro Ser Glu Arg Asp Glu Gly Ser Tyr Tyr Cys Ala
            100                 105                 110

Cys Asp Ala Leu Lys Arg Thr Asp Thr Asp Lys Leu Ile Phe Gly Lys
        115                 120                 125

Gly Thr Arg Val Thr Val Glu Pro Arg Ser Gln Pro His Thr Lys Pro
    130                 135                 140

Ser Val Phe Val Met Lys Asn Gly Thr Asn Val Ala Cys Leu Val Lys
145                 150                 155                 160

Glu Phe Tyr Pro Lys Asp Ile Arg Ile Asn Leu Val Ser Ser Lys Lys
                165                 170                 175

Ile Thr Glu Phe Asp Pro Ala Ile Val Ile Ser Pro Ser Gly Lys Tyr
            180                 185                 190

Asn Ala Val Lys Leu Gly Lys Tyr Glu Asp Ser Asn Ser Val Thr Cys
        195                 200                 205

Ser Val Gln His Asp Asn Lys Thr Val His Ser Thr Asp Phe Glu Val
    210                 215                 220

Lys Thr Asp Ser Thr Asp His Val Lys Pro Lys Glu Thr Glu Asn Thr
225                 230                 235                 240

Lys Gln Pro Ser Lys Ser Cys His Lys Pro Lys Ala Ile Val His Thr
                245                 250                 255

Glu Lys Val Asn Met Met Ser Leu Thr Val Leu Gly Leu Arg Met Leu
            260                 265                 270

Phe Ala Lys Thr Val Ala Val Asn Phe Leu Leu Thr Ala Lys Leu Phe
        275                 280                 285

Phe Leu
    290
```

<210> SEQ ID NO 16
<211> LENGTH: 314
<212> TYPE: PRT
<213> ORGANISM: Artificial
<220> FEATURE:
<223> OTHER INFORMATION: TRG C15

<400> SEQUENCE: 16

```
Met Val Ser Leu Leu His Ala Ser Thr Leu Ala Val Leu Gly Ala Leu
1               5                   10                  15

Cys Val Tyr Gly Ala Gly His Leu Glu Gln Pro Gln Ile Ser Ser Thr
            20                  25                  30

Lys Thr Leu Ser Lys Thr Ala Arg Leu Glu Cys Val Val Ser Gly Ile
        35                  40                  45

Thr Ile Ser Ala Thr Ser Val Tyr Trp Tyr Arg Glu Arg Pro Gly Glu
    50                  55                  60

Val Ile Gln Phe Leu Val Ser Ile Ser Tyr Asp Gly Thr Val Arg Lys
65                  70                  75                  80

Glu Ser Gly Ile Pro Ser Gly Lys Phe Glu Val Asp Arg Ile Pro Glu
                85                  90                  95

Thr Ser Thr Ser Thr Leu Thr Ile His Asn Val Glu Lys Gln Asp Ile
            100                 105                 110

Ala Thr Tyr Tyr Cys Ala Leu Trp Glu Ile Gln Glu Leu Gly Lys Lys
        115                 120                 125

Ile Lys Val Phe Gly Pro Gly Thr Lys Leu Ile Ile Thr Asp Lys Gln
```

```
    130                 135                 140

Leu Asp Ala Asp Val Ser Pro Lys Pro Thr Ile Phe Leu Pro Ser Ile
145                 150                 155                 160

Ala Glu Thr Lys Leu Gln Lys Ala Gly Thr Tyr Leu Cys Leu Leu Glu
                165                 170                 175

Lys Phe Phe Pro Asp Val Ile Lys Ile His Trp Glu Glu Lys Lys Ser
            180                 185                 190

Asn Thr Ile Leu Gly Ser Gln Glu Gly Asn Thr Met Lys Thr Asn Asp
        195                 200                 205

Thr Tyr Met Lys Phe Ser Trp Leu Thr Val Pro Glu Lys Ser Leu Asp
    210                 215                 220

Lys Glu His Arg Cys Ile Val Arg His Glu Asn Asn Lys Asn Gly Val
225                 230                 235                 240

Asp Gln Glu Ile Ile Phe Pro Pro Ile Lys Thr Asp Val Ile Thr Met
                245                 250                 255

Asp Pro Lys Asp Asn Cys Ser Lys Asp Ala Asn Asp Thr Leu Leu Leu
            260                 265                 270

Gln Leu Thr Asn Thr Ser Ala Tyr Tyr Met Tyr Leu Leu Leu Leu Leu
        275                 280                 285

Lys Ser Val Val Tyr Phe Ala Ile Ile Thr Cys Cys Leu Leu Arg Arg
    290                 295                 300

Thr Ala Phe Cys Cys Asn Gly Glu Lys Ser
305                 310


<210> SEQ ID NO 17
<211> LENGTH: 293
<212> TYPE: PRT
<213> ORGANISM: Artificial
<220> FEATURE:
<223> OTHER INFORMATION: TRD Fe11

<400> SEQUENCE: 17

Met Val Phe Ser Ser Leu Leu Cys Val Phe Val Ala Phe Ser Tyr Ser
1               5                   10                  15

Gly Ser Ser Val Ala Gln Lys Val Thr Gln Ala Gln Ser Ser Val Ser
            20                  25                  30

Met Pro Val Arg Lys Ala Val Thr Leu Asn Cys Leu Tyr Glu Thr Ser
        35                  40                  45

Trp Trp Ser Tyr Tyr Ile Phe Trp Tyr Lys Gln Leu Pro Ser Lys Glu
    50                  55                  60

Met Ile Phe Leu Ile Arg Gln Gly Ser Asp Glu Gln Asn Ala Lys Ser
65                  70                  75                  80

Gly Arg Tyr Ser Val Asn Phe Lys Lys Ala Ala Lys Ser Val Ala Leu
                85                  90                  95

Thr Ile Ser Ala Leu Gln Leu Glu Asp Ser Ala Lys Tyr Phe Cys Ala
            100                 105                 110

Leu Gly Asp Ser Tyr Gly Gly Gly Pro Leu Tyr Thr Asp Lys Leu Ile
        115                 120                 125

Phe Gly Lys Gly Thr Arg Val Thr Val Glu Pro Arg Ser Gln Pro His
    130                 135                 140

Thr Lys Pro Ser Val Phe Val Met Lys Asn Gly Thr Asn Val Ala Cys
145                 150                 155                 160

Leu Val Lys Glu Phe Tyr Pro Lys Asp Ile Arg Ile Asn Leu Val Ser
                165                 170                 175

Ser Lys Lys Ile Thr Glu Phe Asp Pro Ala Ile Val Ile Ser Pro Ser
```

```
            180                 185                 190

Gly Lys Tyr Asn Ala Val Lys Leu Gly Lys Tyr Glu Asp Ser Asn Ser
        195                 200                 205

Val Thr Cys Ser Val Gln His Asp Asn Lys Thr Val His Ser Thr Asp
    210                 215                 220

Phe Glu Val Lys Thr Asp Ser Thr Asp His Val Lys Pro Lys Glu Thr
225                 230                 235                 240

Glu Asn Thr Lys Gln Pro Ser Lys Ser Cys His Lys Pro Lys Ala Ile
                245                 250                 255

Val His Thr Glu Lys Val Asn Met Met Ser Leu Thr Val Leu Gly Leu
            260                 265                 270

Arg Met Leu Phe Ala Lys Thr Val Ala Val Asn Phe Leu Leu Thr Ala
        275                 280                 285

Lys Leu Phe Phe Leu
    290


<210> SEQ ID NO 18
<211> LENGTH: 309
<212> TYPE: PRT
<213> ORGANISM: Artificial
<220> FEATURE:
<223> OTHER INFORMATION: TRG Fe11

<400> SEQUENCE: 18

Met Gly Trp Ala Leu Leu Val Leu Leu Ala Phe Leu Ser Pro Ala Ser
1               5                   10                  15

Gln Lys Ser Ser Asn Leu Glu Gly Gly Thr Lys Ser Val Thr Arg Pro
            20                  25                  30

Thr Arg Ser Ser Ala Glu Ile Thr Cys Asp Leu Thr Val Ile Asn Ala
        35                  40                  45

Phe Tyr Ile His Trp Tyr Leu His Gln Glu Gly Lys Ala Pro Gln Arg
    50                  55                  60

Leu Leu Tyr Tyr Asp Val Ser Asn Ser Lys Asp Val Leu Glu Ser Gly
65                  70                  75                  80

Leu Ser Pro Gly Lys Tyr Tyr Thr His Thr Pro Arg Arg Trp Ser Trp
                85                  90                  95

Ile Leu Ile Leu Arg Asn Leu Ile Glu Asn Asp Ser Gly Val Tyr Tyr
            100                 105                 110

Cys Ala Thr Trp Asp Arg Pro Glu Ile Tyr Tyr Lys Lys Leu Phe Gly
        115                 120                 125

Ser Gly Thr Thr Leu Val Val Thr Asp Lys Gln Leu Asp Ala Asp Val
    130                 135                 140

Ser Pro Lys Pro Thr Ile Phe Leu Pro Ser Ile Ala Glu Thr Lys Leu
145                 150                 155                 160

Gln Lys Ala Gly Thr Tyr Leu Cys Leu Leu Glu Lys Phe Phe Pro Asp
                165                 170                 175

Val Ile Lys Ile His Trp Glu Glu Lys Lys Ser Asn Thr Ile Leu Gly
            180                 185                 190

Ser Gln Glu Gly Asn Thr Met Lys Thr Asn Asp Thr Tyr Met Lys Phe
        195                 200                 205

Ser Trp Leu Thr Val Pro Glu Lys Ser Leu Asp Lys Glu His Arg Cys
    210                 215                 220

Ile Val Arg His Glu Asn Asn Lys Asn Gly Val Asp Gln Glu Ile Ile
225                 230                 235                 240

Phe Pro Pro Ile Lys Thr Asp Val Ile Thr Met Asp Pro Lys Asp Asn
```

-continued

```
                245                 250                 255

Cys Ser Lys Asp Ala Asn Asp Thr Leu Leu Leu Gln Leu Thr Asn Thr
            260                 265                 270

Ser Ala Tyr Tyr Met Tyr Leu Leu Leu Leu Leu Lys Ser Val Val Tyr
        275                 280                 285

Phe Ala Ile Ile Thr Cys Cys Leu Leu Arg Arg Thr Ala Phe Cys Cys
    290                 295                 300

Asn Gly Glu Lys Ser
305


<210> SEQ ID NO 19
<211> LENGTH: 14
<212> TYPE: PRT
<213> ORGANISM: Artificial
<220> FEATURE:
<223> OTHER INFORMATION: CDR3  VG4  E113

<400> SEQUENCE: 19

Cys Ala Thr Trp Asp Gly Pro Pro Tyr Tyr Lys Lys Leu Phe
1               5                   10


<210> SEQ ID NO 20
<211> LENGTH: 11
<212> TYPE: PRT
<213> ORGANISM: Artificial
<220> FEATURE:
<223> OTHER INFORMATION: CDR3  VG2  F4

<400> SEQUENCE: 20

Cys Ala Thr Trp Asp Gly Gln Lys Lys Leu Phe
1               5                   10


<210> SEQ ID NO 21
<211> LENGTH: 11
<212> TYPE: PRT
<213> ORGANISM: Artificial
<220> FEATURE:
<223> OTHER INFORMATION: CDR3  VG8  Zi11

<400> SEQUENCE: 21

Cys Ala Thr Trp Asp Asn Tyr Lys Lys Leu Phe
1               5                   10


<210> SEQ ID NO 22
<211> LENGTH: 18
<212> TYPE: PRT
<213> ORGANISM: Artificial
<220> FEATURE:
<223> OTHER INFORMATION: CDR3  VD5  D37

<400> SEQUENCE: 22

Cys Ala Ala Ser Ser Pro Ile Arg Gly Tyr Thr Gly Ser Asp Lys Leu
1               5                   10                  15

Ile Phe


<210> SEQ ID NO 23
<211> LENGTH: 18
<212> TYPE: PRT
<213> ORGANISM: Artificial
<220> FEATURE:
<223> OTHER INFORMATION: CDR3  VD5  E113

<400> SEQUENCE: 23

Cys Ala Ala Ser Ser Pro Ile Arg Gly Tyr Thr Gly Ser Asp Lys Leu
```

-continued 1 5 10 15

Ile Phe

<210> SEQ ID NO 24
<211> LENGTH: 17
<212> TYPE: PRT
<213> ORGANISM: Artificial
<220> FEATURE:
<223> OTHER INFORMATION: CDR3 VD1 F4

<400> SEQUENCE: 24

Cys Ala Leu Gly Glu Leu Arg Tyr Trp Gly Ile Val Asp Lys Leu Ile
1 5 10 15

Phe

<210> SEQ ID NO 25
<211> LENGTH: 25
<212> TYPE: PRT
<213> ORGANISM: Artificial
<220> FEATURE:
<223> OTHER INFORMATION: CDR3 VD1 Zi11

<400> SEQUENCE: 25

Cys Ala Leu Gly Glu Leu Arg Gly Gln Ile Ser Phe Leu Tyr Leu Leu
1 5 10 15

Gly Asp Thr Thr Asp Lys Leu Ile Phe
20 25

<210> SEQ ID NO 26
<211> LENGTH: 895
<212> TYPE: DNA
<213> ORGANISM: Homo sapiens

<400> SEQUENCE: 26
atggccatgc tcctgggggc atcagtgctg attctgtggc ttcagccaga ctgggtaaac 60
agtcaacaga agaatgatga ccagcaagtt aagcaaaatt caccatccct gagcgtccag 120
gaaggaagaa tttctattct gaactgtgac tatactaaca gcatgtttga ttatttccta 180
tggtacaaaa aataccctgc tgaaggtcct acattcctga tatctataag ttccattaag 240
gataaaaatg aagatggaag attcactgtc ttcttaaaca aaagtgccaa gcacctctct 300
ctgcacattg tgccctccca gcctggagac tctgcagtgt acttctgtgc agcaagctcc 360
cctattaggg gatatacagg gtccgataaa ctcatctttg gaaaaggaac ccgtgtgact 420
gtggaaccaa gaagtcagcc tcataccaaa ccatccgttt ttgtcatgaa aaatggaaca 480
aatgtcgctt gtctggtgaa ggaattctac cccaaggata taagaataaa tctcgtgtca 540
tccaagaaga taacagagtt tgatcctgct attgtcatct ctcccagtgg gaagtacaat 600
gctgtcaagc ttggtaaata tgaagattca aattcagtga catgttcagt tcaacacgac 660
aataaaactg tgcactccac tgactttgaa gtgaagacag attctacaga tcacgtaaaa 720
ccaaaggaaa ctgaaaacac aaagcaacct tcaaagagct gccataaacc caaagccata 780
gttcataccg agaaggtgaa catgatgtcc ctcacagtgc ttgggctacg aatgctgttt 840
gcaaagactg ttgccgtcaa ttttctcttg actgccaagt tatttttctt gtaag 895

<210> SEQ ID NO 27
<211> LENGTH: 13
<212> TYPE: PRT
<213> ORGANISM: Artificial
<220> FEATURE:

```
<223> OTHER INFORMATION: CDR3 VG4 C132

<400> SEQUENCE: 27

Cys Ala Thr Trp Asp Gly Phe Tyr Tyr Lys Lys Leu Phe
1               5                   10


<210> SEQ ID NO 28
<211> LENGTH: 18
<212> TYPE: PRT
<213> ORGANISM: Artificial
<220> FEATURE:
<223> OTHER INFORMATION: CDR3 VD5 C132

<400> SEQUENCE: 28

Cys Ala Ala Ser Ser Pro Ile Arg Gly Tyr Thr Gly Ser Asp Lys Leu
1               5                   10                  15

Ile Phe


<210> SEQ ID NO 29
<211> LENGTH: 271
<212> TYPE: PRT
<213> ORGANISM: Homo sapiens

<400> SEQUENCE: 29

Asp Gln Gln Val Lys Gln Asn Ser Pro Ser Leu Ser Val Gln Glu Gly
1               5                   10                  15

Arg Ile Ser Ile Leu Asn Cys Asp Tyr Thr Asn Ser Met Phe Asp Tyr
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ala Ser Ser Pro Ile
                85                  90                  95

Arg Gly Tyr Thr Gly Ser Asp Lys Leu Ile Phe Gly Lys Gly Thr Arg
            100                 105                 110

Val Thr Val Glu Pro Arg Ser Gln Pro His Thr Lys Pro Ser Val Phe
        115                 120                 125

Val Met Lys Asn Gly Thr Asn Val Ala Cys Leu Val Lys Glu Phe Tyr
    130                 135                 140

Pro Lys Asp Ile Arg Ile Asn Leu Val Ser Ser Lys Lys Ile Thr Glu
145                 150                 155                 160

Phe Asp Pro Ala Ile Val Ile Ser Pro Ser Gly Lys Tyr Asn Ala Val
                165                 170                 175

Lys Leu Gly Lys Tyr Glu Asp Ser Asn Ser Val Thr Cys Ser Val Gln
            180                 185                 190

His Asp Asn Lys Thr Val His Ser Thr Asp Phe Glu Val Lys Thr Asp
        195                 200                 205

Ser Thr Asp His Val Lys Pro Lys Glu Thr Glu Asn Thr Lys Gln Pro
    210                 215                 220

Ser Lys Ser Cys His Lys Pro Lys Ala Ile Val His Thr Glu Lys Val
225                 230                 235                 240

Asn Met Met Ser Leu Thr Val Leu Gly Leu Arg Met Leu Phe Ala Lys
                245                 250                 255

Thr Val Ala Val Asn Phe Leu Leu Thr Ala Lys Leu Phe Phe Leu
```

```
        260                 265                 270


<210> SEQ ID NO 30
<211> LENGTH: 290
<212> TYPE: PRT
<213> ORGANISM: Homo sapiens

<400> SEQUENCE: 30

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
        35                  40                  45

Tyr Tyr Asp Ser Tyr Thr Ser Ser Val Val Leu Glu Ser Gly Ile Ser
    50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
                85                  90                  95

Thr Trp Asp Gly Pro Pro Tyr Tyr Lys Lys Leu Phe Gly Ser Gly Thr
            100                 105                 110

Thr Leu Val Val Thr Asp Lys Gln Leu Asp Ala Asp Val Ser Pro Lys
        115                 120                 125

Pro Thr Ile Phe Leu Pro Ser Ile Ala Glu Thr Lys Leu Gln Lys Ala
    130                 135                 140

Gly Thr Tyr Leu Cys Leu Leu Glu Lys Phe Phe Pro Asp Val Ile Lys
145                 150                 155                 160

Ile His Trp Glu Glu Lys Lys Ser Asn Thr Ile Leu Gly Ser Gln Glu
                165                 170                 175

Gly Asn Thr Met Lys Thr Asn Asp Thr Tyr Met Lys Phe Ser Trp Leu
            180                 185                 190

Thr Val Pro Glu Lys Ser Leu Asp Lys Glu His Arg Cys Ile Val Arg
        195                 200                 205

His Glu Asn Asn Lys Asn Gly Val Asp Gln Glu Ile Ile Phe Pro Pro
    210                 215                 220

Ile Lys Thr Asp Val Ile Thr Met Asp Pro Lys Asp Asn Cys Ser Lys
225                 230                 235                 240

Asp Ala Asn Asp Thr Leu Leu Leu Gln Leu Thr Asn Thr Ser Ala Tyr
                245                 250                 255

Tyr Met Tyr Leu Leu Leu Leu Leu Lys Ser Val Val Tyr Phe Ala Ile
            260                 265                 270

Ile Thr Cys Cys Leu Leu Arg Arg Thr Ala Phe Cys Cys Asn Gly Glu
        275                 280                 285

Lys Ser
    290


<210> SEQ ID NO 31
<211> LENGTH: 271
<212> TYPE: PRT
<213> ORGANISM: Homo sapiens

<400> SEQUENCE: 31

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
```

```
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Glu Leu
                85                  90                  95

Arg Tyr Trp Gly Ile Val Asp Lys Leu Ile Phe Gly Lys Gly Thr Arg
            100                 105                 110

Val Thr Val Glu Pro Arg Ser Gln Pro His Thr Lys Pro Ser Val Phe
        115                 120                 125

Val Met Lys Asn Gly Thr Asn Val Ala Cys Leu Val Lys Glu Phe Tyr
    130                 135                 140

Pro Lys Asp Ile Arg Ile Asn Leu Val Ser Ser Lys Lys Ile Thr Glu
145                 150                 155                 160

Phe Asp Pro Ala Ile Val Ile Ser Pro Ser Gly Lys Tyr Asn Ala Val
                165                 170                 175

Lys Leu Gly Lys Tyr Glu Asp Ser Asn Ser Val Thr Cys Ser Val Gln
            180                 185                 190

His Asp Asn Lys Thr Val His Ser Thr Asp Phe Glu Val Lys Thr Asp
        195                 200                 205

Ser Thr Asp His Val Lys Pro Lys Glu Thr Glu Asn Thr Lys Gln Pro
    210                 215                 220

Ser Lys Ser Cys His Lys Pro Lys Ala Ile Val His Thr Glu Lys Val
225                 230                 235                 240

Asn Met Met Ser Leu Thr Val Leu Gly Leu Arg Met Leu Phe Ala Lys
                245                 250                 255

Thr Val Ala Val Asn Phe Leu Leu Thr Ala Lys Leu Phe Phe Leu
            260                 265                 270


<210> SEQ ID NO 32
<211> LENGTH: 287
<212> TYPE: PRT
<213> ORGANISM: Homo sapiens

<400> SEQUENCE: 32

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Asn Gly Tyr
            20                  25                  30

Ile His Trp Tyr Leu His Gln Glu Gly Lys Ala Pro Gln Arg Leu Gln
        35                  40                  45

Tyr Tyr Asp Ser Tyr Asn Ser Lys Val Val Leu Glu Ser Gly Val Ser
    50                  55                  60

Pro Gly Lys Tyr Tyr Thr Tyr Ala Ser Thr Arg Asn Asn Leu Arg Leu
65                  70                  75                  80

Ile Leu Arg Asn Leu Ile Glu Asn Asp Ser Gly Val Tyr Tyr Cys Ala
                85                  90                  95

Thr Trp Asp Gly Gln Lys Lys Leu Phe Gly Ser Gly Thr Thr Leu Val
            100                 105                 110

Val Thr Asp Lys Gln Leu Asp Ala Asp Val Ser Pro Lys Pro Thr Ile
        115                 120                 125
```

```
Phe Leu Pro Ser Ile Ala Glu Thr Lys Leu Gln Lys Ala Gly Thr Tyr
    130                 135                 140

Leu Cys Leu Leu Glu Lys Phe Phe Pro Asp Val Ile Lys Ile His Trp
145                 150                 155                 160

Glu Glu Lys Lys Ser Asn Thr Ile Leu Gly Ser Gln Glu Gly Asn Thr
                165                 170                 175

Met Lys Thr Asn Asp Thr Tyr Met Lys Phe Ser Trp Leu Thr Val Pro
            180                 185                 190

Glu Lys Ser Leu Asp Lys Glu His Arg Cys Ile Val Arg His Glu Asn
        195                 200                 205

Asn Lys Asn Gly Val Asp Gln Glu Ile Ile Phe Pro Pro Ile Lys Thr
    210                 215                 220

Asp Val Ile Thr Met Asp Pro Lys Asp Asn Cys Ser Lys Asp Ala Asn
225                 230                 235                 240

Asp Thr Leu Leu Leu Gln Leu Thr Asn Thr Ser Ala Tyr Tyr Met Tyr
                245                 250                 255

Leu Leu Leu Leu Leu Lys Ser Val Val Tyr Phe Ala Ile Ile Thr Cys
            260                 265                 270

Cys Leu Leu Arg Arg Thr Ala Phe Cys Cys Asn Gly Glu Lys Ser
        275                 280                 285
```

<210> SEQ ID NO 33
<211> LENGTH: 279
<212> TYPE: PRT
<213> ORGANISM: Homo sapiens

<400> SEQUENCE: 33

```
Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Glu Leu
                85                  90                  95

Arg Gly Gln Ile Ser Phe Leu Tyr Leu Leu Gly Asp Thr Thr Asp Lys
            100                 105                 110

Leu Ile Phe Gly Lys Gly Thr Arg Val Thr Val Glu Pro Arg Ser Gln
        115                 120                 125

Pro His Thr Lys Pro Ser Val Phe Val Met Lys Asn Gly Thr Asn Val
    130                 135                 140

Ala Cys Leu Val Lys Glu Phe Tyr Pro Lys Asp Ile Arg Ile Asn Leu
145                 150                 155                 160

Val Ser Ser Lys Lys Ile Thr Glu Phe Asp Pro Ala Ile Val Ile Ser
                165                 170                 175

Pro Ser Gly Lys Tyr Asn Ala Val Lys Leu Gly Lys Tyr Glu Asp Ser
            180                 185                 190

Asn Ser Val Thr Cys Ser Val Gln His Asp Asn Lys Thr Val His Ser
        195                 200                 205

Thr Asp Phe Glu Val Lys Thr Asp Ser Thr Asp His Val Lys Pro Lys
    210                 215                 220
```

Glu Thr Glu Asn Thr Lys Gln Pro Ser Lys Ser Cys His Lys Pro Lys
225 230 235 240

Ala Ile Val His Thr Glu Lys Val Asn Met Met Ser Leu Thr Val Leu
245 250 255

Gly Leu Arg Met Leu Phe Ala Lys Thr Val Ala Val Asn Phe Leu Leu
260 265 270

Thr Ala Lys Leu Phe Phe Leu
275

<210> SEQ ID NO 34
<211> LENGTH: 287
<212> TYPE: PRT
<213> ORGANISM: Homo sapiens

<400> SEQUENCE: 34

Ser Ser Asn Leu Glu Gly Arg Thr Lys Ser Val Thr Arg Pro Thr Gly
1 5 10 15

Ser Ser Ala Val Ile Thr Cys Asp Leu Pro Val Glu Asn Ala Val Tyr
20 25 30

Thr His Trp Tyr Leu His Gln Glu Gly Lys Ala Pro Gln Arg Leu Leu
35 40 45

Tyr Tyr Asp Ser Tyr Asn Ser Arg Val Val Leu Glu Ser Gly Ile Ser
50 55 60

Arg Glu Lys Tyr His Thr Tyr Ala Ser Thr Gly Lys Ser Leu Lys Phe
65 70 75 80

Ile Leu Glu Asn Leu Ile Glu Arg Asp Ser Gly Val Tyr Tyr Cys Ala
85 90 95

Thr Trp Asp Asn Tyr Lys Lys Leu Phe Gly Ser Gly Thr Thr Leu Val
100 105 110

Val Thr Asp Lys Gln Leu Asp Ala Asp Val Ser Pro Lys Pro Thr Ile
115 120 125

Phe Leu Pro Ser Ile Ala Glu Thr Lys Leu Gln Lys Ala Gly Thr Tyr
130 135 140

Leu Cys Leu Leu Glu Lys Phe Phe Pro Asp Val Ile Lys Ile His Trp
145 150 155 160

Gln Glu Lys Lys Ser Asn Thr Ile Leu Gly Ser Gln Glu Gly Asn Thr
165 170 175

Met Lys Thr Asn Asp Thr Tyr Met Lys Phe Ser Trp Leu Thr Val Pro
180 185 190

Glu Lys Ser Leu Asp Lys Glu His Arg Cys Ile Val Arg His Glu Asn
195 200 205

Asn Lys Asn Gly Val Asp Gln Glu Ile Ile Phe Pro Pro Ile Lys Thr
210 215 220

Asp Val Ile Thr Met Asp Pro Lys Asp Asn Cys Ser Lys Asp Ala Asn
225 230 235 240

Asp Thr Leu Leu Leu Gln Leu Thr Asn Thr Ser Ala Tyr Tyr Met Tyr
245 250 255

Leu Leu Leu Leu Leu Lys Ser Val Val Tyr Phe Ala Ile Ile Thr Cys
260 265 270

Cys Leu Leu Arg Arg Thr Ala Phe Cys Cys Asn Gly Glu Lys Ser
275 280 285

<210> SEQ ID NO 35
<211> LENGTH: 271
<212> TYPE: PRT

<213> ORGANISM: Homo sapiens

<400> SEQUENCE: 35

Asp Gln Gln Val Lys Gln Asn Ser Pro Ser Leu Ser Val Gln Glu Gly
1               5                   10                  15

Arg Ile Ser Ile Leu Asn Cys Asp Tyr Thr Asn Ser Met Phe Asp Tyr
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ala Ser Ser Pro Ile
                85                  90                  95

Arg Gly Tyr Thr Gly Ser Asp Lys Leu Ile Phe Gly Lys Gly Thr Arg
            100                 105                 110

Val Thr Val Glu Pro Arg Ser Gln Pro His Thr Lys Pro Ser Val Phe
        115                 120                 125

Val Met Lys Asn Gly Thr Asn Val Ala Cys Leu Val Lys Glu Phe Tyr
    130                 135                 140

Pro Lys Asp Ile Arg Ile Asn Leu Val Ser Ser Lys Lys Ile Thr Glu
145                 150                 155                 160

Phe Asp Pro Ala Ile Val Ile Ser Pro Ser Gly Lys Tyr Asn Ala Val
                165                 170                 175

Lys Leu Gly Lys Tyr Glu Asp Ser Asn Ser Val Thr Cys Ser Val Gln
            180                 185                 190

His Asp Asn Lys Thr Val His Ser Thr Asp Phe Glu Val Lys Thr Asp
        195                 200                 205

Ser Thr Asp His Val Lys Pro Lys Glu Thr Glu Asn Thr Lys Gln Pro
    210                 215                 220

Ser Lys Ser Cys His Lys Pro Lys Ala Ile Val His Thr Glu Lys Val
225                 230                 235                 240

Asn Met Met Ser Leu Thr Val Leu Gly Leu Arg Met Leu Phe Ala Lys
                245                 250                 255

Thr Val Ala Val Asn Phe Leu Leu Thr Ala Lys Leu Phe Phe Leu
            260                 265                 270

<210> SEQ ID NO 36
<211> LENGTH: 287
<212> TYPE: PRT
<213> ORGANISM: Homo sapiens

<400> SEQUENCE: 36

Ser Ser Asn Leu Glu Gly Arg Thr Lys Ser Val Thr Arg Pro Thr Gly
1               5                   10                  15

Ser Ser Ala Val Ile Thr Cys Asp Leu Pro Val Glu Asn Ala Val Tyr
            20                  25                  30

Thr His Trp Tyr Leu His Gln Glu Gly Lys Ala Pro Gln Arg Leu Leu
        35                  40                  45

Tyr Tyr Asp Ser Tyr Asn Ser Arg Val Val Leu Glu Ser Gly Ile Ser
    50                  55                  60

Arg Glu Lys Tyr His Thr Tyr Ala Ser Thr Gly Lys Ser Leu Lys Phe
65                  70                  75                  80

Ile Leu Glu Asn Leu Ile Glu Arg Asp Ser Gly Val Tyr Tyr Cys Ala

-continued

```
                85                  90                  95

Thr Trp Asp Asn Tyr Met Lys Leu Phe Gly Ser Gly Thr Thr Leu Val
            100                 105                 110

Val Thr Asp Lys Gln Leu Asp Ala Asp Val Ser Pro Lys Pro Thr Ile
        115                 120                 125

Phe Leu Pro Ser Ile Ala Glu Thr Lys Leu Gln Lys Ala Gly Thr Tyr
    130                 135                 140

Leu Cys Leu Leu Glu Lys Phe Phe Pro Asp Val Ile Lys Ile His Trp
145                 150                 155                 160

Glu Glu Lys Lys Ser Asn Thr Ile Leu Gly Ser Gln Glu Gly Asn Thr
                165                 170                 175

Met Lys Thr Asn Asp Thr Tyr Met Lys Phe Ser Trp Leu Thr Val Pro
            180                 185                 190

Glu Lys Ser Leu Asp Lys Glu His Arg Cys Ile Val Arg His Glu Asn
        195                 200                 205

Asn Lys Asn Gly Val Asp Gln Glu Ile Ile Phe Pro Pro Ile Lys Thr
    210                 215                 220

Asp Val Ile Thr Met Asp Pro Lys Asp Asn Cys Ser Lys Asp Ala Asn
225                 230                 235                 240

Asp Thr Leu Leu Leu Gln Leu Thr Asn Thr Ser Ala Tyr Tyr Met Tyr
                245                 250                 255

Leu Leu Leu Leu Leu Lys Ser Val Val Tyr Phe Ala Ile Ile Thr Cys
            260                 265                 270

Cys Leu Leu Arg Arg Thr Ala Phe Cys Cys Asn Gly Glu Lys Ser
        275                 280                 285


<210> SEQ ID NO 37
<211> LENGTH: 271
<212> TYPE: PRT
<213> ORGANISM: Homo sapiens

<400> SEQUENCE: 37

Asp Gln Gln Val Lys Gln Asn Ser Pro Ser Leu Ser Val Gln Glu Gly
1               5                   10                  15

Arg Ile Ser Ile Leu Asn Cys Asp Tyr Thr Asn Ser Met Phe Asp Tyr
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ala Ser Ser Pro Ile
                85                  90                  95

Arg Gly Tyr Thr Gly Ser Asp Lys Leu Ile Phe Gly Lys Gly Thr Arg
            100                 105                 110

Val Thr Val Glu Pro Arg Ser Gln Pro His Thr Lys Pro Ser Val Phe
        115                 120                 125

Val Met Lys Asn Gly Thr Asn Val Ala Cys Leu Val Lys Glu Phe Tyr
    130                 135                 140

Pro Lys Asp Ile Arg Ile Asn Leu Val Ser Ser Lys Lys Ile Thr Glu
145                 150                 155                 160

Phe Asp Pro Ala Ile Val Ile Ser Pro Ser Gly Lys Tyr Asn Ala Val
                165                 170                 175
```

```
Lys Leu Gly Lys Tyr Glu Asp Ser Asn Ser Val Thr Cys Ser Val Gln
            180                 185                 190

His Asp Asn Lys Thr Val His Ser Thr Asp Phe Glu Val Lys Thr Asp
        195                 200                 205

Ser Thr Asp His Val Lys Pro Lys Glu Thr Glu Asn Thr Lys Gln Pro
    210                 215                 220

Ser Lys Ser Cys His Lys Pro Lys Ala Ile Val His Thr Glu Lys Val
225                 230                 235                 240

Asn Met Met Ser Leu Thr Val Leu Gly Leu Arg Met Leu Phe Ala Lys
            245                 250                 255

Thr Val Ala Val Asn Phe Leu Leu Thr Ala Lys Leu Phe Phe Leu
        260                 265                 270

<210> SEQ ID NO 38
<211> LENGTH: 289
<212> TYPE: PRT
<213> ORGANISM: Homo sapiens

<400> SEQUENCE: 38

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
        35                  40                  45

Tyr Tyr Asp Ser Tyr Thr Ser Ser Val Val Leu Glu Ser Gly Ile Ser
    50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
            85                  90                  95

Thr Trp Asp Gly Phe Tyr Tyr Lys Lys Leu Phe Gly Ser Gly Thr Thr
        100                 105                 110

Leu Val Val Thr Asp Lys Gln Leu Asp Ala Asp Val Ser Pro Lys Pro
    115                 120                 125

Thr Ile Phe Leu Pro Ser Ile Ala Glu Thr Lys Leu Gln Lys Ala Gly
130                 135                 140

Thr Tyr Leu Cys Leu Leu Glu Lys Phe Phe Pro Asp Val Ile Lys Ile
145                 150                 155                 160

His Trp Glu Glu Lys Lys Ser Asn Thr Ile Leu Gly Ser Gln Glu Gly
            165                 170                 175

Asn Thr Met Lys Thr Asn Asp Thr Tyr Met Lys Phe Ser Trp Leu Thr
        180                 185                 190

Val Pro Glu Lys Ser Leu Asp Lys Glu His Arg Cys Ile Val Arg His
    195                 200                 205

Glu Asn Asn Lys Asn Gly Val Asp Gln Glu Ile Ile Phe Pro Pro Ile
210                 215                 220

Lys Thr Asp Val Ile Thr Met Asp Pro Lys Asp Asn Cys Ser Lys Asp
225                 230                 235                 240

Ala Asn Asp Thr Leu Leu Leu Gln Leu Thr Asn Thr Ser Ala Tyr Tyr
            245                 250                 255

Met Tyr Leu Leu Leu Leu Leu Lys Ser Val Val Tyr Phe Ala Ile Ile
        260                 265                 270

Thr Cys Cys Leu Leu Arg Arg Thr Ala Phe Cys Cys Asn Gly Glu Lys
    275                 280                 285
```

Ser

<210> SEQ ID NO 39
<211> LENGTH: 11
<212> TYPE: PRT
<213> ORGANISM: Artificial
<220> FEATURE:
<223> OTHER INFORMATION: CDR3 VG8 D37

<400> SEQUENCE: 39

Cys Ala Thr Trp Asp Asn Tyr Met Lys Leu Phe
1               5                   10

<210> SEQ ID NO 40
<211> LENGTH: 23
<212> TYPE: PRT
<213> ORGANISM: Artificial
<220> FEATURE:
<223> OTHER INFORMATION: CDR3 VD3 F2

<400> SEQUENCE: 40

Cys Ala Ser Ser Tyr Thr Leu Lys Leu Gly Asp Thr Pro Gly Arg Val
1               5                   10                  15

Arg Asp Trp Lys Leu Ile Phe
            20

<210> SEQ ID NO 41
<211> LENGTH: 924
<212> TYPE: DNA
<213> ORGANISM: Homo sapiens

<400> SEQUENCE: 41
atgcagtggg ccctagcggt gcttctagct ttcctgtctc ctgccagtca gaaatcttcc     60
aacttggaag ggagaacgaa gtcagtcatc aggcagactg ggtcatctgc tgaaatcact    120
tgtgatcttg ctgaaggaag taccggctac atccactggt acctacacca ggaggggaag    180
gccccacagc gtcttctgta ctatgactcc tacacctcca gcgttgtgtt ggaatcagga    240
atcagcccag ggaagtatga tacttatgga agcacaagga agaacttgag aatgatactg    300
cgaaatctta ttgaaaatga ctctggagtc tattactgtg ccacctggga tgggcctcct    360
tattataaga aactctttgg cagtggaaca acactggttg tcacagataa acaacttgat    420
gcagatgttt cccccaagcc cactattttt cttccttcaa ttgctgaaac aaagctccag    480
aaggctggaa catacctttg tcttcttgag aaatttttcc ctgatgttat taagatacat    540
tggcaagaaa agaagagcaa cacgattctg ggatcccagg aggggaacac catgaagact    600
aacgacacat acatgaaatt tagctggtta acggtgccag aaaagtcact ggacaaagaa    660
cacagatgta tcgtcagaca tgagaataat aaaaacggag ttgatcaaga aattatcttt    720
cctccaataa agacagatgt catcacaatg gatcccaaag acaattgttc aaaagatgca    780
aatgatacac tactgctgca gctcacaaac acctctgcat attacatgta cctcctcctg    840
ctcctcaaga gtgtggtcta ttttgccatc atcacctgct gtctgcttag aagaacggct    900
ttctgctgca atggagagaa atca                                           924

<210> SEQ ID NO 42
<211> LENGTH: 877
<212> TYPE: DNA
<213> ORGANISM: Homo sapiens

<400> SEQUENCE: 42

```
atgctgttct ccagcctgct gtgtgtattt gtggccttca gctactctgg atcaagtgtg     60

gcccagaagg ttactcaagc ccagtcatca gtatccatgc cagtgaggaa agcagtcacc    120

ctgaactgcc tgtatgaaac aagttggtgg tcatattata ttttttggta caagcaactt    180

cccagcaaag agatgatttt ccttattcgc cagggttctg atgaacagaa tgcaaaaagt    240

ggtcgctatt ctgtcaactt caagaaagca gcgaaatccg tcgccttaac catttcagcc    300

ttacagctag aagattcagc aaagtacttt tgtgctcttg gggaactccg gtactggggg    360

atagtcgata aactcatctt tggaaaagga acccgtgtga ctgtggaacc aagaagtcag    420

cctcatacca aaccatccgt ttttgtcatg aaaaatggaa caaatgtcgc ttgtctggtg    480

aaggaattct accccaagga tataagaata aatctcgtgt catccaagaa gataacagag    540

tttgatcctg ctattgtcat ctctcccagt gggaagtaca atgctgtcaa gcttggtaaa    600

tatgaagatt caaattcagt gacatgttca gttcaacacg acaataaaac tgtgcactcc    660

actgactttg aagtgaagac agattctaca gatcacgtaa aaccaaagga aactgaaaac    720

acaaagcaac cttcaaagag ctgccataaa cccaaagcca tagttcatac cgagaaggtg    780

aacatgatgt ccctcacagt gcttgggcta cgaatgctgt ttgcaaagac tgttgccgtc    840

aattttctct tgactgccaa gttatttttc ttgtaag                             877
```

<210> SEQ ID NO 43
<211> LENGTH: 915
<212> TYPE: DNA
<213> ORGANISM: Homo sapiens

<400> SEQUENCE: 43

```
atgcagtggg ccctagcggt gcttctagct ttcctgtctc ctgccagtca gaaatcttcc     60

aacttggaag ggagaacgaa gtcagtcatc aggcagactg ggtcatctgc tgaaatcact    120

tgtgatcttg ctgaaggaag taacggctac atccactggt acctacacca ggaggggaag    180

gccccacagc gtcttcagta ctatgactcc tacaactcca aggttgtgtt ggaatcagga    240

gtcagtccag ggaagtatta tacttacgca agcacaagga acaacttgag attgatactg    300

cgaaatctaa ttgaaaatga ctctggggtc tattactgtg ccacctggga cgggcaaaag    360

aaactctttg gcagtggaac aacactggtt gtcacagata aacaacttga tgcagatgtt    420

tcccccaagc ccactatttt tcttccttca attgctgaaa caaagctcca gaaggctgga    480

acatacettt gtcttcttga gaaatttttc cctgatgtta ttaagataca ttggcaagaa    540

aagaagagca acacgattct gggatcccag gaggggaaca ccatgaagac taacgacaca    600

tacatgaaat ttagctggtt aacggtgcca gaaaagtcac tggacaaaga acacagatgt    660

atcgtcagac atgagaataa taaaaacgga gttgatcaag aaattatctt tcctccaata    720

aagacagatg tcatcacaat ggatcccaaa gacaattgtt caaaagatgc aaatgataca    780

ctactgctgc agctcacaaa cacctctgca tattacatgt acctcctcct gctcctcaag    840

agtgtggtct attttgccat catcacctgc tgtctgctta gaagaacggc tttctgctgc    900

aatggagaga aatca                                                     915
```

<210> SEQ ID NO 44
<211> LENGTH: 901
<212> TYPE: DNA
<213> ORGANISM: Homo sapiens

<400> SEQUENCE: 44

```
atgctgttct ccagcctgct gtgtgtattt gtggccttca gctactctgg atcaagtgtg     60
gcccagaagg ttactcaagc ccagtcatca gtatccatgc cagtgaggaa agcagtcacc    120
ctgaactgcc tgtatgaaac aagttggtgg tcatattata tttttggta caagcaactt    180
cccagcaaag agatgatttt ccttattcgc cagggttctg atgaacagaa tgcaaaaagt    240
ggtcgctatt ctgtcaactt caagaaagca gcgaaatccg tcgccttaac catttcagcc    300
ttacagctag aagattcagc aaagtacttt tgtgctcttg ggaacttag gggacaaatt    360
tccttccttt atttactggg ggatacaacc gataaactca tctttggaaa aggaacccgt    420
gtgactgtgg aaccaagaag tcagcctcat accaaaccat ccgtttttgt catgaaaaat    480
ggaacaaatg tcgcttgtct ggtgaaggaa ttctacccca aggatataag aataaatctc    540
gtgtcatcca agaagataac agagtttgat cctgctattg tcatctctcc cagtgggaag    600
tacaatgctg tcaagcttgg taaatatgaa gattcaaatt cagtgacatg ttcagttcaa    660
cacgacaata aaactgtgca ctccactgac tttgaagtga agacagattc tacagatcac    720
gtaaaaccaa aggaaactga aaacacaaag caaccttcaa agagctgcca taaacccaaa    780
gccatagttc ataccgagaa ggtgaacatg atgtccctca cagtgcttgg gctacgaatg    840
ctgtttgcaa agactgttgc cgtcaatttt ctcttgactg ccaagttatt tttcttgtaa    900
g                                                                    901
```

<210> SEQ ID NO 45
<211> LENGTH: 915
<212> TYPE: DNA
<213> ORGANISM: Homo sapiens

<400> SEQUENCE: 45

```
atgctgttgg ctctagctct gcttctagct ttcctgcctc ctgccagtca gaaatcttcc     60
aacttggaag ggagaacaaa gtcagtcacc aggccaactg ggtcatcagc tgtaatcact    120
tgtgatcttc ctgtagaaaa tgccgtctac acccactggt acctacacca ggaggggaag    180
gccccacagc gtcttctgta ctatgactcc tacaactcca gggttgtgtt ggaatcagga    240
atcagtcgag aaaagtatca tacttatgca agcacaggga agagccttaa atttatactg    300
gaaaatctaa ttgaacgtga ctctggggtc tattactgtg ccacctggga taattataag    360
aaactctttg gcagtggaac aacactggtt gtcacagata aacaacttga tgcagatgtt    420
tcccccaagc ccactatttt tcttccttca attgctgaaa caaagctcca gaaggctgga    480
acatacccttt gtcttcttga gaaatttttc cctgatgtta ttaagataca ttggcaagaa    540
aagaagagca acacgattct gggatcccag gaggggaaca ccatgaagac taacgacaca    600
tacatgaaat ttagctggtt aacggtgcca gaaaagtcac tggacaaaga acacagatgt    660
atcgtcagac atgagaataa taaaaacgga gttgatcaag aaattatctt tcctccaata    720
aagacagatg tcatcacaat ggatcccaaa gacaattgtt caaaagatgc aaatgataca    780
ctactgctgc agctcacaaa cacctctgca tattacatgt acctcctcct gctcctcaag    840
agtgtggtct attttgccat catcacctgc tgtctgctta gaagaacggc tttctgctgc    900
aatggagaga aatca                                                     915
```

<210> SEQ ID NO 46
<211> LENGTH: 895
<212> TYPE: DNA
<213> ORGANISM: Homo sapiens

<400> SEQUENCE: 46

```
atggccatgc tcctgggggc atcagtgctg attctgtggc ttcagccaga ctgggtaaac     60

agtcaacaga agaatgatga ccagcaagtt aagcaaaatt caccatccct gagcgtccag    120

gaaggaagaa tttctattct gaactgtgac tatactaaca gcatgtttga ttatttccta    180

tggtacaaaa aataccctgc tgaaggtcct acattcctga tatctataag ttccattaag    240

gataaaaatg aagatggaag attcactgtc ttcttaaaca aaagtgccaa gcacctctct    300

ctgcacattg tgccctccca gcctggagac tctgcagtgt acttctgtgc agcaagctcc    360

cctattaggg gatatacagg gtccgataaa ctcatctttg gaaaaggaac ccgtgtgact    420

gtggaaccaa gaagtcagcc tcataccaaa ccatccgttt ttgtcatgaa aaatggaaca    480

aatgtcgctt gtctggtgaa ggaattctac cccaaggata taagaataaa tctcgtgtca    540

tccaagaaga taacagagtt tgatcctgct attgtcatct ctcccagtgg gaagtacaat    600

gctgtcaagc ttggtaaata tgaagattca aattcagtga catgttcagt tcaacacgac    660

aataaaactg tgcactccac tgactttgaa gtgaagacag attctacaga tcacgtaaaa    720

ccaaaggaaa ctgaaaacac aaagcaacct tcaaagagct gccataaacc caaagccata    780

gttcataccg agaaggtgaa catgatgtcc ctcacagtgc ttgggctacg aatgctgttt    840

gcaaagactg ttgccgtcaa ttttctcttg actgccaagt tatttttctt gtaag         895
```

<210> SEQ ID NO 47
<211> LENGTH: 915
<212> TYPE: DNA
<213> ORGANISM: Homo sapiens

<400> SEQUENCE: 47

```
atgctgttgg ctctagctct gcttctagct ttcctgcctc ctgccagtca gaaatcttcc     60

aacttggaag ggagaacaaa gtcagtcacc aggccaactg ggtcatcagc tgtaatcact    120

tgtgatcttc ctgtagaaaa tgccgtctac acccactggt acctacacca ggaggggaag    180

gccccacagc gtcttctgta ctatgactcc tacaactcca gggttgtgtt ggaatcagga    240

atcagtcgag aaaagtatca tacttatgca agcacaggga agagccttaa atttatactg    300

gaaaatctaa ttgaacgtga ctctggggtc tattactgtg ccacctggga taattatatg    360

aaactctttg gcagtggaac aacactggtt gtcacagata aacaacttga tgcagatgtt    420

tcccccaagc ccactatttt tcttccttca attgctgaaa caaagctcca gaaggctgga    480

acatacctttt gtcttcttga gaaatttttc cctgatgtta ttaagataca ttggcaagaa    540

aagaagagca acacgattct gggatcccag gaggggaaca ccatgaagac taacgacaca    600

tacatgaaat ttagctggtt aacggtgcca gaaaagtcac tggacaaaga acacagatgt    660

atcgtcagac atgagaataa taaaaacgga gttgatcaag aaattatctt tcctccaata    720

aagacagatg tcatcacaat ggatcccaaa gacaattgtt caaaagatgc aaatgataca    780

ctactgctgc agctcacaaa cacctctgca tattacatgt acctcctcct gctcctcaag    840

agtgtggtct attttgccat catcacctgc tgtctgctta gaagaacggc tttctgctgc    900

aatggagaga aatca                                                     915
```

<210> SEQ ID NO 48
<211> LENGTH: 895
<212> TYPE: DNA
<213> ORGANISM: Homo sapiens

<400> SEQUENCE: 48

-continued

```
atggccatgc tcctgggggc atcagtgctg attctgtggc ttcagccaga ctgggtaaac      60

agtcaacaga agaatgatga ccagcaagtt aagcaaaatt caccatccct gagcgtccag     120

gaaggaagaa tttctattct gaactgtgac tatactaaca gcatgtttga ttatttccta     180

tggtacaaaa aataccctgc tgaaggtcct acattcctga tatctataag ttccattaag     240

gataaaaatg aagatggaag attcactgtc ttcttaaaca aaagtgccaa gcacctctct     300

ctgcacattg tgccctccca gcctggagac tctgcagtgt acttctgtgc agcaagctcc     360

cctattaggg gatatacagg gtccgataaa ctcatctttg gaaaaggaac ccgtgtgact     420

gtggaaccaa gaagtcagcc tcataccaaa ccatccgttt ttgtcatgaa aaatggaaca     480

aatgtcgctt gtctggtgaa ggaattctac cccaaggata taagaataaa tctcgtgtca     540

tccaagaaga taacagagtt tgatcctgct attgtcatct ctcccagtgg gaagtacaat     600

gctgtcaagc ttggtaaata tgaagattca aattcagtga catgttcagt tcaacacgac     660

aataaaactg tgcactccac tgactttgaa gtgaagacag attctacaga tcacgtaaaa     720

ccaaaggaaa ctgaaaacac aaagcaacct tcaaagagct gccataaacc caaagccata     780

gttcataccg agaaggtgaa catgatgtcc ctcacagtgc ttgggctacg aatgctgttt     840

gcaaagactg ttgccgtcaa ttttctcttg actgccaagt tatttttctt gtaag          895
```

```
<210> SEQ ID NO 49
<211> LENGTH: 921
<212> TYPE: DNA
<213> ORGANISM: Homo sapiens

<400> SEQUENCE: 49

atgcagtggg ccctagcggt gcttctagct ttcctgtctc ctgccagtca gaaatcttcc      60

aacttggaag ggagaacgaa gtcagtcatc aggcagactg ggtcatctgc tgaaatcact     120

tgtgatcttg ctgaaggaag taccggctac atccactggt acctacacca ggaggggaag     180

gccccacagc gtcttctgta ctatgactcc tacacctcca gcgttgtgtt ggaatcagga     240

atcagcccag ggaagtatga tacttatgga agcacaagga agaacttgag aatgatactg     300

cgaaatctta ttgaaaatga ctctggagtc tattactgtg ccacctggga tggattttat     360

tataagaaac tctttggcag tggaacaaca ctggttgtca cagataaaca acttgatgca     420

gatgtttccc ccaagcccac tatttttctt ccttcaattg ctgaaacaaa gctccagaag     480

gctggaacat acctttgtct tcttgagaaa tttttccctg atgttattaa gatacattgg     540

caagaaaaga agagcaacac gattctggga tcccaggagg ggaacaccat gaagactaac     600

gacacataca tgaaatttag ctggttaacg gtgccagaaa agtcactgga caaagaacac     660

agatgtatcg tcagacatga gaataataaa aacggagttg atcaagaaat tatctttcct     720

ccaataaaga cagatgtcat cacaatggat cccaaagaca attgttcaaa agatgcaaat     780

gatacactac tgctgcagct cacaaacacc tctgcatatt acatgtacct cctcctgctc     840

ctcaagagtg tggtctattt tgccatcatc acctgctgtc tgcttagaag aacggctttc     900

tgctgcaatg gagagaaatc a                                               921
```

```
<210> SEQ ID NO 50
<211> LENGTH: 883
<212> TYPE: DNA
<213> ORGANISM: Homo sapiens

<400> SEQUENCE: 50

atgctgttct ccagcctgct gtgtgtattt gtggccttca gctactctgg atcaagtgtg      60
```

-continued gcccagaagg ttactcaagc ccagtcatca gtatccatgc cagtgaggaa agcagtcacc 120
ctgaactgcc tgtatgaaac aagttggtgg tcatattata ttttttggta caagcaactt 180
cccagcaaag agatgatttt ccttattcgc cagggttctg atgaacagaa tgcaaaaagt 240
ggtcgctatt ctgtcaactt caagaaagca gcgaaatccg tcgccttaac catttcagcc 300
ttacagctag aagattcagc aaagtacttt tgtgctcttg ggattcccta cggtggggga 360
cccctataca ccgataaact catctttgga aaaggaaccc gtgtgactgt ggaaccaaga 420
agtcagcctc ataccaaacc atccgttttt gtcatgaaaa atggaacaaa tgtcgcttgt 480
ctggtgaagg aattctaccc caaggatata agaataaatc tcgtgtcatc caagaagata 540
acagagtttg atcctgctat tgtcatctct cccagtggga agtacaatgc tgtcaagctt 600
ggtaaatatg aagattcaaa ttcagtgaca tgttcagttc aacacgacaa taaaactgtg 660
cactccactg actttgaagt gaagacagat tctacagatc acgtaaaacc aaaggaaact 720
gaaaacacaa agcaaccttc aaagagctgc cataaaccca aagccatagt tcataccgag 780
aaggtgaaca tgatgtccct cacagtgctt gggctacgaa tgctgtttgc aaagactgtt 840
gccgtcaatt ttctcttgac tgccaagtta tttttcttgt aag 883

<210> SEQ ID NO 51
<211> LENGTH: 927
<212> TYPE: DNA
<213> ORGANISM: Homo sapiens

<400> SEQUENCE: 51
atgcggtggg ccctactggt gcttctagct ttcctgtctc ctgccagtca gaaatcttcc 60
aacttggaag gggaacgaa gtcagtcacg aggccgacta ggtcatctgc tgaaatcact 120
tgtgacctta ctgtaataaa tgccttctac atccactggt acctacacca ggaggggaag 180
gccccacagc gtcttctgta ctatgacgtc tccaactcaa aggatgtgtt ggaatcagga 240
ctcagtccag gaaagtatta tactcataca cccaggaggt ggagctggat attgatacta 300
cgaaatctaa ttgaaaatga ttctggggtc tattactgtg ccacctggga caggcctgag 360
atttattata agaaactctt tggcagtgga acaacactgg ttgtcacaga taaacaactt 420
gatgcagatg tttcccccaa gcccactatt tttcttcctt caattgctga aacaaagctc 480
cagaaggctg gaacatacct ttgtcttctt gagaaatttt tccctgatgt tattaagata 540
cattggcaag aaaagaagag caacacgatt ctgggatccc aggaggggaa caccatgaag 600
actaacgaca catacatgaa atttagctgg ttaacggtgc cagaaaagtc actggacaaa 660
gaacacagat gtatcgtcag acatgagaat aataaaaacg gagttgatca agaaattatc 720
tttcctccaa taaagacaga tgtcatcaca atggatccca aagacaattg ttcaaaagat 780
gcaaatgata cactactgct gcagctcaca aacacctctg catattacat gtacctcctc 840
ctgctcctca agagtgtggt ctattttgcc atcatcacct gctgtctgct tagaagaacg 900
gctttctgct gcaatggaga gaaatca 927

<210> SEQ ID NO 52
<211> LENGTH: 891
<212> TYPE: DNA
<213> ORGANISM: Artificial
<220> FEATURE:
<223> OTHER INFORMATION: TRD E113 codon opt.

<400> SEQUENCE: 52

-continued

```
atggccatgc tgctgggagc cagcgtgctg atcctgtggc tgcagcccga ttgggtcaac      60

agccagcaga agaacgacga ccagcaagtg aagcagaaca gccccagcct gagcgtgcag     120

gaaggccgga tcagcatcct gaactgcgac tacaccaact ctatgttcga ctacttcctg     180

tggtacaaga agtaccccgc cgagggcccc accttcctga tctccatcag cagcatcaag     240

gacaagaacg aggacggccg gttcaccgtg tttctgaaca agagcgccaa gcacctgagc     300

ctgcacatcg tgcctagcca gcctggcgat agcgccgtgt acttttgtgc cgccagcagc     360

cccatcagag gctacaccgg cagcgacaag ctgatcttcg gcaagggcac cagagtgacc     420

gtggaaccca gaagccagcc ccacaccaag cccagcgtgt tcgtgatgaa gaacggcacc     480

aacgtggcct gcctcgtgaa agagttctac cccaaggaca tccggatcaa cctggtgtcc     540

agcaagaaga tcaccgagtt cgaccccgcc atcgtgatca gcccctccgg caagtacaac     600

gccgtgaagc tggggaagta cgaggacagc aacagcgtga cctgctccgt gcagcacgac     660

aacaagaccg tgcacagcac cgatttcgaa gtgaaaaccg actccaccga ccacgtgaag     720

cccaaagaga cagagaacac caagcagccc agcaagagct gccacaagcc caaggccatc     780

gtgcacaccg agaaagtgaa catgatgagc ctgaccgtgc tgggcctgcg gatgctgttc     840

gccaaaaccg tggccgtgaa cttcctgctg accgccaagc tgttctttct g              891
```

<210> SEQ ID NO 53
<211> LENGTH: 924
<212> TYPE: DNA
<213> ORGANISM: Artificial
<220> FEATURE:
<223> OTHER INFORMATION: TRG E113 codon opt.

<400> SEQUENCE: 53

```
atggagtggg ccctggccgt gctgctggcc tttctgagcc ctgccagcca gaagtccagc      60

aacctggaag gccggaccaa gagcgtgatc cggcagacag gcagcagcgc cgagatcacc     120

tgtgacctgg ccgagggcag caccggctac atccactggt atctgcacca agaaggcaag     180

gccccccagc ggctgctgta ctacgacagc tacaccagct ccgtggtgct ggaaagcggc     240

atcagccccg ggaagtacga cacctacggc agcacccgga agaacctgcg gatgatcctg     300

cggaacctga tcgagaacga cagcggcgtg tactactgcg ccacctggga cggccccccc     360

tactacaaga agctgttcgg cagcggcacc accctggtgg tgacagacaa gcagctggac     420

gccgacgtgt cccccaagcc taccatcttc ctgccctcaa ttgctgagac aaagctgcag     480

aaggccggca cctacctgtg cctgctggaa aagttcttcc cagacgtgat caagatccac     540

tgggaggaaa agaagtccaa caccatcctg ggcagccaag aaggcaacac catgaagacc     600

aacgacacct acatgaagtt cagctggctg accgtgcccg agaagtccct ggacaaagaa     660

caccggtgca tcgtgcggca cgagaacaac aagaacggcg tggaccaaga aatcatcttc     720

ccacccatca agaccgacgt gatcacaatg gaccccaagg acaactgcag caaggacgcc     780

aacgataccc tgctgctgca gctgacaaac accagcgcct actacatgta cttgttgctg     840

ctgctgaagt ccgtggtgta cttcgccatc atcacatgct gcctgctgcg gcggaccgcc     900

ttctgctgca acggcgagaa gtcc                                            924
```

<210> SEQ ID NO 54
<211> LENGTH: 873
<212> TYPE: DNA
<213> ORGANISM: Artificial
<220> FEATURE:
<223> OTHER INFORMATION: TRD F4 codon opt.

<400> SEQUENCE: 54

```
atggtgttca gcagcctgct gtgcgtgttc gtggccttca gctacagcgg cagcagcgtg     60
gcccagaaag tgacccaggc ccagagcagc gtgtccatgc ctgtgcggaa ggccgtgacc    120
ctgaactgcc tgtacgagac aagctggtgg tcctactaca tcttctggta caagcagctg    180
cccagcaaag agatgatctt cctgatccgg cagggcagcg acgagcagaa cgccaagagc    240
ggccggtaca gcgtgaactt caagaaagcc gccaagtccg tggccctgac catcagcgcc    300
ctgcagctgg aagatagcgc caagtacttc tgcgccctgg gcgagctgcg atattgggga    360
atcgtggaca agctgatctt cggcaagggc accagagtga ccgtggaacc cagaagccag    420
ccccacacca agccctccgt gttcgtgatg aagaacggca ccaacgtggc ctgcctggtg    480
aaagaattct accccaagga catccggatc aacctggtgt ccagcaagaa gatcaccgag    540
ttcgaccccg ccatcgtgat cagccccagc ggcaagtaca acgccgtgaa gctggggaag    600
tacgaggaca gcaacagcgt gacctgcagc gtgcagcacg acaacaagac cgtgcacagc    660
accgacttcg aagtgaaaac cgactccacc gaccacgtga agcccaaaga gacagagaac    720
accaagcagc ccagcaagag ctgccacaag cccaaggcca tcgtgcacac cgagaaagtg    780
aacatgatga gcctgaccgt gctgggcctg cggatgctgt tcgccaagac agtggccgtg    840
aacttcctgc tgaccgccaa gctgttcttt ctg                                 873
```

<210> SEQ ID NO 55
<211> LENGTH: 915
<212> TYPE: DNA
<213> ORGANISM: Artificial
<220> FEATURE:
<223> OTHER INFORMATION: TRG F4 codon opt.

<400> SEQUENCE: 55

```
atggagtggg cactcgcagt gttgctcgct tttttgtctc ctgcctccca gaagtctagt     60
aacctggagg ggcggactaa gtccgtcatt aggcagactg gtagcagtgc cgagattacc    120
tgcgacttgg ctgaaggcag caatggctac atccactggt acttgcacca agaaggcaaa    180
gcaccgcagc gactgcaata ttatgactcc tacaactcaa aggttgtgct cgaaagtgga    240
gtctctcccg gcaagtatta cacttacgca agcacccgaa ataatttgcg acttatcctg    300
agaaacctga tagaaaatga tagcggcgtg tactactgcg ccacctggga cggccaaaag    360
aagctgttcg gcagcggcac caccctggtg gtgacagaca agcagctgga cgccgacgtg    420
tcccccaagc ctaccatctt cctgccctca attgctgaga caaagctgca gaaggccggc    480
acctacctgt gcctgctgga aaagttcttc ccagacgtga tcaagatcca ctgggaggaa    540
aagaagtcca acaccatcct gggcagccaa gaaggcaaca ccatgaagac caacgacacc    600
tacatgaagt tcagctggct gaccgtgccc gagaagtccc tggacaaaga acaccggtgc    660
atcgtgcggc acgagaacaa caagaacggc gtggaccaag aaatcatctt cccacccatc    720
aagaccgacg tgatcacaat ggaccccaag gacaactgca gcaaggacgc caacgatacc    780
ctgctgctgc agctgacaaa caccagcgcc tactacatgt acttgttgct gctgctgaag    840
tccgtggtgt acttcgccat catcacatgc tgcctgctgc ggcggaccgc cttctgctgc    900
aacggcgaga agtcc                                                     915
```

<210> SEQ ID NO 56
<211> LENGTH: 897
<212> TYPE: DNA

<213> ORGANISM: Artificial
<220> FEATURE:
<223> OTHER INFORMATION: TRDZi11 codon opt.

<400> SEQUENCE: 56
atggtcttta gcagcctgct gtgcgtgttc gtggccttca gctacagcgg cagcagcgtg 60
gcccagaaag tgacacaggc tcagagcagc gtgtccatgc ctgtgcggaa ggccgtgacc 120
ctgaactgcc tgtacgagac aagctggtgg tcctactaca tcttctggta caagcagctg 180
cccagcaaag agatgatctt cctgatccgg cagggcagcg acgagcagaa tgccaagagc 240
ggccggtaca gcgtgaactt caagaaagcc gccaagtccg tggccctgac catctctgct 300
ctgcagctgg aagatagcgc caagtacttc tgcgccctgg gcgagctgag aggccagatc 360
agcttcctgt acctgctggg cgacaccacc gacaagctga ttttcggcaa gggcaccaga 420
gtgaccgtgg aacccagaag ccagccccac accaagccct ccgtgtttgt gatgaagaac 480
ggcaccaacg tggcctgcct cgtgaaagag ttctacccca aggacatccg gatcaacctg 540
gtgtccagca agaagatcac cgagttcgac cccgccatcg tgatcagccc cagcggcaag 600
tacaacgccg tgaagctggg gaagtacgag gacagcaaca gcgtgacctg cagcgtgcag 660
cacgacaaca agaccgtgca cagcaccgat ttcgaagtga aaaccgactc caccgaccac 720
gtgaagccca aagagacaga gaacaccaag cagcccagca agagctgcca caagcccaag 780
gccatcgtgc acaccgagaa agtgaacatg atgagcctga ccgtgctggg cctgcggatg 840
ctgttcgcca aaaccgtggc cgtgaatttc ctgctgaccg ccaagctgtt ctttctg 897

<210> SEQ ID NO 57
<211> LENGTH: 915
<212> TYPE: DNA
<213> ORGANISM: Artificial
<220> FEATURE:
<223> OTHER INFORMATION: TRG Zi11 codon opt

<400> SEQUENCE: 57
atggtgctgg ctctggctct gctgctggcc tttctgcctc ccgccagcca gaagtccagc 60
aacctggaag gccggaccaa gagcgtgacc agacctacag gatctagcgc cgtgatcacc 120
tgtgacctgc ccgtggaaaa cgccgtgtac acccactggt atctgcacca ggaaggcaag 180
gccccccagc ggctgctgta ctacgacagc tacaacagcc gggtggtgct ggaaagcggc 240
atcagcagag agaagtacca cacctacgcc agcaccggca agagcctgaa gttcatcctg 300
gaaaacctga tcgagcggga ctccggcgtg tactactgcg ccacctggga caactacaag 360
aagctgttcg gcagcggcac caccctggtc gtgaccgaca aacagctgga cgccgacgtg 420
tcccccaagc ctaccatctt cctgccctct atcgccgaga caaagctgca gaaggccggc 480
acctacctgt gcctgctgga aaagttcttc ccagacgtga tcaagatcca ctggcaggaa 540
aagaagtcca acaccatcct gggcagccag gaagggaaca ccatgaagac caacgacacc 600
tacatgaagt tcagctggct gaccgtgccc gagaagtccc tggacaaaga acaccggtgc 660
atcgtgcggc acgagaacaa caagaacggc gtggaccagg aaatcatctt cccacccatc 720
aagaccgatg tgatcactat ggaccccaag gacaactgca gcaaggacgc caacgatacc 780
ctgctgctgc agctgaccaa caccagcgcc tactacatgt atttgttgct gctgctgaag 840
tccgtggtgt acttcgccat catcacatgc tgcctgctgc ggcggaccgc cttctgctgc 900
aatggcgaga agtct 915

<210> SEQ ID NO 58
<211> LENGTH: 891
<212> TYPE: DNA
<213> ORGANISM: Artificial
<220> FEATURE:
<223> OTHER INFORMATION: TRD D37 codon opt

<400> SEQUENCE: 58

```
atggccatgc tgctgggagc cagcgtgctg atcctgtggc tgcagcccga ttgggtcaac     60
agccagcaga agaacgacga ccagcaagtg aagcagaaca gccccagcct gagcgtgcag    120
gaaggccgga tcagcatcct gaactgcgac tacaccaact ctatgttcga ctacttcctg    180
tggtacaaga agtaccccgc cgagggcccc accttcctga tctccatcag cagcatcaag    240
gacaagaacg aggacggccg gttcaccgtg tttctgaaca agagcgccaa gcacctgagc    300
ctgcacatcg tgcctagcca gcctggcgat agcgccgtgt acttttgtgc cgccagcagc    360
cccatcagag gctacaccgg cagcgacaag ctgatcttcg gcaagggcac cagagtgacc    420
gtggaaccca gaagccagcc ccacaccaag cccagcgtgt tcgtgatgaa gaacggcacc    480
aacgtggcct gcctcgtgaa agagttctac cccaaggaca tccggatcaa cctggtgtcc    540
agcaagaaga tcaccgagtt cgaccccgcc atcgtgatca gcccctccgg caagtacaac    600
gccgtgaagc tggggaagta cgaggacagc aacagcgtga cctgctccgt gcagcacgac    660
aacaagaccg tgcacagcac cgatttcgaa gtgaaaaccg actccaccga ccacgtgaag    720
cccaaagaga cagagaacac caagcagccc agcaagagct gccacaagcc caaggccatc    780
gtgcacaccg agaaagtgaa catgatgagc ctgaccgtgc tgggcctgcg gatgctgttc    840
gccaaaaccg tggccgtgaa cttcctgctg accgccaagc tgttctttct g             891
```

<210> SEQ ID NO 59
<211> LENGTH: 915
<212> TYPE: DNA
<213> ORGANISM: Artificial
<220> FEATURE:
<223> OTHER INFORMATION: TRG D37 codon opt.

<400> SEQUENCE: 59

```
atggtgctgg ccctggctct gctgctggcc tttctgcccc ctgccagcca gaagtccagc     60
aacctggaag gccggaccaa gagcgtgacc agacctaccg gcagcagcgc cgtgatcacc    120
tgtgacctgc ccgtggaaaa cgccgtgtac acccactggt atctgcacca agaaggcaag    180
gccccccagc ggctgctgta ctacgacagc tacaacagcc gggtggtgct ggaaagcggc    240
atcagcagag agaagtacca cacctacgcc agcaccggca agagcctgaa gttcatcctg    300
gaaaacctga tcgagcggga cagcggcgtg tactactgcg ccacctggga caattacatg    360
aagttgtttg ggtctgggac tacattggtt gtaactgaca agcagctgga cgccgacgtg    420
tcccccaagc ctaccatctt cctgccctca attgctgaga caaagctgca gaaggccggc    480
acctacctgt gcctgctgga aaagttcttc ccagacgtga tcaagatcca ctgggaggaa    540
aagaagtcca acaccatcct gggcagccaa gaaggcaaca ccatgaagac caacgacacc    600
tacatgaagt tcagctggct gaccgtgccc gagaagtccc tggacaaaga acaccggtgc    660
atcgtgcggc acgagaacaa caagaacggc gtggaccaag aaatcatctt cccacccatc    720
aagaccgacg tgatcacaat ggaccccaag gacaactgca gcaaggacgc caacgatacc    780
ctgctgctgc agctgacaaa caccagcgcc tactacatgt acttgttgct gctgctgaag    840
tccgtggtgt acttcgccat catcacatgc tgcctgctgc ggcggaccgc cttctgctgc    900
```

aacggcgaga agtcc 915

<210> SEQ ID NO 60
<211> LENGTH: 891
<212> TYPE: DNA
<213> ORGANISM: Artificial
<220> FEATURE:
<223> OTHER INFORMATION: TRD C132 codon opt.

<400> SEQUENCE: 60
atggccatgc tgctgggagc cagcgtgctg atcctgtggc tgcagcccga ttgggtcaac 60
agccagcaga agaacgacga ccagcaagtg aagcagaaca gccccagcct gagcgtgcag 120
gaaggccgga tcagcatcct gaactgcgac tacaccaact ctatgttcga ctacttcctg 180
tggtacaaga agtaccccgc cgagggcccc accttcctga tctccatcag cagcatcaag 240
gacaagaacg aggacggccg gttcaccgtg tttctgaaca agagcgccaa gcacctgagc 300
ctgcacatcg tgcctagcca gcctggcgat agcgccgtgt actttttgtgc cgccagcagc 360 cccatcagag gctacaccgg cagcgacaag ctgatcttcg gcaagggcac cagagtgacc 420
gtggaaccca gaagccagcc ccacaccaag cccagcgtgt tcgtgatgaa gaacggcacc 480
aacgtggcct gcctcgtgaa agagttctac cccaaggaca tccggatcaa cctggtgtcc 540
agcaagaaga tcaccgagtt cgaccccgcc atcgtgatca gcccctccgg caagtacaac 600
gccgtgaagc tggggaagta cgaggacagc aacagcgtga cctgctccgt gcagcacgac 660
aacaagaccg tgcacagcac cgatttcgaa gtgaaaaccg actccaccga ccacgtgaag 720
cccaaagaga cagagaacac caagcagccc agcaagagct gccacaagcc caaggccatc 780
gtgcacaccg agaaagtgaa catgatgagc ctgaccgtgc tgggcctgcg gatgctgttc 840
gccaaaaccg tggccgtgaa cttcctgctg accgccaagc tgttctttct g 891

<210> SEQ ID NO 61
<211> LENGTH: 921
<212> TYPE: DNA
<213> ORGANISM: Artificial
<220> FEATURE:
<223> OTHER INFORMATION: TRG C132 codon opt.

<400> SEQUENCE: 61
atggagtggg ccctggccgt gctgctggcc tttctgagcc ctgccagcca gaagtccagc 60
aacctggaag gccggaccaa gagcgtgatc cggcagacag gcagcagcgc cgagatcacc 120
tgtgacctgg ccgagggcag caccggctac atccactggt atctgcacca agaaggcaag 180
gccccccagc ggctgctgta ctacgacagc tacaccagct ccgtggtgct ggaaagcggc 240
atcagccccg ggaagtacga cacctacggc agcacccgga agaacctgcg gatgatcctg 300
cggaacctga tcgagaacga cagcggcgtg tactactgcg ccacctggga cggcttctac 360
tacaagaagc tgttcggcag cggcaccacc ctggtggtga cagacaagca gctggacgcc 420
gacgtgtccc ccaagcctac catcttcctg ccctcaattg ctgagacaaa gctgcagaag 480
gccggcacct acctgtgcct gctggaaaag ttcttcccag acgtgatcaa gatccactgg 540
gaggaaaaga agtccaacac catcctgggc agccaagaag gcaacaccat gaagaccaac 600
gacacctaca tgaagttcag ctggctgacc gtgcccgaga agtccctgga caaagaacac 660
cggtgcatcg tgcggcacga gaacaacaag aacggcgtgg accaagaaat catcttccca 720
cccatcaaga ccgacgtgat cacaatggac cccaaggaca actgcagcaa ggacgccaac 780
gataccctgc tgctgcagct gacaaacacc agcgcctact acatgtactt gttgctgctg 840

```
ctgaagtccg tggtgtactt cgccatcatc acatgctgcc tgctgcggcg gaccgccttc    900

tgctgcaacg gcgagaagtc c                                              921


<210> SEQ ID NO 62
<211> LENGTH: 882
<212> TYPE: DNA
<213> ORGANISM: Artificial
<220> FEATURE:
<223> OTHER INFORMATION: TRD Fe11 codon opt.

<400> SEQUENCE: 62

atggtgttca gcagcctgct gtgcgtgttc gtggccttca gctacagcgg cagcagcgtg     60

gcccagaaag tgacccaggc ccagagcagc gtgtccatgc ctgtgcggaa ggccgtgacc    120

ctgaactgcc tgtacgagac aagctggtgg tcctactaca tcttctggta caagcagctg    180

cccagcaaag agatgatctt cctgatccgg cagggcagcg acgagcagaa cgccaagagc    240

ggccggtaca gcgtgaactt caagaaagcc gccaagtccg tggccctgac catcagcgcc    300

ctgcagctgg aagatagcgc caagtacttc tgcgccctgg gcgacagcta cggcggaggc    360

cccctgtaca ccgacaagct gatcttcggc aagggcacca gagtgaccgt ggaacccaga    420

agccagcccc acaccaagcc ctccgtgttc gtgatgaaga acggcaccaa cgtggcctgc    480

ctggtcaaag aattctaccc caaggacatc cggatcaacc tggtgtccag caagaagatc    540

accgagttcg accccgccat cgtgatcagc cccagcggca agtacaacgc cgtgaagctg    600

gggaagtacg aggacagcaa cagcgtgacc tgcagcgtgc agcacgacaa caagaccgtg    660

cacagcaccg acttcgaagt gaaaaccgac tccaccgacc acgtgaagcc caaagagaca    720

gagaacacca agcagcccag caagagctgc cacaagccca aggccatcgt gcacaccgag    780

aaagtgaaca tgatgagcct gaccgtgctg ggcctgcgga tgctgttcgc caagacagtg    840

gccgtgaact tcctgctgac cgccaagctg ttctttctgt ga                       882


<210> SEQ ID NO 63
<211> LENGTH: 930
<212> TYPE: DNA
<213> ORGANISM: Artificial
<220> FEATURE:
<223> OTHER INFORMATION: TRG Fe11 codon opt.

<400> SEQUENCE: 63

atgggatggg ccctgctggt gctgctggcc ttcctgagcc ctgccagcca gaagtccagc     60

aacctggaag gcggcaccaa gagcgtgacc cggcctacca gaagcagcgc cgagatcacc    120

tgtgacctga ccgtgatcaa cgccttctac atccactggt atctgcacca ggaaggcaag    180

gccccccagc ggctgctgta ctacgacgtg tccaacagca aggacgtgct ggaaagcggc    240

ctgagccccg gcaagtacta cacccacacc cccagacggt ggtcctggat tctgatcctg    300

cggaacctga tcgagaacga cagcggcgtg tactactgcg ccacctggga ccggcccgag    360

atctactaca agaagctgtt cggcagcggc accaccctgg tcgtgacaga caagcagctg    420

gacgccgacg tgtcccccaa gcctaccatc ttcctgccct caattgctga gacaaagctg    480

cagaaggccg gcacctacct gtgcctgctg gaaaagttct tcccagacgt gatcaagatc    540

cactgggagg aaaagaagtc caacaccatc ctgggcagcc aagaaggcaa caccatgaag    600

accaacgaca cctacatgaa gttcagctgg ctgaccgtgc ccgagaagtc cctggacaaa    660

gaacaccggt gcatcgtgcg gcacgagaac aacaagaacg gcgtggacca agaaatcatc    720
```

-continued

```
ttcccaccca tcaagaccga cgtgatcaca atggacccca aggacaactg cagcaaggac    780

gccaacgata ccctgctgct gcagctgaca aacaccagcg cctactacat gtacttgttg    840

ctgctgctga agtccgtggt gtacttcgcc atcatcacat gctgcctgct gcggcggacc    900

gccttctgct gcaacggcga gaagtcctga                                    930


<210> SEQ ID NO 64
<211> LENGTH: 15
<212> TYPE: PRT
<213> ORGANISM: Artificial
<220> FEATURE:
<223> OTHER INFORMATION: Longer CDR3 VG5 Fe11

<400> SEQUENCE: 64

Cys Ala Thr Trp Asp Arg Pro Glu Ile Tyr Tyr Lys Lys Leu Phe
1               5                   10                  15


<210> SEQ ID NO 65
<211> LENGTH: 14
<212> TYPE: PRT
<213> ORGANISM: Artificial
<220> FEATURE:
<223> OTHER INFORMATION: CDR3 VG4 F2

<400> SEQUENCE: 65

Cys Ala Thr Trp Asp Gly Pro Pro Tyr Tyr Lys Lys Leu Phe
1               5                   10


<210> SEQ ID NO 66
<211> LENGTH: 26
<212> TYPE: PRT
<213> ORGANISM: Artificial
<220> FEATURE:
<223> OTHER INFORMATION: CDR3 VD1 Ze11

<400> SEQUENCE: 66

Cys Ala Leu Gly Asp Tyr Leu Gly Asp Lys Tyr Pro Ser Tyr Asp Leu
1               5                   10                  15

Leu Gly Asp Thr Thr Asp Lys Leu Ile Phe
            20                  25


<210> SEQ ID NO 67
<211> LENGTH: 11
<212> TYPE: PRT
<213> ORGANISM: Artificial
<220> FEATURE:
<223> OTHER INFORMATION: CDR3 VG8 Ze11

<400> SEQUENCE: 67

Cys Ala Thr Trp Asp Asn Tyr Lys Lys Leu Phe
1               5                   10


<210> SEQ ID NO 68
<211> LENGTH: 18
<212> TYPE: PRT
<213> ORGANISM: Artificial
<220> FEATURE:
<223> OTHER INFORMATION: CDR3 VD5 B23

<400> SEQUENCE: 68

Cys Ala Ala Ser Ser Pro Ile Arg Gly Tyr Thr Gly Ser Asp Lys Leu
1               5                   10                  15

Ile Phe
```

-continued

<210> SEQ ID NO 69
<211> LENGTH: 11
<212> TYPE: PRT
<213> ORGANISM: Artificial
<220> FEATURE:
<223> OTHER INFORMATION: CDR3 VG8 B23

<400> SEQUENCE: 69

```
Cys Ala Thr Trp Asp Asn Tyr Lys Lys Leu Phe
1               5                   10
```

<210> SEQ ID NO 70
<211> LENGTH: 280
<212> TYPE: PRT
<213> ORGANISM: Homo sapiens

<400> SEQUENCE: 70

```
Cys Asp Lys Val Thr Gln Ser Ser Pro Asp Gln Thr Val Ala Ser Gly
1               5                   10                  15

Ser Glu Val Val Leu Leu Cys Thr Tyr Asp Thr Val Tyr Ser Asn Pro
            20                  25                  30

Asp Leu Phe Trp Tyr Arg Ile Arg Pro Asp Tyr Ser Phe Gln Phe Val
        35                  40                  45

Phe Tyr Gly Asp Asn Ser Arg Ser Glu Gly Ala Asp Phe Thr Gln Gly
    50                  55                  60

Arg Phe Ser Val Lys His Ile Leu Thr Gln Lys Ala Phe His Leu Val
65                  70                  75                  80

Ile Ser Pro Val Arg Thr Glu Asp Ser Ala Thr Tyr Tyr Cys Ala Ser
                85                  90                  95

Ser Tyr Thr Leu Lys Leu Gly Asp Thr Pro Gly Arg Val Arg Asp Trp
            100                 105                 110

Lys Leu Ile Phe Gly Lys Gly Thr Arg Val Thr Val Glu Pro Arg Ser
        115                 120                 125

Gln Pro His Thr Lys Pro Ser Val Phe Val Met Lys Asn Gly Thr Asn
    130                 135                 140

Val Ala Cys Leu Val Lys Glu Phe Tyr Pro Lys Asp Ile Arg Ile Asn
145                 150                 155                 160

Leu Val Ser Ser Lys Lys Ile Thr Glu Phe Asp Pro Ala Ile Val Ile
                165                 170                 175

Ser Pro Ser Gly Lys Tyr Asn Ala Val Lys Leu Gly Lys Tyr Glu Asp
            180                 185                 190

Ser Asn Ser Val Thr Cys Ser Val Gln His Asp Asn Lys Thr Val His
        195                 200                 205

Ser Thr Asp Phe Glu Val Lys Thr Asp Ser Thr Asp His Val Lys Pro
    210                 215                 220

Lys Glu Thr Glu Asn Thr Lys Gln Pro Ser Lys Ser Cys His Lys Pro
225                 230                 235                 240

Lys Ala Ile Val His Thr Glu Lys Val Asn Met Met Ser Leu Thr Val
                245                 250                 255

Leu Gly Leu Arg Met Leu Phe Ala Lys Thr Val Ala Val Asn Phe Leu
            260                 265                 270

Leu Thr Ala Lys Leu Phe Phe Leu
        275                 280
```

<210> SEQ ID NO 71
<211> LENGTH: 290
<212> TYPE: PRT
<213> ORGANISM: Homo sapiens

<400> SEQUENCE: 71

```
Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
        35                  40                  45

Tyr Tyr Asp Ser Tyr Thr Ser Ser Val Val Leu Glu Ser Gly Ile Ser
    50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
                85                  90                  95

Thr Trp Asp Gly Pro Pro Tyr Tyr Lys Lys Leu Phe Gly Ser Gly Thr
            100                 105                 110

Thr Leu Val Val Thr Asp Lys Gln Leu Asp Ala Asp Val Ser Pro Lys
        115                 120                 125

Pro Thr Ile Phe Leu Pro Ser Ile Ala Glu Thr Lys Leu Gln Lys Ala
    130                 135                 140

Gly Thr Tyr Leu Cys Leu Leu Glu Lys Phe Phe Pro Asp Val Ile Lys
145                 150                 155                 160

Ile His Trp Glu Glu Lys Lys Ser Asn Thr Ile Leu Gly Ser Gln Glu
                165                 170                 175

Gly Asn Thr Met Lys Thr Asn Asp Thr Tyr Met Lys Phe Ser Trp Leu
            180                 185                 190

Thr Val Pro Glu Lys Ser Leu Asp Lys Glu His Arg Cys Ile Val Arg
        195                 200                 205

His Glu Asn Asn Lys Asn Gly Val Asp Gln Glu Ile Ile Phe Pro Pro
    210                 215                 220

Ile Lys Thr Asp Val Ile Thr Met Asp Pro Lys Asp Asn Cys Ser Lys
225                 230                 235                 240

Asp Ala Asn Asp Thr Leu Leu Leu Gln Leu Thr Asn Thr Ser Ala Tyr
                245                 250                 255

Tyr Met Tyr Leu Leu Leu Leu Leu Lys Ser Val Val Tyr Phe Ala Ile
            260                 265                 270

Ile Thr Cys Cys Leu Leu Arg Arg Thr Ala Phe Cys Cys Asn Gly Glu
        275                 280                 285

Lys Ser
    290
```

<210> SEQ ID NO 72
<211> LENGTH: 280
<212> TYPE: PRT
<213> ORGANISM: Homo sapiens

<400> SEQUENCE: 72

```
Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60
```

Val Asn Phe Lys Lys Ala Ala Lys Ser Val Ala Leu Thr Ile Ser Ala
65 70 75 80

Leu Gln Leu Glu Asp Ser Ala Lys Tyr Phe Cys Ala Leu Gly Asp Tyr
85 90 95

Leu Gly Asp Lys Tyr Pro Ser Tyr Asp Leu Leu Gly Asp Thr Thr Asp
100 105 110

Lys Leu Ile Phe Gly Lys Gly Thr Arg Val Thr Val Glu Pro Arg Ser
115 120 125

Gln Pro His Thr Lys Pro Ser Val Phe Val Met Lys Asn Gly Thr Asn
130 135 140

Val Ala Cys Leu Val Lys Glu Phe Tyr Pro Lys Asp Ile Arg Ile Asn
145 150 155 160

Leu Val Ser Ser Lys Lys Ile Thr Glu Phe Asp Pro Ala Ile Val Ile
165 170 175

Ser Pro Ser Gly Lys Tyr Asn Ala Val Lys Leu Gly Lys Tyr Glu Asp
180 185 190

Ser Asn Ser Val Thr Cys Ser Val Gln His Asp Asn Lys Thr Val His
195 200 205

Ser Thr Asp Phe Glu Val Lys Thr Asp Ser Thr Asp His Val Lys Pro
210 215 220

Lys Glu Thr Glu Asn Thr Lys Gln Pro Ser Lys Ser Cys His Lys Pro
225 230 235 240

Lys Ala Ile Val His Thr Glu Lys Val Asn Met Met Ser Leu Thr Val
245 250 255

Leu Gly Leu Arg Met Leu Phe Ala Lys Thr Val Ala Val Asn Phe Leu
260 265 270

Leu Thr Ala Lys Leu Phe Phe Leu
275 280

<210> SEQ ID NO 73
<211> LENGTH: 287
<212> TYPE: PRT
<213> ORGANISM: Homo sapiens

<400> SEQUENCE: 73

Ser Ser Asn Leu Glu Gly Arg Thr Lys Ser Val Thr Arg Pro Thr Gly
1 5 10 15

Ser Ser Ala Val Ile Thr Cys Asp Leu Pro Val Glu Asn Ala Val Tyr
20 25 30

Thr His Trp Tyr Leu His Gln Glu Gly Lys Ala Pro Gln Arg Leu Leu
35 40 45

Tyr Tyr Asp Ser Tyr Asn Ser Arg Val Val Leu Glu Ser Gly Ile Ser
50 55 60

Arg Glu Lys Tyr His Thr Tyr Ala Ser Thr Gly Lys Ser Leu Lys Phe
65 70 75 80

Ile Leu Glu Asn Leu Ile Glu Arg Asp Ser Gly Val Tyr Tyr Cys Ala
85 90 95

Thr Trp Asp Asn Tyr Lys Lys Leu Phe Gly Ser Gly Thr Thr Leu Val
100 105 110

Val Thr Asp Lys Gln Leu Asp Ala Asp Val Ser Pro Lys Pro Thr Ile
115 120 125

Phe Leu Pro Ser Ile Ala Glu Thr Lys Leu Gln Lys Ala Gly Thr Tyr
130 135 140

Leu Cys Leu Leu Glu Lys Phe Phe Pro Asp Val Ile Lys Ile His Trp

-continued

```
145                 150                 155                 160

Gln Glu Lys Lys Ser Asn Thr Ile Leu Gly Ser Gln Glu Gly Asn Thr
                165                 170                 175

Met Lys Thr Asn Asp Thr Tyr Met Lys Phe Ser Trp Leu Thr Val Pro
            180                 185                 190

Glu Lys Ser Leu Asp Lys Glu His Arg Cys Ile Val Arg His Glu Asn
        195                 200                 205

Asn Lys Asn Gly Val Asp Gln Glu Ile Ile Phe Pro Pro Ile Lys Thr
    210                 215                 220

Asp Val Ile Thr Met Asp Pro Lys Asp Asn Cys Ser Lys Asp Ala Asn
225                 230                 235                 240

Asp Thr Leu Leu Leu Gln Leu Thr Asn Thr Ser Ala Tyr Tyr Met Tyr
                245                 250                 255

Leu Leu Leu Leu Leu Lys Ser Val Val Tyr Phe Ala Ile Ile Thr Cys
            260                 265                 270

Cys Leu Leu Arg Arg Thr Ala Phe Cys Cys Asn Gly Glu Lys Ser
        275                 280                 285


<210> SEQ ID NO 74
<211> LENGTH: 271
<212> TYPE: PRT
<213> ORGANISM: Homo sapiens

<400> SEQUENCE: 74

Asp Gln Gln Val Lys Gln Asn Ser Pro Ser Leu Ser Val Gln Glu Gly
1               5                   10                  15

Arg Ile Ser Ile Leu Asn Cys Asp Tyr Thr Asn Ser Met Phe Asp Tyr
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ala Ser Ser Pro Ile
                85                  90                  95

Arg Gly Tyr Thr Gly Ser Asp Lys Leu Ile Phe Gly Lys Gly Thr Arg
            100                 105                 110

Val Thr Val Glu Pro Arg Ser Gln Pro His Thr Lys Pro Ser Val Phe
        115                 120                 125

Val Met Lys Asn Gly Thr Asn Val Ala Cys Leu Val Lys Glu Phe Tyr
    130                 135                 140

Pro Lys Asp Ile Arg Ile Asn Leu Val Ser Ser Lys Lys Ile Thr Glu
145                 150                 155                 160

Phe Asp Pro Ala Ile Val Ile Ser Pro Ser Gly Lys Tyr Asn Ala Val
                165                 170                 175

Lys Leu Gly Lys Tyr Glu Asp Ser Asn Ser Val Thr Cys Ser Val Gln
            180                 185                 190

His Asp Asn Lys Thr Val His Ser Thr Asp Phe Glu Val Lys Thr Asp
        195                 200                 205

Ser Thr Asp His Val Lys Pro Lys Glu Thr Glu Asn Thr Lys Gln Pro
    210                 215                 220

Ser Lys Ser Cys His Lys Pro Lys Ala Ile Val His Thr Glu Lys Val
225                 230                 235                 240
```

-continued

```
Asn Met Met Ser Leu Thr Val Leu Gly Leu Arg Met Leu Phe Ala Lys
                245                 250                 255

Thr Val Ala Val Asn Phe Leu Leu Thr Ala Lys Leu Phe Phe Leu
            260                 265                 270


<210> SEQ ID NO 75
<211> LENGTH: 287
<212> TYPE: PRT
<213> ORGANISM: Homo sapiens

<400> SEQUENCE: 75

Ser Ser Asn Leu Glu Gly Arg Thr Lys Ser Val Thr Arg Pro Thr Gly
1               5                   10                  15

Ser Ser Ala Val Ile Thr Cys Asp Leu Pro Val Glu Asn Ala Val Tyr
            20                  25                  30

Thr His Trp Tyr Leu His Gln Glu Gly Lys Ala Pro Gln Arg Leu Leu
        35                  40                  45

Tyr Tyr Asp Ser Tyr Asn Ser Arg Val Val Leu Glu Ser Gly Ile Ser
    50                  55                  60

Arg Glu Lys Tyr His Thr Tyr Ala Ser Thr Gly Lys Ser Leu Lys Phe
65                  70                  75                  80

Ile Leu Glu Asn Leu Ile Glu Arg Asp Ser Gly Val Tyr Tyr Cys Ala
                85                  90                  95

Thr Trp Asp Asn Tyr Lys Lys Leu Phe Gly Ser Gly Thr Thr Leu Val
            100                 105                 110

Val Thr Asp Lys Gln Leu Asp Ala Asp Val Ser Pro Lys Pro Thr Ile
        115                 120                 125

Phe Leu Pro Ser Ile Ala Glu Thr Lys Leu Gln Lys Ala Gly Thr Tyr
    130                 135                 140

Leu Cys Leu Leu Glu Lys Phe Phe Pro Asp Val Ile Lys Ile His Trp
145                 150                 155                 160

Gln Glu Lys Lys Ser Asn Thr Ile Leu Gly Ser Gln Glu Gly Asn Thr
                165                 170                 175

Met Lys Thr Asn Asp Thr Tyr Met Lys Phe Ser Trp Leu Thr Val Pro
            180                 185                 190

Glu Lys Ser Leu Asp Lys Glu His Arg Cys Ile Val Arg His Glu Asn
        195                 200                 205

Asn Lys Asn Gly Val Asp Gln Glu Ile Ile Phe Pro Pro Ile Lys Thr
    210                 215                 220

Asp Val Ile Thr Met Asp Pro Lys Asp Asn Cys Ser Lys Asp Ala Asn
225                 230                 235                 240

Asp Thr Leu Leu Leu Gln Leu Thr Asn Thr Ser Ala Tyr Tyr Met Tyr
                245                 250                 255

Leu Leu Leu Leu Leu Lys Ser Val Val Tyr Phe Ala Ile Ile Thr Cys
            260                 265                 270

Cys Leu Leu Arg Arg Thr Ala Phe Cys Cys Asn Gly Glu Lys Ser
        275                 280                 285


<210> SEQ ID NO 76
<211> LENGTH: 895
<212> TYPE: DNA
<213> ORGANISM: Homo sapiens

<400> SEQUENCE: 76

atgattctta ctgtgggctt tagctttttg tttttctaca ggggcacgct gtgtgacaaa      60

gtaacccaga gttccccgga ccagacggtg gcgagtggca gtgaggtggt actgctctgc     120
```

acttacgaca ctgtatattc aaatccagat ttattctggt accggataag gccagattat 180
tcctttcagt ttgtctttta tggggataac agcagatcag aaggtgcaga ttttactcaa 240
ggacggtttt ctgtgaaaca cattctgacc cagaaagcct ttcacttggt gatctctcca 300
gtaaggactg aagacagtgc cacttactac tgtgcctcct cctatactct caaactgggg 360
gatacgccgg gtagggtccg tgattggaaa ctcatctttg gaaaaggaac ccgtgtgact 420
gtggaaccaa gaagtcagcc tcataccaaa ccatccgttt ttgtcatgaa aaatggaaca 480
aatgtcgctt gtctggtgaa ggaattctac cccaaggata taagaataaa tctcgtgtca 540
tccaagaaga taacagagtt tgatcctgct attgtcatct ctcccagtgg gaagtacaat 600
gctgtcaagc ttggtaaata tgaagattca aattcagtga catgttcagt tcaacacgac 660
aataaaactg tgcactccac tgactttgaa gtgaagacag attctacaga tcacgtaaaa 720
ccaaaggaaa ctgaaaacac aaagcaacct tcaaagagct gccataaacc caaagccata 780
gttcataccg agaaggtgaa catgatgtcc ctcacagtgc ttgggctacg aatgctgttt 840
gcaaagactg ttgccgtcaa ttttctcttg actgccaagt tatttttctt gtaag 895

<210> SEQ ID NO 77
<211> LENGTH: 924
<212> TYPE: DNA
<213> ORGANISM: Homo sapiens

<400> SEQUENCE: 77
atgcagtggg ccctagcggt gcttctagct ttcctgtctc ctgccagtca gaaatcttcc 60
aacttggaag ggagaacgaa gtcagtcatc aggcagactg ggtcatctgc tgaaatcact 120
tgtgatcttg ctgaaggaag taccggctac atccactggt acctacacca ggaggggaag 180
gccccacagc gtcttctgta ctatgactcc tacacctcca gcgttgtgtt ggaatcagga 240
atcagcccag ggaagtatga tacttatgga agcacaagga agaacttgag aatgatactg 300
cgaaatctta ttgaaaatga ctctggagtc tattactgtg ccacctggga tgggcctcct 360
tattataaga aactctttgg cagtggaaca acactggttg tcacagataa acaacttgat 420
gcagatgttt cccccaagcc cactattttt cttccttcaa ttgctgaaac aaagctccag 480
aaggctggaa catacctttg tcttcttgag aaatttttcc ctgatgttat taagatacat 540
tggcaagaaa agaagagcaa cacgattctg ggatcccagg aggggaacac catgaagact 600
aacgacacat acatgaaatt tagctggtta acggtgccag aaaagtcact ggacaaagaa 660
cacagatgta tcgtcagaca tgagaataat aaaaacggag ttgatcaaga aattatcttt 720
cctccaataa agacagatgt catcacaatg gatcccaaag acaattgttc aaaagatgca 780
aatgatacac tactgctgca gctcacaaac acctctgcat attacatgta cctcctcctg 840
ctcctcaaga gtgtggtcta ttttgccatc atcacctgct gtctgcttag aagaacggct 900
ttctgctgca atggagagaa atca 924

<210> SEQ ID NO 78
<211> LENGTH: 904
<212> TYPE: DNA
<213> ORGANISM: Homo sapiens

<400> SEQUENCE: 78
atgctgttct ccagcctgct gtgtgtattt gtggccttca gctactctgg atcaagtgtg 60
gcccagaagg ttactcaagc ccagtcatca gtatccatgc cagtgaggaa agcagtcacc 120

-continued

```
ctgaactgcc tgtatgaaac aagttggtgg tcatattata tttttggta caagcaactt    180

cccagcaaag agatgatttt ccttattcgc cagggttctg atgaacagaa tgcaaaaagt    240

ggtcgctatt ctgtcaactt caagaaagca gcgaaatccg tcgccttaac catttcagcc    300

ttacagctag aagattcagc aaagtacttt tgtgctcttg ggactatttt aggggacaaa    360

tatccttcct acgatttact gggggataca accgataaac tcatctttgg aaaaggaacc    420

cgtgtgactg tggaaccaag aagtcagcct cataccaaac catccgtttt tgtcatgaaa    480

aatggaacaa atgtcgcttg tctggtgaag gaattctacc ccaaggatat aagaataaat    540

ctcgtgtcat ccaagaagat aacagagttt gatcctgcta ttgtcatctc tcccagtggg    600

aagtacaatg ctgtcaagct tggtaaatat gaagattcaa attcagtgac atgttcagtt    660

caacacgaca ataaaactgt gcactccact gactttgaag tgaagacaga ttctacagat    720

cacgtaaaac caaaggaaac tgaaaacaca aagcaacctt caaagagctg ccataaaccc    780

aaagccatag ttcataccga gaaggtgaac atgatgtccc tcacagtgct tgggctacga    840

atgctgtttg caaagactgt tgccgtcaat ttctcttga ctgccaagtt atttttcttg    900

taag                                                                904
```

<210> SEQ ID NO 79
<211> LENGTH: 915
<212> TYPE: DNA
<213> ORGANISM: Homo sapiens

<400> SEQUENCE: 79

```
atgctgttgg ctctagctct gcttctagct ttcctgcctc ctgccagtca gaaatcttcc     60

aacttggaag ggagaacaaa gtcagtcacc aggccaactg ggtcatcagc tgtaatcact    120

tgtgatcttc ctgtagaaaa tgccgtctac acccactggt acctacacca ggaggggaag    180

gccccacagc gtcttctgta ctatgactcc tacaactcca gggttgtgtt ggaatcagga    240

atcagtcgag aaaagtatca tacttatgca agcacaggga agagccttaa atttatactg    300

gaaaatctaa ttgaacgtga ctctggggtc tattactgtg ccacctggga taattataag    360

aaactctttg gcagtggaac aacactggtt gtcacagata aacaacttga tgcagatgtt    420

tcccccaagc ccactatttt tcttccttca attgctgaaa caaagctcca gaaggctgga    480

acatacottt gtcttcttga gaaatttttc cctgatgtta ttaagataca ttggcaagaa    540

aagaagagca acacgattct gggatcccag gaggggaaca ccatgaagac taacgacaca    600

tacatgaaat ttagctggtt aacggtgcca gaaaagtcac tggacaaaga acacagatgt    660

atcgtcagac atgagaataa taaaaacgga gttgatcaag aaattatctt tcctccaata    720

aagacagatg tcatcacaat ggatcccaaa gacaattgtt caaaagatgc aaatgataca    780

ctactgctgc agctcacaaa cacctctgca tattacatgt acctcctcct gctcctcaag    840

agtgtggtct attttgccat catcacctgc tgtctgctta gaagaacggc tttctgctgc    900

aatggagaga aatca                                                     915
```

<210> SEQ ID NO 80
<211> LENGTH: 895
<212> TYPE: DNA
<213> ORGANISM: Homo sapiens

<400> SEQUENCE: 80

```
atggccatgc tcctgggggc atcagtgctg attctgtggc ttcagccaga ctgggtaaac     60

agtcaacaga agaatgatga ccagcaagtt aagcaaaatt caccatccct gagcgtccag    120
```

```
gaaggaagaa tttctattct gaactgtgac tatactaaca gcatgtttga ttatttccta    180

tggtacaaaa aataccctgc tgaaggtcct acattcctga tatctataag ttccattaag    240

gataaaaatg aagatggaag attcactgtc ttcttaaaca aaagtgccaa gcacctctct    300

ctgcacattg tgccctccca gcctggagac tctgcagtgt acttctgtgc agcaagctcc    360

cctattaggg gatatacagg gtccgataaa ctcatctttg gaaaaggaac ccgtgtgact    420

gtggaaccaa gaagtcagcc tcataccaaa ccatccgttt ttgtcatgaa aaatggaaca    480

aatgtcgctt gtctggtgaa ggaattctac cccaaggata taagaataaa tctcgtgtca    540

tccaagaaga taacagagtt tgatcctgct attgtcatct ctcccagtgg gaagtacaat    600

gctgtcaagc ttggtaaata tgaagattca aattcagtga catgttcagt tcaacacgac    660

aataaaactg tgcactccac tgactttgaa gtgaagacag attctacaga tcacgtaaaa    720

ccaaaggaaa ctgaaaacac aaagcaacct tcaaagagct gccataaacc caaagccata    780

gttcataccg agaaggtgaa catgatgtcc ctcacagtgc ttgggctacg aatgctgttt    840

gcaaagactg ttgccgtcaa ttttctcttg actgccaagt tatttttctt gtaag         895
```

```
<210> SEQ ID NO 81
<211> LENGTH: 915
<212> TYPE: DNA
<213> ORGANISM: Homo sapiens

<400> SEQUENCE: 81

atgctgttgg ctctagctct gcttctagct ttcctgcctc ctgccagtca gaaatcttcc     60

aacttggaag ggagaacaaa gtcagtcacc aggccaactg ggtcatcagc tgtaatcact    120

tgtgatcttc ctgtagaaaa tgccgtctac acccactggt acctacacca ggaggggaag    180

gccccacagc gtcttctgta ctatgactcc tacaactcca gggttgtgtt ggaatcagga    240

atcagtcgag aaaagtatca tacttatgca agcacaggga agagccttaa atttatactg    300

gaaaatctaa ttgaacgtga ctctggggtc tattactgtg ccacctggga taattataag    360

aaactctttg gcagtggaac aacactggtt gtcacagata aacaacttga tgcagatgtt    420

tcccccaagc ccactatttt tcttccttca attgctgaaa caaagctcca gaaggctgga    480

acatacccttt gtcttcttga gaaatttttc cctgatgtta ttaagataca ttggcaagaa    540

aagaagagca acacgattct gggatcccag gaggggaaca ccatgaagac taacgacaca    600

tacatgaaat ttagctggtt aacggtgcca gaaaagtcac tggacaaaga acacagatgt    660

atcgtcagac atgagaataa taaaaacgga gttgatcaag aaattatctt tcctccaata    720

aagacagatg tcatcacaat ggatcccaaa gacaattgtt caaaagatgc aaatgataca    780

ctactgctgc agctcacaaa cacctctgca tattacatgt acctcctcct gctcctcaag    840

agtgtggtct attttgccat catcacctgc tgtctgctta gaagaacggc tttctgctgc    900

aatggagaga aatca                                                     915
```

```
<210> SEQ ID NO 82
<211> LENGTH: 891
<212> TYPE: DNA
<213> ORGANISM: Artificial
<220> FEATURE:
<223> OTHER INFORMATION: TRD F2 codon opt.

<400> SEQUENCE: 82

atggttctta cagtaggatt ttctttcctc ttcttctaca gagggactct ttgcgacaaa     60
```

```
gtgacacaaa gcagtccgga ccaaacggtg gcgtctggtt ccgaagtggt gcttctttgc    120

acttatgata cggtatatag caatccggac ctcttctggt atcgcatacg cccggattat    180

agttttcaat tcgtcttcta tggcgacaac tctcgaagcg aaggcgcaga ttttacccag    240

gggcgctttt cagttaaaca catattgacc cagaaggctt ttcacttggt gatctctcct    300

gtgagaactg aggattccgc gacttattac tgcgcgtctt cttacaccct taaattgggg    360

gacacgccag gcagagtccg cgactggaag ctgatcttcg gcaagggcac cagagtgacc    420

gtggaaccca gaagccagcc ccacaccaag ccctccgtgt tcgtgatgaa gaacggcacc    480

aacgtggcct gcctggtgaa agaattctac cccaaggaca tccggatcaa cctggtgtcc    540

agcaagaaga tcaccgagtt cgaccccgcc atcgtgatca gccccagcgg caagtacaac    600

gccgtgaagc tggggaagta cgaggacagc aacagcgtga cctgcagcgt gcagcacgac    660

aacaagaccg tgcacagcac cgacttcgaa gtgaaaaccg actccaccga ccacgtgaag    720

cccaaagaga cagagaacac caagcagccc agcaagagct gccacaagcc caaggccatc    780

gtgcacaccg agaaagtgaa catgatgagc ctgaccgtgc tgggcctgcg gatgctgttc    840

gccaagacag tggccgtgaa cttcctgctg accgccaagc tgttctttct g             891
```

<210> SEQ ID NO 83
<211> LENGTH: 924
<212> TYPE: DNA
<213> ORGANISM: Artificial
<220> FEATURE:
<223> OTHER INFORMATION: TRG F2 codon opt.

<400> SEQUENCE: 83

```
atggagtggg ccctggccgt gctgctggcc tttctgagcc ctgccagcca gaagtccagc     60

aacctggaag gccggaccaa gagcgtgatc cggcagacag gcagcagcgc cgagatcacc    120

tgtgacctgg ccgagggcag caccggctac atccactggt atctgcacca agaaggcaag    180

gccccccagc ggctgctgta ctacgacagc tacaccagct ccgtggtgct ggaaagcggc    240

atcagccccg ggaagtacga cacctacggc agcacccgga agaacctgcg gatgatcctg    300

cggaacctga tcgagaacga cagcggcgtg tactactgcg ccacctggga cggccccccc    360

tactacaaga agctgttcgg cagcggcacc accctggtgg tgacagacaa gcagctggac    420

gccgacgtgt cccccaagcc taccatcttc ctgccctcaa ttgctgagac aaagctgcag    480

aaggccggca cctacctgtg cctgctggaa aagttcttcc cagacgtgat caagatccac    540

tgggaggaaa agaagtccaa caccatcctg ggcagccaag aaggcaacac catgaagacc    600

aacgacacct acatgaagtt cagctggctg accgtgcccg agaagtccct ggacaaagaa    660

caccggtgca tcgtgcggca cgagaacaac aagaacggcg tggaccaaga aatcatcttc    720

ccacccatca agaccgacgt gatcacaatg gaccccaagg acaactgcag caaggacgcc    780

aacgataccc tgctgctgca gctgacaaac accagcgcct actacatgta cttgttgctg    840

ctgctgaagt ccgtggtgta cttcgccatc atcacatgct gcctgctgcg gcggaccgcc    900

ttctgctgca acggcgagaa gtcc                                           924
```

<210> SEQ ID NO 84
<211> LENGTH: 900
<212> TYPE: DNA
<213> ORGANISM: Artificial
<220> FEATURE:
<223> OTHER INFORMATION: TRD Ze 11 codon opt.

<400> SEQUENCE: 84
atggtgttca gcagcctgct gtgcgtgttc gtggccttca gctacagcgg cagcagcgtg 60
gcccagaaag tgacacaggc tcagagcagc gtgtccatgc ctgtgcggaa ggccgtgacc 120
ctgaactgcc tgtacgagac aagctggtgg tcctactaca tcttctggta caagcagctg 180
cccagcaaag agatgatctt cctgatccgg cagggcagcg acgagcagaa tgccaagagc 240
ggccggtaca gcgtgaactt caagaaagcc gccaagtccg tggccctgac catctctgct 300
ctgcagctgg aagatagcgc caagtacttc tgcgccctgg gcgactacct gggcgataag 360
taccccagct acgacctgct gggcgacacc accgacaagc tgatcttcgg caagggcacc 420
agagtgaccg tggaacccag aagccagccc cacaccaagc cctccgtgtt tgtgatgaag 480
aacggcacca acgtggcctg cctcgtgaaa gagttctacc ccaaggacat ccggatcaac 540
ctggtgtcca gcaagaagat caccgagttc gaccccgcca tcgtgatcag ccccagcggc 600
aagtacaacg ccgtgaagct ggggaagtac gaggacagca acagcgtgac ctgcagcgtg 660
cagcacgaca acaagaccgt gcacagcacc gatttcgaag tgaaaaccga ctccaccgac 720
cacgtgaagc ccaaagagac agagaacacc aagcagccca gcaagagctg ccacaagccc 780
aaggccatcg tgcacaccga gaaagtgaac atgatgagcc tgaccgtgct gggcctgcgg 840
atgctgttcg ccaaaaccgt ggccgtgaat ttcctgctga ccgccaagct gttctttctg 900

<210> SEQ ID NO 85
<211> LENGTH: 915
<212> TYPE: DNA
<213> ORGANISM: Artificial
<220> FEATURE:
<223> OTHER INFORMATION: TRG Ze11 codon opt.

<400> SEQUENCE: 85
atggtgctgg ctctggctct gctgctggcc tttctgcctc ccgccagcca gaagtccagc 60
aacctggaag gccggaccaa gagcgtgacc agacctacag gatctagcgc cgtgatcacc 120
tgtgacctgc ccgtggaaaa cgccgtgtac acccactggt atctgcacca ggaaggcaag 180
gccccccagc ggctgctgta ctacgacagc tacaacagcc gggtggtgct ggaaagcggc 240
atcagcagag agaagtacca cacctacgcc agcaccggca agagcctgaa gttcatcctg 300
gaaaacctga tcgagcggga ctccggcgtg tactactgcg ccacctggga caactacaag 360
aagctgttcg gcagcggcac caccctggtc gtgaccgaca aacagctgga cgccgacgtg 420
tcccccaagc ctaccatctt cctgccctct atcgccgaga caaagctgca gaaggccggc 480
acctacctgt gcctgctgga aaagttcttc ccagacgtga tcaagatcca ctggcaggaa 540
aagaagtcca acaccatcct gggcagccag gaagggaaca ccatgaagac caacgacacc 600
tacatgaagt tcagctggct gaccgtgccc gagaagtccc tggacaaaga acaccggtgc 660
atcgtgcggc acgagaacaa caagaacggc gtggaccagg aaatcatctt cccacccatc 720
aagaccgatg tgatcactat ggaccccaag gacaactgca gcaaggacgc caacgatacc 780
ctgctgctgc agctgaccaa caccagcgcc tactacatgt atttgttgct gctgctgaag 840
tccgtggtgt acttcgccat catcacatgc tgcctgctgc ggcggaccgc cttctgctgc 900
aatggcgaga agtct 915

<210> SEQ ID NO 86
<211> LENGTH: 891
<212> TYPE: DNA
<213> ORGANISM: Artificial
<220> FEATURE:

-continued

<223> OTHER INFORMATION: TRD B23 codon opt.

<400> SEQUENCE: 86
atggccatgc tgctgggagc cagcgtgctg atcctgtggc tgcagcccga ttgggtcaac 60
agccagcaga agaacgacga ccagcaagtg aagcagaaca gccccagcct gagcgtgcag 120
gaaggccgga tcagcatcct gaactgcgac tacaccaact ctatgttcga ctacttcctg 180
tggtacaaga agtaccccgc cgagggcccc accttcctga tctccatcag cagcatcaag 240
gacaagaacg aggacggccg gttcaccgtg tttctgaaca agagcgccaa gcacctgagc 300
ctgcacatcg tgcctagcca gcctggcgat agcgccgtgt acttttgtgc cgccagcagc 360
cccatcagag gctacaccgg cagcgacaag ctgatcttcg gcaagggcac cagagtgacc 420
gtggaaccca gaagccagcc ccacaccaag cccagcgtgt tcgtgatgaa gaacggcacc 480
aacgtggcct gcctcgtgaa agagttctac cccaaggaca tccggatcaa cctggtgtcc 540
agcaagaaga tcaccgagtt cgaccccgcc atcgtgatca gcccctccgg caagtacaac 600
gccgtgaagc tggggaagta cgaggacagc aacagcgtga cctgctccgt gcagcacgac 660
aacaagaccg tgcacagcac cgatttcgaa gtgaaaaccg actccaccga ccacgtgaag 720
cccaaagaga cagagaacac caagcagccc agcaagagct gccacaagcc caaggccatc 780
gtgcacaccg agaaagtgaa catgatgagc ctgaccgtgc tgggcctgcg gatgctgttc 840
gccaaaaccg tggccgtgaa cttcctgctg accgccaagc tgttctttct g 891

<210> SEQ ID NO 87
<211> LENGTH: 915
<212> TYPE: DNA
<213> ORGANISM: Artificial
<220> FEATURE:
<223> OTHER INFORMATION: TRG B23 codon opt.

<400> SEQUENCE: 87
atggtgctgg ctctggctct gctgctggcc tttctgcctc ccgccagcca gaagtccagc 60
aacctggaag gccggaccaa gagcgtgacc agacctacag gatctagcgc cgtgatcacc 120
tgtgacctgc ccgtggaaaa cgccgtgtac acccactggt atctgcacca ggaaggcaag 180
gccccccagc ggctgctgta ctacgacagc tacaacagcc gggtggtgct ggaaagcggc 240
atcagcagag agaagtacca cacctacgcc agcaccggca agagcctgaa gttcatcctg 300
gaaaacctga tcgagcggga ctccggcgtg tactactgcg ccacctggga caactacaag 360
aagctgttcg gcagcggcac caccctggtc gtgaccgaca aacagctgga cgccgacgtg 420
tcccccaagc ctaccatctt cctgccctct atcgccgaga caaagctgca gaaggccggc 480
acctacctgt gcctgctgga aaagttcttc ccagacgtga tcaagatcca ctggcaggaa 540
aagaagtcca acaccatcct gggcagccag gaagggaaca ccatgaagac caacgacacc 600
tacatgaagt tcagctggct gaccgtgccc gagaagtccc tggacaaaga acaccggtgc 660
atcgtgcggc acgagaacaa caagaacggc gtggaccagg aaatcatctt cccacccatc 720
aagaccgatg tgatcactat ggaccccaag gacaactgca gcaaggacgc caacgatacc 780
ctgctgctgc agctgaccaa caccagcgcc tactacatgt atttgttgct gctgctgaag 840
tccgtggtgt acttcgccat catcacatgc tgcctgctgc ggcggaccgc cttctgctgc 900
aatggcgaga agtct 915

<210> SEQ ID NO 88
<211> LENGTH: 20

```
<212> TYPE: PRT
<213> ORGANISM: Artificial
<220> FEATURE:
<223> OTHER INFORMATION: CDR3 VD1 B9

<400> SEQUENCE: 88

Cys Ala Leu Gly Asn Gly Asn His Ile Gly Tyr Trp Arg Tyr Thr Asp
1               5                   10                  15

Lys Leu Ile Phe
            20


<210> SEQ ID NO 89
<211> LENGTH: 13
<212> TYPE: PRT
<213> ORGANISM: Artificial
<220> FEATURE:
<223> OTHER INFORMATION: CDR3 VG5  B9

<400> SEQUENCE: 89

Cys Ala Thr Trp Asp Arg Leu Tyr Tyr Lys Lys Leu Phe
1               5                   10


<210> SEQ ID NO 90
<211> LENGTH: 274
<212> TYPE: PRT
<213> ORGANISM: Homo sapiens

<400> SEQUENCE: 90

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Asn Gly
                85                  90                  95

Asn His Ile Gly Tyr Trp Arg Tyr Thr Asp Lys Leu Ile Phe Gly Lys
            100                 105                 110

Gly Thr Arg Val Thr Val Glu Pro Arg Ser Gln Pro His Thr Lys Pro
        115                 120                 125

Ser Val Phe Val Met Lys Asn Gly Thr Asn Val Ala Cys Leu Val Lys
    130                 135                 140

Glu Phe Tyr Pro Lys Asp Ile Arg Ile Asn Leu Val Ser Ser Lys Lys
145                 150                 155                 160

Ile Thr Glu Phe Asp Pro Ala Ile Val Ile Ser Pro Ser Gly Lys Tyr
                165                 170                 175

Asn Ala Val Lys Leu Gly Lys Tyr Glu Asp Ser Asn Ser Val Thr Cys
            180                 185                 190

Ser Val Gln His Asp Asn Lys Thr Val His Ser Thr Asp Phe Glu Val
        195                 200                 205

Lys Thr Asp Ser Thr Asp His Val Lys Pro Lys Glu Thr Glu Asn Thr
    210                 215                 220

Lys Gln Pro Ser Lys Ser Cys His Lys Pro Lys Ala Ile Val His Thr
225                 230                 235                 240
```

```
Glu Lys Val Asn Met Met Ser Leu Thr Val Leu Gly Leu Arg Met Leu
                245                 250                 255

Phe Ala Lys Thr Val Ala Val Asn Phe Leu Leu Thr Ala Lys Leu Phe
            260                 265                 270

Phe Leu


<210> SEQ ID NO 91
<211> LENGTH: 289
<212> TYPE: PRT
<213> ORGANISM: Homo sapiens

<400> SEQUENCE: 91

Ser Ser Asn Leu Glu Gly Gly Thr Lys Ser Val Thr Arg Pro Thr Arg
1               5                   10                  15

Ser Ser Ala Glu Ile Thr Cys Asp Leu Thr Val Ile Asn Ala Phe Tyr
            20                  25                  30

Ile His Trp Tyr Leu His Gln Glu Gly Lys Ala Pro Gln Arg Leu Leu
        35                  40                  45

Tyr Tyr Asp Val Ser Asn Ser Lys Asp Val Leu Glu Ser Gly Leu Ser
    50                  55                  60

Pro Gly Lys Tyr Tyr Thr His Thr Pro Arg Arg Trp Ser Trp Ile Leu
65                  70                  75                  80

Ile Leu Arg Asn Leu Ile Glu Asn Asp Ser Gly Val Tyr Tyr Cys Ala
                85                  90                  95

Thr Trp Asp Arg Leu Tyr Tyr Lys Lys Leu Phe Gly Ser Gly Thr Thr
            100                 105                 110

Leu Val Val Thr Asp Lys Gln Leu Asp Ala Asp Val Ser Pro Lys Pro
        115                 120                 125

Thr Ile Phe Leu Pro Ser Ile Ala Glu Thr Lys Leu Gln Lys Ala Gly
    130                 135                 140

Thr Tyr Leu Cys Leu Leu Glu Lys Phe Phe Pro Asp Val Ile Lys Ile
145                 150                 155                 160

His Trp Glu Glu Lys Lys Ser Asn Thr Ile Leu Gly Ser Gln Glu Gly
                165                 170                 175

Asn Thr Met Lys Thr Asn Asp Thr Tyr Met Lys Phe Ser Trp Leu Thr
            180                 185                 190

Val Pro Glu Lys Ser Leu Asp Lys Glu His Arg Cys Ile Val Arg His
        195                 200                 205

Glu Asn Asn Lys Asn Gly Val Asp Gln Glu Ile Ile Phe Pro Pro Ile
    210                 215                 220

Lys Thr Asp Val Ile Thr Met Asp Pro Lys Asp Asn Cys Ser Lys Asp
225                 230                 235                 240

Ala Asn Asp Thr Leu Leu Leu Gln Leu Thr Asn Thr Ser Ala Tyr Tyr
                245                 250                 255

Met Tyr Leu Leu Leu Leu Leu Lys Ser Val Val Tyr Phe Ala Ile Ile
            260                 265                 270

Thr Cys Cys Leu Leu Arg Arg Thr Ala Phe Cys Cys Asn Gly Glu Lys
        275                 280                 285

Ser


<210> SEQ ID NO 92
<211> LENGTH: 886
<212> TYPE: DNA
<213> ORGANISM: Homo sapiens

<400> SEQUENCE: 92
```

```
atgctgttct ccagcctgct gtgtgtattt gtggccttca gctactctgg atcaagtgtg     60

gcccagaagg ttactcaagc ccagtcatca gtatccatgc cagtgaggaa agcagtcacc    120

ctgaactgcc tgtatgaaac aagttggtgg tcatattata ttttttggta caagcaactt    180

cccagcaaag agatgatttt ccttattcgc cagggttctg atgaacagaa tgcaaaaagt    240

ggtcgctatt ctgtcaactt caagaaagca gcgaaatccg tcgccttaac catttcagcc    300

ttacagctag aagattcagc aaagtacttt tgtgctcttg gaaacggtaa tcacatcggg    360

tactggcggt acaccgataa actcatcttt ggaaaaggaa cccgtgtgac tgtggaacca    420

agaagtcagc ctcataccaa accatccgtt tttgtcatga aaaatggaac aaatgtcgct    480

tgtctggtga aggaattcta ccccaaggat ataagaataa atctcgtgtc atccaagaag    540

ataacagagt ttgatcctgc tattgtcatc tctcccagtg ggaagtacaa tgctgtcaag    600

cttggtaaat atgaagattc aaattcagtg acatgttcag ttcaacacga caataaaact    660

gtgcactcca ctgactttga agtgaagaca gattctacag atcacgtaaa accaaaggaa    720

actgaaaaca caaagcaacc ttcaaagagc tgccataaac ccaaagccat agttcatacc    780

gagaaggtga acatgatgtc cctcacagtg cttgggctac gaatgctgtt tgcaaagact    840

gttgccgtca attttctctt gactgccaag ttatttttct tgtaag                   886
```

<210> SEQ ID NO 93
<211> LENGTH: 921
<212> TYPE: DNA
<213> ORGANISM: Homo sapiens

<400> SEQUENCE: 93

```
atgcggtggg ccctactggt gcttctagct ttcctgtctc ctgccagtca gaaatcttcc     60

aacttggaag gggaacgaa gtcagtcacg aggccgacta ggtcatctgc tgaaatcact    120

tgtgacctta ctgtaataaa tgccttctac atccactggt acctacacca ggaggggaag    180

gccccacagc gtcttctgta ctatgacgtc tccaactcaa aggatgtgtt ggaatcagga    240

ctcagtccag gaaagtatta tactcataca cccaggaggt ggagctggat attgatacta    300

cgaaatctaa ttgaaaatga ttctggggtc tattactgtg ccacctggga cagactttat    360

tataagaaac tctttggcag tggaacaaca ctggttgtca cagataaaca acttgatgca    420

gatgtttccc ccaagcccac tatttttctt ccttcaattg ctgaaacaaa gctccagaag    480

gctggaacat acctttgtct tcttgagaaa tttttccctg atgttattaa gatacattgg    540

caagaaaaga agagcaacac gattctggga tcccaggagg ggaacaccat gaagactaac    600

gacacataca tgaaatttag ctggttaacg gtgccagaaa agtcactgga caaagaacac    660

agatgtatcg tcagacatga gaataataaa aacggagttg atcaagaaat tatctttcct    720

ccaataaaga cagatgtcat cacaatggat cccaaagaca attgttcaaa agatgcaaat    780

gatacactac tgctgcagct cacaaacacc tctgcatatt acatgtacct cctcctgctc    840

ctcaagagtg tggtctattt tgccatcatc acctgctgtc tgcttagaag aacggctttc    900

tgctgcaatg gagagaaatc a                                              921
```

<210> SEQ ID NO 94
<211> LENGTH: 882
<212> TYPE: DNA
<213> ORGANISM: Artificial
<220> FEATURE:
<223> OTHER INFORMATION: TRD B9 codon opt.

<400> SEQUENCE: 94
atggtgttca gcagcctgct gtgcgtgttc gtggccttca gctacagcgg cagcagcgtg 60
gcccagaaag tgacccaggc ccagagcagc gtgtccatgc ctgtgcggaa ggccgtgacc 120
ctgaactgcc tgtacgagac aagctggtgg tcctactaca tcttctggta caagcagctg 180
cccagcaaag agatgatctt cctgatccgg cagggcagcg acgagcagaa cgccaagagc 240
ggccggtaca gcgtgaactt caagaaagcc gccaagtccg tggccctgac catcagcgcc 300
ctgcagctgg aagatagcgc caagtacttc tgcgccctgg gcaatggcaa tcatattgga 360
tactggcgat ataccgacaa gctgatcttc ggcaagggca ccagagtgac cgtggaaccc 420
agaagccagc cccacaccaa gccctccgtg ttcgtgatga agaacggcac caacgtggcc 480
tgcctggtga aagaattcta ccccaaggac atccggatca acctggtgtc cagcaagaag 540
atcaccgagt tcgaccccgc catcgtgatc agccccagcg gcaagtacaa cgccgtgaag 600
ctggggaagt acgaggacag caacagcgtg acctgcagcg tgcagcacga caacaagacc 660
gtgcacagca ccgacttcga agtgaaaacc gactccaccg accacgtgaa gcccaaagag 720
acagagaaca ccaagcagcc cagcaagagc tgccacaagc ccaaggccat cgtgcacacc 780
gagaaagtga acatgatgag cctgaccgtg ctgggcctgc ggatgctgtt cgccaagaca 840
gtggccgtga acttcctgct gaccgccaag ctgttctttc tg 882

<210> SEQ ID NO 95
<211> LENGTH: 921
<212> TYPE: DNA
<213> ORGANISM: Artificial
<220> FEATURE:
<223> OTHER INFORMATION: TRG B9 codon opt.

<400> SEQUENCE: 95
atggtgtggg ccctgctggt gctgctggcc ttcctgagcc ccgccagcca gaagagcagc 60
aacctggagg gcggcaccaa gagcgtgacc cggcccaccc ggagcagcgc cgagatcacc 120
tgcgacctga ccgtgatcaa cgccttctac atccactggt atctgcacca ggagggcaag 180
gccccccagc ggctgctgta ctacgacgtg agcaacagca aggacgtgct ggagagcggc 240
ctgagccccg gcaagtacta cacccacacc ccccggcggt ggagctggat tctgatcctg 300
cggaacctga tcgagaacga cagcggcgtg tactactgcg ccacctggga ccggctgtac 360
tacaagaagc tgttcggcag cggcaccacc ctggtggtga ccgacaagca gctggacgcc 420
gacgtgtccc ccaagcctac catcttcctg ccctcaattg ctgagacaaa gctgcagaag 480
gccggcacct acctgtgcct gctggaaaag ttcttcccag acgtgatcaa gatccactgg 540
gaggaaaaga agtccaacac catcctgggc agccaagaag gcaacaccat gaagaccaac 600
gacacctaca tgaagttcag ctggctgacc gtgcccgaga agtccctgga caaagaacac 660
cggtgcatcg tgcggcacga gaacaacaag aacggcgtgg accaagaaat catcttccca 720
cccatcaaga ccgacgtgat cacaatggac cccaaggaca actgcagcaa ggacgccaac 780
gataccctgc tgctgcagct gacaaacacc agcgcctact acatgtactt gttgctgctg 840
ctgaagtccg tggtgtactt cgccatcatc acatgctgcc tgctgcggcg gaccgccttc 900
tgctgcaacg gcgagaagtc c 921

<210> SEQ ID NO 96
<211> LENGTH: 273
<212> TYPE: PRT
<213> ORGANISM: Homo sapiens -continued

<400> SEQUENCE: 96

```
Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Asp Ser
                85                  90                  95

Tyr Gly Gly Gly Pro Leu Tyr Thr Asp Lys Leu Ile Phe Gly Lys Gly
            100                 105                 110

Thr Arg Val Thr Val Glu Pro Arg Ser Gln Pro His Thr Lys Pro Ser
        115                 120                 125

Val Phe Val Met Lys Asn Gly Thr Asn Val Ala Cys Leu Val Lys Glu
    130                 135                 140

Phe Tyr Pro Lys Asp Ile Arg Ile Asn Leu Val Ser Ser Lys Lys Ile
145                 150                 155                 160

Thr Glu Phe Asp Pro Ala Ile Val Ile Ser Pro Ser Gly Lys Tyr Asn
                165                 170                 175

Ala Val Lys Leu Gly Lys Tyr Glu Asp Ser Asn Ser Val Thr Cys Ser
            180                 185                 190

Val Gln His Asp Asn Lys Thr Val His Ser Thr Asp Phe Glu Val Lys
        195                 200                 205

Thr Asp Ser Thr Asp His Val Lys Pro Lys Glu Thr Glu Asn Thr Lys
    210                 215                 220

Gln Pro Ser Lys Ser Cys His Lys Pro Lys Ala Ile Val His Thr Glu
225                 230                 235                 240

Lys Val Asn Met Met Ser Leu Thr Val Leu Gly Leu Arg Met Leu Phe
                245                 250                 255

Ala Lys Thr Val Ala Val Asn Phe Leu Leu Thr Ala Lys Leu Phe Phe
            260                 265                 270

Leu
```

<210> SEQ ID NO 97
<211> LENGTH: 291
<212> TYPE: PRT
<213> ORGANISM: Homo sapiens

<400> SEQUENCE: 97

```
Ser Ser Asn Leu Glu Gly Gly Thr Lys Ser Val Thr Arg Pro Thr Arg
1               5                   10                  15

Ser Ser Ala Glu Ile Thr Cys Asp Leu Thr Val Ile Asn Ala Phe Tyr
            20                  25                  30

Ile His Trp Tyr Leu His Gln Glu Gly Lys Ala Pro Gln Arg Leu Leu
        35                  40                  45

Tyr Tyr Asp Val Ser Asn Ser Lys Asp Val Leu Glu Ser Gly Leu Ser
    50                  55                  60

Pro Gly Lys Tyr Tyr Thr His Thr Pro Arg Arg Trp Ser Trp Ile Leu
65                  70                  75                  80
```

```
Ile Leu Arg Asn Leu Ile Glu Asn Asp Ser Gly Val Tyr Tyr Cys Ala
                85                  90                  95

Thr Trp Asp Arg Pro Glu Ile Tyr Tyr Lys Lys Leu Phe Gly Ser Gly
            100                 105                 110

Thr Thr Leu Val Val Thr Asp Lys Gln Leu Asp Ala Asp Val Ser Pro
        115                 120                 125

Lys Pro Thr Ile Phe Leu Pro Ser Ile Ala Glu Thr Lys Leu Gln Lys
    130                 135                 140

Ala Gly Thr Tyr Leu Cys Leu Leu Glu Lys Phe Phe Pro Asp Val Ile
145                 150                 155                 160

Lys Ile His Trp Glu Glu Lys Lys Ser Asn Thr Ile Leu Gly Ser Gln
                165                 170                 175

Glu Gly Asn Thr Met Lys Thr Asn Asp Thr Tyr Met Lys Phe Ser Trp
            180                 185                 190

Leu Thr Val Pro Glu Lys Ser Leu Asp Lys Glu His Arg Cys Ile Val
        195                 200                 205

Arg His Glu Asn Asn Lys Asn Gly Val Asp Gln Glu Ile Ile Phe Pro
    210                 215                 220

Pro Ile Lys Thr Asp Val Ile Thr Met Asp Pro Lys Asp Asn Cys Ser
225                 230                 235                 240

Lys Asp Ala Asn Asp Thr Leu Leu Leu Gln Leu Thr Asn Thr Ser Ala
                245                 250                 255

Tyr Tyr Met Tyr Leu Leu Leu Leu Leu Lys Ser Val Val Tyr Phe Ala
            260                 265                 270

Ile Ile Thr Cys Cys Leu Leu Arg Arg Thr Ala Phe Cys Cys Asn Gly
        275                 280                 285

Glu Lys Ser
    290
```

<210> SEQ ID NO 98
<211> LENGTH: 269
<212> TYPE: PRT
<213> ORGANISM: Homo sapiens

<400> SEQUENCE: 98

```
Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Leu
                85                  90                  95

Leu Gly Tyr Thr Asp Lys Leu Ile Phe Gly Lys Gly Thr Arg Val Thr
            100                 105                 110

Val Glu Pro Arg Ser Gln Pro His Thr Lys Pro Ser Val Phe Val Met
        115                 120                 125

Lys Asn Gly Thr Asn Val Ala Cys Leu Val Lys Glu Phe Tyr Pro Lys
    130                 135                 140

Asp Ile Arg Ile Asn Leu Val Ser Ser Lys Lys Ile Thr Glu Phe Asp
145                 150                 155                 160
```

Pro Ala Ile Val Ile Ser Pro Ser Gly Lys Tyr Asn Ala Val Lys Leu
165 170 175

Gly Lys Tyr Glu Asp Ser Asn Ser Val Thr Cys Ser Val Gln His Asp
180 185 190

Asn Lys Thr Val His Ser Thr Asp Phe Glu Val Lys Thr Asp Ser Thr
195 200 205

Asp His Val Lys Pro Lys Glu Thr Glu Asn Thr Lys Gln Pro Ser Lys
210 215 220

Ser Cys His Lys Pro Lys Ala Ile Val His Thr Glu Lys Val Asn Met
225 230 235 240

Met Ser Leu Thr Val Leu Gly Leu Arg Met Leu Phe Ala Lys Thr Val
245 250 255

Ala Val Asn Phe Leu Leu Thr Ala Lys Leu Phe Phe Leu
260 265

<210> SEQ ID NO 99
<211> LENGTH: 293
<212> TYPE: PRT
<213> ORGANISM: Homo sapiens

<400> SEQUENCE: 99

Ala Gly His Leu Glu Gln Pro Gln Ile Ser Ser Thr Lys Thr Leu Ser
1 5 10 15

Lys Thr Ala Arg Leu Glu Cys Val Val Ser Gly Ile Thr Ile Ser Ala
20 25 30

Thr Ser Val Tyr Trp Tyr Arg Glu Arg Pro Gly Glu Val Ile Gln Phe
35 40 45

Leu Val Ser Ile Ser Tyr Asp Gly Thr Val Arg Lys Glu Ser Gly Ile
50 55 60

Pro Ser Gly Lys Phe Glu Val Asp Arg Ile Pro Glu Thr Ser Thr Ser
65 70 75 80

Thr Leu Thr Ile His Asn Val Glu Lys Gln Asp Ile Ala Thr Tyr Tyr
85 90 95

Cys Ala Leu Trp Glu Glu Glu Leu Gly Lys Lys Ile Lys Val Phe Gly
100 105 110

Pro Gly Thr Lys Leu Ile Ile Thr Asp Lys Gln Leu Asp Ala Asp Val
115 120 125

Ser Pro Lys Pro Thr Ile Phe Leu Pro Ser Ile Ala Glu Thr Lys Leu
130 135 140

Gln Lys Ala Gly Thr Tyr Leu Cys Leu Leu Glu Lys Phe Phe Pro Asp
145 150 155 160

Val Ile Lys Ile His Trp Glu Glu Lys Lys Ser Asn Thr Ile Leu Gly
165 170 175

Ser Gln Glu Gly Asn Thr Met Lys Thr Asn Asp Thr Tyr Met Lys Phe
180 185 190

Ser Trp Leu Thr Val Pro Glu Lys Ser Leu Asp Lys Glu His Arg Cys
195 200 205

Ile Val Arg His Glu Asn Asn Lys Asn Gly Val Asp Gln Glu Ile Ile
210 215 220

Phe Pro Pro Ile Lys Thr Asp Val Ile Thr Met Asp Pro Lys Asp Asn
225 230 235 240

Cys Ser Lys Asp Ala Asn Asp Thr Leu Leu Leu Gln Leu Thr Asn Thr
245 250 255

Ser Ala Tyr Tyr Met Tyr Leu Leu Leu Leu Leu Lys Ser Val Val Tyr

```
            260                 265                 270

Phe Ala Ile Ile Thr Cys Cys Leu Leu Arg Arg Thr Ala Phe Cys Cys
        275                 280                 285

Asn Gly Glu Lys Ser
    290


<210> SEQ ID NO 100
<211> LENGTH: 271
<212> TYPE: PRT
<213> ORGANISM: Homo sapiens

<400> SEQUENCE: 100

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Ala
                85                  90                  95

Leu Lys Arg Thr Asp Thr Asp Lys Leu Ile Phe Gly Lys Gly Thr Arg
            100                 105                 110

Val Thr Val Glu Pro Arg Ser Gln Pro His Thr Lys Pro Ser Val Phe
        115                 120                 125

Val Met Lys Asn Gly Thr Asn Val Ala Cys Leu Val Lys Glu Phe Tyr
    130                 135                 140

Pro Lys Asp Ile Arg Ile Asn Leu Val Ser Ser Lys Lys Ile Thr Glu
145                 150                 155                 160

Phe Asp Pro Ala Ile Val Ile Ser Pro Ser Gly Lys Tyr Asn Ala Val
                165                 170                 175

Lys Leu Gly Lys Tyr Glu Asp Ser Asn Ser Val Thr Cys Ser Val Gln
            180                 185                 190

His Asp Asn Lys Thr Val His Ser Thr Asp Phe Glu Val Lys Thr Asp
        195                 200                 205

Ser Thr Asp His Val Lys Pro Lys Glu Thr Glu Asn Thr Lys Gln Pro
    210                 215                 220

Ser Lys Ser Cys His Lys Pro Lys Ala Ile Val His Thr Glu Lys Val
225                 230                 235                 240

Asn Met Met Ser Leu Thr Val Leu Gly Leu Arg Met Leu Phe Ala Lys
                245                 250                 255

Thr Val Ala Val Asn Phe Leu Leu Thr Ala Lys Leu Phe Phe Leu
            260                 265                 270


<210> SEQ ID NO 101
<211> LENGTH: 294
<212> TYPE: PRT
<213> ORGANISM: Homo sapiens

<400> SEQUENCE: 101

Ala Gly His Leu Glu Gln Pro Gln Ile Ser Ser Thr Lys Thr Leu Ser
1               5                   10                  15

Lys Thr Ala Arg Leu Glu Cys Val Val Ser Gly Ile Thr Ile Ser Ala
```

-continued

```
            20                  25                  30

Thr Ser Val Tyr Trp Tyr Arg Glu Arg Pro Gly Glu Val Ile Gln Phe
        35                  40                  45

Leu Val Ser Ile Ser Tyr Asp Gly Thr Val Arg Lys Glu Ser Gly Ile
    50                  55                  60

Pro Ser Gly Lys Phe Glu Val Asp Arg Ile Pro Glu Thr Ser Thr Ser
65                  70                  75                  80

Thr Leu Thr Ile His Asn Val Glu Lys Gln Asp Ile Ala Thr Tyr Tyr
                85                  90                  95

Cys Ala Leu Trp Glu Ile Gln Glu Leu Gly Lys Lys Ile Lys Val Phe
            100                 105                 110

Gly Pro Gly Thr Lys Leu Ile Ile Thr Asp Lys Gln Leu Asp Ala Asp
        115                 120                 125

Val Ser Pro Lys Pro Thr Ile Phe Leu Pro Ser Ile Ala Glu Thr Lys
    130                 135                 140

Leu Gln Lys Ala Gly Thr Tyr Leu Cys Leu Leu Glu Lys Phe Phe Pro
145                 150                 155                 160

Asp Val Ile Lys Ile His Trp Glu Glu Lys Lys Ser Asn Thr Ile Leu
                165                 170                 175

Gly Ser Gln Glu Gly Asn Thr Met Lys Thr Asn Asp Thr Tyr Met Lys
            180                 185                 190

Phe Ser Trp Leu Thr Val Pro Glu Lys Ser Leu Asp Lys Glu His Arg
        195                 200                 205

Cys Ile Val Arg His Glu Asn Asn Lys Asn Gly Val Asp Gln Glu Ile
    210                 215                 220

Ile Phe Pro Pro Ile Lys Thr Asp Val Ile Thr Met Asp Pro Lys Asp
225                 230                 235                 240

Asn Cys Ser Lys Asp Ala Asn Asp Thr Leu Leu Leu Gln Leu Thr Asn
                245                 250                 255

Thr Ser Ala Tyr Tyr Met Tyr Leu Leu Leu Leu Leu Lys Ser Val Val
            260                 265                 270

Tyr Phe Ala Ile Ile Thr Cys Cys Leu Leu Arg Arg Thr Ala Phe Cys
        275                 280                 285

Cys Asn Gly Glu Lys Ser
    290
```